(12) United States Patent
Chan et al.

(10) Patent No.: US 11,981,911 B2
(45) Date of Patent: May 14, 2024

(54) COMPOSITIONS AND METHODS FOR INHIBITING VIRAL VECTOR-INDUCED INFLAMMATORY RESPONSES

(71) Applicant: President and Fellows of Harvard College, Cambridge, MA (US)

(72) Inventors: Ying Kai Chan, Cambridge, MA (US); George M. Church, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 687 days.

(21) Appl. No.: 16/762,356

(22) PCT Filed: Nov. 8, 2018

(86) PCT No.: PCT/US2018/059756
§ 371 (c)(1),
(2) Date: May 7, 2020

(87) PCT Pub. No.: WO2019/094548
PCT Pub. Date: May 16, 2019

(65) Prior Publication Data
US 2020/0270637 A1    Aug. 27, 2020

Related U.S. Application Data

(60) Provisional application No. 62/595,433, filed on Dec. 6, 2017, provisional application No. 62/583,449, filed on Nov. 8, 2017.

(51) Int. Cl.
*C12N 15/86* (2006.01)
*C12N 15/117* (2010.01)

(52) U.S. Cl.
CPC ............ *C12N 15/86* (2013.01); *C12N 15/117* (2013.01); *C12N 2710/10343* (2013.01)

(58) Field of Classification Search
None
See application file for complete search history.

(56) References Cited

U.S. PATENT DOCUMENTS

| | | |
|---|---|---|
| 5,618,696 A | 4/1997 | Norris et al. |
| 5,643,890 A | 7/1997 | Iversen et al. |
| 6,194,206 B1 | 2/2001 | West et al. |
| 6,225,292 B1 | 5/2001 | Raz et al. |
| 7,271,156 B2 | 9/2007 | Krieg et al. |
| 7,314,926 B1 | 1/2008 | Miller et al. |

(Continued)

FOREIGN PATENT DOCUMENTS

| | | |
|---|---|---|
| CN | 101712957 A | 5/2010 |
| CN | 102925485 A | 2/2013 |

(Continued)

OTHER PUBLICATIONS

GenBank: HP047598.1 (2012) (Year: 2012).*

(Continued)

*Primary Examiner* — Michelle S Horning
(74) *Attorney, Agent, or Firm* — Wolf, Greenfield & Sacks, P.C.

(57) ABSTRACT

Provided herein, in some embodiments, are recombinant viral genomes comprising an inhibitory oligonucleotide that reduces inflammation for use, for example, in gene therapy.

18 Claims, 20 Drawing Sheets

Specification includes a Sequence Listing.

(56) References Cited

U.S. PATENT DOCUMENTS

| | | |
|---|---|---|
| 7,514,414 B2 | 4/2009 | Klinman et al. |
| 7,514,415 B2 | 4/2009 | Klinman et al. |
| 7,723,054 B2 | 5/2010 | Latz et al. |
| 7,879,812 B2 | 2/2011 | Ashman et al. |
| 8,030,289 B2 | 10/2011 | Wang et al. |
| 8,053,422 B2 | 11/2011 | Klinman et al. |
| 8,153,141 B2 | 4/2012 | Lipford et al. |
| 8,377,898 B2 | 2/2013 | Kandimalla et al. |
| 8,486,908 B2 | 7/2013 | Kandimalla et al. |
| 8,771,669 B1 | 7/2014 | Bermudes |
| 8,853,177 B2 | 10/2014 | Zhu et al. |
| 8,895,521 B2 | 11/2014 | Klinman et al. |
| 8,933,011 B2 | 1/2015 | O'Neill et al. |
| 9,006,203 B2 | 4/2015 | Klinman et al. |
| 9,096,858 B2 | 8/2015 | Kandimalla et al. |
| 9,540,651 B2 | 1/2017 | Kandimalla et al. |
| 10,124,062 B2 | 11/2018 | O'Neil |
| 10,441,654 B2 | 10/2019 | Korneluk et al. |
| 11,339,396 B2 | 5/2022 | Chan et al. |
| 2003/0176376 A1 | 9/2003 | Klem |
| 2004/0097455 A1 | 5/2004 | Borunda et al. |
| 2004/0132682 A1 | 7/2004 | Klinman et al. |
| 2004/0248834 A1 | 12/2004 | Klinman et al. |
| 2005/0239733 A1 | 10/2005 | Jurk et al. |
| 2006/0074039 A1 | 4/2006 | Klinman et al. |
| 2007/0020624 A1 | 1/2007 | Rubenfield et al. |
| 2009/0081157 A1 | 3/2009 | Kornbluth et al. |
| 2009/0082288 A1 | 3/2009 | Klinman et al. |
| 2009/0142310 A1 | 6/2009 | Klinman et al. |
| 2009/0208468 A1 | 8/2009 | Klinman et al. |
| 2010/0069467 A1 | 3/2010 | Boye et al. |
| 2010/0081706 A1* | 4/2010 | Ashman ............. A61P 37/00 536/23.1 |
| 2010/0144839 A1 | 6/2010 | Klinman et al. |
| 2011/0033448 A1 | 2/2011 | Gilliet et al. |
| 2011/0070241 A1 | 3/2011 | Yang |
| 2011/0077289 A1 | 3/2011 | Klinman et al. |
| 2011/0182927 A1 | 7/2011 | Raz et al. |
| 2011/0201676 A1 | 8/2011 | Klinman et al. |
| 2011/0236392 A1 | 9/2011 | O'Neill et al. |
| 2011/0251264 A1 | 10/2011 | McArthur et al. |
| 2012/0009170 A1 | 1/2012 | Klinman et al. |
| 2012/0016013 A1 | 1/2012 | Klinman et al. |
| 2012/0076763 A1 | 3/2012 | Anderson et al. |
| 2012/0128699 A1 | 5/2012 | Kandimalla et al. |
| 2012/0258144 A1 | 10/2012 | Klinman et al. |
| 2013/0018089 A1 | 1/2013 | Klinman et al. |
| 2013/0101558 A1 | 4/2013 | Gao et al. |
| 2013/0281518 A1 | 10/2013 | Klinman et al. |
| 2014/0004100 A1 | 1/2014 | Kandimalla et al. |
| 2014/0134233 A1 | 5/2014 | Klinman et al. |
| 2014/0234252 A1* | 8/2014 | Campbell ............. A61K 47/14 435/320.1 |
| 2014/0271550 A1 | 9/2014 | Rabinowitz et al. |
| 2015/0238550 A1 | 8/2015 | McCown et al. |
| 2015/0299710 A1 | 10/2015 | Esashi et al. |
| 2015/0320800 A1 | 11/2015 | Contag et al. |
| 2017/0035864 A1 | 2/2017 | Theriault |
| 2017/0190778 A1 | 7/2017 | Layne et al. |
| 2017/0233741 A1 | 8/2017 | Kandimalla et al. |
| 2018/0023085 A1 | 1/2018 | Kandimalla et al. |
| 2018/0275120 A1 | 9/2018 | Lee |
| 2018/0325890 A1 | 11/2018 | De Lonlay-Debeney et al. |
| 2019/0177731 A1 | 6/2019 | Chan et al. |
| 2019/0316151 A1 | 10/2019 | Chan et al. |
| 2022/0259599 A1 | 8/2022 | Chan et al. |

FOREIGN PATENT DOCUMENTS

| | | |
|---|---|---|
| CN | 109451729 A | 3/2019 |
| EP | 3329004 B1 | 6/2018 |
| JP | 2002-505580 A | 2/2002 |
| JP | 2010-035488 A | 2/2010 |
| JP | 2013-544816 A | 12/2013 |
| JP | 2015-532095 A | 11/2015 |
| JP | 2015-536659 A | 12/2015 |
| WO | WO 98/055495 A2 | 12/1998 |
| WO | WO 2003/103586 A2 | 12/2003 |
| WO | WO 2004/048511 A2 | 6/2004 |
| WO | WO 2005/013891 A2 | 2/2005 |
| WO | WO 2005/035579 A1 | 4/2005 |
| WO | WO 2005/111211 A2 | 11/2005 |
| WO | WO 2005/116250 A2 | 12/2005 |
| WO | WO 2006/028742 A2 | 3/2006 |
| WO | WO 2006/035939 A1 | 4/2006 |
| WO | WO 2006/066003 A2 | 6/2006 |
| WO | WO 2007/047396 A2 | 4/2007 |
| WO | WO 2007/147011 A2 | 12/2007 |
| WO | WO 2008/104985 A2 | 9/2008 |
| WO | WO 2009/006141 A2 | 1/2009 |
| WO | WO 2009/023819 A2 | 2/2009 |
| WO | WO 2009/055076 A2 | 4/2009 |
| WO | WO 2009/089399 A2 | 7/2009 |
| WO | WO 2009/089401 A2 | 7/2009 |
| WO | WO 2009/143292 A2 | 11/2009 |
| WO | WO 2010/141483 A2 | 12/2010 |
| WO | WO 2011/005942 A2 | 1/2011 |
| WO | WO 2011/159328 A1 | 12/2011 |
| WO | WO 2011/159958 A2 | 12/2011 |
| WO | WO 2012/022948 A1 | 2/2012 |
| WO | WO 212/051491 A1 | 4/2012 |
| WO | WO 2012/068470 A2 | 5/2012 |
| WO | WO 2013/116590 A1 | 8/2013 |
| WO | WO 2014/001422 A2 | 1/2014 |
| WO | WO 2014/052789 A1 | 4/2014 |
| WO | WO 2014/082254 A1 | 6/2014 |
| WO | WO 2014/105870 A1 | 7/2014 |
| WO | WO 2014/110081 A1 | 7/2014 |
| WO | WO 2016/020377 A1 | 2/2016 |
| WO | WO 2016/070045 A1 | 5/2016 |
| WO | WO 2016/130832 A1 | 8/2016 |
| WO | WO 2016/149612 A2 | 9/2016 |
| WO | WO 2016/183370 A1 | 11/2016 |
| WO | WO 2017/111045 A1 | 6/2017 |
| WO | WO 2017/214378 A1 | 12/2017 |
| WO | WO 2018/095697 A1 | 5/2018 |
| WO | WO 2019/094548 A1 | 5/2019 |

OTHER PUBLICATIONS

Phillips MI. Antisense inhibition and adeno-associated viral vector delivery for reducing hypertension. Hypertension. Jan. 1997;29(1 Pt 2):177-87. (Year: 1997).*

Yan Z, Zak R, Zhang Y, Engelhardt JF. Inverted terminal repeat sequences are important for intermolecular recombination and circularization of adeno-associated virus genomes. J Virol. Jan. 2005;79(1):364-79. (Year: 2005).*

Eckmann CR, Rammelt C, Wahle E. Control of poly(A) tail length. Wiley Interdiscip Rev RNA. May-Jun. 2011;2(3):348-61. Abstact Only. (Year: 2011).*

Gray JT, Zolotukhin S. Design and construction of functional AAV vectors. Methods Mol Biol. 2011;807:25-46. (Year: 2011).*

International Search Report and Written Opinion dated May 3, 2019, for Application No. PCT/US2018/059756.

International Preliminary Report on Patentability dated May 22, 2020, for Application No. PCT/US2018/059756.

Extended European Search Report dated Dec. 5, 2019, for Application No. EP 17811006.0.

International Search Report and Written Opinion dated Oct. 25, 2017, for Application No. PCT/US2017/036525.

International Preliminary Report on Patentability dated Dec. 20, 2018, for Application No. PCT/US2017/036525.

[No Author Listed], ODN 2088 control. InvivoGen. Accessed on May 27, 2020. Accessible at www.invivogen.com/odn2088-control. 2 pages.

[No Author Listed], ODN 2088. InvivoGen. Accessed on May 27, 2020. Accessible at www.invivogen.com/odn2088. 2 pages.

[No Author Listed], ODN 4084-F. InvivoGen. Accessed on May 27, 2020. Accessible at www.invivogen.com/odn4084-f. 2 pages.

(56) References Cited

OTHER PUBLICATIONS

[No Author Listed], ODN INH-18. InvivoGen. Accessed on May 27, 2020. Accessible at www.invivogen.com/odn-inh18. 2 pages.

[No Author Listed], ODG TTAGGG (A151). InvivoGen. Accessed on May 27, 2020. Accessible at www.invivogen.com/odn2088. 2 pages.

[No Author Listed], ODG TTAGGG control. InvivoGen. Accessed on May 27, 2020. Accessible at www.invivogen.com/odn2088. 2 pages.

Arbuckle et al., The molecular biology of human herpesvirus-6 latency and telomere integration. Microbes Infect. Aug. 2011; 13(8-9):731-41.

Ashman et al., Optimal oligonucleotide sequences for TLR9 inhibitory activity in human cells: lack of correlation with TLR9 binding. Int Immunol. Mar. 2011;23(3):203-14. doi: 10.1093/intimm/dxq473.

Ashman et al., Sequence requirements for oligodeoxyribonucleotide inhibitory activity. Int Immunol. Apr. 2005;17(4):411-20.

Bessis et al., Immune responses to gene therapy vectors: influence on vector function and effector mechanisms. Gene Ther. Oct. 2004;11 Suppl 1:S10-7.

Beutler et al., TLRs and innate immunity. Blood. Feb. 2009;113(7):1399-1407. Online print version. https://www.ncbi.nlm.nih.gov/pmc/articles/PMC2644070/?report=printable. 21 pages.

Cerullo et al., Toll-like receptor 9 triggers an innate immune response to helper-dependent adenoviral vectors. Mol Ther. Feb. 2007;15(2):378-85.

Chan et al., Viral evasion of intracellular DNA and RNA sensing. Nat Rev Microbiol. Jun. 2016;14:360-73. Epub May 13, 2016. Author Manuscript, 43 pages.

Chan, Manipulating the Immune Response to Viral Pathogens and Gene Therapy Viral Vectors. Powerpoint Presentation slides. Loyola Seminar. 46 pages. Jun. 30, 2016.

Chinnery et al., Retinal microglial activation following topical application of intracellular toll-like receptor ligands. Invest Ophthalmol Vis Sci. 2015;56(12):7377-86. doi: 10.1167/iovs.15-17587.

Chinnery et al., TLR9 ligand CpG-ODN applied to the injured mouse cornea elicits retinal inflammation. Am J Pathol. Jan. 2012;180(1):209-20. doi: 10.1016/j.ajpath.2011.09.041.

Doi et al., Microglia activated with the toll-like receptor 9 ligand CpG attenuate oligomeric amyloid { beta } neurotoxicity in in vitro and in vivo models of Alzheimer's disease. Am J Pathol. Nov. 2009;175(5):2121-32. doi: 10.2353/ajpath.2009.090418.

Faust et al., CpG-depleted adeno-associated virus vectors evade immune detection. J Clin Invest. Jul. 2013;123(7):2994-3001.

Gursel et al., Repetitive elements in mammalian telomeres suppress bacterial DNA-induced immune activation. J Immunol. 2003;171(3):1393-400.

Hartmann et al., Mechanism and function of a newly identified CpG DNA motif in human primary B cells. J Immunol. Jan. 15, 2000;164(2):944-53.

Hensley et al., Toll-like receptors impact on safety and efficacy of gene transfer vectors. Mol Ther. Aug. 2007;15(8):1417-22. doi: 10.1038/sj.mt.6300217.

Ho et al., An immunomodulatory GpG oligonucleotide for the treatment of autoimmunity via the innate and adaptive immune systems. J Immunol. 2003;171(9):4920-4926. doi:10.4049/jimmunol. 171.9.4920.

Huang et al., Targeting the TLR9-MyD88 pathway in the regulation of adaptive immune responses. Expert Opin Ther Targets. Aug. 2010;14(8):787-96. doi: 10.1517/14728222.2010.501333. Review.

Kaminski et al., Synthetic oligodeoxynucleotides containing suppressive TTAGGG motifs inhibit AIM2 inflammasome activation. J Immunol. 2013;191(7):3876-83. doi: 10.4049/jimmunol.1300530. Author Manuscript, 19 pages.

Krieg et al., CpG motifs in bacterial DNA trigger direct B-cell activation. Nature. Apr. 6, 1995;374(6522):546-9.

Krieg et al., Sequence motifs in adenoviral DNA block immune activation by stimulatory CpG motifs. Proc Natl Acad Sci U S A. Oct. 1998;95(21):12631-6.

Krieg, Therapeutic potential of Toll-like receptor 9 activation. Nat Rev. Jun. 2006;5(6):471-84.

Kumagai et al., TLR9 as a key receptor for the recognition of DNA. Adv Drug Deliv Rev. Apr. 2008;60(7):795-804. doi: 10.1016/j.addr. 2007.12.004.

Latz et al., Ligand-induced conformational changes allosterically activate Toll-like receptor 9. Nat Immunol. Jul. 2007;8(7):772-9.

Lee et al., Nucleic acid-binding polymers as anti-inflammatory agents. Proc Natl Acad Sci U S A. Aug. 23, 2011;108(34):14055-60. doi: 10.1073/pnas.1105777108. Epub Aug. 15, 2011.

Lenert et al., Classification, mechanisms of action, and therapeutic applications of inhibitory oligonucleotides for Toll-like receptors (TLR) 7 and 9. Mediators Inflamm. 2010;2010:986596. 10 pages. doi: 10.1155/2010/986596.

Lenert et al., DNAlike class R inhibitory oligonucleotides (INH-ODNs) preferentially block autoantigen-induced B-cell and dendritic cell activation in vitro and autoantibody production in lupus-prone MRL-Fas(lpr/lpr) mice in vivo. Arthritis Res Ther. 2009;11(3):R79. doi: 10.1186/ar2710. Available online http://arthritis-research.com/content/11/3/R79. 16 pages. Epub May 28, 2009.

Lenert et al., Structural characterization of the inhibitory DNA motif for the type A (D)-CpG-induced cytokine secretion and NK-cell lytic activity in mouse spleen cells. DNA Cell Biol. 2003;22(10):621-31. doi: 10.1089/104454903770238094.

Lenert et al., Targeting Toll-like receptor signaling in plasmacytoid dendritic cells and autoreactive B cells as a therapy for lupus. Arthritis Res Ther. 2006;8(1):203(1-11). doi: 10.1186/ar1888. Epub Jan. 10, 2006.

Li et al., A novel antagonist of TLR9 blocking all classes of immunostimulatory CpG-ODNs. Vaccine. 2011;29(11):2193-8. doi: 10.1016/j.vaccine.2010.10.042.

Martino et al., The genome of self-complementary adeno-associated viral vectors increases Toll-like receptor 9-dependent innate immune responses in the liver. Blood. Jun. 16, 2011;117(24):6459-68. Epub Apr. 7, 2011. https:///www.ncbi.nlm.nih.gov/pmc/articles/PMC3123017/?report=printable. 21 pages.

Ohto et al., Structural basis of CpG and inhibitory DNA recognition by Toll-like receptor 9. Nature. Apr. 2015;520(7549):702-5. doi: 10.1038/nature14138.

Olson et al., Microglia initiate central nervous system innate and adaptive immune responses through multiple TLRs. J Immunol. Sep. 15, 2004;173(6):3916-24.

Peter et al., Characterization of suppressive oligodeoxynucleotides that inhibit Toll-like receptor-9-mediated activation of innate immunity. Immunology. 2008;123(1):118-28. doi: 10.1111/j.1365-2567. 2007.02718.x.

Rogers et al., Innate immune responses to AAV vectors. Frontiers in Microbiology. Sep. 19, 2011;2(194):1-10.

Sanftner et al., Recombinant AAV-mediated delivery of a tet-inducible reporter gene to the rat retina. Mol Ther. May 2001;3(5 Pt 1):688-96.

Shirota et al., Suppressive oligodeoxynucleotides protect mice from lethal endotoxic shock. J Immunol. 2005;174(8):4579-83.

Stunz et al., Inhibitory oligonucleotides specifically block effects of stimulatory CpG oligonucleotides in B cells. Eur J Immunol. 2002;32(5):1212-22.

Takeda et al., TLR signaling pathways. Semin Immunol. Feb. 2004;16(1):3-9.

Trieu et al., DNA motifs suppressing TLR9 responses. Crit Rev Immunol. 2006;26(6):527-44.

Yew et al., Reducing the immunostimulatory activity of CpG-containing plasmid DNA vectors for non-viral gene therapy. Expert Opin Drug Deliv. Nov. 2004;1(1):115-25. Review. Erratum in: Expert Opin Drug Deliv. Jan. 2005;2(1):199.

Zhu et al., The TLR9-MyD88 pathway is critical for adaptive immune responses to adeno-associated virus gene therapy vectors in mice. J Clin Invest. Aug. 2009;119(8):2388-98. doi: 10.1172/JCI37607.

U.S. Appl. No. 16/167,764, filed Oct. 23, 2018, Published, 2019-0316151.

U.S. Appl. No. 16/308,420, filed Dec. 7, 2018, Published, 2019-0177731.

(56) References Cited

OTHER PUBLICATIONS

PCT/US2018/059756, May 3, 2019, International Search Report and Written Opinion.
PCT/US2018/059756, May 22, 2020, International Preliminary Report on Patentability.
EP 17811006.0, Dec. 5, 2019, Extended European Search Report.
PCT/US2017/036525, Oct. 25, 2017, International Search Report and Written Opinion.
PCT/US2017/036525, Dec. 20, 2018, International Preliminary Report on Patentability.
Invitation to Pay Additional Fees for Application No. PCT/US2020/032819, dated Aug. 27, 2020.
International Search Report and Written Opinion for Application No. PCT/US2020/032819, dated Oct. 23, 2020.
International Preliminary Report on Patentability dated Nov. 16, 2021, for Application No. PCT/US2020/032819.
Ballas et al., Induction of NK activity in murine and human cells by CpG motifs in oligodeoxynucleotides and bacterial DNA. J Immunol. Sep. 1, 1996;157(5):1840-5.
Chan et al., Engineering adeno-associated viral vectors to evade innate immune and inflammatory responses. Sci Transl Med. Feb. 10, 2021;13(580):eabd3438. doi: 10.1126/scitranslmed.abd3438.
Chen et al., Identification of methylated CpG motifs as inhibitors of the immune stimulatory CpG motifs. Gene Ther. Jul. 2001;8(13):1024-32. doi: 10.1038/sj.gt.3301482.
Cui et al., Transcriptional regulation of gene expression by microRNAs as endogenous decoys of transcription factors. Cell Physiol Biochem. 2014;33(6):1698-714. Epub May 20, 2014.
Duramad et al., Inhibitors of TLR-9 act on multiple cell subsets in mouse and man in vitro and prevent death in vivo from systemic inflammation. J Immunol. May 1, 2005;174(9):5193-200. doi: 10.4049/jimmunol.174.9.5193.
Klinman et al., Contribution of CpG motifs to the immunogenicity of DNA vaccines. J Immunol. Apr. 15, 1997;158(8):3635-9.
Patole et al., G-rich DNA suppresses systemic lupus. J Am Soc Nephrol. Nov. 2005;16(11):3273-80. doi: 10.1681/ASN.2005060658. Epub Sep. 21, 2005.
Sato et al., Immunostimulatory DNA sequences necessary for effective intradermal gene immunization. Science. Jul. 19, 1996;273(5273):352-4. doi: 10.1126/science.273.5273.352.
Schwerk et al., Translating the untranslated region. J Immunol. Oct. 1, 2015;195(7):2963-71.
Shirota et al., Suppressive oligodeoxynucleotides inhibit Th1 differentiation by blocking IFN-gamma- and IL-12-mediated signaling. J Immunol. Oct. 15, 2004;173(8):5002-7. doi: 10.4049/jimmunol.173.8.5002.
Yamamoto et al., DNA from bacteria, but not from vertebrates, induces interferons, activates natural killer cells and inhibits tumor growth. Microbiol Immunol. 1992;36(9):983-97. doi: 10.1111/j.1348-0421.1992.tb02102.x.
[No Author Listed], Genbank Accession No. HP047598.1. Oct. 2, 2012. 1 page.

* cited by examiner

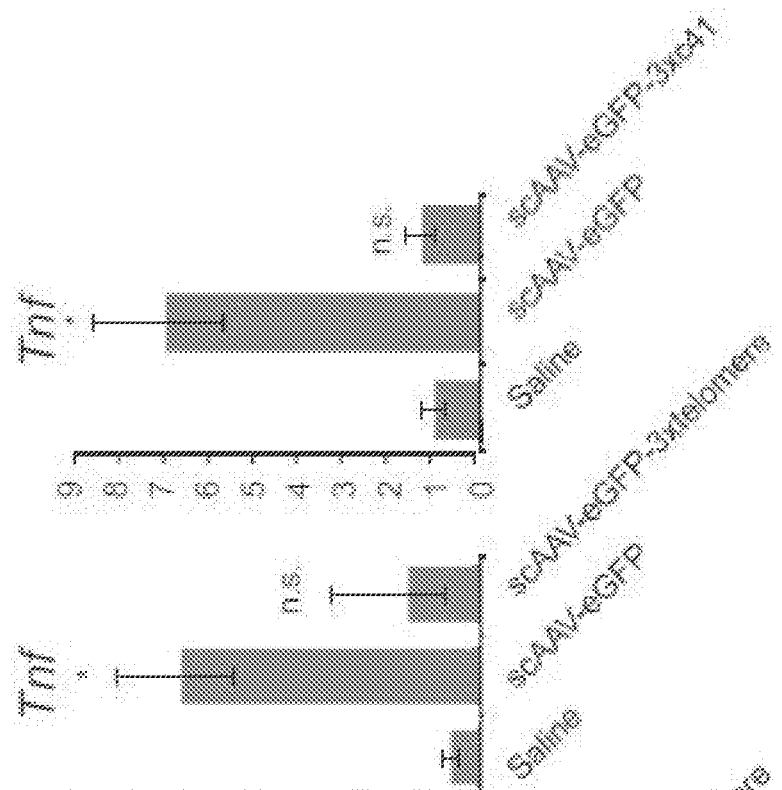

FIG. 4 ssAAV-eGFP:

| ITR | promoter | intron | eGFP | LPA | ITR | ssAAV-eGFP-5xtelomere:

| ITR | promoter | intron | eGFP | LPA | ▓ | ITR |

[3 copies of "telomere" with AAAAA linkers] – [reverse complementary of 5 copies of telomere with linkers]

ssAAV-eGFP-3xtelo3xINH18:

| ITR | promoter | intron | eGFP | LPA | ▓ | ITR |

[3 copies of "telomere" with AAAAA linkers] – [reverse complementary of 3 copies of INH18 with linkers]

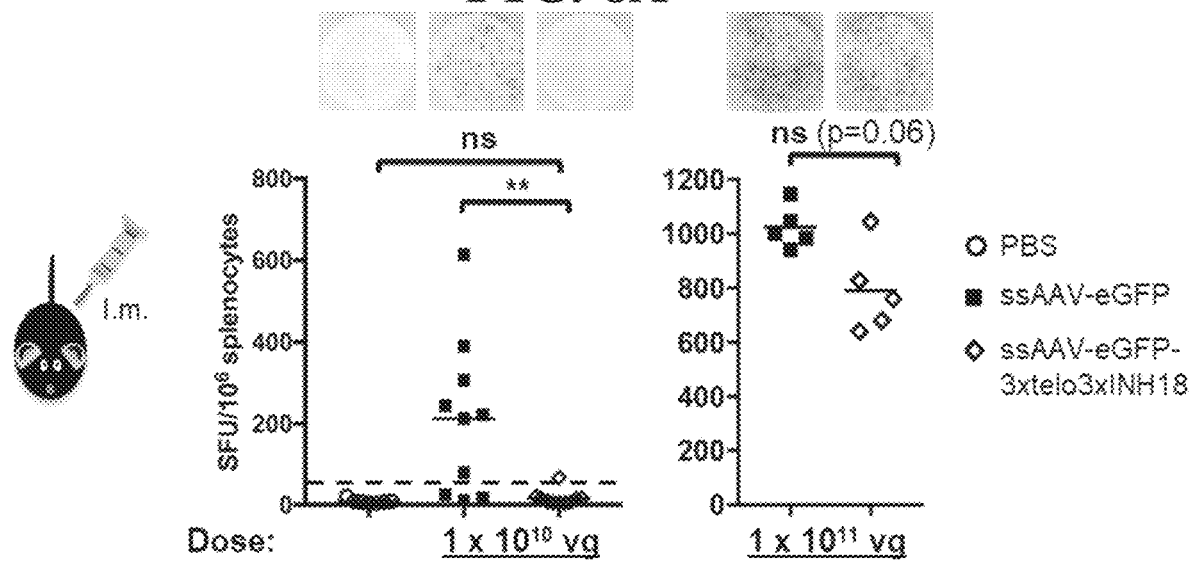
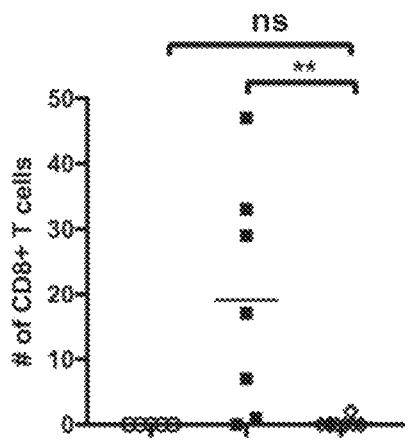
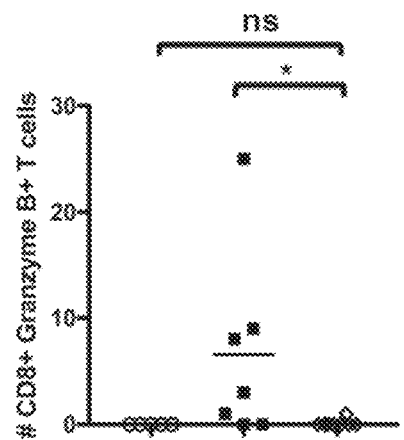

FIG. 13 ssAAV-eGFP-WPRE:
| ITR | promoter | intron | eGFP | LPA | WPRE | ITR | ssAAV-eGFP-WPRE-3xtelo3xiNH18:
| ITR | promoter | intron | eGFP | LPA | WPRE | ITR |

[3 copies of "telomere" with AAAAA linkers] – [reverse complementary of 3 copies of iNH18 with linkers]

COMPOSITIONS AND METHODS FOR INHIBITING VIRAL VECTOR-INDUCED INFLAMMATORY RESPONSES

RELATED APPLICATIONS

This application is a national stage filing under 35 U.S.C. § 371 of international application number PCT/US2018/059756, filed Nov. 8, 2018, which claims the benefit under 35 U.S.C. § 119(e) of U.S. provisional application No. 62/583,449, filed Nov. 8, 2017 and U.S. provisional application No. 62/595,433, filed Dec. 6, 2017, each of which is incorporated by reference herein in its entirety.

FEDERALLY SPONSORED RESEARCH

This invention was made with government support under Grant No. HG008525 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Oct. 6, 2022, is named H049870653US02-SUB-SEQ-KVC and is 139,521 bytes in size.

BACKGROUND

Viruses have evolved to become highly efficient at nucleic acid delivery to specific cell types while avoiding immunosurveillance by an infected host. These properties make viruses attractive gene-delivery vehicles, or vectors, for gene therapy. Several types of viruses, including retrovirus, adenovirus, adeno-associated virus (AAV), and herpes simplex virus, have been modified in the laboratory for use in gene therapy (Robbins, P D et al. *Pharmol Ther,* 1998; 80(1):35-47). Nonetheless, viral vectors have been shown to elicit an inflammatory response.

SUMMARY

Provided herein, in some embodiments, are viral molecular therapy vectors that inhibit nucleic acid-mediated inflammatory responses while boosting expression of a desired therapeutic molecule (e.g., a therapeutic gene of interest). The vectors of the present disclosure include a recombinant viral genome linked in cis to an inhibitory oligonucleotide sequence that prevents virally-induced production of proinflammatory cytokines. In some embodiments, the inhibitory oligonucleotide inhibits nucleic acid-mediated activation of toll-like receptors and/or inhibits nucleic acid-mediated toll-like receptor (TLR) signaling (e.g., TLR9). Surprisingly, inclusion of the inhibitory oligonucleotide in the viral genome not only inhibits the inflammatory response, but it also increases transduction efficiency and/or efficacy of the therapeutic nucleotide sequence and/or expression levels of expression products encoded by nucleic acids, as appropriate. Thus, the amount of recombinant viral genome needed to be therapeutically effective is less than the amount needed with conventional viral vector delivery systems that do not include an inhibitory oligonucleotide.

Thus, some aspects of the present disclosure provide recombinant viral genomes comprising a therapeutic nucleic acid (e.g., DNA encoding a gene (e.g., Cas9) or gene fragment (e.g., a replacement exon of interest) and an inhibitory oligonucleotide that inhibits the production of proinflammatory cytokines. Also provided herein, in some aspects, are methods comprising administering to a subject a recombinant viral genome that comprises a therapeutic nucleic acid (e.g., DNA) and an inhibitory oligonucleotide that inhibits the production of proinflammatory cytokines. In some embodiments, the recombinant viral genomes are administered intramuscularly. In other embodiments, the recombinant viral genomes are administered intravenously. In some embodiments, the recombinant viral genomes are administered to the eye (e.g., intravitreally).

Other aspects of the present disclosure provide recombinant viral genomes comprising a therapeutic nucleotide sequence and an inhibitory oligonucleotide that inhibits nucleic acid-sensing TLR activation and/or signaling. Also provided herein, in some aspects, are methods comprising administering to a subject a recombinant viral genome comprising a therapeutic nucleotide sequence and an inhibitory oligonucleotide that inhibits nucleic acid-sensing TLR activation and/or signaling.

In some embodiments, the TLR is TLR9. In some embodiments, the inhibitory oligonucleotide binds to the TLR. In other embodiments, the inhibitory oligonucleotide binds to inflammatory nucleic acids. In some embodiments, the inflammatory nucleic acids comprise CpG oligodeoxynucleotides. In some embodiments, the inhibitory oligonucleotide comprises a CCx(not-C)(not-C)xxGGG (SEQ ID NO: 63) motif, wherein x is any nucleic acid.

BRIEF DESCRIPTION OF THE DRAWINGS

FIG. 1A: TLR9 activating nucleic acid (ODN 2006) linked to each of the indicated sequences on the X-axis was tested in the HEK293-TLR9 reporter system. The left graph in FIG. 1A shows results using 0.5 μM of the constructs. The right graph in FIG. 1A shows results using 5 μM of the constructs. FIG. 1B: TLR9 activating nucleic acid (ODN 2006) linked through a AAAAA (SEQ ID NO: 8) linker to each of the indicated sequences on the X-axis was tested in the HEK293-TLR9 reporter system. FIG. 1C: TLR9 activating nucleic acid (ODN 2006) linked to each of the sequences indicated on the X-axis was tested in the HEK293-TLR9 reporter system.

FIG. 2A: shows data relating to the impact of indicated constructs or control saline on expression of proinflammatory cytokines, using qRT-PCR. Adult C57BL/6 mice were infected with indicated AAV2 viruses ($10^{11}$ vg per mouse) by intramuscular injection in the quadricep. 2 hours (h) later, the animals were euthanized and a piece of the quadricep was analyzed for indicated gene expression by qRT-PCR. Saline injection was set to 1-fold expression for each gene. Data shown are mean±s.d. of n=4 or 5 mice per condition. FIG. 2B: shows data relating to the impact of indicated AAV vectors on GFP expression. Adult C57BL/6 mice were infected with indicated AAV2 viruses similar to FIG. 2A and a piece of the quadricep was analyzed for GFP gene expression by qRT-PCR 28 d later. scAAV-eGFP infection was set to 1-fold expression for GFP. Data shown are n=5 mice per condition. Each triangle represents an animal and mean values are indicated.

FIGS. 3A-3C includes liver tissue data relating to the impact of three copies of telomere ("3×telomere" SEQ ID NO: 35) and three copies of c41 (3×c41)oligonucleotides on the inflammatory response elicited by a linked self-complementary adeno-associated virus (scAAV) in infected mice. All three panels show data relating to the impact of indicated constructs or control saline on expression of proinflammatory cytokines, using qRT-PCR. Adult C57BL/6 mice were infected with indicated AAV2 viruses ($10^{11}$ vg per mouse) by tail vein injections. 2 h later, the animals were euthanized and a piece of the liver was analyzed for indicated gene expression by qRT-PCR. Saline injection was set to 1-fold expression for each gene. FIG. 3A: data shown are mean±s.d. of n=3 mice per condition. FIGS. 3B and 3C: data shown are mean±s.d. of n=4 mice per condition. *P<0.05 (unpaired t-test) compared to saline condition. N.s.: not significant (P>0.05).

FIG. 4 is a schematic representation of a single-stranded AAV vector encoding GFP (ssAAV-eGFP). Two engineered forms are shown. ssAAV-eGFP-5×telomere carries an insertion of 5 copies of telomere oligonucleotide (5 X SEQ ID NO: 9) with AAAAA (SEQ ID NO: 8) linkers, followed by reverse complementary sequences of another 5 copies with AAAAA linkers (in anti-sense orientation). ssAAV-eGFP-3×telo3×INH18 carries an insertion of 3 copies of telomere oligonucleotide (3 X SEQ ID NO: 9) with AAAAA (SEQ ID NO: 8) linkers, followed by reverse complementary sequences of 3 copies of INH-18 (3 X SEQ ID NO: 5) with AAAAA (SEQ ID NO: 8) linkers (in anti-sense orientation) ("3×telo3×INH18 SEQ ID NO 39). LpA: polyA signal.

FIG. 6A shows results using HEK293-TLR7 reporter cells and FIG. 6B shows results using HEK293-TLR2 reporter cells.

FIGS. 7A-7E show the effects of incorporation of three copies of the telomere sequence ("3×telomere" SEQ ID NO: 35) into a self-complementary AAV vector encoding human factor IX on innate immune response and transgene expression in vivo in liver tissue. FIG. 7A shows a schematic diagram of vector organization of scAAV-FIX (the original "wild-type" vector, SEQ ID NO: 33) and scAAV-FIX-3×telomere (SEQ ID NO: 34). AAV vectors were packaged in an AAV8 capsid. FIGS. 7B and 7C show innate immune responses in mouse liver assayed by qPCR 2 h after intravenous administration of indicated vector at indicated dose. PBS injection was set to 1-fold expression for each gene. Data shown are mean±s.e.m. of n=5-7 animals per condition. * p<0.05 by two-tailed Mann-Whitney test and compared against PBS condition. ns, not significant, p>0.05. FIGS. 7D and 7E show human factor IX levels in plasma of mice at indicated time points. Data shown are mean±s.d. of n=5-8 animals per condition. ** p<0.005 by two-tailed Mann-Whitney test. ns, not significant, p>0.05. ITR, inverted terminal repeat; TTR, transthyretin promoter; hFIX, human factor IX; bGH, bovine growth hormone poly(A) signal; TRS, terminal resolution site.

FIGS. 8A-8D include data showing the effects of multiple copies of inhibitory oligonucleotides (multiple copies of telomere (multiple copies of SEQ ID NO: 9) and multiple copies of INH-18 (multiple copies of SEQ ID NO: 5)) on AAV-induced T cell reactivity and T cell infiltration. FIG. 8A includes data where mice received indicated doses of AAVrh32.33 vectors (single-stranded AAV) via intramuscular injections and 21 d later, splenocytes were subject to IFN-γ ELISPOT assays to quantify CD8+ T cell responses to an immunodominant epitope of rh32.33 capsid. Representative images of the ELISPOT well for animals with median responses for each condition are shown. The dotted line (50 SFU/$10^6$ splenocytes) indicates the cutoff for a positive T cell response in this assay. ssAAV-eGFP is provided as SEQ ID NO: 36. ssAAV-eGFP-3×telo3×INH18 is provided as SEQ ID NO: 37. FIGS. 8B-8C show the number of CD8+ T cells and CD8+ Granzyme B+ T cells in the muscle sections (four fields examined per sample) for PBS and 1×$10^{10}$ vg rh32.33 vectors 21 dpi. (FIG. 8D) Representative images of GFP expression by immunohistochemistry staining in muscle sections at 21 dpi. Scale bar, 50 μm. n=5-10 animals per condition as indicated. *p<0.05 and ** p<0.005 by two-tailed Mann-Whitney test. ns, not significant, p>0.05. SFU, spot forming units.

FIG. 9A is a silver staining comparison of 1×10¹⁰ vg AAV8 vectors. FIG. 9B is a series of transmission electron microscopy images showing negatively stained AAV, and representative empty particles are shown with white arrows. Representative images are shown for each vector. Scale bar: 100 nm.

FIG. 10A shows immunohistochemical images of ONL of retina 6 weeks after subretinal injections. Outer segments of cone photoreceptors were visualized by anti-red-green cone opsin staining. Scale bars, 10 µm. FIG. 10B shows microglia proliferation and activation in the retina indicated by anti-Iba1 staining. Scale bars, 50 µm. FIG. 10C shows cytotoxic T cell infiltration into the retina indicated by anti-CD8 staining. Scale bars, 50 µm. Each animal is indicated by an identification number and the two images are from the two treated eyes of each animal. ONL, outer nuclear layer; Iba1, ionized calcium-binding adaptor protein 1.

FIG. 13 shows a schematic representation of a different single-stranded AAV vector encoding GFP (ssAAV-eGFP-WPRE). An engineered form is shown. ssAAV-eGFP-WPRE-3×telo3×INH18 (SEQ ID NO: 42) carries an insertion of 3 copies of telomere oligonucleotide (3 X SEQ ID NO: 9) with AAAAA (SEQ ID NO: 8) linkers, followed by reverse complementary sequences of 3 copies of INH-18 (3 X SEQ ID NO: 5) with AAAAA linkers (in anti-sense orientation, i.e., anti-sense orientation of SEQ ID NO: 8) in the 3' untranslated region (between the polyA signal and right ITR). WPRE: Woodchuck Hepatitis Virus Posttranscriptional Regulatory Element. LpA: polyA signal.

DETAILED DESCRIPTION

Figure 1A:
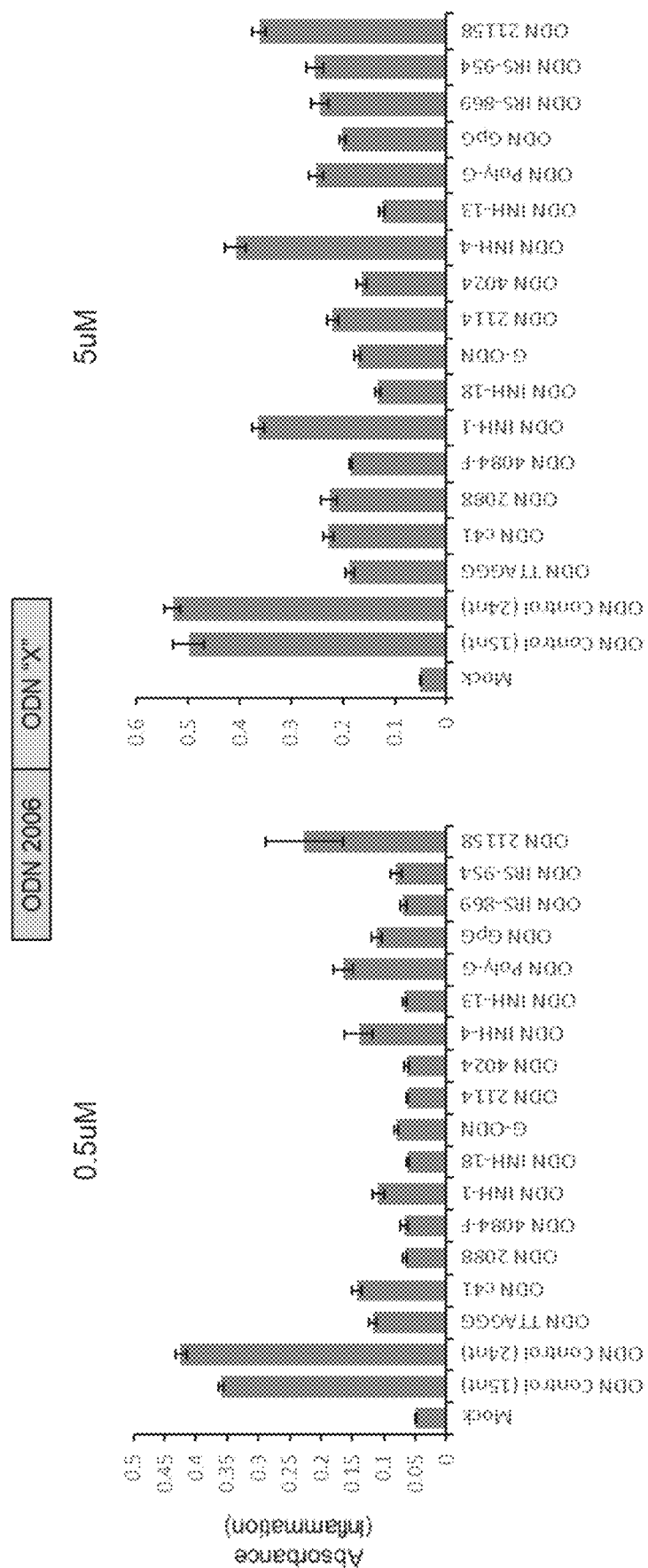
FIGS. 1A-1C includes data showing the impact of exemplary inhibitory oligonucleotides on TLR9 activation in vitro. HEK293-TLR9 reporter cells were treated with the indicated constructs (single-stranded DNA with a phosphorothioate backbone) at the indicated concentrations for 18 hours. A 50-μl sample of cell supernatant was incubated with 100 μl HEK-Blue Detection and then analyzed on a plate reader for absorbance at 639 nm. The data shown are mean±s.d. of n=3 technical replicates.

Despite recent advances, the effectiveness of viral vectors as gene delivery vehicles has been limited, in part, due to vector-induced inflammation. Thus, clinically, gene therapy with viral vectors often includes systemic treatment with an immunosuppressive agent. Such immunosuppressive and anti-inflammatory drugs, however, can compromise the patient's immune system during treatment and patients often still develop neutralizing antibodies or T cells to exogenous biological materials (e.g., against AAV capsid), precluding future re-administration or leading to destruction of transduced cells.

Provided herein, in some embodiments, are recombinant viral genomes that may be used as delivery vehicles, without inducing a substantial inflammatory response. In some embodiments, the recombinant viral genomes induce less of an inflammatory response than would otherwise be induced without the presence of the inhibitory oligonucleotide. The recombinant viral genomes of the present disclosure include an inhibitory oligonucleotide that inhibits production of proinflammatory cytokines, thus, inhibiting the inflammatory response. In some embodiments, the inhibitory oligonucleotide inhibits an inflammatory response induced by the toll-like receptor (TLR) pathway, for example, by inhibiting (preventing) TLR activation and/or inhibiting TLR signaling.

Inflammatory Response to Viral Vectors

Viral vectors are often studied in experimental and clinical models as agents for gene therapy. Recent generations of viral vectors have the majority of viral genes removed and result in vectors with a large carrying capacity, reduced host immune responses and improved gene transfer efficiency. Some viral vectors, such as adenovirus vectors and adeno-associated virus vectors, however, still activate innate immune responses following administration in vivo. Unlike the adaptive response, the innate response to viral vectors is independent of immunological memory and is caused by recognition of conserved features of microbes, commonly termed pattern-associated molecular patterns (PAMPs). This response results in inflammation of transduced tissues and can reduce viral transduction efficiency. Viral infection can activate a number of signaling pathways following cell entry that ultimately lead to expression of inflammatory (proinflammatory) genes. Various cytokines, chemokines and leukocyte adhesion molecules are induced by the viral vector in a wide range of cell types providing a molecular basis for the inflammatory properties of these vectors. See Liu, Q. et al. *Gene Therapy* 2003; 10:935-940.

Toll-Like Receptor Signaling Pathway

One of the signaling pathways activated following in vivo administration (in a subject) of viral vectors is the toll-like receptor (TLR) signaling pathway. TLRs are immune pattern-recognition receptors that detect pathogens and damaged cells. For example, TLR9 is well-known, and TLR9 amino acid sequences can be found in publically-available gene databases, such as GenBank and UnitProtKB. For example, the amino acid sequence of wild-type human TLR9 can be identified as UniProtKB entryQ9NR96 (TLR9_Human).

TLR9 is generally located on endosomal membranes in immune cells. TLR9 is an exemplary nucleic acid-sensing TLRs that detects exogenous nucleic acids (inflammatory nucleic acids) that have entered a cell (see, e.g. Takeda, K et al., *Semin Immunol.* 2004; 16(1):3-9; Lee, J et al. *Proc Natl Acad Sci USA.* 2011; 108(34):14055-60). Nucleic acids recognized by TLR9 include those that originate from bacteria, viruses or even endogenous nucleic acids. 'Nucleic acid-sensing TLRs' are TLRs that can bind to nucleic acids, such as ssRNA, dsRNA, and DNA containing unmethylated CpG (cytosine-phosphate-guanine) motifs. This binding typically results in the dimerization of TLR and activation of TLR signaling, which results in the production of (expression of and/or activation of) proinflammatory molecules, such as proinflammatory cytokines. In particular, TLR9 recognizes nucleic acids with unmethylated CpGs (Kumagai, Y, et al. *Adv Drug Deliv Rev.* 2008; 60(7)795-804).

As used herein, unless otherwise specified, 'inflammatory nucleic acids' are nucleic acids that activate TLR signaling (e.g., bind to TLR to activate TLR signaling). In some embodiments, the inflammatory nucleic acids comprise deoxycytidyl-deoxyguanosine (CpG) oligodeoxynucleotides. CpG oligodeoxynucleotides are sequences that comprise at least one unmethylated CpG motif and activate an immune response. See, e.g., Krieg, A M et al. *Nature.* 1995; 374(6522):546-9. In some embodiments, the inflammatory nucleic acids (e.g., CpG oligodeoxynucleotides) activate TLR9 signaling (e.g., by binding to TLR9). An exemplary inflammatory nucleic acid is provided in Example 1 (ODN 2006).

TLR signaling results in an inflammatory response characterized by gene expression of antiviral molecules and proinflammatory cytokines, including type I interferons and NF-kB (p25-RelA complex) target genes. Thus, TLR signaling may be used as means to determine the impact of an inhibitory oligonucleotide on the inflammatory response. In some embodiments, a TLR reporter cell line may be used to assess the inhibitory nature of an oligonucleotide, for example, by determining the level of cytokine (e.g. IL6, CXCL10 and/or TNF) production, which reflects the level of TLR signaling (see, e.g., Example 1). As an example, recognition of unmethylated CpG motifs in exogenous DNA activates TLR9, and TLR9 signaling leads to an increase in expression of proinflammatory cytokines, including IL6, CXCL10, and/or TNF. See, e.g., Krieg A M *Nat Rev Drug Discov.* 2006; 5(6):471-84. In some embodiments, the level of a particular cytokine is measured using quantitative PCR with primers targeting the cytokine of interest (see, e.g., Examples 3 and 4). Additional methods of measuring cytokine levels include enzyme-linked immunosorbent assay (ELISA) and Western blot analysis with an anti-cytokine antibody.

Inhibition of an inflammatory response may be measured as a decrease in TLR signaling. For example, a decrease in cytokine activity level or expression level (e.g., a 2-fold, 5-fold, 10-fold, 50-fold reduction) relative to a control may indicate inhibition (partial or complete inhibition) of the inflammatory response (see, e.g., Examples 3 and 4).

Inhibitory Oligonucleotides

An inhibitory oligonucleotide is an oligonucleotide that, when co-delivered in vivo with another nucleic acid (such as a viral genome, a single-stranded RNA, or a single-stranded DNA), inhibits the production of proinflammatory cytokines, relative to proinflammatory cytokine production in the absence of the inhibitory oligonucleotide. See, e.g., Stunz, L L et al. *Eur J Immunol.* 2002; 32(5):1212-22; Lenert, P et al. *DNA Cell Biol.* 2003; 22(10):621-31; Lenert, P et al. *Arthritis Res Ther.* 2009; 11(3):R79; Lenert, P S et al. *Arthritis Res Ther.* 2006; 8(1):203; Kaminski, J J et al. *J Immunol.* 2013; 191(7):3876-83; Shirota, H et al. *J Immunol.* 2005; 174(8): 4579-83; Peter, M et al. *Immunology.* 2008; 123(1):118-28. The inhibitory oligonucleotides of the present disclosure comprise at least two nucleotides covalently linked together, and in some instances, may contain phosphodiester bonds (e.g., a phosphodiester "backbone"). In some instances, the oligonucleotide may contain phosphorothioate bonds (e.g., a phosphorothioate backbone). The length of an inhibitory oligonucleotide may vary, but is should be understood that the length of an inhibitory oligonucleotide is typically 4 to 200 nucleotides. In some embodiments, an inhibitory oligonucleotide has a length of 4 to 100 nucleotides. In some embodiments, an inhibitory oligonucleotide has a length of 4 to 10, 4 to 20, 4 to 30, 4 to 50, 4 to 60, 4 to 70, 4 to 80, or 4 to 90 nucleotides. In some embodiments, an inhibitory oligonucleotide has a length of 5 to 10, 5 to 20, 5 to 30, 5 to 50, 5 to 60, 5 to 70, 5 to 80, 5 to 90, or 5 to 100 nucleotides. In some embodiments, an inhibitory oligonucleotide has a length of 6 to 10, 6 to 20, 6 to 30, 6 to 50, 6 to 60, 6 to 70, 6 to 80, 6 to 90, or 6 to 100 nucleotides. In some embodiments, an inhibitory oligonucleotide has a length of 7 to 10, 7 to 20, 7 to 30, 7 to 50, 7 to 60, 7 to 70, 7 to 80, 7 to 90, or 7 to 100 nucleotides. In some embodiments, an inhibitory oligonucleotide has a length of 8 to 10, 8 to 20, 8 to 30, 8 to 50, 8 to 60, 8 to 70, 8 to 80, 8 to 90, or 8 to 100 nucleotides. In some embodiments, an inhibitory oligonucleotide has a length of 9 to 10, 9 to 20, 9 to 30, 9 to 50, 9 to 60, 9 to 70, 9 to 80, 9 to 90, or 9 to 100 nucleotides. In some embodiments, an inhibitory oligonucleotide has a length of 10 to 10, 10 to 20, 10 to 30, 10 to 50, 10 to 60, 10 to 70, 10 to 80, 10 to 90, or 10 to 100 nucleotides. Inhibitory oligonucleotides may be produced recombinantly or synthetically, for example.

In some embodiments, the inhibitory oligonucleotide comprises or consists of deoxyribonucleotides. Thus, in some embodiments, the inhibitory oligonucleotide is an inhibitory DNA oligonucleotide. In some embodiments, the inhibitory oligonucleotide does not include RNA. It should be understood that the definition of inhibitory oligonucleotides, as provided herein, specifically excludes RNA interference molecules (RNAi), such as short interfering RNA (siRNA) molecules.

In some embodiments, the inhibitory oligonucleotides inhibit the activation of nucleic acid-sensing TLRs. For example, the inhibitory oligonucleotides may act as molecular scavengers and bind to (and sequester) inflammatory nucleic acids, thus preventing the inflammatory nucleic acids from binding the TLR and activating TLR signaling.

In some instances, the inhibitory oligonucleotides may prevent dimerization of a TLR.

In some embodiments, the inhibitory oligonucleotides inhibit TLR signaling (to downstream molecules). For example, the inhibitory oligonucleotides may bind indirectly or directly to a TLR (e.g., TLR9) to block TLR-mediated production of proinflammatory cytokines (e.g., induction of proinflammatory cytokine activity and/or expression). See, e.g. Lenert, P S *Mediators Inflamm.* 2010; 2010:986596; Ohto, U et al. *Nature.* 2015; 520(7549):702-5; Lee, J et al. *Proc Natl Acad Sci U.S.A.* 2011; 108(34):14055-60. In some embodiments, the inhibitor oligonucleotide competes for receptor-mediated endocytosis or phagocytosis. In some embodiments, the inhibitor oligonucleotide inhibits TLR9 trafficking. In some embodiments, the inhibitor oligonucleotide inhibits TLR9 processing into a functionally active product. In some embodiments, the inhibitor oligonucleotide inhibits endosomal acidification or activity of key proteases in endosomes. In some embodiments, the inhibitor oligonucleotide blocks signaling proteins downstream of TLR9.

It should be understood that the term "inhibits" encompasses complete (100%) inhibition and partial (less than 100%) inhibition, otherwise referred to as reduction. Thus, an inhibitory oligonucleotide may reduce nucleic acid-sensing TLR activation and/or signaling by at least 10%, at least 20%, at least 30%, at least 40%, at least 50%, at least 60%, at least 70%, at least 80%, at least 90%, or at least 95%, relative to control (nucleic acid-sensing TLR activation and/or signaling in the absence of the inhibitory oligonucleotide).

In some embodiments, the inhibitory oligonucleotides of the present disclosure inhibit production of proinflammatory cytokines. Non-limiting examples of proinflammatory cytokines include interleukins (e.g., IL-1, IL-6, IL-17 and IL-18), interferons (IFNs, e.g., interferon α (IFNα), interferon β (IFNβ), and interferon γ (IFNγ)), tumor necrosis factors (TNFs) (e.g., TNF-α) and chemokines (e.g., CCL2, CXCL10 and CCLS). In some embodiments, the inhibitory oligonucleotide inhibits IL-6, CXCL10 and/or TNF production. In some embodiments, the inhibitory oligonucleotide inhibits IL-6 production. In some embodiments, the inhibitory oligonucleotide inhibits CXCL10 production. In some embodiments, the inhibitory oligonucleotide inhibits TNF production. As discussed herein, the level of inflammatory cytokine production may be measured using Western blot analysis, quantitative PCR and/or enzyme-linked immunosorbent assay. Other assays for assessing the inflammatory response are known and may be used as provided herein.

In some embodiments, an inhibitory oligonucleotide reduces production of (activity of and/or expression of) proinflammatory cytokines by at least 10%, at least 20%, at least 30%, at least 40%, at least 50%, at least 60%, at least 70%, at least 80%, at least 90%, or at least 95%, relative to control (inflammatory cytokine production in the absence of the inhibitory oligonucleotide).

The inhibitory oligonucleotides of the present disclosure may include different motifs that contribute to anti-inflammatory properties of the inhibitory oligonucleotide. In some embodiments, the inhibitory oligonucleotide comprises at least one CCx(not-C)(not-C)xxGGG (SEQ ID NO: 63) motif, wherein x is any nucleic acid (e.g., A, T, C or G (but not C where specified)). See, e.g., Ashman, R F et al. *Int Immunol.* 2011; 23(3):203-14. Non-limiting examples of inhibitory oligonucleotides that comprise at least one CCx(not-C)(not-C)xxGGG (SEQ ID NO: 63) motif include ODN 4228 (see, e.g., Ashman, R F et al. *Int Immunol.* 2011; 23(3):203-14), SEQ ID NO: 2, SEQ ID NO: 3, SEQ ID NO: 4, SEQ ID NO: 5, SEQ ID NO: 7, SEQ ID NO: 16, SEQ ID NO: 17, SEQ ID NO: 18, SEQ ID NO: 19, SEQ ID NO: 21, SEQ ID NO: 22, SEQ ID NO: 23, and SEQ ID NO: 24.

In some embodiments, an inhibitory oligonucleotide comprises at least one TTAGGG motif (SEQ ID NO: 61). For example, an inhibitory oligonucleotide may comprise at least 2, 3, 4, 5, 6, 7, 8, 9 or 10 TTAGGG motifs. In some embodiments, the inhibitory oligonucleotide includes two TTAGGG motifs. In some embodiments, the inhibitory oligonucleotide includes three TTAGGG motifs. In some embodiments, the inhibitory oligonucleotide includes four TTAGGG motifs. Exemplary inhibitory oligonucleotides comprising at least one TTAGGG motif include those identified by SEQ ID NO:6 and/or SEQ ID NO: 9.

In some embodiments, the inhibitory oligonucleotide includes at least one sequence that is identical to a nucleotide sequence of any one of SEQ ID NOS: 1-7, 9-25, or 27-32.

In some embodiments, the inhibitory oligonucleotide includes a nucleotide sequence that is identical to the nucleotide sequence identified by SEQ ID NO: 1. In some embodiments, the inhibitory oligonucleotide includes a nucleotide sequence that is identical to SEQ ID NO: 6. In some embodiments, the inhibitory oligonucleotide includes a nucleotide sequence that is identical to the nucleotide sequence identified by SEQ ID NO: 9.

In some embodiments, the inhibitory oligonucleotide includes multiple tandem repeats of a nucleotide sequence of any one of SEQ ID NOS: 1-7, 9-25, or 27-32. As used herein, unless otherwise noted, tandem repeats are sequences that that follow one another. In some examples, the tandem repeats may be directly next to one another (e.g., TTAGGGTTAGGGTTAGGG (SEQ ID NO: 62) (repeated sequence underlined)). In some examples, the tandem repeats may be separated by another sequence (e.g., a linker sequence) (e.g., TTAGGG-linker-TTAGGG-linker-TTAGGG). In some embodiments, the inhibitory oligonucleotide includes multiple tandem repeat sequences (e.g. two, three, four or five tandem repeats). In some embodiments, the inhibitory oligonucleotide includes multiple tandem repeats (e.g. two, three, four or five repeats) of SEQ ID NO: 1. In some embodiments, the inhibitory oligonucleotide includes multiple tandem repeats (e.g. two, three, four or five repeats) of SEQ ID NO: 9. In some embodiments, the inhibitory oligonucleotide includes multiple tandem repeats (e.g. two, three, four or five repeats) of SEQ ID NO: 6.

In some embodiments, the multiple tandem repeat sequences in an inhibitory oligonucleotide are separated by a linker. The linker may be oriented in the sense or antisense direction. As an example, a linker may be oriented in the sense direction if it is separating multiple tandem repeat sequences that are also oriented in the sense direction. In certain embodiments, a linker is oriented in the antisense direction when it is separating multiple tandem repeat sequences that are also oriented in the antisense direction.

In some embodiments, the linker is a polyA linker (a string of "A" nucleotides). In some embodiments, the polyA linker comprises at least one nucleotide sequence that is identified by SEQ ID NO: 8. In some embodiments, the polyA linker comprises two nucleotide sequences that is identified by SEQ ID NO: 8. In some embodiments, the polyA linker comprises three nucleotide sequences that is identified by SEQ ID NO: 8. For example, an inhibitory oligonucleotide may have three tandem repeats of the sequence in SEQ ID NO:1 and each of the tandem repeats may be separated by a linker identified by SEQ ID NO: 8. In certain embodiments, the linker comprises at least one nucleotide sequence (e.g., at least 2, 3, 4, 5, 6, 7, 8, 9, or 10 nucleotide sequences) that is the antisense sequence of SEQ ID NO: 8 (i.e., SEQ ID NO: 8 oriented in the antisense direction).

As a non-limiting example, an inhibitory oligonucleotide may have three tandem repeats of the sequence in SEQ ID NO: 9 or SEQ ID NO: 6 and each of the tandem repeats may be separated by a linker identified by SEQ ID NO: 8. In some embodiments, the viral genome comprises a sequence that is at least 90% (e.g., at least 91%, at least 92%, at least 93%, at least 94%, at least 95%, at least 96%, at least 97%, at least 98%, at least 99%, or is 100%) identical to SEQ ID NO: 35. In certain embodiments, a recombinant viral genome is single-stranded and comprises the sequence in SEQ ID NO: 35 that is located upstream (5') of a therapeutic nucleotide sequence (e.g., Factor IX) (e.g., in the 5' UTR). In certain embodiments, a recombinant viral genome is single-stranded and comprises the sequence in SEQ ID NO: 35 that is located downstream (3') of a therapeutic nucleotide sequence (e.g., Factor IX) (e.g., downstream from (3') a polyA tail linked to the therapeutic nucleic acid, including in the 3' UTR). In some embodiments, the viral genome comprises a sequence that is at least 90% (e.g., at least 91%, at least 92%, at least 93%, at least 94%, at least 95%, at least 96%, at least 97%, at least 98%, at least 99%, or is 100%) identical to SEQ ID NO: 34.

In some embodiments, the inhibitory oligonucleotide includes a combination of nucleotide sequences of any one of SEQ ID NOS: 1-7, 9-25, or 27-32. For example, the inhibitory oligonucleotide may include at least one copy (e.g., one, two, three, four, five, six or seven copies) of a nucleotide sequence of of any one of SEQ ID NOS: 1-7, 9-25, or 27-32 combined with at least one copy (e.g., one, two, three, four, five, six or seven copies) of a nucleotide sequence of any one of SEQ ID NOS: 1-7, 9-25, or 27-32. In some embodiments, the inhibitory oligonucleotide includes three copies of SEQ ID NO: 9 and three copies of SEQ ID NO: 5 (e.g., SEQ ID NO: 39). In some embodiments, the inhibitory oligonucleotide comprises three copies of SEQ ID NO: 3 and three copies of SEQ ID NO: 2. In some embodiments, the inhibitory oligonucleotide includes five copies of SEQ ID NO: 1 and three copies of SEQ ID NO: 9. See also Example 8 and Materials and Methods section of the Examples below.

As discussed in the Examples section, a single expression construct (e.g., ssAAV) may include more than one (e.g., at least 2, at least 3, at least 4, at least 5, at least 6, at least 7, at least 8, at least 9, at least 10, at least 15, or at least 20) type of inhibitory oligonucleotides, one type (one or more copies, e.g., 2, 3, 4 or 5 tandem copies) in the sense orientation and another type (one or more copies, e.g., 2, 3, 4 or 5 tandem copies) in the antisense orientation. Without being bound by a particular theory, inclusion of two different types of inhibitory oligonucleotides may prevent self-annealing between the inhibitory oligonucleotides and formation of unwanted hairpin structures. In some embodiments, a recombinant single-stranded viral genome comprising an inhibitory oligonucleotide in the sense orientation and another inhibitory oligonucleotide in the antisense direction increases the probability that each packaged viral genome comprises at least one inhibitory oligonucleotide in the correct orientation.

As a non-limiting example, an inhibitory oligonucleotide may have three tandem repeats of the sequence in SEQ ID NO: 9 or SEQ ID NO: 6 and three tandem repeats of the sequence in SEQ ID NO: 5. The tandem repeats of the sequence in SEQ ID NO: 9 or SEQ ID NO: 6 may be oriented in the opposite direction of the tandem repeats of the sequence in SEQ ID NO: 5. For example, the tandem repeats of the sequence in SEQ ID NO: 9 or SEQ ID NO: 6 may be oriented in the sense direction and the tandem repeats of the sequence in SEQ ID NO: 5 may be oriented in the antisense direction or vice versa. The tandem repeats of SEQ ID NO: 9 or SEQ ID NO: 6 may be upstream (5') or downstream (3') of the tandem repeats of the sequence in SEQ ID NO: 5. Each of the tandem repeats (e.g., repeats of SEQ ID NOS: 5, 6, 9, or any combination thereof) may be separated by a linker identified by SEQ ID NO: 8 oriented in the sense or antisense direction. In some embodiments, the viral genome comprises a sequence that is at least 90% (e.g., at least 91%, at least 92%, at least 93%, at least 94%, at least 95%, at least 96%, at least 97%, at least 98%, at least 99%, or is 100%) identical to SEQ ID NO: 39. In certain embodiments, a recombinant viral genome is single-stranded and comprises the sequence in SEQ ID NO: 39 that is located upstream (5') (e.g., in the 5' UTR) of a therapeutic nucleotide sequence. In certain embodiments, a recombinant viral genome is single-stranded and comprises the sequence in SEQ ID NO: 39 that is located downstream (3') (e.g., downstream from (3') a polyA tail linked to the therapeutic nucleic acid, including in the 3' UTR) of a therapeutic nucleotide sequence.

In certain embodiments, an inhibitory oligonucleotide may have three tandem repeats of the sequence in SEQ ID NO: 3 and three tandem repeats of the sequence in SEQ ID NO: 2. The tandem repeats of the sequence in SEQ ID NO: 3 may be oriented in the opposite direction of the tandem repeats of the sequence in SEQ ID NO: 2. For example, the tandem repeats of the sequence in SEQ ID NO: 3 may be oriented in the sense direction and the tandem repeats of the sequence in SEQ ID NO: 2 may be oriented in the antisense direction or vice versa. The tandem repeats of SEQ ID NO: 3 may be upstream (5') or downstream (3') of the tandem repeats of the sequence in SEQ ID NO: 2. Each of the tandem repeats (e.g., repeats of SEQ ID NOS: 2, 3, or any combination thereof) may be separated by a linker identified by SEQ ID NO: 8 that is oriented in the sense or antisense direction. In some embodiments, the viral genome comprises a sequence that is at least 90% (e.g., at least 91%, at least 92%, at least 93%, at least 94%, at least 95%, at least 96%, at least 97%, at least 98%, at least 99%, or is 100%) identical to SEQ ID NO: 40. In certain embodiments, a recombinant viral genome is single-stranded and comprises the sequence in SEQ ID NO: 40 that is located upstream (5') (e.g., in the 5' UTR) of a therapeutic nucleotide sequence. In certain embodiments, a recombinant viral genome is single-stranded and comprises the sequence in SEQ ID NO: 40 that is located downstream (3') (e.g., downstream from (3') a polyA tail linked to the therapeutic nucleic acid, including in the 3' UTR) of a therapeutic nucleotide sequence.

It should be understood that the present disclosure encompasses the use of any inhibitory oligonucleotide, such as those described herein, as well as inhibitory oligonucleotides that share a certain degree of sequence identity (percent identity) with a reference inhibitory oligonucleotide (e.g., SEQ ID NO:1, SEQ ID NO:6, or SEQ ID NO: 9). Percent identity refers to a relationship between the sequences of two or more polynucleotides (nucleic acids), as determined by comparing the sequences. Identity measures the percent of identical matches between the smaller of two or more sequences with gap alignments (if any) addressed by a particular mathematical model or computer program (e.g., "algorithms"). Identity of related molecules can be readily calculated by known methods. "Percent (%) identity" as it applies to nucleic acid sequences is defined as the percentage of nucleic acid residues in the candidate nucleic acid sequence that are identical with the residues in the nucleic acid sequence of a second sequence after aligning the sequences and introducing gaps, if necessary, to achieve the maximum percent identity. Identity depends on a calculation of percent identity but may differ in value due to gaps and penalties introduced in the calculation. Variants of a particular inhibitory oligonucleotide may have at least 90%, 91%, 92%, 93%, 94%, 95%, 96%, 97%, 98%, 99% but less than 100% sequence identity to that particular reference inhibitory oligonucleotide sequence, as determined by sequence alignment programs and parameters described herein and known to those skilled in the art.

Thus, in some embodiments, the inhibitory oligonucleotide includes at least one sequence that is at least 80% identical to a nucleotide sequence of any one of SEQ ID NOS: 1-7, 9-25, or 27-32. In some embodiments, the inhibitory oligonucleotide includes at least one sequence that is at least 90% identical to a nucleotide sequence of any one of SEQ ID NOS: 1-7, 9-25, or 27-32.

The comparison of sequences and determination of percent identity between two sequences can be accomplished using a mathematical algorithm. Techniques for determining identity are codified in publicly available computer programs. Exemplary computer software to determine homology between two sequences include, but are not limited to, the GCG program package (Devereux, J. et al. Nucleic Acids Research, 12(1): 387, 1984), the BLAST suite (Altschul, S. F. et al. *Nucleic Acids Res.* 25: 3389, 1997), and FASTA (Altschul, S. F. et al. *J. Molec. Biol.* 215: 403, 1990). Other techniques include: the Smith-Waterman algorithm (Smith, T. F. et al. *J. Mol. Biol.* 147: 195, 1981; the Needleman-Wunsch algorithm (Needleman, S. B. et al. *J. Mol. Biol.* 48: 443, 1970; and the Fast Optimal Global Sequence Alignment Algorithm (FOGSAA) (Chakraborty, A. et al. Sci Rep. 3: 1746, 2013).

Recombinant Viral Genomes

The present disclosure provides recombinant viral genomes in which an (at least one) inhibitory oligonucleotide is included in the viral genome. In some embodiments, two or more inhibitory oligonucleotide is included in the viral genome. Multiple inhibitory oligonucleotides may be located in different locations throughout the viral genome (relative to each other). The viral genomes typically include a therapeutic nucleotide sequence and an inhibitory oligonucleotide. The inhibitory oligonucleotide may be located, for example, in the 3' untranslated region (UTR) of the viral genome (see, e.g., scAAV-eGFP-3×c41 and scAAV-eGFP-3× telomere in Example 2 described below). In certain embodiments, the inhibitory oligonucleotide is downstream (3') relative to the therapeutic nucleotide sequence. In certain embodiments, the inhibitory oligocnuleotide is located downtream from (3') a polyA tail linked to the therapeutic nucleic acid. In some embodiments, the inhibitory oligonucleotide is located in the 5' UTR of the viral genome. In some embodiments, the inhibitory oligonucleotide is located upstream (5') of a promoter operably linked to the therapeutic nucleotide sequence. In some instances, the inhibitory oligonucleotide is located upstream (5') relative to the therapeutic nucleotide sequence. As a non-limiting example, a recombinant viral genome may comprise an inhibitory oligonucleotide located downstream (3') (e.g., downstream from (3') a polyA tail linked to the therapeutic nucleic acid, including in the 3' UTR) and an inhibitory oligonucleotide located upstream (5') (e.g., in the 5' UTR) of the therapeutic nucleotide sequence. Surprisingly, the location of the inhibitory oligonucleotide in the viral genome, relative to the promoter, does not impact the inhibitory function of the oligonucleotide. The recombinant viral genome may comprise inflammatory nucleic acids (e.g., CpG oligodeoxynucleotides). The inflammatory nucleic acids may be located anywhere in the viral genome (e.g., the viral ITR, the promoter, the intron, the transgene, the 5' UTR, the 3' UTR, etc.). For example, the therapeutic nucleotide sequence may comprise inflammatory nucleic acids (e.g., CpG oligodeoxynucleotide).

The inhibitory oligonucleotides of the present disclosure may be oriented in the sense direction and/or antisense direction in the viral genome. In some embodiments, a viral genome includes 1, 2, 3, 4, or 5 copies of an inhibitory oligonucleotide (e.g., 1, 2, 3, 4, or 5 copies of SEQ ID NO: 9) in the sense direction. In some embodiments, the same viral genome includes 1, 2, 3, 4, or 5 copies of the same inhibitory oligonucleotide (e.g., 1, 2, 3, 4, or 5 of reverse complement of SEQ ID NO:9) or a different oligonucleotide (e.g., reverse complement of SEQ ID NO: 1 or SEQ ID NO:5) in the antisense direction. See also Example 6 and Materials and Methods section of the Examples below.

The recombinant viral genomes, as provided herein, may be used, in some embodiments, to deliver (to a subject) a therapeutic nucleotide sequence of interest (e.g., a therapeutic DNA, a therapeutic RNA, and/or a therapeutic protein encoded by the nucleotide sequence). In some embodiments, the recombinant viral genomes of the present disclosure are gene delivery vectors. Thus, in some embodiments, the therapeutic nucleotide sequence is a gene encoding a therapeutic protein, as discussed elsewhere herein.

A recombinant viral genome, generally, is a viral genome that is not naturally occurring. The viral genomes may be from adeno-associated virus (AAV), adenovirus, herpes simplex virus, varicella, variola virus, hepatitis B, cytomegalovirus, JC polyomavirus, BK polyomavirus, monkeypox virus, Herpes Zoster, Epstein-Barr virus, human herpes virus 7, Kaposi's sarcoma-associated herpesvirus, or human parvovirus B19. Other viral genomes are encompassed by the present disclosure.

In some embodiments, a viral genome is an AAV genome. AAV is a small, non-enveloped virus that packages a single-stranded linear DNA genome that is approximately 5 kb long, and has been adapted for use as a gene transfer vehicle (Samulski, R J et al., *Annu Rev Virol.* 2014; 1(1):427-51). The coding regions of AAV are flanked by inverted terminal repeats (ITRs), which act as the origins for DNA replication and serve as the primary packaging signal (McLaughlin, S K et al. *J Virol.* 1988; 62(6):1963-73; Hauswirth, W W et al. 1977; 78(2):488-99). Both positive and negative strands are packaged into virions equally well and capable of infection (Zhong, L et al. *Mol Ther.* 2008; 16(2):290-5; Zhou, X et al. *Mol Ther.* 2008; 16(3):494-9; Samulski, R J et al. *J Virol.* 1987; 61(10):3096-101). In addition, a small deletion in one of the two ITRs allows packaging of self-complementary vectors, in which the genome self-anneals after viral uncoating. This results in more efficient transduction of cells but reduces the coding capacity by half (McCarty, D M et al. *Mol Ther.* 2008; 16(10):1648-56; McCarty, D M et al. *Gene Ther.* 2001; 8(16):1248-54).

In some embodiments, the recombinant viral genomes of the present disclosure include a single-stranded nucleotide sequence. In some embodiments, the viral genome is self-complementary. A self-complementary viral genome is a viral genome that forms an intramolecular double-stranded nucleotide sequence. Examples of methods for making recombinant viral genomes and self-complementary (sc) viral genomes are provided in Example 2 and in the Materials and Methods section of the Examples below.

In some embodiments, the viral genome is a single-stranded nucleotide sequence (e.g., ssAAV). In some embodiments, the single-stranded viral genome does not form an intramolecular double-stranded nucleotide sequence. In certain embodiments, a recombinant viral genome is a single-stranded viral genome comprising an inhibitory oligonucleotide downstream (3') of the therapeutic nucleotide sequence (e.g., downstream from (3') a polyA tail linked to the therapeutic nucleic acid, including in the 3' UTR of the viral genome). In certain embodiments, a recombinant viral genome is a single-stranded viral genome comprising an inhibitory oligonucleotide upstream (5') of the therapeutic nucleotide sequence (e.g., in the 5' UTR of the viral genome). As a non-limiting example, a single-stranded viral genome comprising an inhibitory oligonucleotide that is located upstream (5') of a therapeutic nucleotide sequence (e.g., Factor IX) is provided as SEQ ID NO: 34. In certain embodiments, a recombinant viral genome is a single-stranded viral genome comprising an inhibitory oligonucleotide upstream (5') of the therapeutic nucleotide sequence (e.g., in the 5' UTR of the viral genome) and an inhibitory oligonucleotide downstream (3') of the therapeutic nucleotide sequence (e.g., in the 3' UTR of the viral genome).

As a non-limiting example, a recombinant viral genome may comprise at least two different inhibitory oligonucleotides located upstream (5') of a therapeutic nucleotide sequence and at least two different inhibitory oligonucleotides sequences located downstream (3') of the therapeutic nucleotide sequence. In some instances, all inhibitory oligonucleotides sequences are different in a recombinant viral genome. For example, a recombinant viral genome may comprise inhibitory oligonucleotides that each comprise different multiple tandem repeats of a sequence that is at least 90% identical to a sequence of any one of SEQ ID NOS: 1-7, 9-25, or 27-32. In some instances, an inhibitory oligonucleotide comprises multiple tandem repeats of two different sequences selected from to a sequence of any one of SEQ ID NOS: 1-7, 9-25, or 27-32.

In some instances, a recombinant viral genome comprises 1) an inhibitory oligonucleotide sequence that is at least 90% (e.g., at least 91%, 92%, 93%, 94%, 95%, 96%, 97%, 98%, 99%, or is identical) to SEQ ID NO: 39 located upstream (5') of a therapeutic nucleotide sequence (e.g., in the 5' UTR) and 2) an inhibitory oligonucleotide that is at least 90% (e.g., at least 91%, 92%, 93%, 94%, 95%, 96%, 97%, 98%, 99%, or is identical) to SEQ ID NO: that is located downstream (3') of a therapeutic nucleotide sequence (e.g., in the 3' UTR). Alternatively, the inhibitory oligonucleotide that is at least 90% identical to SEQ ID NO: 39 may be located downstream (3') of a therapeutic nucleotide sequence (e.g., in the 3' UTR) and the inhibitory oligonucleotide that is at least 90% identical to SEQ ID: 40 may be located upstream (5') of a therapeutic nucleotide sequence (e.g., in the 5' UTR).

Exemplary methods for making a single-stranded viral genome with limited self-annealing are provided in Example 8 and in the Materials and Methods section of the Examples below.

The recombinant viral genomes of the present disclosure may comprise a therapeutic nucleotide sequence. A therapeutic nucleotide sequence is a nucleotide sequence (e.g., RNA or DNA) that confers a therapeutic benefit or encodes a molecule (e.g., protein) that confers a therapeutic benefit to a subject when administered in vivo. In some embodiments, the therapeutic nucleotide sequence is a therapeutic RNA sequence (e.g., an RNAi molecule). In some embodiments, the therapeutic nucleotide sequence is a therapeutic DNA sequence (e.g. a DNA aptamer that binds a target). In some embodiments, the therapeutic nucleotide sequence encodes a therapeutic protein or peptide. For example, the therapeutic nucleotide sequence may encode a wild-type (unmodified) protein to compensate for a modified (e.g., mutated or truncated) version of the protein present in a subject or to compensate for a protein the subject lacks. Non-limiting examples of proteins encoded by a therapeutic nucleotide sequence include antibodies, enzymes, hormones, growth factors, cytokines and fusion proteins.

In some embodiments, the therapeutic nucleotide sequence is configured to replace a disease allele. For example, the therapeutic nucleotide sequence could be designed to facilitate nonhomologous end joining or homologous recombination. In some embodiments, the therapeutic gene sequence is a programmable nuclease. Non limiting examples of programmable nucleases include Cas9, Cpf1, C2c2, zinc finger, zinc finger nucleases, TALEs, TALENs, meganucleases, and fusions thereof to effector domains. Effector domains include transcriptional activators, transcription repressors, transposes, recombinases and deaminases. In some embodiments, the therapeutic nucleotide sequence encodes a guide RNA (e.g., for gene editing) or a DNA template (e.g., for homologous recombination).

In some examples, the therapeutic nucleotide sequence itself is a therapeutic molecule. In some embodiments, the nucleotide sequence is a DNA aptamer that binds a molecular target (e.g., protein target). A process termed SELEX (systematic evolution of ligands by exponential enrichment) is frequently used to select oligonucleotides from a DNA library that bind strongly to a target (Zhou J et al. Ther Nucleic Acids. 2014; 3:e169). Examples of DNA aptamers include AS1411, which binds to the cellular protein nucleolin and has been tested as an anticancer agent (Bates P J et al. Exp Mol Pathol. 2009; 86(3):151-64; Soundararajan S et al. Cancer Res. 2008; 68(7):2358-65), and ARC1779, a PEGylated DNA aptamer which binds to von Willebrand factor to inhibit its interaction with platelets, thereby inducing an antithrombotic effect (Markus H S et al. Stroke. 2011; 42(8):2149-53).

In certain embodiments, the therapeutic nucleotide sequence encodes a sequence that is capable of reducing expression of a disease gene. In some embodiments, the therapeutic nucleotide sequence is complementary to a mRNA encoding a disease gene. As a non-limiting example, the therapeutic nucleotide sequence may be a guide RNA (e.g., for use in CRISPR systems), a siRNA, a microRNA (miRNA), or a short hairpin RNA (shRNA). In some embodiments, a therapeutic nucleotide sequence targets a mutant allele.

In some embodiments, the recombinant viral genome comprises a promoter operably linked to the therapeutic nucleotide sequence. A promoter is a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. A promoter drives expression or drives transcription of the nucleic acid sequence that it regulates. A promoter is considered to be 'operably linked' to a nucleotide sequence when it is in a correct functional location and orientation in relation to the nucleotide sequence to control ('drive') transcriptional initiation and/or expression of that sequence. Promoters may be constitutive or inducible. An inducible promoter is a promoter that is regulated (e.g., activated or inactivated) by the presence or absence of a particular factor.

In some instances, a suitable host cell line (e.g., HEK293T, HeLa cells and Sf9 insect cells) may be used for producing viral particles encoding the recombinant viral genomes disclosed herein following routine practice. One or more expression vectors (e.g. viral vectors) encoding viral components, at least one therapeutic nucleotide sequence and at least one inhibitory oligonucleotide described herein may be introduced into the suitable host cells, which can then be cultured under suitable conditions allowing for production of the viral particles. When needed, a helper virus can be used to facilitate replication and/or assembly of the viral particles. Alternatively, a host cell line producing one or more of essential viral components for viral genome replication and/or viral particle assembly may be used. The supernatant of the cell culture may be collected and the viral particles contained therein can be collected via routine methodology. As an example, a method for AAV production is provided in the Materials and Methods section below.

The recombinant viral genomes as provided herein may be administered by intravenous, intramuscular, subretinal, intravitreal, intrathecal, intraparenchymal, and intracranial injections. In some embodiments, the recombinant viral genomes is delivered by intramuscular injection. In some embodiments, the recombinant viral genomes is delivered by intravenous injection.

In some embodiments, the recombinant viral genomes are used to transduce cells in the liver, skeletal muscle, cardiac muscle, eye (e.g., retina), central nervous system or any combination thereof.

Pharmaceutical Compositions

In some aspects, the present disclosure provides compositions comprising any of the recombinant viral genomes as disclosed herein. In some embodiments, the compositions further comprise a pharmaceutically-acceptable excipient. Non-limiting examples of pharmaceutically-acceptable excipients include water, saline, dextrose, glycerol, ethanol and combinations thereof. The excipient may be selected on the basis of the mode and route of administration, and standard pharmaceutical practice.

Recombinant viral genomes, in some embodiments, may be formulated in a delivery vehicle. Non-limiting examples of delivery vehicles include nanoparticles, such as nanocapsules and nanospheres. See, e.g., Sing, R et al. *Exp Mol Pathol.* 2009; 86(3):215-223. A nanocapsule is often comprised of a polymeric shell encapsulating a drug (e.g., recombinant viral genome of the present disclosure). Nanospheres are often comprised of a solid polymeric matrix throughout which the drug (e.g. recombinant viral genome) is dispersed. In some embodiments, the nanoparticle is a lipid particle, such as a liposome. See, e.g., Puri, A et al. *Crit Rev Ther Drug Carrier Syst.* 2009; 26(6):523-80. The term 'nanoparticle' also encompasses microparticles, such as microcapsules and microspheres.

Methods developed for making particles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, J. Controlled Release 5:13-22, 1987; Mathiowitz et al. Reactive Polymers 6:275-283, 1987; Mathiowitz et al. J. Appl. Polymer Sci. 35:755-774, 1988; each of which is incorporated herein by reference).

General considerations in the formulation and/or manufacture of pharmaceutical agents, such as compositions comprising any of the recombinant viral genomes disclosed herein may be found, for example, in Remington's Pharmaceutical Sciences, 18th edition, Mack Publishing Co., Easton, Pa (1990) (incorporated herein by reference in its entirety).

Methods of Delivery

Any of the recombinant viral genomes or compositions disclosed herein may be administered to a subject (e.g., mammalian subject, such as a human, mouse, rabbit, goat, sheep or pig) to inhibit the inflammatory response (e.g., inhibit induction of the inflammatory response). In some embodiments, the subject is in need of gene therapy. For example, the subject may have a genetic disorder (e.g., characterized by chromosomal abnormality and/or gene defects including mutation, truncation, insertion and deletion).

The subject may have, may be suspected of having, or may be at risk for a disease. In some embodiments, the disease is an ocular disease. As used herein, an "ocular disease" or "eye disease" is a disease or condition of the eye (e.g., retinal disease). Non-limiting examples of conditions that affect the eye include Ectropion, Lagophthalmos, Blepharochalasis, Ptosis, Stye, Xanthelasma, Dermatitis, Demodex, leishmaniasis, loiasis, onchocerciasis, phthiriasis, (herpes simplex), leprosy, molluscum contagiosum, tuberculosis, yaws, zoster, impetigo, Dacryoadenitis, Epiphora, exophthalmos, Conjunctivitis, Scleritis, Keratitis, Corneal ulcer/Corneal abrasion, Snow blindness/Arc eye, Thygeson's superficial punctate keratopathy, Corneal neovascularization, Fuchs' dystrophy, Keratoconus, Keratoconjunctivitis sicca, Iritis, iris, Uveitis, Sympathetic ophthalmia, Cataract, Chorioretinal inflammation, Focal chorioretinal inflammation, chorioretinitis, choroiditis, retinitis, retinochoroiditis, Disseminated chorioretinal inflammation, exudative retinopathy, Posterior cyclitis, Pars planitis, chorioretinal inflammations, Harada's disease, Chorioretinal inflammation, choroid, Chorioretinal scars, Macula scars, posterior pole (postinflammatory) (post-traumatic),Solar retinopathy, Choroidal degeneration, Atrophy, Sclerosis, angioid streaks, choroidal dystrophy, Choroideremia, choroidal, areolar, (peripapillary), Gyrate atrophy, choroid, ornithinaemia, Choroidal haemorrhage, Choroidal haemorrhage, NOS (Not Otherwise Specified), Choroidal detachment, Chorioretinal, Chorioretinal inflammation, infectious and parasitic diseases, Chorioretinitis, syphilitic, toxoplasma, tuberculosis, chorioretinal, Retinal detachment, distorted vision, Retinoschisis, Hypertensive retinopathy, Diabetic retinopathy, Retinopathy, Retinopathy of prematurity, Age-related macular degeneration, macula, Macular degeneration, Bull's Eye Maculopathy, Epiretinal membrane, Peripheral retinal degeneration, Hereditary retinal dystrophy, Retinitis pigmentosa, Retinal haemorrhage, retinal layers, Central serous retinopathy, Retinal detachment, retinal disorders, Macular edema, macula, Retinal disorder, Diabetic retinopathy, Glaucoma, optic neuropathy, ocular hypertension, open-angle glaucoma, angle-closure glaucoma, Normal Tension glaucoma, open-angle glaucoma, angle-closure glaucoma, Floaters, Leber's hereditary optic neuropathy, Optic disc drusen, Strabismus, Ophthalmoparesis, eye muscles, Progressive external ophthaloplegia, Esotropia, Exotropia, Disorders of refraction, accommodation, Hypermetropia, Myopia, Astigmatism, Anisometropia, Presbyopia, ophthalmoplegia, Amblyopia, Leber's congenital amaurosis, Scotoma, Anopsia, Color blindness, Achromatopsia/Maskun, Nyctalopia, Blindness, River blindness, Micropthalmia/coloboma, Red eye, Argyll Robertson pupil, pupils, Keratomycosis, Xerophthalmia, and Aniridia.

In certain embodiments, the disease affects muscle. Non-limiting examples of muscle diseases include Barth syndrome, Duchenne muscular dystrophy, Becker muscular dystrophy, myotonic dystrophy, facioscapulohumeral muscular dystrophy, mitochondrial encephalomyopathy, MELAS syndrome, MERRF syndrome, MNGIE syndrome, mitochondrial myopathy, Kearns-Sayre syndrome, myalgia, fibromyalgia, polymyalgia rheumatica, myoma, myositis, dermatomyositis, neuromuscular disease, Kearns-Sayre syndrome, muscular dystrophy, myasthenia, congenital myasthenic syndrome, Lambert-Eaton myasthenic syndrome, myasthenia gravis, myotonia, myotonia congenita, spinal muscular atrophy, tetany, ophthalmoplegia, and rhabdomyolysis.

Suitable routes of administration include parenterally, by injection, for example, intravenously, subcutaneously, intramuscularly intrathecally, intraperitoneally, intraparenchymal, intracuteanously, intrasternally, intraarticularlly, intracranially, intralesionally, intrarectually, intravaginally, intranasally, intragastically, intratracheally, or intrapulmonarily. Alternatively, other modes of administration including suppositories, oral formulations, enteral, nasal, topical or transmucosal administration may be desirable. Oral formulations may include normally employed incipients such as, for example, pharmaceutical grades of saccharine, cellulose, magnesium carbonate and the like. These compositions may take the form of solutions, suspensions, tablets, pills, capsules, sustained release formulations or powders.

In some embodiments, a recombinant viral genome comprising an inhibitory oligonucleotide is administered intramuscularly. In some embodiments, the intramuscularly administered recombinant viral genome comprises an adeno-associated viral genome, which comprises a therapeutic nucleotide sequence and an inhibitory nucleotide sequence. In some embodiments, the inhibitory nucleotide sequence comprises a nucleotide sequence of any one of SEQ ID NOS: 1-7, 9-25, or 27-32. In some embodiments, the adeno-associated viral genome administered intramuscularly comprises a therapeutic nucleotide sequence and three tandem repeats of SEQ ID NO: 1. In some embodiments, the adeno-associated viral genome administered intramuscularly comprises a therapeutic nucleotide sequence and three tandem repeats of SEQ ID NO: 9. In some embodiments, the viral genome administered intramuscularly is expressed in muscle cells.

In some embodiments, the recombinant viral genomes of the present disclosure are administered intravenously to a subject. In some embodiments, the recombinant viral genomes are administered peritoneally to a subject. In some embodiments, the intravenously or peritoneally administered recombinant viral genome comprises an adeno-associated viral genome, which includes a therapeutic nucleotide sequence and an inhibitory nucleotide sequence. In some embodiments, the inhibitory nucleotide sequence comprises a nucleotide sequence of any one of SEQ ID NOS: 1-7, 9-25, or 27-32. In some embodiments, the adeno-associated viral genome administered intravenously or peritoneally comprises a therapeutic nucleotide sequence and three tandem repeats of SEQ ID NO: 1. In some embodiments, the adeno-associated viral genome administered intravenously or peritoneally comprises a therapeutic nucleotide sequence and three tandem repeats of SEQ ID NO: 9. In some embodiments, the recombinant viral genome administered intravenously or peritoneally is expressed in the liver cells of a subject.

An inflammatory response (e.g., local or systemic) may be assessed by measuring the level of cytokine activity and/or expression in a subject. In some embodiments, the level of expression and/or activity of IL-6, TNF, interferon (e.g., IFNα, IFNβ, and IFNγ), and/or CXCL10 is measured. Typically, the level of cytokine expression and/or activity correlates with the degree of the inflammatory response. Thus, a subject who has received a recombinant viral genome of the present disclosure (comprising a therapeutic nucleotide sequence and an inhibitory oligonucleotide) may have a reduction of or undetectable expression and/or activity levels of certain cytokines, indicative of a reduced or no inflammatory response, compared to a subject who has received a recombinant viral genome that does not include an inhibitory oligonucleotide. In some embodiments, the control inflammatory response for comparison is the inflammatory response elicited by a viral genome that does not comprise an inhibitory oligonucleotide as determined by the same or a substantially similar assay under the same or substantially similar conditions. Exemplary control viral genomes for adeno-associated virus include scAAV-eGFP-3xcontrol and scAAV-eGFP used in Examples 2, 3, 4 and 5 below.

In some embodiments, a recombinant viral genome of the present disclosure elicits an inflammatory response in the subject that is at least 2-fold lower than a control. For example, a recombinant viral genome may elicit an inflammatory response in the subject that is at least 3-fold, 4-fold, 5-fold, 6-fold, 7-fold, 8-fold, 9-fold, 10-fold, 25-fold or 50-fold lower than a control. In some embodiments, a recombinant viral genome elicits an inflammatory response in the subject that is at least 10% lower than a control. For example, a recombinant viral genome may elicit an inflammatory response in the subject that is at least 15%, 20%, 25%, 30%, 35%, 40%, 45%, 55%, 60%, 70%, 80% or 90% lower than a control. In some embodiments, a recombinant viral genome may inhibit induction of an inflammatory response compared to a control, such that the inflammatory response is undetectable. A control, in some embodiments, is an inflammatory response elicited in a subject by a viral genome that does not comprise an inhibitory oligonucleotide.

In certain embodiments, a recombinant viral genome of the present disclosure reduces AAV-induced pathology in the eye of a subject compared to control. A control, in some embodiments, is the pathology, including tissue damage and alteration in morphology, elicited in an organ by a viral genome that does not comprise an inhibitory oligonucleotide. For example, a recombinant viral genome of the present disclosure may reduce loss of cone outer segments, reduce shortening of cone outer segments, or alter the morphology of cone outer segments less than a control. For example, an eye receiving a recombinant viral genome of the present disclosure may have better preservation of cone outer segments and appeared morphologically closer to an eye receiving no viral genome.

Morphology of the eye or tissues of the eye can be determined using methods known in the art, including cone arrestin staining and opsin staining. Retinal images from in vivo optical coherence tomography (OCT) b-scans may be used to determine damage to outer retinal lamination. As a non-limiting example, the lengths of various types of damage (e.g., retinal detachment, non-severe laminar disruption, or severe laminar damage) on the optical coherence tomography (OCT) b-scans may be measured (see, e.g., Example 9). In some instances, a recombinant viral genome of the present disclosure elicits less or no severe laminar damage compared to a viral genome without an inhibitory oligonucleotide.

In some embodiments, a recombinant viral genome (and thus the therapeutic nucleotide sequence of the recombinant viral genome) of the present disclosure is expressed in cells of the subject at a level that is at least 2-fold greater than a control. For example, a recombinant viral genome may be expressed in cells of the subject at a level that is at least 3-fold, 4-fold, 5-fold, 6-fold, 7-fold, 8-fold, 9-fold, 10-fold, 25-fold or 50-fold higher than a control. In some embodiments, a recombinant viral genome of the present disclosure is expressed in cells of the subject at a level that is at least 10% higher than a control. For example, a recombinant viral genome may be expressed in cells of the subject at a level that is at least 15%, 20%, 25%, 30%, 35%, 40%, 45%, 55%, 60%, 70%, 80% or 90% higher than a control. A control, in some embodiments, is the expression level of a viral genome that does not comprise an inhibitory oligonucleotide.

In some embodiments, a therapeutically effective amount of a recombinant viral genome of the present disclosure is administered to a subject to treat a genetic disorder, such as a muscle disorder or a liver disorder. A therapeutically effective amount, in some embodiments, is an amount of a therapeutic nucleotide sequence (and/or a recombinant viral genomes) required to confer therapeutic effect on the subject. In some embodiments, a therapeutically effective amount is an amount of inhibitory oligonucleotide required to inhibit induction of an inflammatory response following administration of a recombinant viral genome (comprising a therapeutic nucleotide sequence and an inhibitory nucleotide sequence) of the present disclosure. Effective amounts vary, as recognized by those skilled in the art, depending on the route of administration, excipient usage, and co-usage with other active agents. Effective amounts depend on the subject to be treated, including, for example, the weight, sex and age of the subject as well as the strength of the subject's immune system and/or genetic predisposition. Suitable dosage ranges are readily determinable by one skilled in the art. The effective amount (and thus the dosage and/or dosing schedule) of the compositions disclosed herein may also depend on the type of the viral genome, the type of therapeutic nucleotide sequence, and/or the type of inhibitory oligonucleotide.

In some embodiments, the therapeutically effective amount of a recombinant viral genome of the present disclosure is at least 20% lower than the therapeutically effective amount of a viral genome not comprising an inhibitory oligonucleotide. For example, the therapeutically effective amount of a recombinant viral genome of the present disclosure may be at least at least 25%, 30%, 40%, 50% or 60% (but less than 100%) lower than the therapeutically effective amount of a viral genome not comprising an inhibitory oligonucleotide. In some embodiments, administration of a recombinant viral genome of the present disclosure at a reduced therapeutically effective amount results in expression of an encoded therapeutic molecule at a level that is equal to or greater than (e.g., at least 5%, 10%, 20%, 30%, 40%, or 50% greater than) expression of the same encoded therapeutic molecule from a viral genome not comprising an inhibitory oligonucleotide sequence.

ADDITIONAL EMBODIMENTS

The present disclosure also provides the following additional embodiments encompassed by numbered paragraphs.

1. A method comprising administering to a subject a recombinant viral genome comprising a therapeutic nucleotide sequence and an inhibitory oligonucleotide that inhibits nucleic acid-sensing toll-like receptor (TLR) activation and/or signaling, wherein the recombinant viral genome inhibits inflammatory response to the recombinant viral genome in a target tissue.
2. The method of paragraph 1, wherein the target tissue is muscle.
3. The method of paragraph 1, wherein the target tissue is liver.
4. The method of paragraph 1, wherein the viral genome is adeno-associated virus (AAV).
5. The method of any one of paragraphs 1-4, wherein the TLR is TLR9.
6. The method of any one of paragraphs 1-5, wherein the inhibitory oligonucleotide binds to TLR9.
7. The method of any one of paragraphs 6, wherein the inhibitory oligonucleotide binds to TLR9 without activating TLR9 mediated signaling.
8. The method of paragraph 7, wherein the inflammatory nucleic acids comprise CpG oligodeoxynucleotides.
9. The method of any one of paragraphs 1-7, wherein the inhibitory oligonucleotide comprises a CCx(not-C)(not-C)xxGGG (SEQ ID NO: 63) motif, wherein x is any nucleic acid.
10. The method of any one of paragraphs 1-7, wherein the inhibitory oligonucleotide comprises a nucleotide sequence that is at least 90% identical to the nucleotide sequence of any one of SEQ ID NOS: 1-7, 9-25, or 27-32.
11. The method of paragraph 10, wherein the inhibitory oligonucleotide comprises a nucleotide sequence that is identical to the nucleotide sequence of any one of SEQ ID NOS: 1-7, 9-25, or 27-32.
12. The method of any one of paragraphs 1-7, wherein the inhibitory oligonucleotide comprises a TTAGGG motif.
13. The method of paragraph 12, wherein the inhibitory oligonucleotide comprises at least two tandem repeats of the TTAGGG motif.
14. The method of paragraph 13, wherein the inhibitory oligonucleotide comprises at least three tandem repeats of the TTAGGG motif.
15. The method of paragraph 14, wherein the inhibitory oligonucleotide comprises a nucleotide sequence that is identical to the nucleotide sequence identified by SEQ ID NO: 6 or SEQ ID NO: 9.
16. The method of paragraph 11, wherein the inhibitory oligonucleotide comprises a nucleotide sequence that is identical to the nucleotide sequence identified by SEQ ID NO: 1.
17. The method of paragraph 16, wherein the inhibitory oligonucleotide comprises multiple tandem repeats of the nucleotide sequence that is identical to the nucleotide sequence identified by SEQ ID NO: 1.
18. The method of any one of paragraphs 13-17, wherein the tandem repeat sequence are separated from each other by a polyA linker.
19. The method of any one of paragraphs 1-18, wherein the viral genome is from adeno-associated virus (AAV), adenovirus, herpes simplex virus, varicella, variola virus, hepatitis B, cytomegalovirus, JC polyomavirus, BK polyomavirus, monkeypox virus, Herpes Zoster, Epstein-Barr virus, human herpes virus 7, Kaposi's sarcoma-associated herpesvirus, or human parvovirus B19.
20. The method of paragraph 19, wherein the viral genome is an AAV genome.
21. The method of any one of paragraphs 1-20, wherein the inhibitory oligonucleotide is located in the 5' untranslated region of the viral genome.
22. The method of any one of paragraphs 1-21, wherein the recombinant viral genome is expressed in cells of the subject at a level that is at least 2-fold greater than a control.
23. The method of paragraph 22, wherein the recombinant viral genome is expressed in cells of the subject at a level that is at least 5-fold greater than a control.
24. The method of paragraph 23, wherein the recombinant viral genome is expressed in cells of the subject at a level that is at least 10-fold greater than a control.
25. The method of paragraph 24, wherein the recombinant viral genome is expressed in cells of the subject at a level that is at least 15-fold greater than a control.
26. The method of any one of paragraphs 1-25, wherein administration of the recombinant viral genome elicits an inflammatory response in the subject that is at least 2-fold lower than a control.

27. The method of paragraph 26, wherein administration of the recombinant viral genome elicits an inflammatory response in the subject that is at least 5-fold lower than a control.
28. The method of paragraph 27, wherein administration of the recombinant viral genome elicits an inflammatory response in the subject that is at least 10-fold lower than a control.
29. The method of paragraph 28, wherein administration of the recombinant viral genome elicits an inflammatory response in the subject that is at least 50-fold lower than a control.
30. The method of any one of paragraphs 22-29, wherein the control is expression of a viral genome that does not comprise the inhibitory oligonucleotide.
31. The method of any one of paragraphs 1-30, wherein the recombinant viral genome is administered intramuscularly.
32. The method of paragraph 31, wherein the recombinant viral genome is expressed in muscle cells of the subject.
33. The method of any one of paragraphs 1-30, wherein the recombinant viral genome is administered intravenously.
34. The method of paragraph 33, wherein the recombinant viral genome is expressed in liver cells of the subject.
35. The method of any one of paragraphs 1-34, wherein the subject is in need of gene therapy.
36. The method of any one of paragraphs 1-35, wherein the therapeutic nucleotide sequence encodes a therapeutic molecule.
37. The method of paragraph 36, wherein the therapeutic molecule is a therapeutic RNA or therapeutic DNA.
38. The method of paragraph 36, wherein the therapeutic molecule is a therapeutic protein or peptide.
39. The method of paragraph 37 or 38, wherein a therapeutically effective amount of the recombinant viral genomes is administered to the subject to treat a genetic disorder.
40. The method of paragraph 39, wherein the therapeutically effective amount is reduced by at least 20% relative to the therapeutically effective amount of a control, wherein the control is a recombinant viral genome that does not comprise an inhibitory oligonucleotide that inhibits nucleic acid-sensing TLR activation and/or signaling.
41. The method of paragraphs 40, wherein the therapeutic molecule is expressed in cells of the subject at a level that is equal to or greater than the expression level of a control, wherein the control is the therapeutic molecule encoded by a viral genome that does not comprise an an inhibitory oligonucleotide that inhibits nucleic acid-sensing TLR activation and/or signaling.
42. A recombinant viral genome comprising a therapeutic nucleotide sequence and an inhibitory oligonucleotide that inhibits nucleic acid-sensing toll-like receptor (TLR) activation and/or signaling.
43. The recombinant viral genome of paragraph 42, wherein the TLR is TLR3, TLR7, TLR8 or TLR9.
44. The recombinant viral genome of paragraph 43, wherein the TLR is TLR9.
45. The recombinant viral genome of any one of paragraphs 42-44, wherein the inhibitory oligonucleotide binds to the TLR.
46. The recombinant viral genome of any one of paragraphs 42-45, wherein the inhibitory oligonucleotide binds to inflammatory nucleic acids.
47. The recombinant viral genome of paragraph 46, wherein the inflammatory nucleic acids comprise CpG oligodeoxynucleotides.
48. The recombinant viral genome of any one of paragraphs 42-47, wherein the inhibitory oligonucleotide comprises a CCx(not-C)(not-C)xxGGG (SEQ ID NO: 63) motif, wherein x is any nucleic acid.
49. The recombinant viral genome of any one of paragraphs 42-48, wherein the inhibitory oligonucleotide comprises a nucleotide sequence that is at least 90% identical to the nucleotide sequence of any one of SEQ ID NOS: 1-7, 9-25, or 27-32.
50. The recombinant viral genome of paragraph 9, wherein the inhibitory oligonucleotide comprises a nucleotide sequence that is identical to the nucleotide sequence of any one of SEQ ID NOS: 1-7, 9-25, or 27-32.
51. The recombinant viral genome of any one of paragraphs 42-48, wherein the inhibitory oligonucleotide comprises a TTAGGG motif.
52. The recombinant viral genome of paragraph 51, wherein the inhibitory oligonucleotide comprises at least two tandem repeats of the TTAGGG motif.
53. The recombinant viral genome of paragraph 52, wherein the inhibitory oligonucleotide comprises at least three tandem repeats of the TTAGGG motif.
54. The recombinant viral genome of paragraph 53, wherein the inhibitory oligonucleotide comprises a nucleotide sequence that is identical to the nucleotide sequence identified by SEQ ID NO: 6 or SEQ ID NO: 9.
55. The recombinant viral genome of paragraph 50, wherein the inhibitory oligonucleotide comprises a nucleotide sequence that is identical to the nucleotide sequence identified by SEQ ID NO: 1.
56. The recombinant viral genome of paragraph 55, wherein the inhibitory oligonucleotide comprises multiple tandem repeats of the nucleotide sequence that is identical to the nucleotide sequence identified by SEQ ID NO: 1.
57. The recombinant viral genome of any one of paragraphs 52-56, wherein the tandem repeat sequence are separated from each other by a polyA linker.
58. The recombinant viral genome of any one of paragraphs 42-57, wherein the viral genome is from adeno-associated virus (AAV), adenovirus, herpes simplex virus, varicella, variola virus, hepatitis B, cytomegalovirus, JC polyomavirus, BK polyomavirus, monkeypox virus, Herpes Zoster, Epstein-Barr virus, human herpes virus 7, Kaposi's sarcoma-associated herpesvirus, or human parvovirus B19.
59. The recombinant viral genome of paragraph 58, wherein the viral genome is an AAV genome.
60. The recombinant viral genome of any one of paragraphs 42-59, wherein the inhibitory oligonucleotide is located in the 3' untranslated region of the viral genome.
61. The recombinant viral genome of any one of paragraphs 42-60, wherein the therapeutic nucleotide sequence encodes a therapeutic molecule.
62. The recombinant viral genome of paragraph 61, wherein the therapeutic molecule is a therapeutic RNA.
63. The recombinant viral genome of paragraph 61, wherein the therapeutic molecule is a therapeutic protein or peptide.
64. A method of treating a condition in a subject comprising administering by intramuscular injection or intravenous injection to the subject a therapeutically effective amount of a recombinant adeno-associated viral genome comprising a therapeutic nucleotide sequence and an inhibitory oligonucleotide that comprises a nucleotide sequence that is identical to the nucleotide sequence identified by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 or SEQ ID NO: 24, to treat the condition in the subject without eliciting an inflammatory response.

65. A recombinant adeno-associated viral genome comprising a therapeutic nucleotide sequence and an inhibitory oligonucleotide that comprises a nucleotide sequence that is identical to the nucleotide sequence of any one of SEQ ID NOS: 1-7, 9-25, or 27-32.
66. A method comprising administering to a subject a recombinant viral genome comprising a therapeutic nucleic acid and an inhibitory oligonucleotide that inhibits the production of inflammatory cytokines.
67. A recombinant viral genome comprising a therapeutic nucleic acid and an inhibitory oligonucleotide that inhibits the production of inflammatory cytokines.
68. The recombinant viral genome of any one of paragraphs 42-59, wherein the inhibitory oligonucleotide is located in the 3' untranslated region of the viral genome.
69. The method of paragraph 37, wherein therapeutic molecule is a therapeutic DNA.
70. The method of paragraph 69, wherein the therapeutic DNA is an aptamer.
71. The method of any one of paragraphs 1-41, wherein the recombinant viral genome further comprises at least one other inhibitory oligonucleotide that inhibits nucleic acid-sensing TLR activation and/or signaling.
72. The method of paragraph 71, wherein one of the inhibitory oligonucleotides is oriented in the sense direction of the viral genome and another of the inhibitory oligonucleotides is oriented in the antisense direction of the viral genome.
73. The method of paragraph 71 or 72, wherein each of the inhibitory oligonucleotides comprises a nucleotide sequence that is at least 90% identical to the nucleotide sequence of any one of SEQ ID NOS: 1-7, 9-25, or 27-32.
74. The method of any one of paragraphs 71-73, wherein one of the inhibitory oligonucleotides comprises SEQ ID NO: 9.
75. The method of any one of paragraphs 71-74, wherein one of the inhibitory oligonucleotides comprises SEQ ID NO: 5.
76. The recombinant viral genome of any one of paragraphs 42-63, wherein the recombinant viral genome further comprises at least one other inhibitory oligonucleotide that inhibits nucleic acid-sensing TLR activation and/or signaling.
77. The recombinant viral genome of paragraph 76, wherein one of the inhibitory oligonucleotides is oriented in the sense direction of the viral genome and another of the inhibitory oligonucleotides is oriented in the antisense direction of the viral genome.
78. The recombinant viral genome of paragraph 76 or 77, wherein each of the inhibitory oligonucleotides comprises a nucleotide sequence that is at least 90% identical to the nucleotide sequence of any one of SEQ ID NOS: 1-7, 9-25, or 27-32.
79. The recombinant viral genome of any one of paragraphs 76-78, wherein one of the inhibitory oligonucleotides comprises SEQ ID NO: 9.
80. The recombinant viral genome of any one of paragraphs 76-80, wherein one of the inhibitory oligonucleotides comprises SEQ ID NO: 5.
81. A method comprising administering to an eye of a subject a recombinant viral genome comprising a therapeutic nucleotide sequence and an inhibitory oligonucleotide that inhibits nucleic acid-sensing toll-like receptor (TLR) activation and/or signaling, wherein the recombinant viral genome inhibits an inflammatory response to the recombinant viral genome in the eye, optionally wherein the recombinant viral genome is administered intravitreally.

EXAMPLES

Example 1: Impact of Oligonucleotides on TLR9 Activation In Vitro

This example provides data indicating that incorporating TLR9 inhibitory oligonucleotides into DNA can reduce TLR9-mediated inflammation. Inhibitory oligonucleotides were covalently linked to a short nucleic acid that normally activates TLR signaling to determine whether the inhibitory oligonucleotides would block TLR9 activation by the short nucleic acid. The inhibitory oligonucleotides tested included: c41 oligonucleotide (SEQ ID NO: 1), ODN 2088 (SEQ ID NO: 2), ODN 4084-F (SEQ ID NO: 3), ODN INH-1 (SEQ ID NO: 4), ODN INH-18 (SEQ ID NO: 5), ODN TTAGGG (SEQ ID NO: 6), G-ODN (SEQ ID NO: 7), ODN 2114 (SEQ ID NO: 16), ODN 4024 (SEQ ID NO: 17), ODN INH-4 (SEQ ID NO: 18), ODN INH-13 (SEQ ID NO: 19), ODN Poly-G (SEQ ID NO: 20), ODN GpG (SEQ ID NO: 21), ODN IRS-869 (SEQ ID NO: 22), ODN IRS-954 (SEQ ID NO: 23) and ODN 21158 (SEQ ID NO: 24). ODN Control (15 nt) and ODN Control (24 nt) were used as controls.

Several single-stranded DNA oligonucleotides were generated in which ODN 2006, a CpG-containing oligonucleotide known to strongly activate TLR9, is immediately followed by a control or experimental oligonucleotide (i.e. ODN 2006 is on the 5' end). All oligonucleotides were synthesized with a phosphorothioate backbone for increased stability. A HEK293-based reporter cell line that constitutively expresses TLR9 to measure TLR9-mediated inflammation was used. When oligonucleotides were applied at the low concentration of 0.5 µM, both oligonucleotides containing control sequences induced robust inflammation compared to mock treatment (FIG. 1A on the left). In contrast, all the oligonucleotides containing TLR9 inhibitory oligonucleotides showed markedly reduced inflammation (FIG. 1A on the left). A similar trend at the high concentration of 5 µM was observed (FIG. 1A on the right).

Figure 1B:
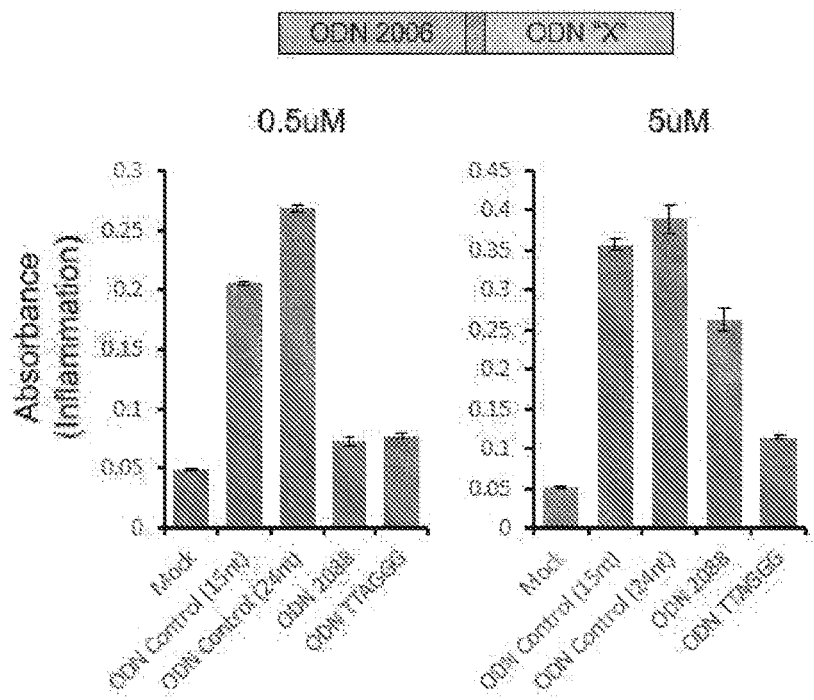

Oligonucleotides with an AAAAA linker (SEQ ID NO: 8) between ODN 2006 and the following sequence were also tested, and similar results were observed with reduction in inflammation (FIG. 1B), suggesting the TLR9 inhibitory sequence can be distal to the inflammatory sequence.

Figure 1C:
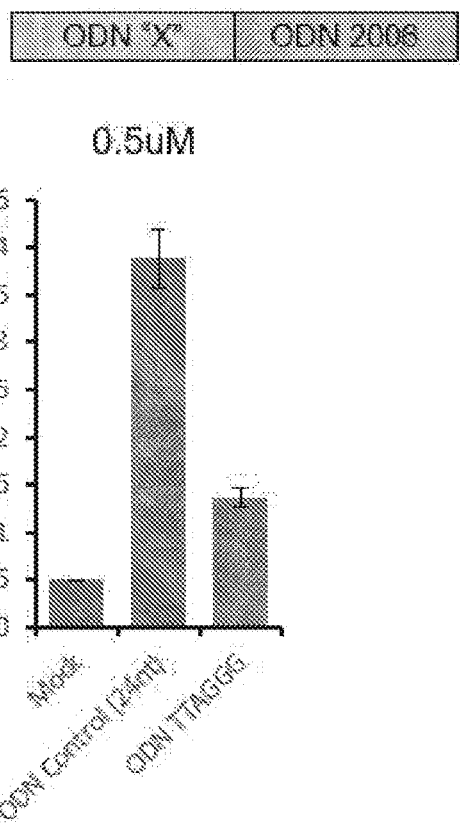

When oligonucleotides in which the order of ODN 2006 and the covalently linked sequence is reversed were tested, the oligonucleotide containing TLR9 inhibitory oligonucleotide ODN TTAGGG was also able to reduce inflammation (FIG. 1C). Taken together, these results show that incorporation of a TLR9 inhibitory oligonucleotide in a DNA inhibits inflammatory responses.

Figure 5:
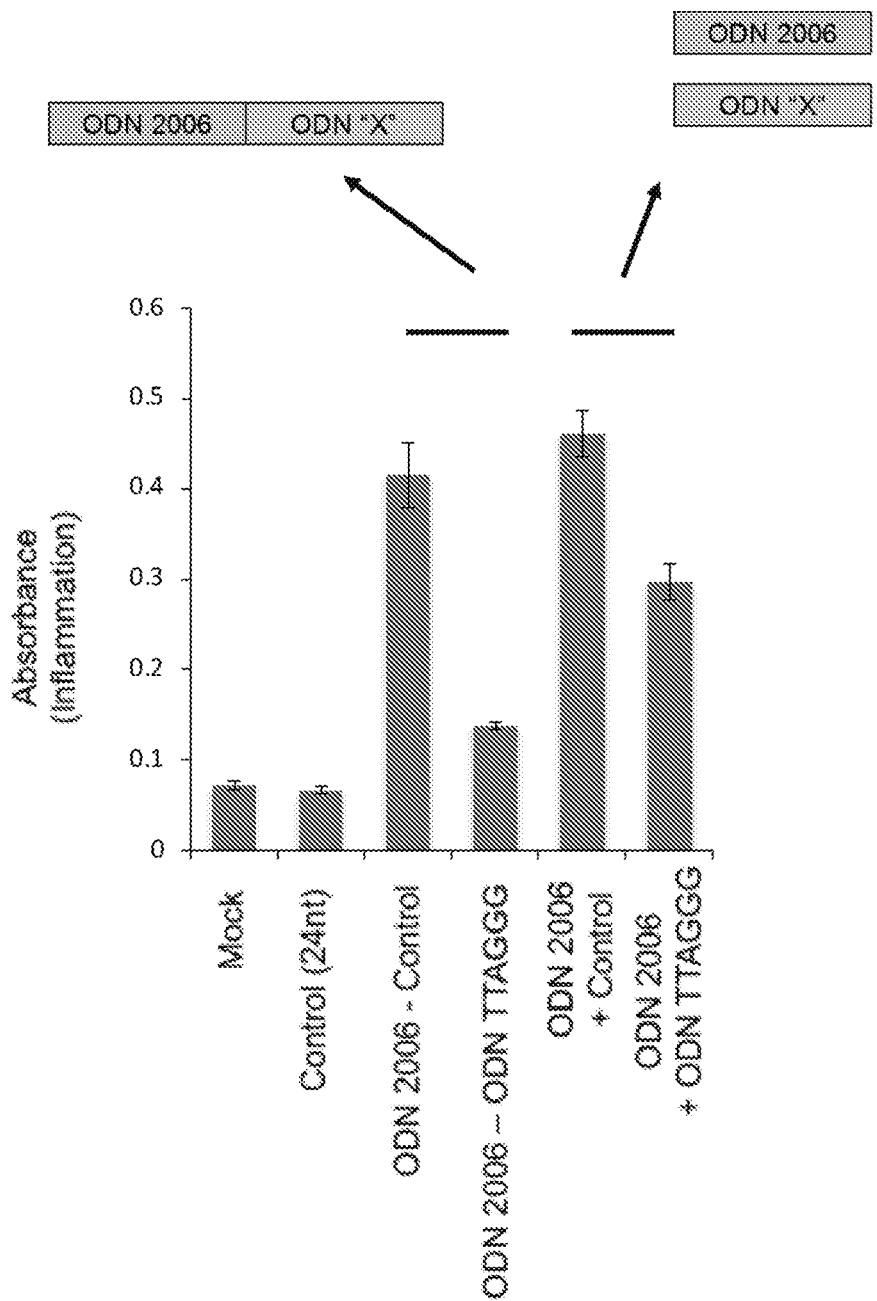
FIG. 5 includes a graph showing inflammatory responses to various inhibitory oligonucleotides in HEK293-TLR9 reporter cells in vitro. HEK293-TLR9 reporter cells were treated with 0.02 μM of the indicated oligonucleotides (see Example 1) for 18 hours. A 50 μl sample of cell supernatant was incubated with 150 μl HEK-Blue Detection and then analyzed on a plate reader for absorbance at 630 nm. Cells were treated with (1) a random 24 nucleotide strand ("control") that does not contain CG, (2) ODN 2006 (SEQ ID NO: 26) fused to ODN TTAGGG (SEQ ID NO: 6) (in cis), or (3) ODN 2006 co-administered with ODN TTAGGG (in trans). Data shown are mean±s.d. of n=3 technical replicates.

A condition was identified where ODN 2006 covalently linked to a control sequence (in cis) gave comparable inflammation as ODN 2006 and the control ODN co-administered at the same concentration (in trans), and observed that ODN 2006-TTAGGG (fusion of SEQ ID NOS: 26 and SEQ ID NO: 6) blocked ~80% of induced inflammation while co-administration of ODN 2006 (SEQ ID NO: 26) and ODN TTAGGG (SEQ ID NO: 6) only inhibited ~35% of induced inflammation (FIG. 5). Thus, linking a TLR9 inhibitory sequence to an otherwise inflammatory nucleic acid (in cis), for example, can be more effective at preventing inflammation than administering the TLR9 inhibitory sequence as an independent molecule (in trans).

Figures 6A, 6B:
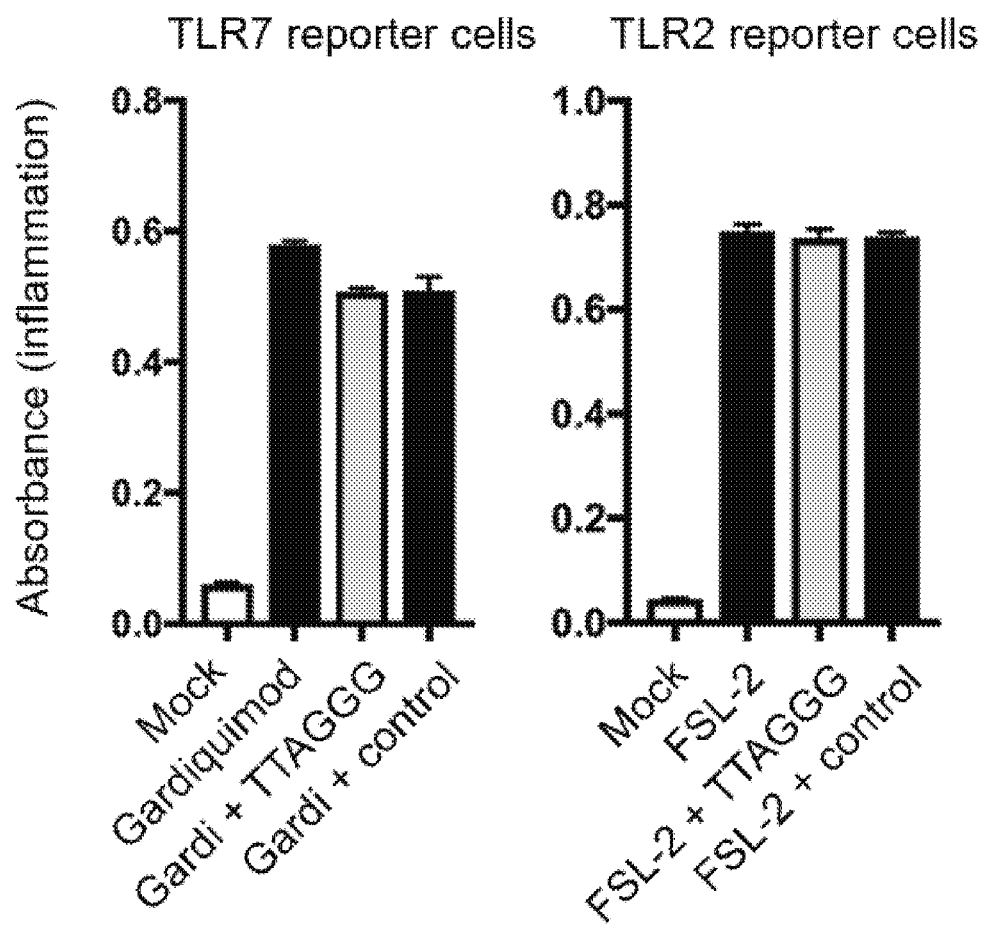
FIGS. 6A-6B includes data showing the impact of exemplary inhibitory oligonucleotides on TLR7 and TLR2 activation in vitro. HEK293-TLR7 or HEK293-TLR2 reporter cells were treated with or without a high concentration of 5 μM of the indicated constructs (single-stranded DNA with a phosphorothioate backbone), along with the appropriate TLR7 stimulant (1 vg/ml of Gardiquimod) or TLR2 stimulant (100 ng/ml of FSL-2), for 18 hours. TTAGGG in FIGS. 6A-6B refers to ODN TTAGGG (SEQ ID NO: 6). A 50-μl sample of cell supernatant was incubated with 100 μl HEK-Blue Detection and then analyzed on a plate reader for absorbance at 639 nm. The data shown are mean±s.d. of n=3 technical replicates.

ODN TTAGGG did not reduce inflammatory responses by TLR7 stimulation (FIG. 6A) or TLR2 stimulation (FIG. 6B) even at high concentration of 5 uM, supporting its specificity for TLR9.

Example 2: Engineering a Self-Complementary AAV Vector

It is unknown if the inhibitory oligonucleotides retain functionality in the context of a much larger viral genome (i.e., the sequence is covalently linked on both ends to much longer sequences). To test this possibility, a self-complementary (sc) AAV vector encoding enhanced green fluorescent protein (eGFP) was used, and 3 copies of c41 oligonucleotide (3 X SEQ ID NO: 1) or telomere (SEQ ID NO: 9), derived from bacteria and mammalian telomeres respectively (Gursel, I et al. *J Immunol.* 2003; 171(3):1393-400; Kaminski, J J et al. *J Immunol.* 2013; 191(7):3876-83; Shirota, H et al. *J Immunol.* 2005; 174(8):4579-83; Li, Y et al. *Vaccine.* 2011; 29(11):2193-8), were inserted into a plasmid harboring the vector genome. sc AAV vectors were used as they have been shown to be more efficient at triggering TLR9 activation and inducing more inflammation in the mouse liver than single-stranded (ss) AAV vectors. As c41 oligonucleotide and telomere oligonucleotides are predicted to have strong secondary structure, an AAAAA (SEQ ID NO: 8) linker was inserted between copies of the inhibitory oligonucleotide. In addition, 3×c41 and 3×telomere sequences were placed after the polyA sequence and upstream of the right inverted terminal repeat (ITR) so they would be present in the DNA genome during viral entry, but would be absent from subsequent mRNA transcripts upon successful transduction (scAAV-eGFP-3×c41 and scAAV-eGFP-3×telomere). Finally, to determine if the location of inhibitory oligonucleotide in the viral genome matters, a vector where 3× telomere was located between the left ITR and the promoter was generated (scAAV-3×telomere-eGFP) (data not shown).

Figure 2B:
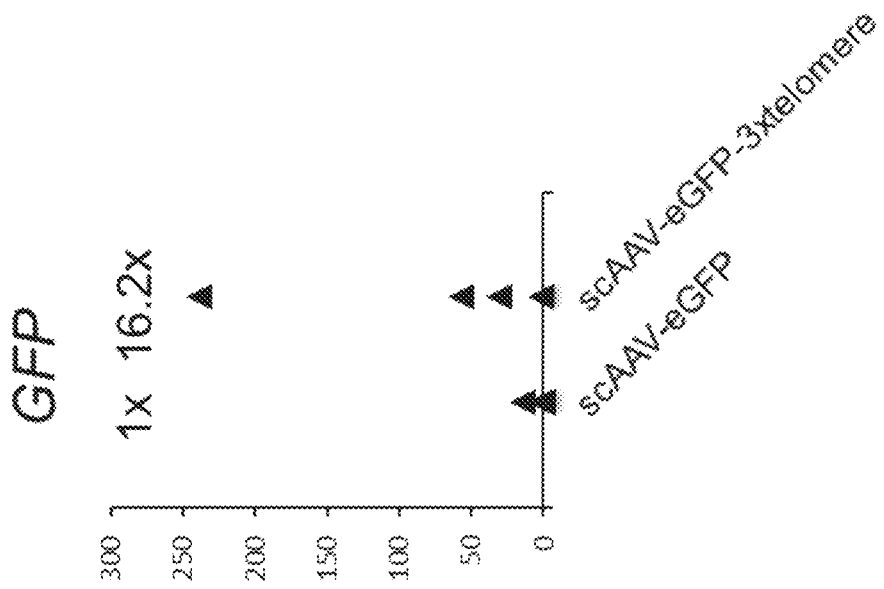
FIGS. 2A-2B show muscle tissue data relating to the impact of three copies of the telomere oligonucleotide ("3×telomere" SEQ ID NO: 35) on the inflammatory response elicited by a linked self-complementary adeno-associated virus (scAAV) genome and on AAV transgene expression in infected mice.
Figure 2A:
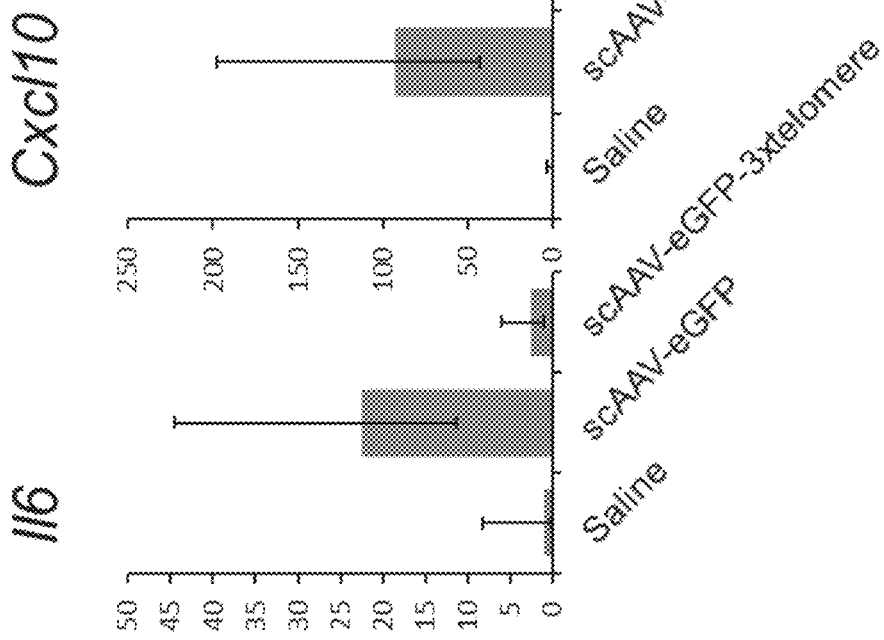

Example 3: Impact of Three Copies of Telomere Oligonucleotide ("3×Telomere" SEQ ID NO: 35) on the Inflammatory Response Elicited by a Self-Complementary Adeno-Associated Virus (scAAV) Genome and on Transgene Expression in Muscle Tissue of Mice In Vivo Muscle is an important tissue target for gene therapy. The scAAV-eGFP-3×telomere was selected for in vivo characterization as the telomere oligonucleotide is derived from human sequences and might be preferable for clinical use. To determine whether three copies of the telomere oligonucleotide ("3×telomere" SEQ ID NO: 35) could prevent an inflammatory response induced by AAV, the following was delivered to the quadriceps of adult C57BL/6 mice via intramuscular injections: control saline, scAAV-eGFP or scAAV-eGFP-3×telomere (described in example 2). Consistent with the literature, scAAV-eGFP increased Il6 and Cxcl10 expression in muscle tissues 2 h post-administration (approximately 20 to 100 fold, compared to saline), indicating inflammation (FIG. 2A). In contrast, scAAV-eGFP-3×telomere showed little to no increase in inflammatory markers (FIG. 2A). Furthermore, 28 d after AAV administration, scAAV-eGFP-3×telomere showed 16.2× higher gene expression of GFP than scAAV-eGFP, demonstrating increased transgene expression (FIG. 2B). Therefore, when linked to an AAV-encoding a transgene, the telomere oligonucleotide could also increase viral genome expression.

Example 4: Impact of Telomere and c41 Oligonucleotides on Inflammatory Response Elicited by a Self-Complementary Adeno-Associated Virus (scAAV) Genome in Liver Tissue of Mice in Vivo Intravenous delivery of AAV is often used to transduce hepatocytes for gene therapy. Previous work has shown that upon intravenous administration of AAV, Kupffer cells (resident hepatic antigen-presenting cells) in the liver of mice are capable of sensing sc AAV genomes and triggering inflammatory and innate immune responses 1-9 h later (Martino, A T et al., *Blood.* 2011; 117(24):6459-68). These responses include induction of proinflammatory cytokines such as TNF and IL6. In addition, immune cells such as neutrophils, macrophages and natural killer (NK) cells infiltrate the liver 2 h after AAV administration.

Figure 3D:
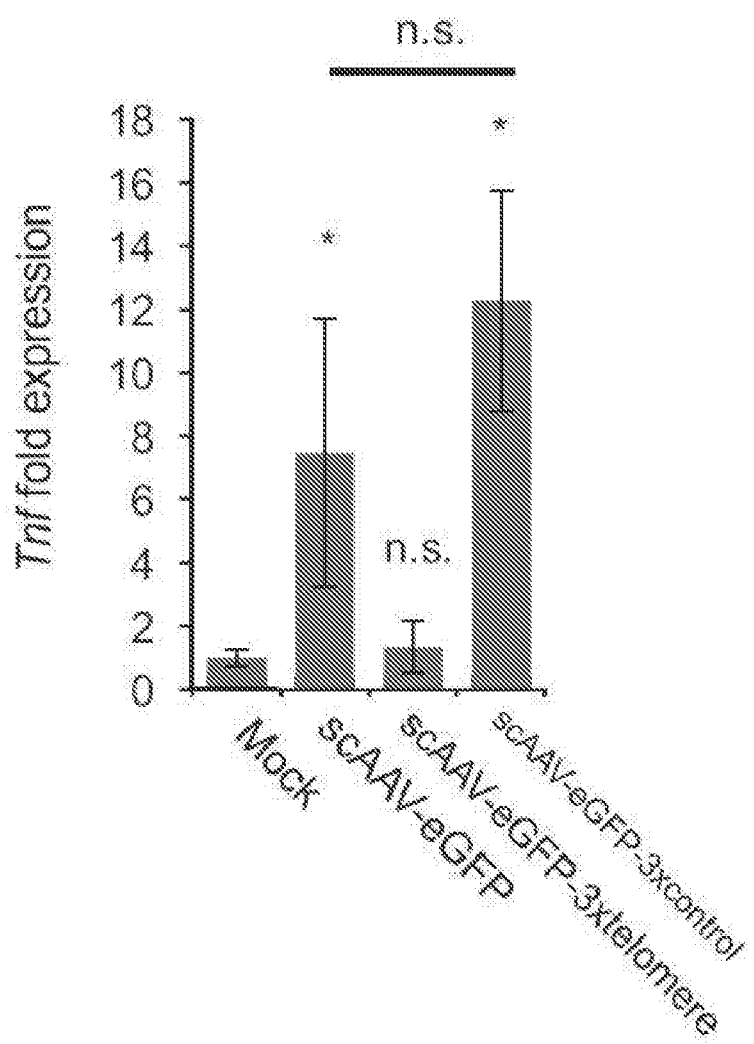
FIG. 3D includes liver tissue data relating to the impact of the inhibitory oligonucleotide sequence or a control sequence on the inflammatory response elicited by a linked scAAV genome in infected mice. Adult C57BL/6 mice were infected with indicated AAV2 viruses and a piece of the liver was analyzed for indicated gene expression by qRT-PCR. Data shown are mean±s.d. of n=5 mice per condition except n=3 mice for scAAV-eGFP-3×control. *P<0.05 (unpaired t-test) compared to saline condition. N.s.: not significant (P>0.05).

To determine if the engineered vectors can reduce inflammation in the liver in vivo, PBS or equal amounts of scAAV-eGFP or scAAV-eGFP-3×telomere was administered via tail vein injection. In agreement with previous work, scAAV-eGFP stimulated increased Tnf and Il6 expression in the liver (approximately 3 to 10 fold, compared to saline), indicating inflammation (FIG. 3A). In contrast, scAAV-eGFP-3×telomere showed little to no increase in inflammatory markers (FIG. 3A). More mice were tested in subsequent experiments and scAAV-eGFP stimulated statistically significant Tnf induction in the liver compared to saline, while scAAV-eGFP-3×telomere and scAAV-eGFP-3×c41 did not (FIGS. 3B-3C), demonstrating their ability to evade eliciting inflammation in the liver. Finally, it was determined that scAAV-eGFP-3×control is not able to prevent inflammation in the liver compared to scAAV-eGFP, demonstrating that the inhibitory oligonucleotide sequence plays a role in preventing inflammation (FIG. 3D).

Figure 3E:
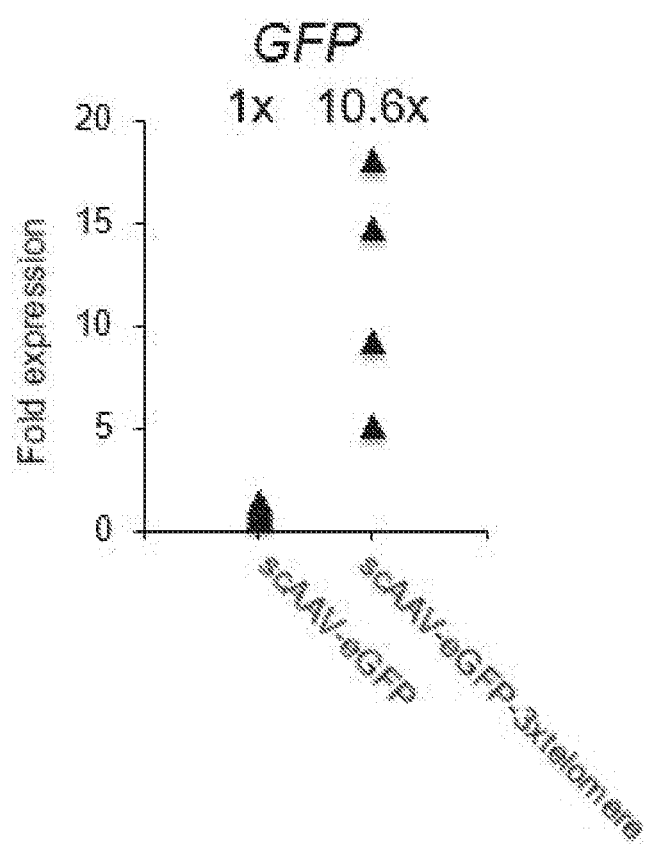
FIG. 3E includes liver tissue data relating to the impact of three copies of telomere oligonucleotide ("3×telomere" SEQ ID NO: 35) on scAAV transgene expression in infected mice. Adult C57BL/6 mice were infected with indicated AAV2 viruses ($10^{11}$ vg per mouse) by tail vein injections. 14 d later, the animals were euthanized and a piece of the liver was analyzed for GFP gene expression by qRT-PCR. scAAV-eGFP injection was set to 1-fold expression for GFP. Data shown are n=4 mice per condition. Each triangle represents an animal and mean values are indicated.

Example 5: Impact of Three Copies of Telomere Oligonucleotide on Transgene Expression by a scAAV In Vivo in Liver Tissue To determine if the engineered vectors can also increase transgene expression in the liver in vivo, scAAV-eGFP or scAAV-eGFP-3×telomere was administered to mice via intravenous injection and GFP gene expression was measured in the liver 14 d later. 10.6× higher gene expression of GFP by scAAV-eGFP-3×telomere was observed (FIG. 3E), suggesting that the engineered vectors also increase transgene expression in the liver.

Figure 7A:
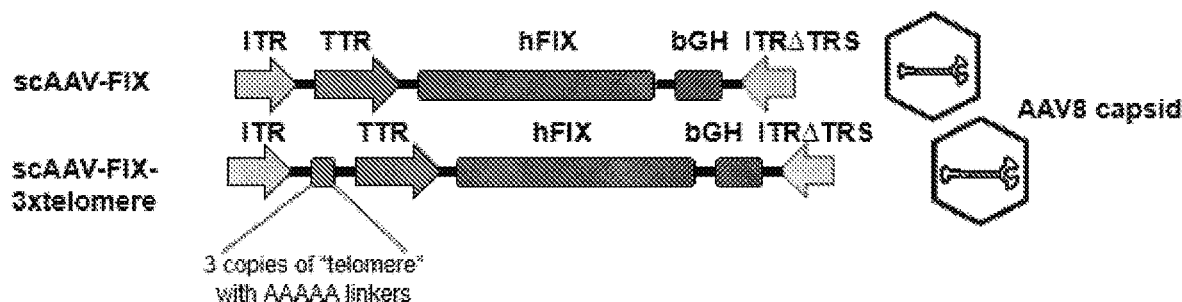
Figure 7A:
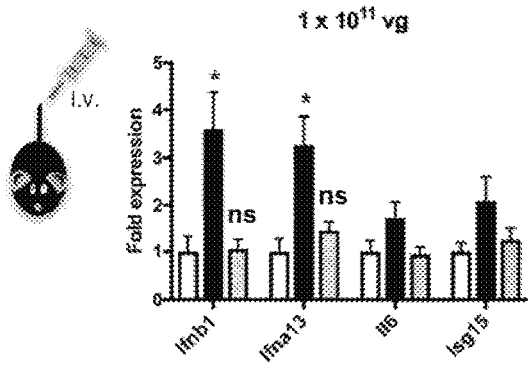
Figure 7A:
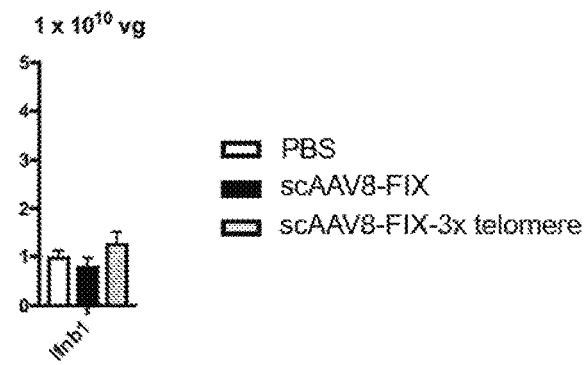
Figure 7A:
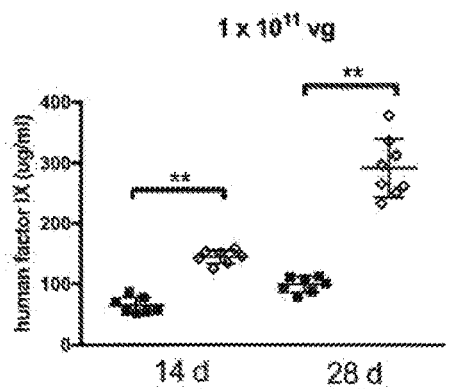
Figure 7A:
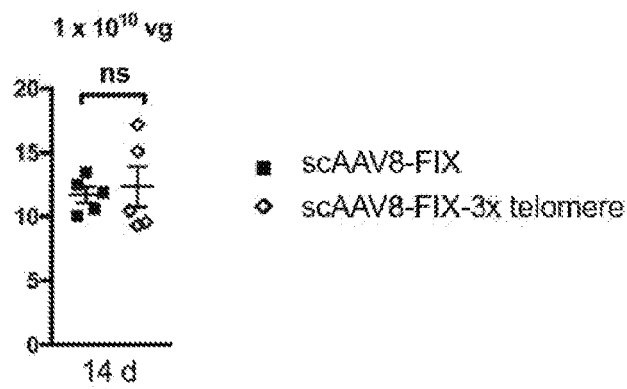

Example 6: Engineering a Self-Complementary AAV Vector Encoding Human Factor IX (FIX) and the Impact of Three Copies of Telomere Oligonucleotide on Innate Immune Response and Transgene Expression In Vivo in Liver Tissue Three copies of SEQ ID NO: 9 were inserted into a plasmid harboring a vector genome for a self-complementary AAV vector expressing human FIX (FIG. 7A). An AAAAA (SEQ ID NO: 8) linker was inserted between copies of the inhibitory oligonucleotide (FIG. 7A). The 3×telomere sequences were placed after the left inverted terminal repeat (ITR) but before the transthyretin (TTR) promoter so they would be present in the DNA genome during viral entry, but would be absent from subsequent mRNA transcripts upon successful transduction. To determine if the engineered vectors can reduce inflammation in the liver in vivo, PBS or equal amounts of scAAV-FIX or scAAV-FIX-3×telomere ($1\times10^{11}$ vg of each, or $1\times10^{10}$ vg of each, in an AAV8 capsid) was administered via tail vein injection. In agreement with previous work, scAAV-FIX stimulated increased interferon (Ifnb1 and Ifna13) gene expression in the liver compared to saline 2 h after administration, indicating innate immune responses (FIG. 7B). In contrast, scAAV-FIX-3×telomere showed little to no increase in interferon expression (FIG. 7B). Furthermore, scAAV-FIX-3×telomere-treated mice expressed more human FIX protein in plasma compared to scAAV-FIX treatment 14 d and 28 d later (FIG. 7D). A 10-fold lower dose of AAV vectors did not result in interferon responses (FIG. 7C) or differences in human FIX protein expression in plasma (FIG. 7E), suggesting that the two vectors do not have inherently different potencies and that evading interferon responses enhances transgene expression.

Example 7: Intramuscular Injection of Engineered Single-Stranded AAV Vector In Vivo in Mice ssAAV-eGFP and ssAAV-eGFP-3×telo3×INH18 (FIG. 4) were packaged in an AAVrh32.33 capsid and intramuscularly injected into the quadriceps muscle of mice. While dose-dependent immune responses are well-appreciated in clinical use, robust immune responses are generally not observed in mice upon AAV administration, especially ss AAV vectors which are more widely used and have a larger coding capacity. Thus, the more clinically relevant immunogenic condition was modeled in mice by utilizing AAVrh32.33 capsid (hereafter referred to as rh32.33) and intramuscular delivery. This combination has been shown to lead to robust CD8+ T cell responses against rh32.33 capsid, local infiltration of cytotoxic T cells into the muscle, and a decline in transgene expression over time in wild-type mice (Faust et al., J Clin Invest 123, 2994-3001 (2013); Mays et al., J Immunol 182, 6051-6060 (2009). Furthermore, the authors found that Tlr9$^{-/-}$ mice showed substantially reduced T cell responses against rh32.33 capsid and maintained stable transgene expression, and similar benefits were observed in wild-type mice by partially depleting the AAV vector genome of CpG motifs (Faust et al., J Clin Invest 123, 2994-3001 (2013)).

Figure 8D:
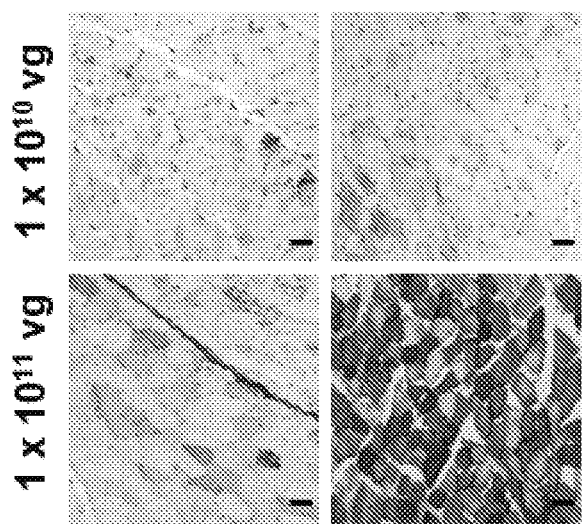

At a lower dose of $1\times10^{10}$ vg, ssAAV-eGFP triggered a range of CD8+ T cell responses against rh32.33 capsid, with 7 of 10 animals showing positive T cell reactivity (FIG. 8A). In contrast, ssAAV-eGFP-3×telo3×INH18, which harbors the inhibitory oligonucleotide designed for single-stranded vectors, showed nearly no CD8+ T cell response against rh32.33 capsid (1 of 10 animals positive) and was not statistically different from PBS treatment (FIG. 8A). At a higher dose of $1\times10^{11}$ vg, both vectors elicited extremely high capsid-directed T cell responses (~800-1000 SFU/million splenocytes); while not statistically significant, the engineered vector elicited a modestly weaker T cell capsid response than the parental vector, consistent with the idea that the inhibitory oligonucleotide functions in an AAV dose-dependent manner (FIG. 8A). Cytotoxic T cell infiltrates have been observed in muscle biopsies of patients receiving intramuscular AAV gene therapy (Ferreira et al., Front Immunol 5, 82 (2014); Flotte et al., Hum Gene Ther 22, 1239-1247 (2011)). Thus, immune cell infiltration into the local tissue environment was further characterized. RobustCD8+ T cell infiltration was observed into muscle samples from ssAAV-eGFP-injected animals, and approximately one-third were granzyme B+, a maker for activated cytotoxic T cells, while no CD8+ T cell infiltration was observed in all eight ssAAV-eGFP-3×telo3×INH18-injected muscle samples, strongly suggesting that the presence of the inhibitory oligonucleotide prevented capsid-directed T cell responses and infiltration (FIG. 8B-8C). The engineered vector showed comparable or higher GFP expression than the parental vector by immunohistochemical analysis (FIG. 8D).

Example 8: Engineering a Single-Stranded AAV Vector

A single-stranded AAV vector, ssAAV-eGFP, was modified by inserting 5 copies of the telomere sequence (5 X SEQ ID NO: 9) with an AAAAA (SEQ ID NO: 8) linker between each copy, followed by another 5 copies of the telomere sequence (5 X SEQ ID NO: 9) in anti-sense direction with a linker between each copy, giving ssAAV-eGFP-5×telomere (FIG. 4). Since both positive and negative strands of the viral genome are equally likely to be packaged into a viral particle, this ensures that each packaged viral genome would have 5 copies of the telomere sequence (5 X SEQ ID NO: 9) in the correct orientation. ssAAV-eGFP-3×telo3×INH18, which carries 3 copies of the telomere sequence (3 X SEQ ID NO: 9) with AAAAA (SEQ ID NO: 8) linkers, followed by 3 copies of INH-18 (3 X SEQ ID NO: 5) with linkers but in anti-sense direction was also engineered (FIG. 4). INH-18 (SEQ ID NO: 5) was chosen as it showed potent inhibition of TLR9-mediated inflammation in the oligonucleotide assays described above (FIG. 1A on the right). Furthermore, having 3 copies of the telomere sequence (3 X SEQ ID NO: 9) in the sense direction followed by 3 copies of INH-18 (3 X SEQ ID NO: 5) in the anti-sense direction avoids the possibility of self-annealing via complementarity, which may hamper viral packaging. Finally, since both positive and negative strands of the viral genome are equally likely to be packaged into a viral particle, this design increases the probability that each packaged viral genome will have either 3 copies of the telomere sequence (3 X SEQ ID NO: 9) in the correct orientation or 3 copies of INH-18 (3 X SEQ ID NO: 5) in the correct orientation.

The three vectors were produced as purified AAV8 viruses and total yield of viruses was measured via PCR of viral genomes. ssAAV-eGFP and ssAAV-eGFP-3×telo3×INH18 gave similar yields of $3.97\times10^{13}$ vg and $3.60\times10^{13}$ vg, while ssAAV-eGFP-5×telomere gave ~10-fold lower yield of $3.11\times10^{12}$ vg (Table 1). Table 1 includes yields of indicated AAV8 viruses produced after triple transfection and purification and yield is shown as total amount of viral genomes (vg) obtained for each vector. Thus, ssAAV-eGFP-5×telomere may have packaging issues and results in lower viral yields compared to the parental ssAAV-eGFP vector, while ssAAV-eGFP-3xtelo3xINH18 gives comparable viral yields.

TABLE 1

| Name of virus | Total yield (vg) |
|---|---|
| ssAAV-eGFP | $3.97 \times 10^{13}$ |
| ssAAV-eGFP-5xtelomere | $3.11 \times 10^{12}$ |
| ssAAV-eGFP-3xtelo3xINH18: | $3.60 \times 10^{13}$ |

Figure 9A:
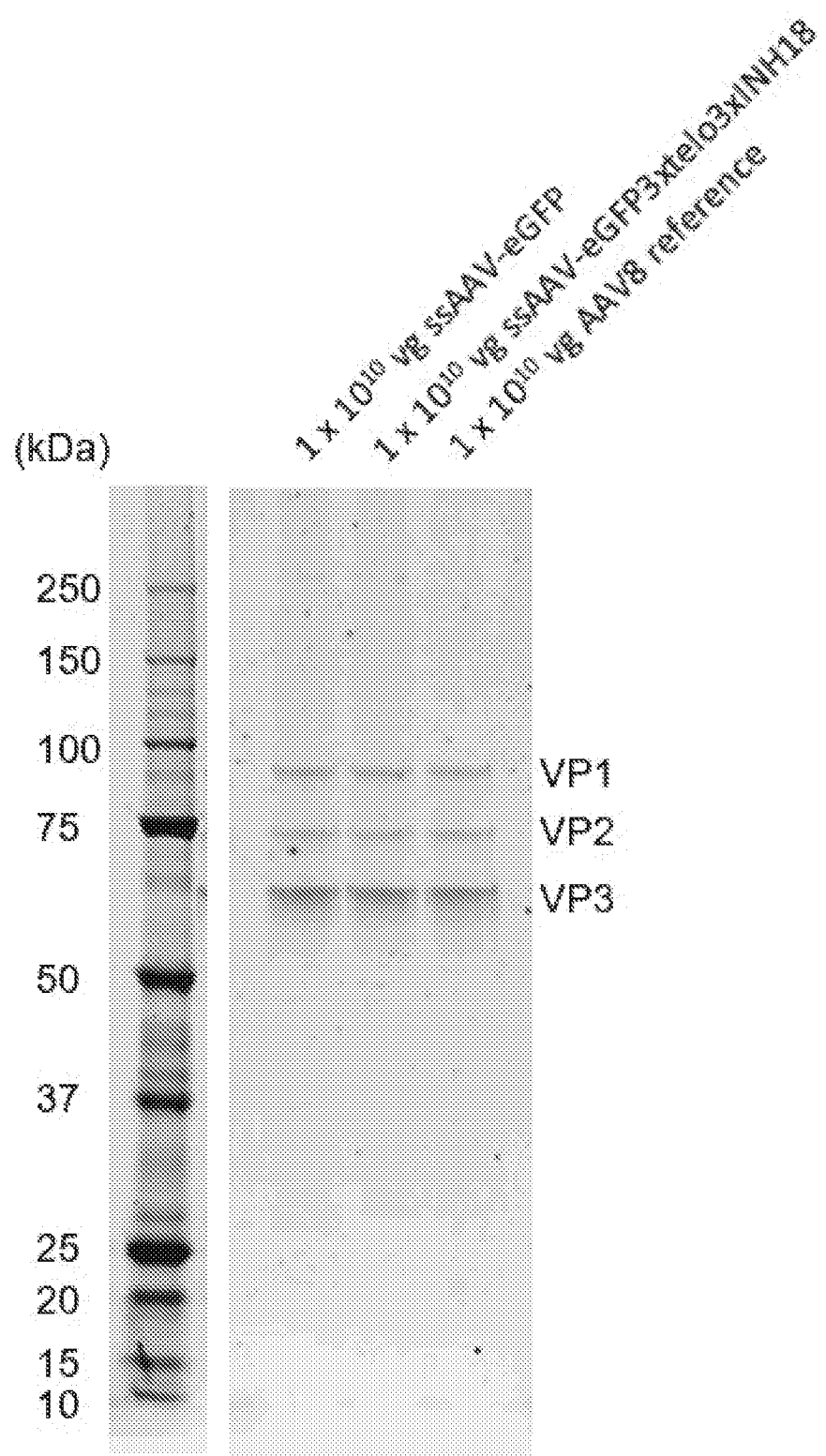
FIGS. 9A-9B show characterization of AAV8 vectors used in a pig study. ssAAV-eGFP vector is provided as SEQ ID NO: 36. ssAAV-eGFP-3×telo3×INH18 vector is provided as SEQ ID NO: 37.
Figure 9B:
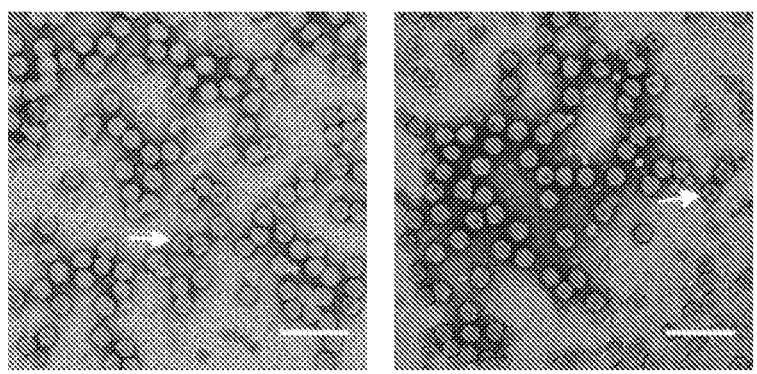

Example 9: Subretinal Injection of Engineered Single-Stranded AAV Vector In Vivo in Outbred Pigs The eye is often described as "immune-privileged" due in part to the presence of a blood-retina barrier that limits the entry of immune cells and immune factors. However, innate and adaptive immune responses have been reported in both large animal studies and clinical trials following subretinal AAV administration with dose-dependent severity (Bainbridge et al., N Engl J Med 372, 1887-1897 (2015); Ramachandran et al., Hum Gene Ther 28, 154-167 (2017); Reichel et al., Mol Ther 25, 2648-2660 (2017)). To determine immune responses and pathology in the retina with AAV, a subretinal AAV pig model was used as the pig eye shares a similar size and morphology as the human eye (Sanchez et al., Graefes Arch Clin Exp Ophthalmol 249, 475-482 (2011)). Table 2 shows design of study evaluating subretinal delivery of AAV vectors in wild-type pigs. Six wild-type female pigs were injected subretinally with 75 µl of indicated AAV8 vectors (dose of $4 \times 10^{11}$ vg per eye) or with vehicle control. The animals received clinical examinations at weekly intervals and OCT imaging at 2 wpi and 6 wpi, and were euthanized 6 wpi. wpi, weeks post-injection; OD, oculus dextrus (right eye); OS, oculus sinister (left eye); N.A., not applicable.

ssAAV-eGFP and ssAAV-eGFP-3xtelo3xINH18 were used and packaged in an AAV8 capsid (FIG. 4, Tables 2-4 and FIGS. 9A-9B). Endotoxin testing of AAV8 vectors using a limulus amebocyte lysate assay showed that both vectors were endotoxin free (<1 EU/ml) (Table 3). The percentage of full particles was determined by negatively staining AAV with 0.5% uranyl acetate and viewing under a transmission electron microscope. Empty particles show an electron-dense circle in the middle of the capsid (example shown with arrow in FIG. 9B). The number of empty and full particles was counted directly from electron micrographs of ten random images for each vector (Table 4). 1183 particles were counted for ssAAV-eGFP and 1221 particles were counted for ssAAV-eGFP-3xtelo3xINH18. The average percent full particles per image is reported with standard deviation. Representative images are shown for each vector with scale bar: 100 nm (FIG. 9B).

An intermediate dose of $4 \times 10^{11}$ vg was selected per eye based on a recently approved gene therapy for biallelic RPE65 mutation-associated retinal dystrophy (LUXTURNA™, dose=$1.5 \times 10^{11}$ vg per eye) and previous reports showing ocular inflammation in patients at $1 \times 10^{11}$ vg and $1 \times 10^{12}$ vg per eye (Bainbridge et al., N Engl J Med 372, 1887-1897 (2015); Xue et al., Nat Med. 2018 October; 24(10):1507-1512; Dimopoulos et al., Am J Ophthalmol. 2018 September; 193:130-142).

TABLE 2

Study Design.

| Animal ID number | Dose (vg)/eye | OD | OS |
|---|---|---|---|
| 23583 | $4 \times 10^{11}$ | ssAAV-eGFP-3xtelo3xINH18 | ssAAV-eGFP |
| 23584 | $4 \times 10^{11}$ | ssAAV-eGFP-3xtelo3xINH18 | ssAAV-eGFP |
| 23585 | $4 \times 10^{11}$ | ssAAV-eGFP-3xtelo3xINH18 | ssAAV-eGFP |
| 23586 | $4 \times 10^{11}$ | ssAAV-eGFP-3xtelo3xINH18 | ssAAV-eGFP |
| 23587 | $4 \times 10^{11}$ | ssAAV-eGFP-3xtelo3xINH18 | ssAAV-eGFP |
| 23588 | N.A. | Vehicle | Uninjected |

TABLE 3

Endotoxin testing (LAL assay).

| Vector | EU/ml |
|---|---|
| ssAAV-GFP | <1.0 |
| ssAAV-eGFP-3xtelo3xINH18 | <1.0 |

TABLE 4

Percent full particles.

| Vector | % full |
|---|---|
| ssAAV-eGFP | 90.97 ± 3.36 |
| ssAAV-eGFP-3xtelo3xINH18 | 91.08 ± 2.11 |

Figure 10A:
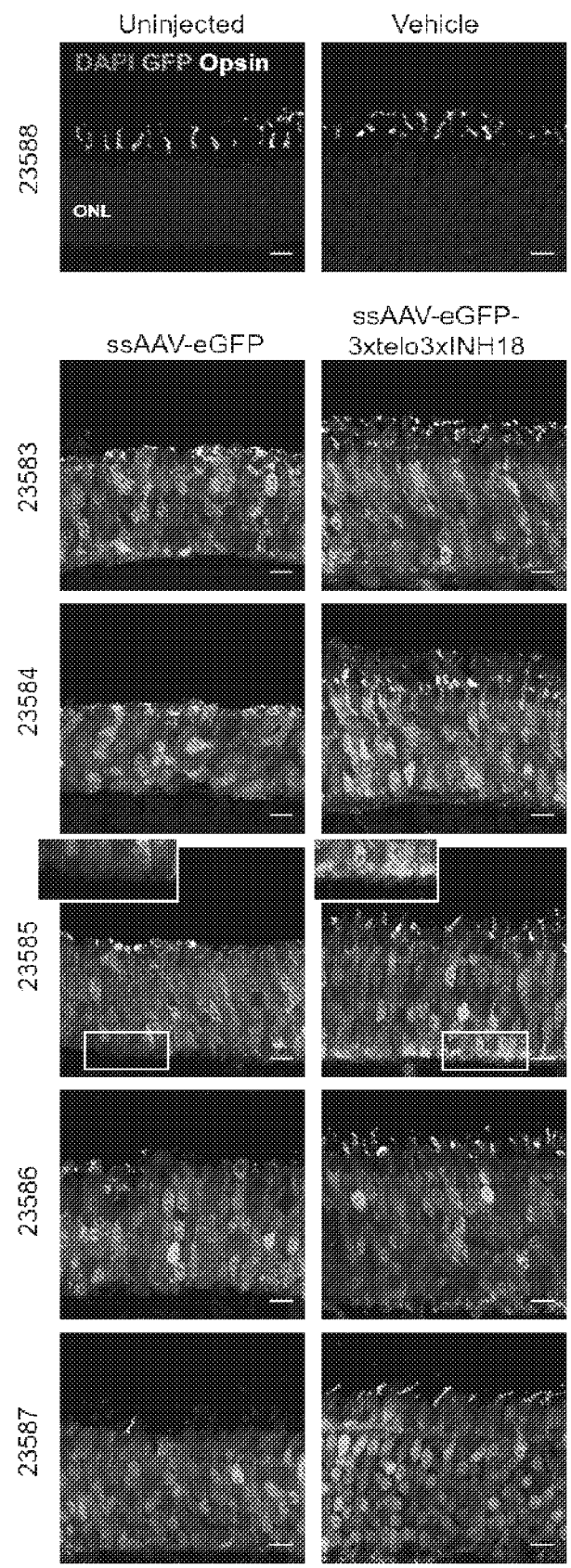
FIGS. 10A-10C show that engineered vector evades photoreceptor pathology and immune responses in subretinal-injected pig eyes. ssAAV-eGFP is provided as SEQ ID NO: 36. ssAAV-eGFP-3×telo3×INH18 is provided as SEQ ID NO: 37.
Figure 11:
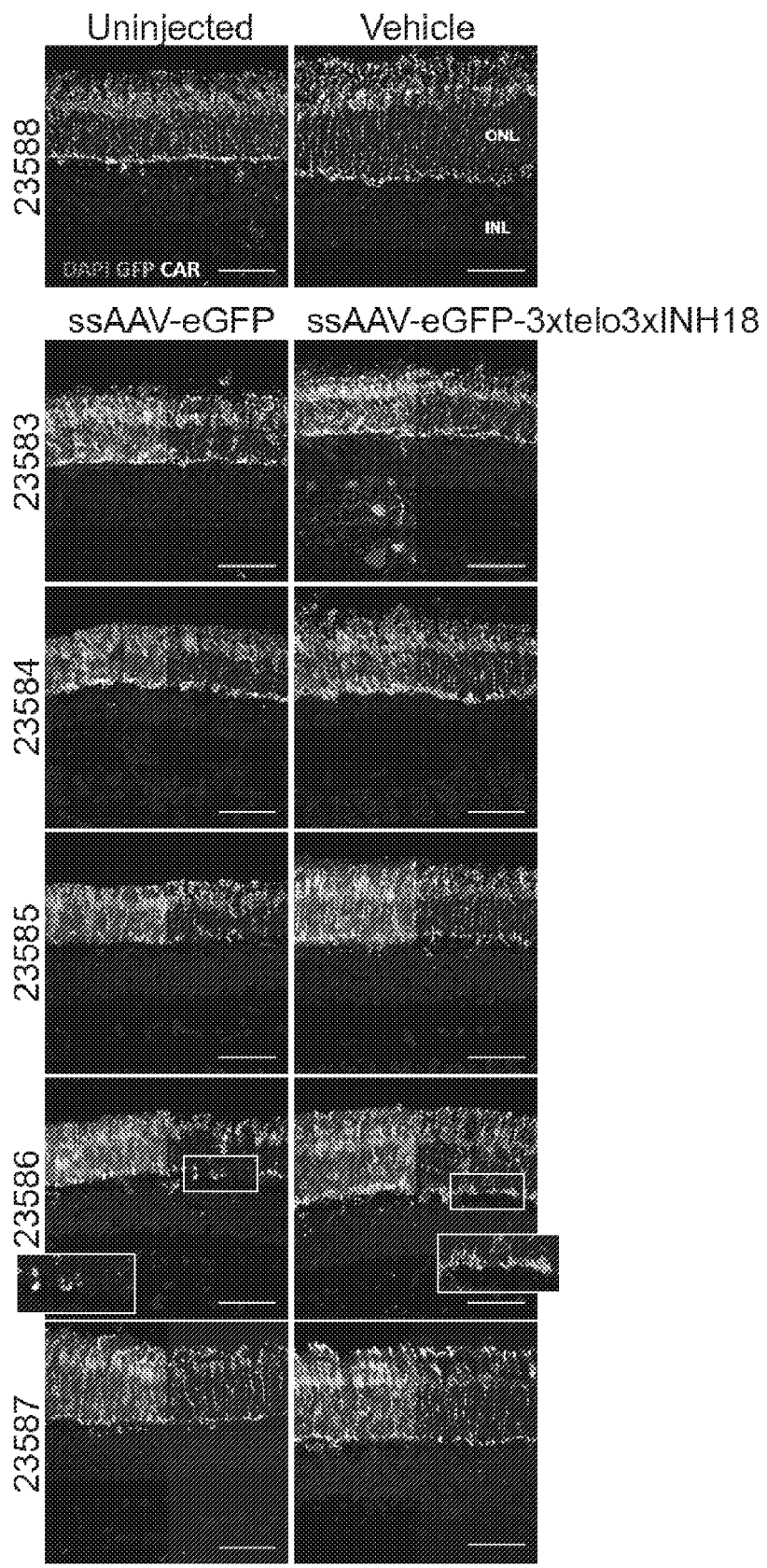
FIG. 11 shows that engineered vector comprising an inhibitory oligonucleotide evades photoreceptor pathology in subretinal-injected pig eyes. Immunohistochemical images of retina 6 weeks after subretinal injections. Cone photoreceptors were visualized by anti-human cone arrestin staining. Scale bars, 50 µm. Each animal is indicated by an identification number and the two images are from the two treated eyes of each animal. Regions shown for AAV8-injected eyes are GFP+, but GFP signal from the right half of each image was digitally removed to allow better visualization of arrestin staining. ssAAV-eGFP is provided as SEQ ID NO: 36. ssAAV-eGFP-3×telo3×INH18 is provided as SEQ ID NO: 37.

Using red-green opsin staining, it was observed that all five AAV-injected outbred pigs, ssAAV-eGFP led to a marked loss, shortening, or altered morphology of cone outer segments, suggesting AAV-induced pathology in the cone photoreceptors which are critical for high-acuity vision (FIG. 10A). In contrast, contralateral eyes injected with ssAAV-eGFP-3xtelo3xINH18 showed substantially better preservation of cone outer segments and appeared morphologically closer to uninjected or vehicle-injected eyes. These findings were confirmed by performing cone arrestin staining which labels the entire cone photoreceptor (FIG. 11). In addition, in two of five animals—animals 23585 and 23586—substantial loss or retraction of cone pedicles (the synaptic terminals of cone photoreceptors important for transferring the light signal onto the dendrites of bipolar cells and horizontal cells) was observed with ssAAV-eGFP; no such loss was observed in animals injected with ssAAV-eGFP-3xtelo3xINH18 (see FIG. 10A and FIG. 11).

Retinal images from in vivo optical coherence tomography (OCT) b-scans for damage to outer retinal lamination. As used in this example, OCT indicates Optical coherence tomography, RPE indicates retinal pigment epithelium, IS/OS indicates inner segment/outer segment, and wpi indicates weeks post injection. Representative OCT b-scan measurements in a vehicle-treated eye and from two different pigs whose left eye was injected with ssAAV-eGFP (OS) and whose right eye was injected with ssAAV-eGFP-3×telo3xINH18 (OD) are shown in Table 5. In areas without damage, the outermost hyper-reflective band (located at the bottom of each b-scan, data not shown) represents the choroid/sclera. Moving inward, the next hyper-reflective band represents the RPE and the third band the IS/OS of the photoreceptors (data not shown). Severe damage were areas where both the photoreceptor and RPE layers were disrupted, non-severe damage were areas where the hyper-reflective bands for one or both of these layers were thinner and less well defined. Severe damage always surrounded the retinotomy and non-severe damage always surrounded areas of severe damage. Areas outside of the calipers had normal retinal lamination. The length of each type of damage (mm) is indicated in Table 5. Two length values for a particular type of damage indicate that there were two areas with that particular type of damage. Scale bars were used in each b-scan as controls (data not shown). The fundus image indicated the location of each b-scan on the retina (data not shown). Images at 2 (left) and 6 wpi (right) were used for each eye to determine whether damage changed with time after injection. At 2 wpi, the vehicle-treated eye had retinal detachment created by the subretinal injection, which was smaller at 6 wpi. Only animals 23586 and 23587 were analyzed as b-scans were available for most of the GFP+ region (mean=30 mm²) for all eyes. Animal 23583 was excluded as the area of GFP+ region was unusually small (1.4 mm² in each eye) and there was concern that the entire inoculum volume had not been deposited subretinally.

telo3×INH18, the area of severe damage decreased between 2 and 6 wpi (~84% smaller). In contrast, in the eyes injected with ssAAV-eGFP, the area with severe damage tended to remain the same.

It was found that outer retinal laminar pathology measured by OCT was consistent with retinal histology and that engineered vector comprising inhibitory oligonucleotide sequences ameliorated outer retina laminar pathology in subretinal-injected pig eyes. The vehicle-injected eye showed a small area of non-severe damage surrounding a similarly sized area of severe damage around the retinotomy site and the areas of damage were reduced between 2 wpi and 6 wpi (e.g., compare 2 wpi measurements with 6 wpi measurements for Vehicle Injection: 23588 OD in Table 5 and fundus images described above). In this eye, retinal detachment created by the subretinal injection was noted. For two animals (23586 and 23587) where b-scans were available for most of the GFP+ region for both eyes, similar damage between the two eyes at 2 wpi was observed (e.g., Table 5 below) However, at 6 wpi, the area of severe damage was largely reduced for both ssAAV-eGFP-3×telo3×INH18 eyes, but not the two ssAAV-eGFP-treated eyes (e.g., severe laminar damage measurements at 6 wpi in Table 5).

TABLE 5

Non-limiting example of types of damage observed in the retina as measured by representative OCT b-scans.

| | 2 wpi | | | 6 wpi | | |
|---|---|---|---|---|---|---|
| | Retinal Detachment | Non-severe Laminar Disruption | Severe Laminar Damage | Retinal Detachment | Non-severe Laminar Disruption | Severe Laminar Damage |
| Treatment and Animal Vehicle Injection: 23588 OD | 2.493 mm | 0.964 mm | 0.665 mm | 0.834 mm; 0.840 mm | 1.041 mm; 0.523 mm | 1.468 mm |
| ssAAV-eGFP: 23586 OS | n/a | 1.77 mm | 3.658 mm | n/a | 1.78 mm | 4.083 mm |
| ssAAV-eGFP-3×telo3×INH18: 23586 OD | n/a | 1.569 mm | 2.394 mm | n/a | 1.266 mm; 3.158 mm | 1.283 mm |
| ssAAV-eGFP: 23587 OS | n/a | 2.389 mm; 0.763 mm | 2.947 mm | n/a | 4.508 mm; 0.804 mm | 3.208 mm |
| ssAAV-eGFP-3×telo3×INH18: 23587 OD | n/a | n/a | 6.598 mm | n/a | 3.155 mm; 2.605 mm | 0.858 mm |

Summary data for the extent of each type of damage (see description of Table 5 above) were shown on fundus images for eyes injected subretinally with vehicle or two pigs whose left eye was injected with ssAAV-eGFP (OS) and whose right eye was injected with ssAAV-eGFP-3×telo3×INH18 (OD) (fundus images not shown). Superimposed on each fundus image were the areas of severe and non-severe damage that were determined from OCT b-scans at 2 and at 6 wpi. Retinal areas with normal outer retina lamination are indicated in green. Severe damage always surrounded the retinotomy and was defined as loss of the hyper-reflective outer retinal bands that represent the RPE and photoreceptor inner/outer segments. Non-severe damage was usually found surrounding areas of severe damage and was defined as areas where the outer retinal hyper-reflective bands were thinner and/or more poorly defined. The fluorescence images of each eye cup were used and the GFP+ boundary was then superimposed on the fundus images. This analysis demonstrated that the areas of damage correspond to the GFP+ areas. In the eyes injected with ssAAV-eGFP-3×

Together, these data demonstrate that subretinal administration of higher doses of AAV can trigger photoreceptor pathology and that the engineered vector significantly reduces the induction of such pathology.

Figure 10B:
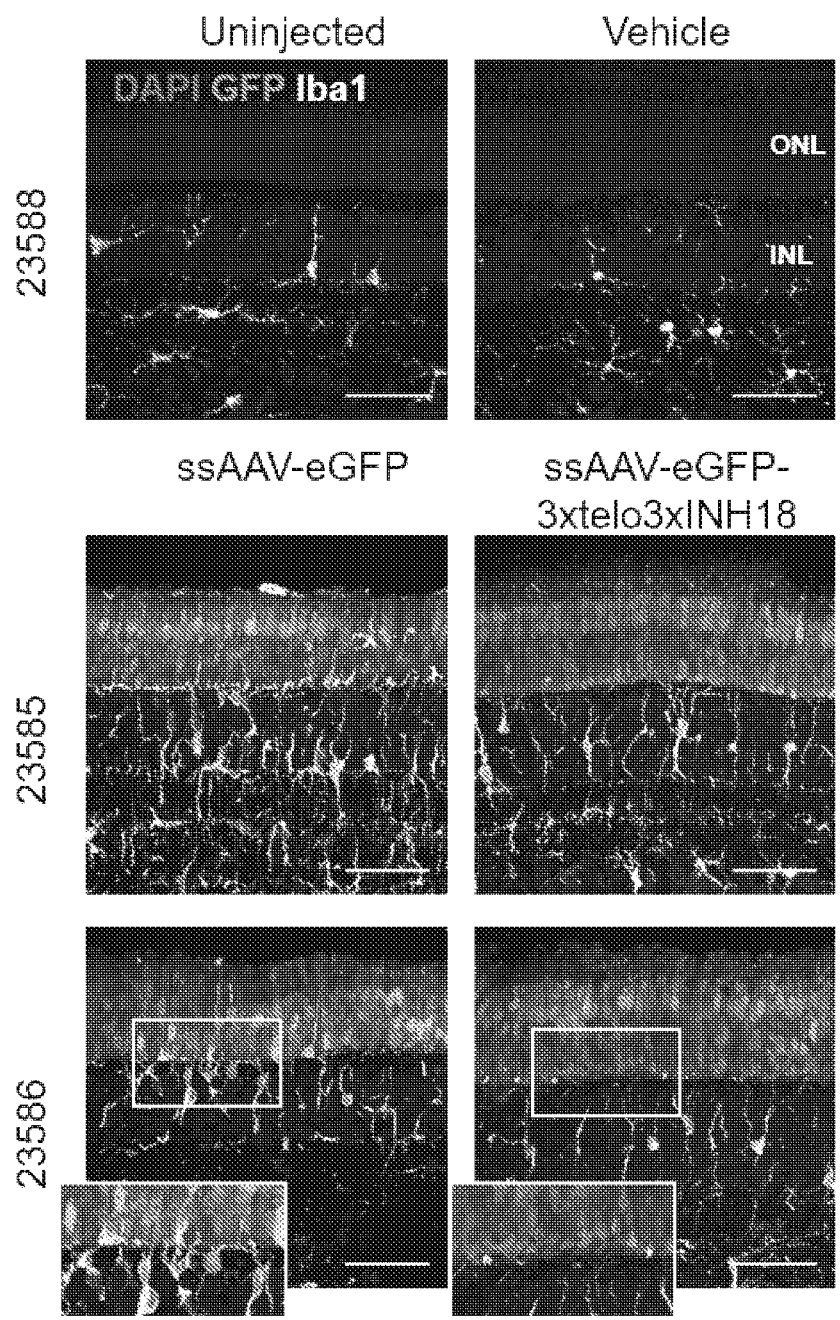
Figure 10C:
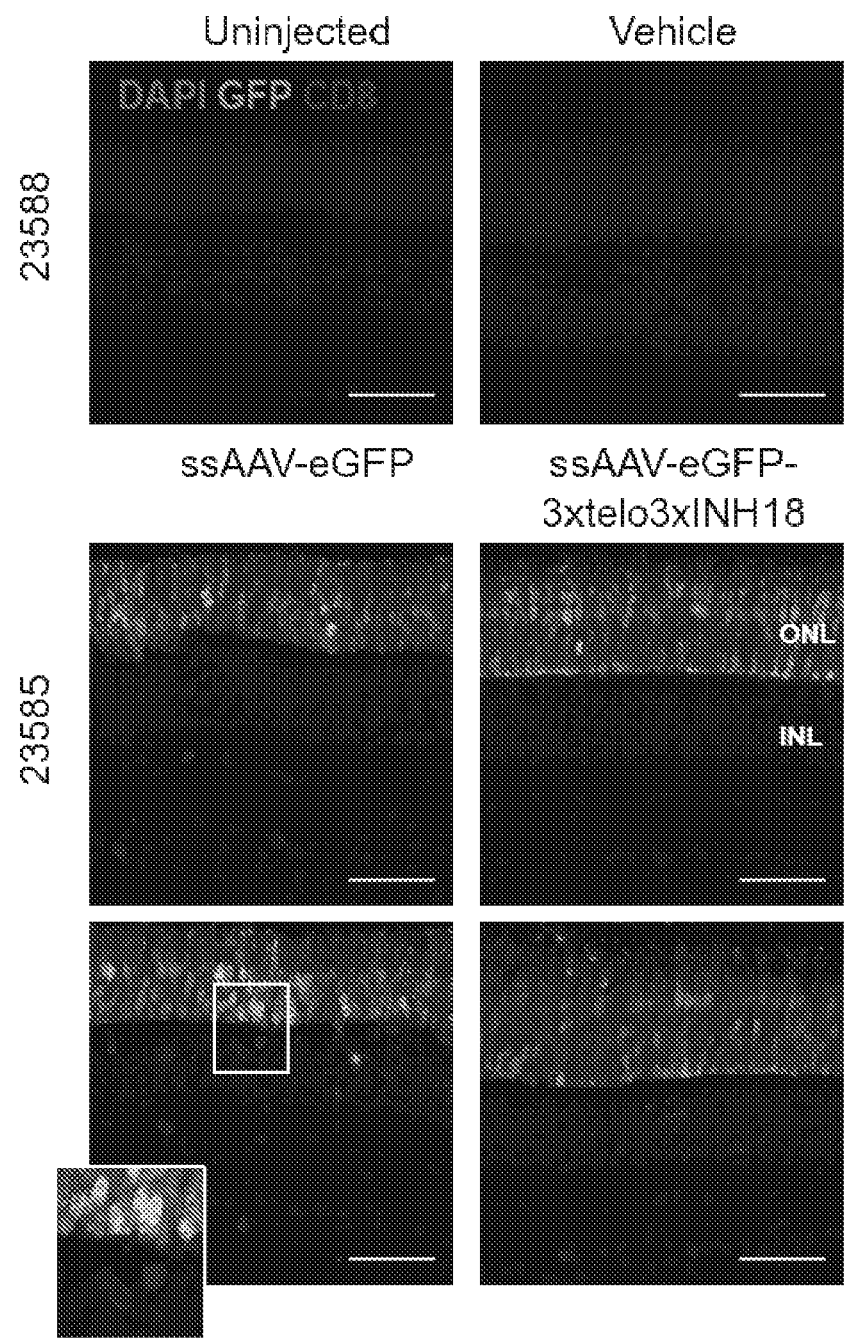

Next the immune responses in the retina were studied. Microglia cells are the resident innate immune cells of the retina and various reports in the literature suggest that CNS microglia can respond to CpG ligands (Olson et al., J Immunol 173, 3916-3924 (2004)). As expected, Iba1 staining of uninjected and vehicle-injected eyes showed a ramified staining pattern outside the outer nuclear layer (ONL), consistent with resting microglia (FIG. 10B). It was found that Iba1 signal increased significantly in all AAV-injected eyes (FIG. 10B and data not shown), suggesting microglia activation and proliferation, but only ssAAV-eGFP stimulated robust microglia infiltration into the ONL in animals 23585 and 23586, which was not seen with the engineered vector in the contralateral eyes. Furthermore, it was found that cytotoxic T cells infiltrating the outer and inner retina in the same two eyes that received ssAAV-eGFP, but not the contralateral ssAAV-eGFP-3xtelo3xINH18 eyes of the same animals or other AAV-treated animals. (FIG. 10C and data not shown).

A summary of the pig study findings, including histology and clinical examinations (inflammation scores) is included in Table 6. Immunohistochemical staining in the retina were performed 6 wpi at the terminus of the study. Vitritis (inflammation of the eye/retina via the SUN classification) was followed at weekly intervals from 2 wpi to 6 wpi. OCT imaging was performed at baseline (day of injection), 2 wpi and 6 wpi and area of damage to photoreceptor layers are shown for 6 wpi (terminus).

Taken together (see summary in Table 6), the engineered vector carrying the inhibitory oligonucleotide can evade eliciting undesirable innate immune and adaptive immune cell responses in the retina compared to the parental vector.

TABLE 6

Summary of pig study findings, including histology and clinical examinations (inflammation scores).

| Animal ID number | Condition | Substantial loss of cone outer segments | Microglia infiltration | Cytotoxic T cell infiltration | In-life vitritis (score 0-5) |
|---|---|---|---|---|---|
| 23583 | ssAAV-eGFP | Yes | No | No | No |
|  | ssAAV-eGFP-3xtelo3xINH18 | No | No | No | No |
| 23584 | ssAAV-eGFP | Yes | No | No | No |
|  | ssAAV-eGFP-3xtelo3xINH18 | No | No | No | No |
| 23585 | ssAAV-eGFP | Yes* | Yes | Yes | Yes** |
|  | ssAAV-eGFP-3xtelo3xINH18 | No | No | No | No |
| 23586 | ssAAV-eGFP | Yes* | Yes | Yes | No |
|  | ssAAV-eGFP-3xtelo3xINH18 | No | No | No | No |
| 23587 | ssAAV-eGFP | Yes | No | No | No |
|  | ssAAV-eGFP-3xtelo3xINH18 | No | No | No | No |
| 23588 | Uninjected Vehicle | N.A. N.A. | No No | No No | No No |

*Loss of cone pedicles observed as well.
**3+ flare at 2 wpi, 1+ flare at 3 wpi, 0.5 flare at 4 wpi, traces of vitritis at 5 wpi, and vitritis resolved at 6 wpi. No steroid treatment was used throughout the course of vitritis.
wpi, week post-injection; SUN, Standardization of Uveitis Nomenclature; OCT, optical coherence tomography; N.A., not applicable.

Example 10: Engineering a Single-Stranded AAV Vector and Testing Intravitreal Administration Single-stranded AAV vectors ssAAV2-eGFP-WPRE (SEQ ID NO: 41) and ssAAV2-eGFP-WPRE-3xtelo3xINH18 (SEQ ID NO: 42) (FIG. 14) were administered intravitreally to the eyes of African Green monkey (one vector per eye). The engineered vector with the inhibitory oligonucleotide reduced the immune response relative to the control vector. For example, 2 weeks after intravitreal injection, animal A983, which received ssAAV-eGFP-WPRe in its OS eye had several signs of ocular inflammation by opthalmic examination, while the vehicle-injected OD eye did not (Table 7). Animal A982, which received ssAAV-eGFP-WPRE-3xtelo3xINH18 in its OS eye, did not have signs of ocular inflammation.

TABLE 7

Non-limiting example of inflammation as measured by clinical examinations of the eye.

| | 2 wpi | | | |
|---|---|---|---|---|
| Treatment: Animal ID and eye | Anterior chamber cells score (0-4) | Aqueous flare score (0-4) | Fibrin strands score (0-3) | Iris hyperemia score 0-4) |
| $5 \times 10^{11}$ vg ssAAV-eGFP-WPRE: A983 OS | 2 | 1 | 2 | 2 |
| Vehicle injection: A983 OD | 0 | 0 | 0 | 0 |
| $5 \times 10^{11}$ vg ssAAV-eGFP-WPRE-3xtelo3xINH18: A982 OS | 0 | 0 | 0 | 0 |
| Vehicle injection: A982 OD | 0 | 0 | 0 | 0 |

More specifically, in animal A983, the eye that was administered ssAAV-eGFP-WPRE (SEQ ID NO: 41) (control) showed greater inflammation following clinical examination compared to the eye in animal A982 that was administered ssAAV-eGFP-WPRE-3xtelo3xINH18 (SEQ ID NO: 42). The eye with control treatment (SEQ ID NO: 41) showed a moderate anterior chamber cell score with 11-20 cells, mild aqueous flare that was just detectable (i.e., the Tyndall effect was barely discernable; the intensity of the light beam in the anterior chamber was less than the intensity of the slit beam as it passes through the lens), moderated fibrin strands (large fibrinous strands/clots, or more than 5 small fibrinous strands), mild injection of tertiary vessels and minimal to moderate injection of the secondary vessels observed for the iris hyperemia score, moderate lens capsule deposits, and mild lens opacity or vacuoles/clefts between the lens fibers, and fundus detail was visible. In contrast, no such signs of inflammation were visible in the eye with ssAAV-eGFP-WPRE-3xtelo3xINH18 (SEQ ID NO: 42) administration.

Example 11: Additional Engineering of Single-Stranded AAV Vector and Testing by Intramuscular Injection In Vivo in Mice ssAAV-eGFP-3xtelo3xINH18 (packaged in rh32.33 capsid) showed reduced immune responses compared to ssAAV-eGFP and this occurs in an AAV dose-dependent fashion (FIG. 8A). Thus, to further reduce immunogenicity, 3 copies of 4084-F (3 X SEQ ID NO: 3) were added with AAAAA (SEQ ID NO: 8) linkers followed by 3 copies of 2088 (3 X SEQ ID NO: 2) with linkers but in the anti-sense direction between the left ITR and promoter (the 5' untranslated region) of ssAAV-eGFP-3xtelo3xINH18 and term this ssAAV-eGFP-double. This vector, packaged in rh32.33 capsid, showed further reduction immune responses in mice upon intramuscular injection. Thus, it is possible to insert inhibitory oligonucleotides in various locations of the vector genome to reduce immune responses, and it is possible to further reduce immune responses by using more inhibitory oligonucleotides in combination.

Materials and Methods

C57BL/6 mice (male, 7-9 weeks old) were purchased from the Jackson Laboratory.

AAV Vectors

Self-complementary (sc) were used in this study. Self-complementary vectors lack the terminal resolution sequence in one ITR. All vector genomes were flanked by AAV2 ITRs. scAAV-eGFP was purchased from Cell Biolabs (VPK-430) and has been previously described (Gray, J T et al., Methods Mol. Biol. 2011; 807:25-46). scAAV-eGFP expressed enhanced green fluorescent protein (eGFP) from the cytomegalovirus (CMV) promoter, and included an SV40 intron and SV40 polyA sequence. The sequences of c41 oligonucleotide (5'-TGGCGCGCACCCACGGCCTG-3'; SEQ ID NO: 1) derived from *Pseudomonas aeruginosa* and telomere oligonucleotide (5'-TTTAGGGTTAGGGT-TAGGGTTAGGG-3'; SEQ ID NO: 9; initial T nucleotide is optional for function) derived from mammalian telomeres have been described (Gursel, I et al., *J Immunol.* 2003; 171(3):1393-400; Kaminski, J J et al., *J Immunol.* 2013; 191(7):3876-83; Shirota, H et al., *J Immunol.* 2005; 174(8): 4579-83; Li, Y et al., *Vaccine.* 2011; 29(11):2193-8). A telomere oligonucleotide (manufactured by Invivogen, catalog code: tlrl-ttag) harbored an additional T (in bold) compared to published studies and thus was included in the sequence. During the course of this study, Invivogen removed the additional T in their manufactured telomere oligonucleotide (catalog code: tlrl-ttag151). In addition, control (5'-GCTAGATGTTAGCGT-3'; SEQ ID NO: 34) was used as a negative control sequence that does not inhibit TLR9 activation (Invivogen, catalog code: t1r1-2088c).

To engineer scAAV-eGFP, sequences were inserted into the unique SpeI site found immediately 5' of the right ITR. To facilitate sub-cloning, a unique ClaI site was created immediately 5' of the inserted sequences, thus allowing ClaI/SpeI sub-cloning of sequences. 3 copies of c41, telomere, or control oligonucleotide were inserted, separated by AAAAA (SEQ ID NO: 8) linkers, giving scAAV-eGFP-3× c41, scAAV-eGFP-3×telomere and scAAV-eGFP-3×control, respectively. Alternatively, one copy of telomere was inserted, with an AAAAA linker (SEQ ID NO: 8), giving scAAV-eGFP-1x telomere (data not shown).

Self-complementary vectors were packaged into AAV2 (Vigene Biosciences) by triple transfection of HEK293 cells and purified using iodixanol gradient ultracentrifugation and then concentrated to 500 ul using Amicon Ultra-15 columns in PBS. The purified viruses were titered by qPCR using primers derived from ITR and an AAV standard. The final yield of the viruses ranged from 0.5-3×10$^{13}$ vg.

scAAV.FIX (Martino, A T et al. *Blood* 2011; 117(24): 6459-68) expressed human factor IX (FIX) under the control of a liver-specific transthyretin (TTR) mouse promoter and included a bovine growth hormone (bGH) polyA sequence. To engineer scAAV.FIX, sequences were inserted into the unique KpnI site found immediately 5' of the TTR promoter. This vector was packaged into AAV8 by the core facility Gene Transfer Vector Core (GTVC) at Massachusetts Eye and Ear Infirmary (MEEI). The viral titers were determined by digital PCR using primers against the polyA sequence and total yield for each vector was calculated by multiplying viral titer (vg/ml) by volume.

Figure 12:
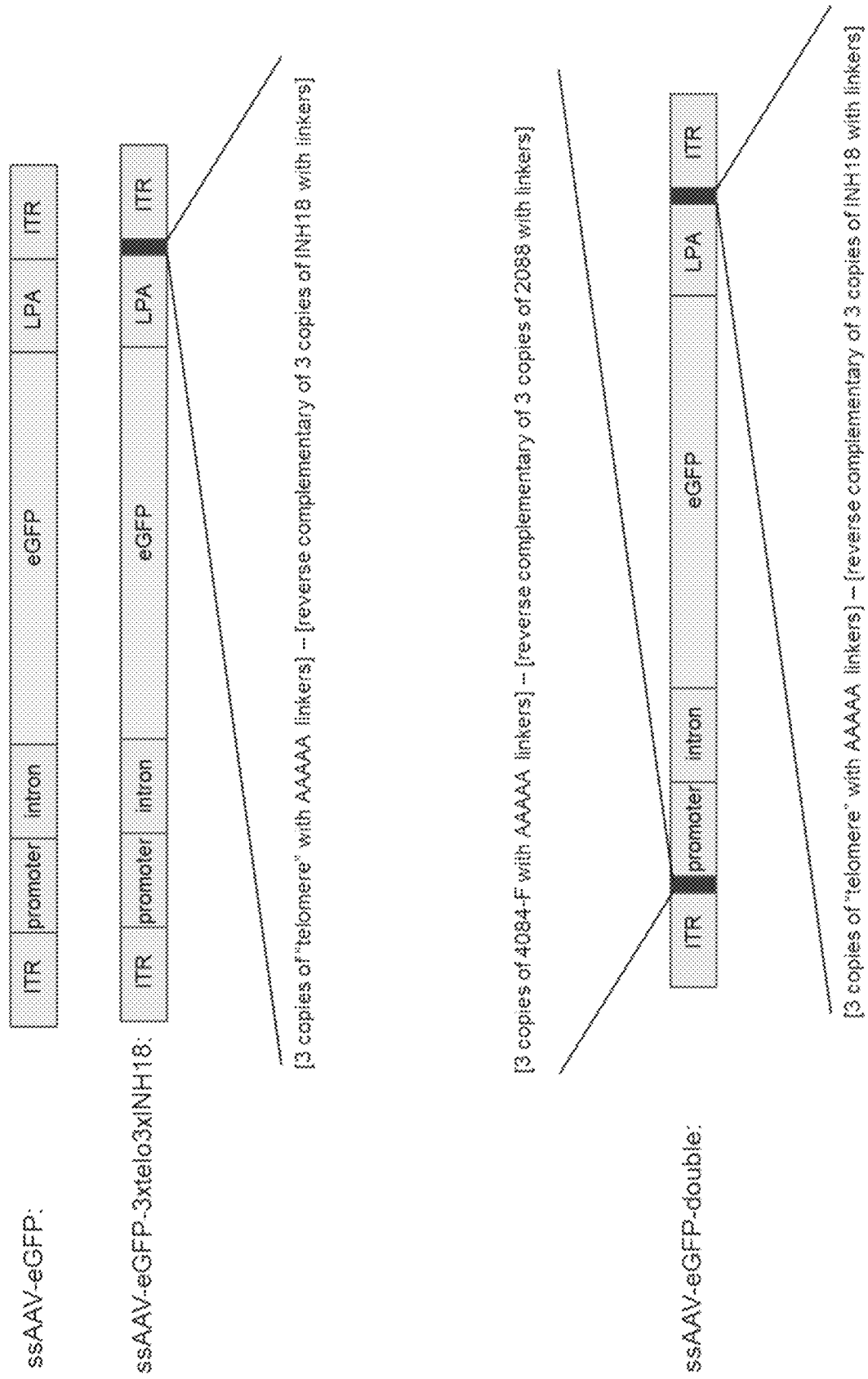
FIG. 12 shows a schematic representation of a single-stranded AAV vector encoding GFP (ssAAV-eGFP). Two engineered forms are shown. ssAAV-eGFP-3×telo3×INH18 (SEQ ID NO: 37) carries an insertion of 3 copies of telomere oligonucleotide (3 X SEQ ID NO: 9) with AAAAA (SEQ ID NO: 8) linkers, followed by reverse complementary sequences of 3 copies of INH-18 (3 X SEQ ID NO: 5) with AAAAA linkers (in anti-sense orientation, i.e., anti-sense orientation of SEQ ID NO: 8) in the 3' untranslated region (between the polyA signal and right ITR). ssAAV-eGFP-double (SEQ ID NO: 38) carries the same insertion, but additionally carries an insertion of 3 copies of 4084-F (3 X SEQ ID NO: 3) oligonucleotide with AAAAA (SEQ ID NO: 8) linkers, followed by reverse complementary sequences of 3 copies of 2088 (3 X SEQ ID NO: 2) oligonucleotide with AAAAA linkers (in anti-sense orientation, i.e., anti-sense orientation of SEQ ID NO: 8) in the 5' untranslated region (between the left ITR and the promoter). LpA: polyA signal.

The single-stranded AAV vector ssAAV-eGFP has been previously described (Xiong, W. et al., *J Clin Invest.,* 2015; 125(4):1433-45) and was originally obtained from the Harvard DF/HCC DNA Resource Core (clone ID: EvN000061595). ssAAV-eGFP contained a CMV enhancer/promoter, human β-globin intron, eGFP, and β-globin polyA sequence. To engineer ssAAV-eGFP, KpnI-5×telomere (sense)-5×telomere(anti-sense)-NheI was inserted immediately 5' of the XbaI site adjacent to the right ITR. Again, AAAAA (SEQ ID NO: 8) was used as a linker between copies of the telomere sequence (SEQ ID NO: 9). Alternatively, KpnI-3×telomere(sense)-3×INH-18(anti-sense)-NheI was inserted at the same site, similarly using AAAAA (SEQ ID NO: 8) as a linker between copies of the telomere sequence (SEQ ID NO: 9) or INH-18 (SEQ ID NO: 5). Both sense and anti-sense sequences of telomere (SEQ ID NO: 9) or INH-18 (SEQ ID NO: 5) were added as single-stranded AAV vectors have an equal chance of packaging positive or negative strands of the viral genome, thus ensuring that all packaged AAV genomes will carry copies of the telomere sequence (SEQ ID NO: 9) or INH-18 (SEQ ID NO: 5) in the right orientation. Finally, SpeI-3×4084-F(sense)-3×2088 (anti-sense)-SpeI were additional inserted into the unique SpeI site found after the left ITR and before the promoter in ssAAV-eGFP-3×telo3×INH18, and this vector was termed ssAAV-eGFP-double (FIG. 12). Single-stranded vectors were packaged into AAV8 (subretinal pig studies) or AAVrh32.33 (intramuscular mouse studies) and purified by the core facility Gene Transfer Vector Core (GTVC) at Massachusetts Eye and Ear Infirmary (MEEI). The viral titers were determined by digital PCR using primers against the CMV promoter and total yield for each vector was calculated by multiplying viral titer (vg/ml) by volume. The purity of vector preps was evaluated by running 1×10$^{10}$ vg (viral genome) on an SDS-PAGE gel. In addition, vector preps had <1 EU/ml of endotoxin using a limulus amebocyte lysate assay (ToxinSensor Chromogenic LAL Endotoxin Assay Kit, Genscript). No significant differences in viral yield (viral titer×volume) were observed between parental vectors and corresponding engineered vectors for >20 purifications, suggesting that insertion of the described sequences do not hamper viral packaging.

A different single-stranded vector, ssAAV-eGFP-WPRE contains a CMV promoter and woodchuck hepatitis virus posttranscriptional regulatory element (WPRE) for eGFP expression. To engineer ssAAV-eGFP-WPRE, KpnI-3×telomere(sense)-3×INH-18(anti-sense) was inserted immediately 5' of the XhoI site just upstream of the right ITR (FIG. 13). The parental vector and engineered vector were packaged into AAV2 and purified by cesium purification.

HEK293-TLR9 Reporter Cell Line

A HEK293-based reporter cell line stably expressing human TLR9 and an inducible SEAP (secreted embryonic alkaline phosphatase) reporter gene was obtained (HEK-Blue hTLR9, Invivogen). The SEAP gene is under the control of the IFN-β minimal promoter fused to five NF-kB and AP-1 binding sites. Stimulation with a TLR9 ligand such as ODN 2006 activates NF-kB and AP-1 and therefore induces the production of SEAP, which can subsequently be measured to determine the amount of inflammation. All designed single-stranded DNA oligonucleotides were synthesized with a phosphorothioate backbone for increased stability (IDT). ODN 2006 was directly linked to indicated sequence with no intervening nucleotides, or with a AAAAA (SEQ ID NO: 8) linker sequence. ODN Control (15 nt) and ODN Control (24 nt) were 5'-TCC TGA GCT TGA AGT-3' (SEQ ID NO: 43) and 5'-TTA TTA TTA TTA TTA TTA TTA TTA-3' (SEQ ID NO: 44) respectively, and the two control sequences were selected to match the approximate range of lengths of the various TLR9 inhibitory oligonucleotides. Indicated concentrations of oligonucleotides were incubated with 6×10$^4$ HEK293-TLR9 cells in 200 ul of DMEM growth media per well in 96-well flat bottom plates for 18 h, and 50 ul media was aspirated and incubated with 100 ul HEK-Blue Detection media (Invivogen) for 4-6 h at 37° C. and then absorbance at 639 nm was read on a plate reader. Similarly, HEK293 reporter cell lines stably expressing inducible SEAP reporter gene and human TLR7 ($1 \times 10^5$ cells) or TLR2 ($6 \times 10^4$ cells) (both from Invivogen) were stimulated with 1 vg/ml of Gardiquimod or 100 ng/ml of FSL-2 (both from Invivogen) respectively with or without control oligonucleotides or TLR9 inhibitory oligonucleotides for 18 h and SEAP activity was measured.

Muscle Studies In Vivo

Adult C57BL/6 mice were injected intramuscularly with 50 ul PBS or AAV2 viruses ($10^{11}$ vg per animal, self-complementary vector) in the quadricep. 2 h later, the animals were sacrificed and a portion of the quadricep was saved in RNAlater solution (Thermo Scientific). The muscle tissues were subjected to RNA extraction, reverse transcription, and qPCR as described in the liver studies. For GFP expression studies, the quadricep was harvested 28 d later.

Similarly, adult mice were injected intramuscularly with 50 ul PBS or AAVrh32.33 viruses ($10^{10}$ or $10^{11}$ vg per animal, single-stranded vector) in the quadriceps. 21 d later, the animals were scarified and spleens were harvested (see ELISPOT below) and muscle tissues were fixed in 10% formalin overnight and transferred to 70% ethanol. For histology, muscle samples were processed at DF/HCC Specialized Histopathology Services (SHS) and Beth Israel Deaconess Medical Center (BIDMC) histology core facilities, embedded in paraffin, and stained for CD8 (1:500, D4W2Z, CST) and granzyme B (1:500, polyclonal, catalog #AF1865, R&D). Antibodies were tagged with AlexaFluor 488 Tyramide (B40957, Thermo) or AlexaFluor 647 Tyramide (B40958, Thermo). All immunohistochemistry was performed on the Leica Bond automated staining platform using the Leica Biosystems Refine Detection Kit with citrate antigen retrieval. Muscle sections were also stained for GFP by immunohistochemistory (IHC) with IHC chromogen substrate DAB (3,3'-diaminobenzidine).

IFN-γ T Cell ELISPOT Assays

Spleens were harvested from C57BL/6 mice injected i.m. with AAVrh32.33 single-stranded vectors 21 d post-injection. Spleens were passed through a 70 μm cell strainer (Fisher Scientific), and dissociated cells were spun down. The cell pellet was treated with 1 ml of ACK lysing buffer (Life Technologies) to lyse red blood cells. To determine the number of cells secreting IFN-γ in response to antigenic stimulation, an IFN-γ ELISPOT assay was used based on manufacturer's instructions (R&D Systems). Briefly, 96-well plates were pre-blocked with RPMI growth media for 2 h at room temperature and rinsed twice with PBS. $5 \times 10^5$ splenocytes were seeded per well in T cell medium (DMEM supplemented with 10% heat-inactivated FBS, 1% penicillin/streptomycin, 1% L-glutamine, 10 mMHEPES buffer, 0.1 mM non-essential amino acids, 2 mM sodium pyruvate and $10^{-6}$ M beta-mercaptoethanol), with 2 μg/ml of a CD8+ h2-$k^b$ restricted dominant epitope of AAVrh32.33 capsid (SSYELPYWM, purchased from Genemed Synthesis) or incubated with PMA/ionomycin as a non-specific positive control. ELISPOT plates were evaluated in blinded fashion (ZellNet Consulting, Inc., Fort Lee, NJ) using an automated Elispot reader system (KS ELISpot reader, Zeiss, Thornwood, USA) with KS ELISpot software version 4.9.16. The plate evaluation process including the setup of optimal reading parameters followed the International guidelines on Elispot plate evaluation[6].

Liver Studies In Vivo

Adult C57BL/6 mice were injected intravenously with 100 ul PBS or AAV2 viruses ($10^{11}$ vg per animal) or AAV8 viruses ($10^{10}$ or $10^{11}$ vg) by tail vein injection as previously described (Martino, A T et al. *Blood* 2011; 117(24):6459-68) 2 h later, the animals were sacrificed and a portion of the right median lobe of the liver was saved in RNAlater solution (Thermo Scientific). Total RNA was extracted from 10-30 mg of mechanically disrupted liver sample by using an RNA extraction kit (OMEGA Bio-Tek). Similar amounts of RNA were reverse transcribed into cDNA with a high-capacity RNA-to-cDNA kit (Thermo Scientific) and similar amounts of cDNA were assayed with quantitative PCR (qPCR) using TaqMan Fast Advanced Master Mix (Thermo Scientific) and commercially available pre-designed primers/probes with FAM reporter dye for the indicated target genes (IDT). Expression level for each gene was calculated by normalizing against the housekeeping genes Actb or Gapdh using the MET method and expressed as fold levels compared to saline-injected mice. All qPCR reactions were run on a realplex 4 Mastercycle (Eppendorf). For GFP expression studies, the liver was harvested 14 d later. For human FIX expression, plasma (EDTA) were obtained 14 d and 28 d after AAV administration and human FIX expression was quantified by analyzing diluted plasma samples using an ELISA kit specific for human factor IX (ab188393, Abcam). Plasma from PBS-injected mice gave signals similar to that of a blank control, demonstrating specificity of the kit for human factor IX. The kit had a sensitivity of at least 0.78 ng/ml.

Subretinal Injection of AAV in Domestic Pigs

All experimental protocols using pigs were performed at the University of Louisville, were approved by the University of Louisville Institutional Animal Care and Use Committee and adhered to the ARVO Statement for Use of Animals in Ophthalmic and Vision Research. Six 50 day old wild-type domestic female pigs were purchased (Oak Hill Genetics, Ewing Indiana). Surgery to inject AAV into the subretinal space was performed after a one week acclimatization period at the University of Louisville AALAC-approved facility. Details have been published previously[7-9]. Animals were sedated via intravenous administration of: Ketamine (10 mg/kg) and Dexmedetomidine (0.04 mg/kg) and treated with Atropine (0.25 mg/kg). An endotracheal tube was inserted and through it Isoflurane was administered to achieve a surgical plane of anesthesia (1-3%). An IV line inserted in the ear vein was used to deliver IV fluids (Lactated Ringers Solution with or without 5% dextrose; 10-15 mL/kg/h) to maintain blood pressure and normal glycemic levels (60-140 mg/dL). Body temperature was monitored every 30 min with a rectal thermometer and maintained via a heated procedure table. Heart and respiration rates and oxygen saturation were recorded every 10 min throughout the procedures and anesthesia adjusted to maintain a normal range for these physiological parameters.

After anesthesia and aseptic surgical preparation, a vitreoretinal surgical approach was used to gain access to the subretinal space (between the retina and the pigment epithelium at the back of the eye) and to deposit an inoculum containing AAV in final formulation buffer (FFB) or FFB alone (vehicle). A lateral canthotomy was performed to increase exposure in the surgical field. After insertion of an eyelid speculum, two 25 g trocars were placed at 1.5 mm posterior to the limbus; one in superior-nasal and the other in inferior-nasal quadrant. An anterior chamber fluid paracentesis was performed to make space for the injected volume. A light pipe was inserted into one trochar to help visualize the retina. A 41 gauge subretinal cannula needle was placed through the other trochar and used to make a local retinal detachment (bleb) followed by injection of inoculum (~75 μl). Either AAV8.GFP.io2 or AAV8.GFP was injected into OD or OS of two pigs (4 eyes) in each of three surgery sessions. After the injection, the light pipe, needle and the trochars were removed (they are self-sealing). The lateral canthotomy was sutured closed with 4-0 Nylon. Antibiotic and steroid ointment was placed topically at the end of the surgery.

From 2 weeks post-injection (wpi) to 6 wpi, a complete clinical examination assessed the health of the retina at weekly intervals in anesthetized pigs. This included a slit lamp examination to inspect the anterior segment of the eye and to characterize damage to the cornea/lens, indirect ophthalmoscopy to inspect the health of the fundus and fundus photography to document the state of the retina, its optic nerve, the blood vessel pattern, and any damage that resulted from surgical procedures or viral expression. In addition, each eye was scored for inflammation of the eye/retina using the SUN classification[10]. The retinal surgeon performing the injections was blinded to the test article, and similarly, clinical examinations and scoring of inflammation were performed blinded.

Prior to surgery and at 2 and 6 wpi, ocular coherence tomography (OCT; Bioptigen/Leica Biosciences) was performed to image the retinal layers in vivo. Pupils were dilated and accommodation relaxed with topical applications of 2.5% phenylephrine hydrochloride and 1% Tropicamide. Lid specula held the eyelids open and corneas were wet throughout the imaging with artificial tears (Tears Again, OcuSoft, Inc, Richmond, TX). Using the OCT b-scans, the retinotomy site was identified and lamination pattern of the hypo- and hyper-reflective bands was characterized as a function of distance from that area in both the axial and lateral dimensions. Two types of damage were identified: severe damage represented areas where the hyper-reflective bands representing the RPE and photoreceptor inner/outer segments were disrupted. Non-severe damage were areas where these hyper-reflective bands were present, but were thinner and thus, less well defined than areas without damage. The shape, location and size of these two types of damage were measured using the software provided with the OCT system. Specifically, calipers were placed over severe and flanking non-severe damage in b-scans across the fundus and their areas were computed and summed over the entire extent of damage. These areas were then superimposed on the fundus image and the areas of damage compared to the areas of GFP expression (see below).

At 6 wpi (terminus), pigs were anesthetized and killed with a solution of Beuthanasia (390 mg pentobarbital sodium, 50 mg phenytoin sodium/ml; 1 mL/5 kg), and their eyes were enucleated. The cornea and lens were removed and the eyecup was dissected and fixed in 4% paraformaldehyde in PBS for 1 h at room temperature and then washed in PBS. Wholemount retinas were examined using a low power fluorescent microscope (Olympus MVX10) and the region of GFP+ expression was located and images acquired and plotted on the fundus images relative to the blood vessels and optic nerve head. The retina was dissected so that the piece used for histology included all of the GFP+ region, as well as GFP-flanking regions.

The pig retinal tissue was cryoprotected in graded sucrose solutions up to 30% sucrose in PBS, then embedded in a 1:1 mixture of 30% sucrose and optimal cutting temperature (OCT) compound (Tissue-Tek) followed by cryosectioning on a Leica CM3050S (Leica Microsystems). Transverse sections of retinal tissue were cut at 20 μm. For immunohistochemistry, tissue sections were first blocked with 5% donkey serum (if the secondary antibody was donkey-origin) or 5% goat serum (if the secondary antibody was goat-origin) in PBS with 0.1% Triton X-100 for 1 h at room temperature. Sections were then stained overnight at 4° C. in blocking solution with primary antibodies against red-green opsin (1:600, AB5405, EMD Millipore), human cone arrestin[11] (1:10000), Iba1 (1:200, ab5076, Abcam) and CD8 (1:200, MCA1223GA, Bio-Rad), followed by staining for 2 h at room temperature with goat anti-rabbit, donkey anti-mouse, or donkey anti-goat AlexaFluor 594-labeled secondary antibodies (111-585-144, 715-585-150 and 705-586-147, all from Jackson ImmunoResearch) used at 1:1000 in PBS. Tissues were lastly stained with 4',6-diamidino-2-phenylindole (DAPI) for 5 min and mounted using Fluoromount-G (Southern Biotech). The slides were examined using a LSM710 laser scanning confocal microscope (Zeiss) with a 40× oil-immersion objective, and image processing was performed using ZEN software and ImageJ. For sections from AAV-injected eyes, care was taken to acquire images of GFP+ regions near, but not directly at, the retinotomy scar (where there is damage to photoreceptors from the injection). Similar laser settings were used when acquiring images of the two eyes of each animal.

Intravitreal Injection of AAV in African Green Monkeys

African Green monkeys received intravitreal injections of 100 ul of ssAAV-eGFP-WPRE or ssAAV-eGFP-WPRE-3× telo3×INH18 (both packaged in AAV2 capsid) in one eye, and the vehicle control (buffer) in the other eye. Ophthalmic examinations by slit lamp biomicroscopy and retinoscopy, as well as fundus imaging (both color photos and fluorescence photos), were performed at various time points. Vitreous haze was graded on a scale of 0 to 4 using the Nussenblatt scale, and anterior chamber cells and aqueous flare were graded using a modified Hackett-McDonald scoring system. Optical coherence tomography (OCT) was also performed to image the retina. At termins, animals were euthanized and aqueous humor collected from the eyes. The enucleated eyes were fixed in 4% paraformaldehyde followed by sectioning and histological analysis for pathology and cellular immune responses.

Statistics

Unpaired two-tailed Student's t-tests were used to compare differences between two unpaired experimental groups in most cases. A two-tailed Mann-Whitney test was used for some in vivo studies as indicated. A P value of <0.05 was considered statistically significant. No pre-specified effect size was assumed and in general three to ten replicates or animals for each condition was used.

Sequences c41 oligonucleotide sequence:

(SEQ ID NO: 1)

TGGCGCGCACCCACGGCCTG.

-continued

| Sequences | |
|---|---|
| ODN 2088:<br>TCC TGG CGG GGA AGT | (SEQ ID NO: 2) |
| ODN 4084-F:<br>CCTGGATGGGAA | (SEQ ID NO: 3) |
| ODN INH-1:<br>CCTGGATGGGAATTCCCATCCAGG | (SEQ ID NO: 4) |
| ODN INH-18:<br>CCT GGA TGG GAA CTT ACC GCT GCA | (SEQ ID NO: 5) |
| ODN TTAGGG:<br>TT AGG GTT AGG GTT AGG GTT AGG G | (SEQ ID NO: 6) |
| G-ODN:<br>CTC CTA TTG GGG GTT TCC TAT | (SEQ ID NO: 7) |
| linker sequence<br>AAAAA | (SEQ ID NO: 8) |
| telomere:<br>TTTAGGGTTAGGGTTAGGGTTAGGG | (SEQ ID NO: 9) |
| ODN 4137:<br>TCCTGGAGGGGAACC. | (SEQ ID NO: 10) |
| ODN 4033:<br>CCTGGAGGGGAAGT. | (SEQ ID NO: 11) |
| ODN 4171:<br>CCTGGAGGGG. | (SEQ ID NO: 12) |
| ODN 4352:<br>TCCTTCCTGGAGGGGAAG. | (SEQ ID NO: 13) |
| ODN 4191:<br>TCCTATCCTGGAGGGGAAG. | (SEQ ID NO: 14) |
| ODN 4351:<br>TCCTATCCTATCCTGGAGGGGAAG. | (SEQ ID NO: 15) |
| ODN 2114:<br>TCCTGGAGGGGAAGT | (SEQ ID NO: 16) |
| ODN 4024:<br>TCCTGGATGGGAAGT | (SEQ ID NO: 17) |
| ODN INH-4:<br>TTCCCATCCAGGCCTGGATGGGAA | (SEQ ID NO: 18) |
| ODN INH-13:<br>CTTACCGCTGCACCTGGATGGGAA | (SEQ ID NO: 19) |
| ODN Poly-G:<br>GGGGGGGGGGGGGGGGGGGG | (SEQ ID NO: 20) |

| Sequences |
| --- |

ODN GpG:

TGACTGTGAAGGTTAGAGATGA (SEQ ID NO: 21)

ODN IRS-869:

TCCTGGAGGGGTTGT (SEQ ID NO: 22)

ODN IRS-954:

TGCTCCTGGAGGGGTTGT (SEQ ID NO: 23)

ODN 21158:

CCTGGCGGGG.

(SEQ ID NO: 24)

ODN super:

CCTCAATAGGGTGAGGGG.

(SEQ ID NO: 25)

ODN 2006:

Tcgtcgttttgtcgttttgtcgtt.

(SEQ ID NO: 26)

ODN 4348:

TCGTATCCTGGAGGGGAAG.

(SEQ ID NO: 27)

ODN 4349:

TAATATCCTGGAGGGGAAG.

(SEQ ID NO: 28)

ODN 4347:

CCTATCCTGGAGGGGAAG.

(SEQ ID NO: 29)

ODN A:

GGGTGGGTGGGTATTACCATTA.

(SEQ ID NO: 30)

ODN B:

TGGGCGGTTCAACCTTCA.

(SEQ ID NO: 31)

ODN C:

CCTCAAGCTTGAGGGG.

(SEQ ID NO: 32)

scAAV-FIX:

(SEQ ID NO: 33)

gcgcgctcgctcgctcactgaggccgcccgggcaaagcccgggcgtcgggcgacctttggtcgcccggcctcagtgagcgagcgagc gcgcagagagggagtggccaactccatcactaggggttccttgtagttaatgattaacccgccatgctacttatctacgtagccatgctcgat ctgaattcggtaccacgcgtgtctgtctgcacatttcgtagagcgagtgttccgatactctaatctccctaggcaaggttcatatttgtgtaggtt acttattctccttttgttgactaagtcaataatcagaatcagcaggtttggagtcagcttggcagggatcagcagcctggggtggaaggaggg ggtataaaagcccccttcaccaggagaagccgtcacacagatccacaagctcctgctagcaggtaagtgccgtgtgtggttcccgcgggcc tggcctctttacgggttatggcccttgcgtgccttgaattactgacactgacatccactttttcttttttctccacaggtatcgattgaattccaccat gcagcgcgtgaacatgatcatggcagaatcaccaggcctcatcaccatctgccttttaggatatctactcagtgctgaatgtacagttttttcttg atcatgaaaacgccaacaaaattctgaatcggccaaagaggtataattcaggtaaattggaagagtttgttcaagggaaccttgagagagaa tgtatggaagaaaagtgtagttttgaagaagcacgagaagttttttgaaaacactgaaagaacaactgaattttggaagcagtatgttgatgga gatcagtgtgagtccaatccatgtttaaatggcggcagttgcaaggatgacattaattcctatgaatgttggtgtccctttggatttgaaggaaa gaactgtgaattagatgtaacatgtaacattaagaatggcagatgcgagcagttttgtaaaaatagtgctgataacaaggtggtttgctcctgta ctgagggatatcgacttgcagaaaaccagaagtcctgtgaaccagcagtgccatttccatgtggaagagtttctgtttcacaaacttctaagct cacccgtgctgagactgttttttcctgatgtggactatgtaaattctactgaagctgaaaccatttttggataacatcactcaaagcacccaatcatt taatgacttcactcgggttgttggtggagaagatgccaaaccaggtcaattcccttggcaggttgttttgaatggtaaagttgatgcattctgtg -continued Sequences gaggctctatcgttaatgaaaaatggattgtaactgctgcccactgtgttgaaactggtgttaaaattacagttgtcgcaggtgaacataatatt gaggagacagaacatacagagcaaaagcgaaatgtgattcgaattattcctcaccacaactacaatgcagctattaataagtacaaccatga cattgcccttctggaactggacgaaccctttagtgctaaacagctacgttacacctatttgcattgctgacaaggaatacacgaacatcttcctc aaatttggatctggctatgtaagtggctggggaagagtcttccacaaagggagatcagctttagttcttcagtaccttagagttccacttgttga ccgagccacatgtcttcgatctacaaagttcaccatctataacaacatgttctgtgctggcttccatgaaggaggtagagattcatgtcaagga gatagtgggggaccccatgttactgaagtggaagggaccagtttcttaactggaattattagctggggtgaagagtgtgcaatgaaaggca aatatggaatatataccaaggtatcccggtatgtcaactggattaaggaaaaaacaaagctcacttaatgaaagatggagatctgcggcctc gactagagctcgctgatcagcctcgactgtgccttctagttgccagccatctgttgtttgcccctccccgtgccttccttgaccctggaaggt gccactcccactgtcctttcctaataaaatgaggaaattgcatcgcattgtctgagtaggtgtcattctattctgggggtggggtggggcagg acagcaaggggaggattgggaagacaatagcaggaacccactccctctctgcgcgctcgctcgctcactgaggccgggcgaccaaa ggtcgcccgacgcccgggctttgcccgggcggcctcagtgagcgagcgagcgcgcag.

scAAV-FIX-3xtelomere (inhibitory oligonucleotide in underlined and bold text):
(SEQ ID NO: 34)
gcgcgctcgctcgctcactgaggccgcccgggcaaagcccgggcgtcgggcgacctttggtcgcccggcctcagtgagcgagcgagc gcgcagagagggagtggccaactccatcactaggggttccttgtagttaatgattaacccgccatgctacttatctacgtagccatgctcgat ctgaattcggtacctttagggttagggttagtttagggAAAAAtttagggttagtttagggttagggAAAAAtttagggtt agggttagggttagggAAAAAggtaccacgcgtgtctgtctgcacatttcgtagagcgagtgttccgatactctaatctccctaggcaa ggttcatatttgtgtaggttacttattctccttttgttgactaagtcaataatcagaatcagcaggtttggagtcagcttggcagggatcagcagc ctgggttggaaggaggggtataaaagccccttcaccaggagaagccgtcacacagatccacaagctcctgctagcaggtaagtgccgt gtgtggttcccgcgggcctggcctctttacgggttatggcccttgcgtgccttgaattactgacactgacatccactttttctttttctccacaggt atcgattgaattccaccatgcagcgcgtgaacatgatcatggcagaatcaccaggcctcatcaccatctgccttttaggatatctactcagtgc tgaatgtacagttttttcttgatcatgaaaacgccaacaaaattctgaatcggccaaagaggtataattcaggtaaattggaagagtttgttcaag ggaaccttgagagaatgtatggaagaaaagtgtagtttttgaagaagcacgagaagtttttgaaaacactgaaagaacaactgaatttttgg aagcagtatgttgatggagatcagtgtgagtccaatccatgtttaaatggcggcagttgcaaggatgacattaattcctatgaatgttggtgtcc ctttggatttgaaggaaagaactgtgaattagatgtaacatgaacattaagaatggcagatgcgagcagtttttgtaaaaatagtgctgataac aaggtggtttgctcctgtactgagggatatcgacttgcagaaaaccagaagtcctgtgaaccagcagtgccatttccatgtggaagagtttct gttcacaaacttctaagctcaccgtgctgagactgtttttcctgatgtggactatgtaaattctactgaagctgaaaccatttttggataacatca ctcaaagcacccaatcatttaatgactcactcggttgttggtggagaagatgccaaaccaggtcaattcccttggcaggttgtttttgaatggt aaagttgatgcattctgtggaggctctatcgttaatgaaaaatggattgtaactgctgcccactgtgttgaaactggtgttaaaattacagttgtc gcaggtgaacataatattgaggagacagaacatacagagcaaaagcgaaatgtgattcgaattattcctcaccacaactacaatgcagctat

taataagtacaaccatgacattgcccttctggaactggacgaacccttagtgctaaacagctacgttacacctattttgcattgctgacaaggaa tacacgaacatcttcctcaaatttggatctggctatgtaagtggctggggaagagtcttccacaaagggagatcagctttagttcttcagtacct

tagagttccacttgttgaccgagccacatgtcttcgatctacaaagttcaccatctataacaacatgttctgtgctggcttccatgaaggagta gagattcatgtcaaggagatagtgggggaccccatgttactgaagtggaagggaccagtttcttaactggaattattagctggggtgaagag tgtgcaatgaaaggcaaatatggaatatataccaaggtatcccggtatgtcaactggattaaggaaaaaacaaagctcacttaatgaaagat ggagatctgcggcctcgactagagctcgctgatcagcctcgactgtgccttctagttgccagccatctgttgtttgcccctccccgtgccttc cttgaccctggaaggtgccactcccactgtcctttcctaataaaatgaggaaattgcatcgcattgtctgagtaggtgtcattctattctggggg gtgggtggggcaggacagcaaggggaggattgggaagacaatagcaggaacccactccctctctgcgcgctcgctcgctcactga ggccgggcgaccaaaggtcgcccgacgcccgggctttgcccgggcggcctcagtgagcgagcgagcgcgcag.

| Sequences |
|---|
| "3xtelomere" oligo: (SEQ ID NO: 35)<br>tttagggttagggttagggttagggAAAAAtttagggttagggttagggttagggAAAAAtttagggttagggttagggttagggAAAAA. |
| ssAAV-eGFP: (SEQ ID NO: 36)<br>tgcgcgctcgctcgctcactgaggccgcccgggcaaagcccgggcgtcgggcgacctttggtcgcccggcctcagtgagcgagcgag<br>cgcgcagagagggagtggccaactccatcactaggggttccttgtagttaatgattaacccgccatgctacttatctacgtagccatgctcta<br>gcggcctcggcctctgcataaataaaaaaaattagtcagccatgagcttggcccattgcatacgttgtatccatatcataatatgtacatttatat<br>tggctcatgtccaacattaccgccatgttgacattgattattgactagttattaatagtaatcaattacggggtcattagttcatagcccatatatgg<br>agttccgcgttacataacttacggtaaatggcccgcctggctgaccgcccaacgacccccgcccattgacgtcaataatgacgtatgttccc<br>atagtaacgccaatagggactttccattgacgtcaatgggtggagtatttacggtaaactgcccacttggcagtacatcaagtgtatcatatgc<br>caagtacgccccctattgacgtcaatgacggtaaatggcccgcctggcattatgcccagtacatgaccttatgggactttcctacttggcagt<br>acatctacgtattagtcatcgctattaccatggtgatgcggttttggcagtacatcaatgggcgtggatagcggtttgactcacggggatttcca<br>agtctccaccccattgacgtcaatgggagtttgttttggcaccaaaatcaacgggactttccaaaatgtcgtaacaactccgccccattgacg<br>caaatgggcggtaggcgtgtacggtgggaggtctatataagcagagctcgtttagtgaaccgtcagatcgcctggagacgccatccacgc<br>tgttttgacctccatagaagacaccgggaccgatccagcctccctcgaagctgatcctgagaacttcagggtgagtctatgggacccttga<br>tgttttctttcccctctttttctatggttaagttcatgtcataggaaggggagaagtaacagggtacacatattgaccaaatcagggtaattttgcat<br>ttgtaattttaaaaatgctttcttcttttaatatactttttgtttatcttatttctaatactttccctaatctctttctttcagggcaataatgat<br>acaatgtatcatgcctcttgcaccattctaaagaataacagtgataatttctgggttaaggcaatagcaatatttctgcatataaatatttctgcat<br>ataaattgtaactgatgtaagaggtttcatattgctaatagcagctacaatccagctaccattctgcttttattttatggttgggataaggctggatt<br>attctgagtccaagctaggcccttttgctaatcatgttcatacctcttatcttcctcccacagctcctgggcaacgtgctggtctgtgtgctggccca<br>tcactttggcaaagaattccgcgggcccgggatccaccggtcgccaccatggtgagcaagggcgaggagctgttcaccggggtggtgcccatcct<br>ggtcgagctggacggcgacgtaaacggccacaagttcagcgtgtccggcgagggcgagggcgatgccacctacggcaagctgaccct<br>gaagttcatctgcaccaccggcaagctgcccgtgccctggcccaccctcgtgaccaccctgacctacggcgtgcagtgcttcagccgcta<br>ccccgaccacatgaagcagcacgacttcttcaagtccgccatgcccgaaggctacgtccaggagcgcaccatcttcttcaaggacgacgg<br>caactacaagacccgcgccgaggtgaagttcgagggcgacaccctggtgaaccgcatcgagctgaagggcatcgacttcaaggaggac<br>ggcaacatcctggggcacaagctggagtacaactacaacagccacaacgtctatatcatggccgacaagcagaagaacggcatcaaggt<br>gaacttcaagatccgccacaacatcgaggacggcagcgtgcagctcgccgaccactaccagcagaacacccccatcggcgacggccc<br>cgtgctgctgcccgacaaccactacctgagcacccagtccgccctgagcaaagaccccaacgagaagcgcgatcacatggtcctgctgg<br>agttcgtgaccgccgccgggatcactctcggcatggacgagctgtacaagtaaagcggccgctctagaggatccaagcttatcgataccgt<br>cgacctcgagggcccagatctaattcaccccaccagtgcaggctgcctatcagaaagtggtggctggtgtggctaatgccctggcccaca<br>agtatcactaagctcgctttcttgctgtccaatttctattaaaggttcctttgttccctaagtccaactactaaactggggatattatgaagggcct<br>tgagcatctggattctgcctaataaaaaacatttattttcattgcaatgatgtatttaaattatttctgaatattttactaaaaagggaatgtgggagg<br>tcagtgcatttaaaacataaagaaatgaagagctagttcaaaccttgggaaaatacactatatcttaaactccatgaaagaaggtgaggctgc<br>aaacagctaatgcacattggcaacagcccctgatgcctatgccttattcatccctcagaaaaggattcaagtagaggcttgatttggaggttaa<br>agttttgctatgctgtattttacattacttattgttttagctgtcctcatgaatgtcttttcactacccatttgcttatcctgcatctctcagccttgac<br>tccactcagttctcttgcttagagataccacctttcccctgaagtgttccttccatgtttttacggcgagatggttctcctcgcctggccactcagcctt<br>agttgtctctgttgtcttatagaggtctacttgaagaaggaaaaacaggggcatggtttgactgtcctgtgagcccttcttccctgcctccccc<br>actcacagtgacccggaatccctcgacatctagagcatggctacgtagataagtagcatggcgggttaatcattaactacaaggaaccccta<br>gtgatggagttggccactccctctctgcgcgctcgctcgctcactgaggccgggcgaccaaaggtcgcccgacgcccgggctttgcccg |

| Sequences |
| --- |
| ggcggcctcagtgagcgagcgagcgc. | ssAAV-eGFP-3xtelo3xINH18 (inhibitory oligonucleotide in underlined and bold text):

(SEQ ID NO: 37)

tgcgcgctcgctcgctcactgaggccgcccgggcaaagcccgggcgtcgggcgacctttggtcgcccggcctcagtgagcgagcgag cgcgcagagagggagtggccaactccatcactaggggttccttgtagttaatgattaacccgccatgctacttatctacgtagccatgctcta gcggcctcggcctctgcataaataaaaaaaattagtcagccatgagcttggcccattgcatacgttgtatccatatcataatatgtacatttatat tggctcatgtccaacattaccgccatgttgacattgattattgactagttattaatagtaatcaattacggggtcattagttcatagcccatatatgg agttccgcgttacataacttacggtaaatggcccgcctggctgaccgcccaacgaccccgcccattgacgtcaataatgacgtatgttccc atagtaacgccaatagggactttccattgacgtcaatgggtggagtatttacggtaaactgcccacttggcagtacatcaagtgtatcatatgc caagtacgccccctattgacgtcaatgacggtaaatggcccgcctggcattatgcccagtacatgaccttatgggactttcctacttggcagt acatctacgtattagtcatcgctattaccatggtgatgcggttttggcagtacatcaatgggcgtggatagcggtttgactcacggggatttcca agtctccaccccattgacgtcaatgggagtttgttttggcaccaaaatcaacgggactttccaaaatgtcgtaacaactccgccccattgacg caaatgggcggtaggcgtgtacggtgggaggtctatataagcagagctcgtttagtgaaccgtcagatcgcctggagacgccatccacgc tgttttgacctccatagaagacaccgggaccgatccagcctcccctcgaagctgatcctgagaacttcagggtgagtctatgggacccttga tgttttctttccccttcttttctatggttaagttcatgtcataggaaggggagaagtaacagggtacacatattgaccaaatcagggtaatttttgcat ttgtaattttaaaaaatgcttttcttcttttaatatacttttttgtttatcttatttctaatacttttccctaatctctttctttcagggcaataatgat acaatgtatcatgcctctttgcaccattctaaagaataacagtgataatttctgggttaaggcaatagcaatatttctgcatataaatatttctgcat ataaattgtaactgatgtaagaggtttcatattgctaatagcagctacaatccagctaccattctgcttttattttatggttgggataaggctggatt attctgagtccaagctaggccttttgctaatcatgttcatacctcttatcttcctcccacagctcctgggcaacgtgctggtctgtgtgctggccca tcactttggcaaagaattccgcgggcccgggatccaccggtcgccaccatggtgagcaagggcgaggagctgttcaccggggtggtgcccatcct ggtcgagctggacggcgacgtaaacggccacaagttcagcgtgtccggcgagggcgagggcgatgccacctacggcaagctgaccct gaagttcatctgcaccaccggcaagctgcccgtgccctggcccaccctcgtgaccaccctgacctacggcgtgcagtgcttcagccgcta ccccgaccacatgaagcagcacgacttcttcaagtccgccatgcccgaaggctacgtccaggagcgcaccatcttcttcaaggacgacgg caactacaagacccgcgccgaggtgaagttcgagggcgacaccctggtgaaccgcatcgagctgaagggcatcgacttcaaggaggac ggcaacatcctggggcacaagctggagtacaactacaacagccacaacgtctatatcatggccgacaagcagaagaacggcatcaaggt gaacttcaagatccgccacaacatcgaggacggcagcgtgcagctcgccgaccactaccagcagaacacccccatcggcgacggccc cgtgctgctgcccgacaaccactacctgagcacccagtccgccctgagcaaagaccccaacgagaagcgcgatcacatggtcctgctgg agttcgtgaccgccgccgggatcactctcggcatggacgagctgtacaagtaaagcggccgctctagaggatccaagcttatcgataccgt cgacctcgagggcccagatctaattcaccccaccagtgcaggctgcctatcagaaagtggtggctggtgtggctaatgccctggcccaca agtatcactaagctcgctttcttgctgtccaatttctattaaaggttcctttgttccctaagtccaactactaaactgggggatattatgaagggcct tgagcatctggattctgcctaataaaaaacatttattttcattgcaatgatgtatttaaattatttctgaatattttactaaaaagggaatgtgggagg tcagtgcatttaaaacataaagaaatgaagagctagttcaaaccttgggaaaatacactatatcttaaactccatgaaagaaggtgaggctgc aaacagctaatgcacattggcaacagcccctgatgcctatgccttattcatccctcagaaaaggattcaagtagaggcttgatttggaggttaa agttttgctatgctgtattttacattacttattgttttagctgtcctcatgaatgtcttttcactacccatttgcttatcctgcatctctcagccttga ctccactcagttctcttgcttagagataccacctttcccctgaagtgttccttccatgttttacggcgagatggtttctcctcgcctggccactcagcc ttagttgtctctgttgtcttatagaggtctacttgaagaaggaaaaacaggggcatggtttgactgtcctgtgagcccttcttccctgcctccccc actcacagtgacccggaatccctcgacaGGTACCtttagggttagggttagggttagggAAAAAtttagggttagggttagg gttagggAAAAAtttagggttaguttaggttagggAAAAATGCAGCGGTAAGTTCCCATCCAGG

TTTTTTGCAGCGGTAAGTTCCCATCCAGGTTTTTTGCAGCGGTAAGTTCCCATC

| Sequences |
| --- |
| CAGGTTTTTGCTAGCtctagagcatggctacgtagataagtagcatggcgggttaatcattaactacaaggaacccctagtg atggagttggccactccctctctgcgcgctcgctcgctcactgaggccgggcgaccaaaggtcgcccgacgcccgggctttgcccgggc ggcctcagtgagcgagcgagcgc. |
| ssAAV-eGFP-double (inhibitory oligonucleotides in underlined and bold text): (SEQ ID NO: 38) tgcgcgctcgctcgctcactgaggccgcccgggcaaagcccgggcgtcgggcgacctttggtcgcccggcctcagtgagcgagcgag cgcgcagagagggagtggccaactccatcactaggggttccttgtagttaatgattaacccgccatgctacttatctacgtagccatgctcta gcggcctcggcctctgcataaataaaaaaaattagtcagccatgagcttggcccattgcatacgttgtatccatatcataatatgtacatttatat tggctcatgtccaacattaccgccatgttgacattgattattgactagtcctggatgggaaAAAAAcctggatgggaaAAAAAcc tggatgggaaAAAAAACTTCCCCGCCAGGATTTTTACTTCCCCGCCAGGATTTTTACT TCCCCGCCAGGATTTTTactagttattaatagtaatcaattacggggtcattagttcatagcccatatatggagttccgcgtta cataacttacggtaaatggcccgcctggctgaccgcccaacgaccccgcccattgacgtcaataatgacgtatgttcccatagtaacgcca atagggactttccattgacgtcaatgggtggagtatttacggtaaactgcccacttggcagtacatcaagtgtatcatatgccaagtacgcccc ctattgacgtcaatgacggtaaatggcccgcctggcattatgcccagtacatgaccttatgggactttcctacttggcagtacatctacgtatta gtcatcgctattaccatggtgatgcggttttggcagtacatcaatgggcgtggatagcggtttgactcacggggatttccaagtctccacccca ttgacgtcaatgggagtttgttttggcaccaaaatcaacgggactttccaaaatgtcgtaacaactccgccccattgacgcaaatgggcggta ggcgtgtacggtgggaggtctatataagcagagctcgtttagtgaaccgtcagatcgcctggagacgccatccacgctgttttgacctccat agaagacaccgggaccgatccagcctccctcgaagctgatcctgagaacttcagggtgagtctatgggacccttgatgttttctttcccctt cttttctatggttaagttcatgtcataggaaggggagaagtaacagggtacacatattgaccaaatcagggtaatttgtcatttgtaattttaaaa aatgctttcttcttttaatatacttttttgtttatcttatttctaatactttccctaatctctttctttcagggcaataatgatacaatgtatcat gcctctttgcaccattctaaagaataacagtgataatttctgggttaaggcaatagcaatatttctgcatataaatatttctgcatataaattgta actgatgtaagaggtttcatattgctaatagcagctacaatccagctaccattctgcttttatttatggttgggataaggctggattattctgag tccaagctaggccctttgtaatcatgttcatacctcttatcttcctcccacagctcctgggcaacgtgctggtctgtgtgctggcccatcactt tggcaaagaattccgcgggcccgggatccaccggtcgccaccatggtgagcaagggcgaggagctgttcaccggggtggtgcccatcctggtcgag ctggacggcgacgtaaacggccacaagttcagcgtgtccggcgagggcgagggcgatgccacctacggcaagctgaccctgaagttcatctgc accaccggcaagctgcccgtgccctggcccaccctcgtgaccaccctgacctacggcgtgcagtgcttcagccgctaccccgaccacat gaagcagcacgacttcttcaagtccgccatgcccgaaggctacgtccaggagcgcaccatcttcttcaaggacgacggcaactacaagac ccgcgccgaggtgaagttcgagggcgacaccctggtgaaccgcatcgagctgaagggcatcgacttcaaggaggacggcaacatcctg gggcacaagctggagtacaactacaacagccacaacgtctatatcatggccgacaagcagaagaacggcatcaaggtgaacttcaagat ccgccacaacatcgaggacggcagcgtgcagctcgccgaccactaccagcagaacacccccatcggcgacggccccgtgctgctgcc cgacaaccactacctgagcacccagtccgccctgagcaaagaccccaacgagaagcgcgatcacatggtcctgctggagttcgtgaccg ccgccgggatcactctcggcatggacgagctgtacaagtaaagcggccgctctagaggatccaagcttatcgataccgtcgacctcgagg gcccagatctaattcaccccaccagtgcaggctgcctatcagaaagtggtggctggtgtggctaatgccctggcccacaagtatcactaag ctcgctttcttgctgtccaatttctattaaaggttcctttgttccctaagtccaactactaaactggggggatattatgaagggccttgagcatctgg attctgcctaataaaaaacatttattttcattgcaatgatgtatttaaattatttctgaatattttactaaaaagggaatgtgggaggtcagtgcat ttaaaacataaagaaatgaagagctagttcaaaccttgggaaaatacactatatcttaaactccatgaaagaaggtgaggctgcaaacagctaat gcacattggcaacagcccctgatgcctatgccttattcatccctcagaaaaggattcaagtagaggcttgatttggaggttaaagttttgctatg ctgtattttacattacttattgttttagctgtcctcatgaatgtctttttcactacccatttgcttatcctgcatctctcagccttgactccactcagt tctcttgcttagagataccacctttccccgaagtgttccttccatgttttacggcgagatggtttctcctcgcctggccactcagccttagttgtct ctgttgtcttatagaggtctacttgaagaaggaaaaacaggggggcatggtttgactgtcctgtgagcccttcttccctgcctccccactcacagtga |

| Sequences |
|---|
| cccggaatccctcgacaGGTACCtttagggttagggttagggttagggAAAAAtttagggttagggttagggttagggAA |
| AAAtttagggttagggttagggttagggAAAAATGCAGCGGTAAGTTCCCATCCAGGTTTTTT |
| GCAGCGGTAAGTTCCCATCCAGGTTTTTTGCAGCGGTAAGTTCCCATCCAGGT |
| TTTTGCTAGCtctagagcatggctacgtagataagtagcatggcgggttaatcattaactacaaggaaccctagtgatggagttg |
| gccactccctctctgcgcgctcgctcgctcactgaggccgggcgaccaaaggtcgcccgacgcccgggctttgcccgggcggcctcagt |
| gagcgagcgagcgc. |
| "3xtelo3xINH18" oligo: (SEQ ID NO: 39) |
| tttagggttagggttagggttagggAAAAAtttagggttagggttagggttagggAAAAAtttagggttagggttagggttagggA |
| AAAATGCAGCGGTAAGTTCCCATCCAGGTTTTTTGCAGCGGTAAGTTCCCATCCAGG |
| TTTTTTGCAGCGGTAAGTTCCCATCCAGGTTTTT. |
| "3x4084-F3x2088" oligo: (SEQ ID NO: 40) |
| cctggatgggaaAAAAAcctggatgggaaAAAAAcctggatgggaaAAAAAACTTCCCCGCCAGGATTT |
| TTACTTCCCCGCCAGGATTTTTACTTCCCCGCCAGGATTTTT. |
| ssAAV-eGFP-WPRE: (SEQ ID NO: 41) |
| ctgcgcgctcgctcgctcactgaggccgcccgggcaaagcccgggcgtcgggcgacctttggtcgcccggcctcagtgagcgagcga |
| gcgcgcagagagggagtggccaactccatcactagggttccttgtagttaatgattaacccgccatgctacttatctacgtagccatgctct |
| aggaagatcggaattcgcccttaagctagctagttattaatagtaatcaattacgggtcattagttcatagcccatatatggagttccgcgtta |
| cataacttacggtaaatggcccgcctggctgaccgcccaacgaccccgcccattgacgtcaataatgacgtatgttcccatagtaacgcca |
| tagggactttccattgacgtcaatgggtggagtatttacggtaaactgcccacttggcagtacatcaagtgtatcatatgccaagtacgcccc |
| ctattgacgtcaatgacggtaaatggcccgcctggcattatgcccagtacatgaccttatgggactttcctacttggcagtacatctacgtatta |
| gtcatcgctattaccatggtgatgcggttttggcagtacatcaatgggcgtggatagcggtttgactcacggggatttccaagtctccaccca |
| ttgacgtcaatgggagtttgttttggcaccaaaatcaacgggactttccaaaatgtcgtaacaactccgccccattgacgcaaatgggcggta |
| ggcgtgtacggtgggaggtctatataagcagagctggtttagtgaaccgtcagatcctgcagaagttggtcgtgaggcactgggcaggtaa |
| gtatcaaggttacaagacaggtttaaggagaccaatagaaactgggcttgtcgagacagagaagactcttgcgtttctgataggcacctattg |
| gtcttactgacatccactttgcctttctctccacaggtgtccagcggccgccatggtgagcaagggcgaggagctgttcaccggggtggtg |
| cccatcctggtcgagctggacggcgacgtaaacggccacaagttcagcgtgtccggcgagggcgagggcgatgccacctacggcaag |
| ctgaccctgaagttcatctgcaccaccggcaagctgcccgtgccctggcccaccctcgtgaccaccctgacctacggcgtgcagtgcttca |
| gccgctaccccgaccacatgaagcagcacgacttcttcaagtccgccatgcccgaaggctacgtccaggagcgcaccatcttcttcaagg |
| acgacggcaactacaagacccgcgccgaggtgaagttcgagggcgacaccctggtgaaccgcatcgagctgaagggcatcgacttcaa |
| ggaggacggcaacatcctggggcacaagctggagtacaactacaacagccacaacgtctatatcatggccgacaagcagaagaacggc |
| atcaaggtgaacttcaagatccgccacaacatcgaggacggcagcgtgcagctcgccgaccactaccagcagaacacccccatcggcg |
| acggccccgtgctgctgcccgacaaccactacctgagcacccagtccgccctgagcaaagaccccaacgagaagcgcgatcacatggt |
| cctgctggagttcgtgaccgccgccgggatcactctcggcatggacgagctgtacaagtaataagcttggatccaatcaacctctggattac |
| aaaatttgtgaaagattgactggtattcttaactatgttgctccttttacgctatgtggatacgctgctttaatgcctttgtatcatgctattgct |
| tcccgtatggctttcattttctcctccttgtataaatcctggttgctgtctctttatgaggagttgtggcccgttgtcaggcaacgtggcgtggtg |
| tgcactgtgtttgctgacgcaaccccactggttggggcattgccaccacctgtcagctcctttccgggactttcgctttccccctccctattgcc |
| acggcggaactcatcgccgcctgccttgcccgctgctggacaggggctcggctgttgggcactgacaattccgtggtgttgtcggggaaatcatc |
| gtcctttccttggctgctcgcctgtgttgccacctggattctgcgcgggacgtccttctgctacgtcccttcggccctcaatccagcggaccttc |

| Sequences |
|---|
| cttcccgcggcctgctgccggctctgcggcctcttccgcgtcttcgagatctgcctcgactgtgccttctagttgccagccatctgttgtttgcc |
| cctccccgtgccttccttgaccctggaaggtgccactcccactgtcctttcctaataaaatgaggaaattgcatcgcattgtctgagtaggtgt |
| cattctattctgggggtgggtggggcaggacagcaaggggaggattgggaagacaatagcaggcatgctgggactcgagttaag |
| ggcgaattcccgataaggatcttcctagagcatggctacgtagataagtagcatggcgggttaatcattaactacaaggaaccccctagtgat |
| ggagttggccactccctctctgcgcgctcgctcgctcactgaggccgggcgaccaaaggtcgcccgacgcccgggctttgcccgggcg |
| gcctcagtgagcgagcgagcgcgcag | ssAAV-GFP-WPRE-3xtelo3xINH18 (inhibitory oligonucleotides in underlined and bold text):

(SEQ ID NO: 42)

| |
|---|
| ctgcgcgctcgctcgctcactgaggccgcccgggcaaagcccgggcgtcgggcgacctttggtcgcccggcctcagtgagcgagcga |
| gcgcgcagagagggagtggccaactccatcactaggggttccttgtagttaatgattaacccgccatgctacttatctacgtagccatgctct |
| aggaagatcggaattcgcccttaagctagctagttattaatagtaatcaattacggggtcattagttcatagcccatatatggagttccgcgtta |
| cataacttacggtaaatggcccgcctggctgaccgcccaacgacccccgcccattgacgtcaataatgacgtatgttcccatagtaacgcca |
| atagggactttccattgacgtcaatgggtggagtatttacggtaaactgcccacttggcagtacatcaagtgtatcatatgccaagtacgcccc |
| ctattgacgtcaatgacggtaaatggcccgcctggcattatgcccagtacatgaccttatgggactttcctacttggcagtacatctacgtatta |
| gtcatcgctattaccatggtgatgcggttttggcagtacatcaatgggcgtggatagcggtttgactcacggggatttccaagtctccacccca |
| ttgacgtcaatgggagtttgttttggcaccaaaatcaacgggactttccaaaatgtcgtaacaactccgccccattgacgcaaatgggcggta |
| ggcgtgtacggtgggaggtctatataagcagagctggtttagtgaaccgtcagatcctgcagaagttggtcgtgaggcactgggcaggtaa |
| gtatcaaggttacaagacaggtttaaggagaccaatagaaactgggcttgtcgagacagagaagactcttgcgtttctgataggcacctattg |
| gtcttactgacatccactttgcctttctctccacaggtgtccaggcggccgccatggtgagcaagggcgaggagctgttcaccggggtggtg |
| cccatcctggtcgagctggacggcgacgtaaacggccacaagttcagcgtgtccggcgagggcgagggcgatgccacctacggcaag |
| ctgaccctgaagttcatctgcaccaccggcaagctgcccgtgccctggcccaccctcgtgaccaccctgacctacggcgtgcagtgcttca |
| gccgctaccccgaccacatgaagcagcacgacttcttcaagtccgccatgcccgaaggctacgtccaggagcgcaccatcttcttcaagg |
| acgacggcaactacaagacccgcgccgaggtgaagttcgagggcgacaccctggtgaaccgcatcgagctgaagggcatcgacttcaa |
| ggaggacggcaacatcctggggcacaagctggagtacaactacaacagccacaacgtctatatcatggccgacaagcagaagaacggc |
| atcaaggtgaacttcaagatccgccacaacatcgaggacggcagcgtgcagctcgccgaccactaccagcagaacacccccatcggcg |
| acggccccgtgctgctgcccgacaaccactacctgagcacccagtccgccctgagcaaagaccccaacgagaagcgcgatcacatggt |
| cctgctggagttcgtgaccgccgccgggatcactctcggcatggacgagctgtacaagtaataagcttggatccaatcaacctctggattac |
| aaaatttgtgaaagattgactggtattcttaactatgttgctccttttacgctatgtggatacgctgctttaatgcctttgtatcatgctattgct |
| tcccgtatggctttcattttctcctccttgtataaatcctggttgctgtctctttatgaggagttgtggcccgttgtcaggcaacgtggcgtggtg |
| tgcactgtgtttgctgacgcaaccccccactggttggggcattgccaccacctgtcagctcctttccgggactttcgctttccccctccctattgcc |
| acggcggaactcatcgccgcctgccttgcccgctgctggacaggggctcggctgttgggcactgacaattccgtggtgttgtcggggaaatcatc |
| gtcctttccttggctgctcgcctgtgttgccacctggattctgcgcgggacgtccttctgctacgtcccttcggccctcaatccagcggaccttc |
| cttcccgcggcctgctgccggctctgcggcctcttccgcgtcttcgagatctgcctcgactgtgccttctagttgccagccatctgttgtttgcc |
| cctccccgtgccttccttgaccctggaaggtgccactcccactgtcctttcctaataaaatgaggaaattgcatcgcattgtctgagtaggtgt |
| cattctattctgggggtgggtggggcaggacagcaaggggaggattgggaagacaatagcaggcatgctgggaGGTACCtt |
| tagggttagggttagggttagggAAAAAtttagggttagggttagggttagggAAAAAtttagggttagggttagggttag |
| ggAAAAAATGCAGCGGTAAGTTCCCATCCAGGTTTTTTGCAGCGGTAAGTTCCCA |

| Sequences |
|---|
| TCCAGGTTTTTTGCAGCGGTAAGTTCCCATCCAGGTTTTTctcgagttaagggcgaattcccga<br><br>taaggatcttcctagagcatggctacgtagataagtagcatggcgggttaatcattaactacaaggaacccctagtgatggagttggccactc<br><br>cctctctgcgcgctcgctcgctcactgaggccgggcgaccaaaggtcgcccgacgcccgggctttgcccgggcggcctcagtgagcga<br><br>gcgagcgcgcag<br><br>TTAGGG motif:<br><br>TTAGGG (SEQ ID NO: 61) |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of and "consisting essentially of shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A nucleic acid comprising an inhibitory oligonucleotide that comprises the nucleotide sequence of SEQ ID NO: 39, wherein the nucleic acid is a recombinant viral genome.

2. The nucleic acid of claim 1, wherein the nucleic acid further comprises a therapeutic nucleotide sequence.

3. The nucleic acid of claim 2, wherein the therapeutic nucleotide sequence encodes a protein or peptide.

4. The nucleic acid of claim 2, wherein the recombinant viral genome is from adeno-associated virus (AAV), adenovirus, herpes simplex virus, varicella, variola virus, hepatitis B, cytomegalovirus, JC polyomavirus, BK polyomavirus, monkeypox virus, Herpes Zoster, Epstein-Barr virus, human herpes virus 7, Kaposi's sarcoma-associated herpesvirus, or human parvovirus B19.

5. The nucleic acid of claim 2, wherein the recombinant viral genome is single-stranded or self-complementary.

6. The nucleic acid of claim 2, wherein the inhibitory oligonucleotide is located 5' to a promoter operably linked to the therapeutic nucleotide sequence.

7. The nucleic acid of claim 2, wherein the inhibitory oligonucleotide is located in a 5' untranslated region (UTR) of the recombinant viral genome.

8. The nucleic acid of claim 2, wherein the inhibitory oligonucleotide is located 3' to a polyA tail linked to the therapeutic nucleotide sequence.

9. The nucleic acid of claim 2, wherein the inhibitory oligonucleotide is located in a 3' UTR of the recombinant viral genome.

10. The nucleic acid of claim 2, wherein the recombinant viral genome further comprises at least one additional inhibitory oligonucleotide that inhibits nucleic-acid sensing TLR activation and/or signaling.

11. The nucleic acid of claim 10, wherein the inhibitory oligonucleotides are in different locations of the viral genome.

12. The nucleic acid of claim 10, wherein one of the inhibitory oligonucleotides is oriented in the sense direction of the recombinant viral genome and another of the inhibitory oligonucleotides is oriented in the antisense direction of the recombinant viral genome.

13. The nucleic acid of claim 10, wherein at least one of the inhibitory oligonucleotides binds to inflammatory nucleic acids.

14. The nucleic acid of claim 13, wherein the inflammatory nucleic acids comprise CpG oligodeoxynucleotides.

15. A viral particle comprising of the nucleic acid of claim 1.

16. A pharmaceutical composition comprising the nucleic acid of claim 1.

17. A method comprising administering to a subject in need thereof the nucleic acid of claim 1.

18. A method of making a recombinant viral genome, the method comprising introducing into a viral genome the nucleic acid of claim 1.

* * * * *

SEQUENCE LISTING

```
<160> NUMBER OF SEQ ID NOS: 63

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
tggcgcgcac ccacggcctg                                            20

<210> SEQ ID NO 2
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 2
tcctggcggg gaagt                                                 15

<210> SEQ ID NO 3
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 3
cctggatggg aa                                                    12

<210> SEQ ID NO 4
<211> LENGTH: 24
<212> TYPE: DNA
```

```
<213> ORGANISM: Artificial Sequence
<220> FEATURE:
<223> OTHER INFORMATION: Synthetic polynucleotide

<400> SEQUENCE: 4
cctggatggg aattcccatc cagg                                        24

<210> SEQ ID NO 5
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 5
cctggatggg aacttaccgc tgca                                        24

<210> SEQ ID NO 6
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 6
ttagggttag ggttagggtt aggg                                        24

<210> SEQ ID NO 7
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 7
ctcctattgg gggtttccta t                                           21

<210> SEQ ID NO 8
<211> LENGTH: 5
<212> TYPE: DNA
<213> ORGANISM: Artificial Sequence
<220> FEATURE:
<223> OTHER INFORMATION: Synthetic polynucleotide

<400> SEQUENCE: 8 aaaaa                                                              5

<210> SEQ ID NO 9
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 9
tttagggtta gggttagggt taggg                                       25

<210> SEQ ID NO 10
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 10
tcctggaggg gaacc                                                  15
```

<210> SEQ ID NO 11
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 11
cctggagggg aagt                                                        14

<210> SEQ ID NO 12
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 12
cctggagggg                                                             10

<210> SEQ ID NO 13
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 13
tccttcctgg aggggaag                                                    18

<210> SEQ ID NO 14
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 14
tcctatcctg gaggggaag                                                   19

<210> SEQ ID NO 15
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 15
tcctatccta tcctggaggg gaag                                             24

<210> SEQ ID NO 16
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 16
tcctggaggg gaagt                                                       15

<210> SEQ ID NO 17
<211> LENGTH: 15
<212> TYPE: DNA
<213> ORGANISM: Artificial Sequence
<220> FEATURE:

<223> OTHER INFORMATION: Synthetic polynucleotide

<400> SEQUENCE: 17
tcctggatgg gaagt                                                          15

<210> SEQ ID NO 18
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 18
ttcccatcca ggcctggatg ggaa                                                24

<210> SEQ ID NO 19
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 19
cttaccgctg cacctggatg ggaa                                                24

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
gggggggggg gggggggggg                                                     20

<210> SEQ ID NO 21
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 21
tgactgtgaa ggttagagat ga                                                  22

<210> SEQ ID NO 22
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 22
tcctggaggg gttgt                                                          15

<210> SEQ ID NO 23
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 23
tgctcctgga ggggttgt                                                       18

```
<210> SEQ ID NO 24
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 24
cctggcgggg                                                              10

<210> SEQ ID NO 25
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 25
cctcaatagg gtgagggg                                                     18

<210> SEQ ID NO 26
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 26
tcgtcgtttt gtcgttttgt cgtt                                              24

<210> SEQ ID NO 27
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 27
tcgtatcctg gaggggaag                                                    19

<210> SEQ ID NO 28
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 28
taatatcctg gaggggaag                                                    19

<210> SEQ ID NO 29
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 29
cctatcctgg aggggaag                                                     18

<210> SEQ ID NO 30
<211> LENGTH: 22
<212> TYPE: DNA
<213> ORGANISM: Artificial Sequence
<220> FEATURE:
<223> OTHER INFORMATION: Synthetic polynucleotide
```

<400> SEQUENCE: 30
gggtgggtgg gtattaccat ta                                         22

<210> SEQ ID NO 31
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 31
tgggcggttc aaccttca                                              18

<210> SEQ ID NO 32
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 32
cctcaagctt gagggg                                                16

<210> SEQ ID NO 33
<211> LENGTH: 2298
<212> TYPE: DNA
<213> ORGANISM: Artificial Sequence
<220> FEATURE:
<223> OTHER INFORMATION: Synthetic polynucleotide

<400> SEQUENCE: 33
gcgcgctcgc tcgctcactg aggccgcccg ggcaaagccc gggcgtcggg cgacctttgg     60
tcgcccggcc tcagtgagcg agcgagcgcg cagagaggga gtggccaact ccatcactag    120
gggttccttg tagttaatga ttaacccgcc atgctactta tctacgtagc catgctcgat    180
ctgaattcgg taccacgcgt gtctgtctgc acatttcgta gagcgagtgt tccgatactc    240
taatctccct aggcaaggtt catatttgtg taggttactt attctccttt tgttgactaa    300
gtcaataatc agaatcagca ggtttggagt cagcttggca gggatcagca gcctgggttg    360
gaaggagggg gtataaaagc cccttcacca ggagaagccg tcacacagat ccacaagctc    420
ctgctagcag gtaagtgccg tgtgtggttc ccgcgggcct ggcctcttta cgggttatgg    480
cccttgcgtg ccttgaatta ctgacactga catccacttt ttcttttttct ccacaggtat    540 cgattgaatt ccaccatgca gcgcgtgaac atgatcatgg cagaatcacc aggcctcatc    600
accatctgcc ttttaggata tctactcagt gctgaatgta cagttttctct tgatcatgaa    660 aacgccaaca aaattctgaa tcggccaaag aggtataatt caggtaaatt ggaagagttt    720
gttcaaggga accttgagag agaatgtatg gaagaaaagt gtagttttga agaagcacga    780 gaagttttg aaaacactga agaacaact gaatttgga agcagtatgt tgatggagat    840
cagtgtgagt ccaatccatg tttaaatggc ggcagttgca aggatgacat taattcctat    900
gaatgttggt gtccctttgg atttgaagga aagaactgtg aattagatgt aacatgtaac    960
attaagaatg gcagatgcga gcagttttgt aaaaatagtg ctgataacaa ggtggtttgc   1020
tcctgtactg agggatatcg acttgcagaa aaccagaagt cctgtgaacc agcagtgcca   1080
tttccatgtg gaagagtttc tgtttcacaa acttctaagc tcacccgtgc tgagactgtt   1140
tttcctgatg tggactatgt aaattctact gaagctgaaa ccattttgga taacatcact   1200
caaagcaccc aatcatttaa tgacttcact cgggttgttg gtggagaaga tgccaaacca   1260

```
ggtcaattcc cttggcaggt tgttttgaat ggtaaagttg atgcattctg tggaggctct    1320
atcgttaatg aaaaatggat tgtaactgct gcccactgtg ttgaaactgg tgttaaaatt    1380
acagttgtcg caggtgaaca taatattgag gagacagaac atacagagca aaagcgaaat    1440
gtgattcgaa ttattcctca ccacaactac aatgcagcta ttaataagta caaccatgac    1500
attgcccttc tggaactgga cgaacccttc gtgctaaaca gctacgttac acctatttgc    1560
attgctgaca aggaatacac gaacatcttc ctcaaatttg gatctggcta tgtaagtggc    1620
tggggaagag tcttccacaa agggagatca gctttagttc ttcagtacct tagagttcca    1680
cttgttgacc gagccacatg tcttcgatct acaaagttca ccatctataa caacatgttc    1740
tgtgctggct tccatgaagg aggtagagat tcatgtcaag agatagtgg gggaccccat    1800 gttactgaag tggaagggac cagtttctta actggaatta ttagctgggg tgaagagtgt    1860
gcaatgaaag gcaaatatgg aatatatacc aaggtatccc ggtatgtcaa ctggattaag    1920
gaaaaaacaa agctcactta tgaaagatg gagatctgcg gcctcgacta gagctcgctg    1980
atcagcctcg actgtgcctt ctagttgcca gccatctgtt gtttgcccct ccccgtgcc    2040 ttccttgacc ctggaaggtg ccactcccac tgtcctttcc taataaaatg aggaaattgc    2100
atcgcattgt ctgagtaggt gtcattctat tctgggggt ggggtggggc aggacagcaa    2160
gggggaggat tgggaagaca atagcaggaa ccccactccc tctctgcgcg ctcgctcgct    2220
cactgaggcc gggcgaccaa aggtcgcccg acgcccgggc tttgcccggg cggcctcagt    2280
gagcgagcga gcgcgcag                                                  2298

<210> SEQ ID NO 34
<211> LENGTH: 2394
<212> TYPE: DNA
<213> ORGANISM: Artificial Sequence
<220> FEATURE:
<223> OTHER INFORMATION: Synthetic polynucleotide

<400> SEQUENCE: 34
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttccttg tagttaatga ttaacccgcc atgctactta tctacgtagc catgctcgat     180
ctgaattcgg tacctttagg gttagggtta gggttaggga aaatttagg gttagggtta     240 gggttaggga aaatttagg gttagggtta gggttaggga aaaggtacc acgcgtgtct     300 gtctgcacat ttcgtagagc gagtgttccg atactctaat ctccctaggc aaggttcata     360
tttgtgtagg ttacttattc tccttttgtt gactaagtca ataatcagaa tcagcaggtt     420
tggagtcagc ttggcaggga tcagcagcct gggttggaag gaggggtat aaaagcccct     480 tcaccaggag aagccgtcac acagatccac aagctcctgc tagcaggtaa gtgccgtgtg     540
tggttcccgc gggcctggcc tctttacggg ttatggccct tgcgtgcctt gaattactga     600
cactgacatc cacttttcct ttttctccac aggtatcgat tgaattccac catgcagcgc     660
gtgaacatga tcatggcaga atcaccaggc ctcatcacca tctgcctttt aggatatcta     720
ctcagtgctg aatgtacagt ttttcttgat catgaaaacg ccaacaaaat tctgaatcgg     780
ccaaagaggt ataattcagg taaattggaa gagtttgttc aagggaacct tgagagagaa     840 tgtatgaag aaaagtgtag ttttgaagaa gcacgagaag ttttttgaaaaa cactgaaaga     900 acaactgaat tttggaagca gtatgttgat ggagatcagt gtgagtccaa tccatgttta     960
```

```
aatggcggca gttgcaagga tgacattaat tcctatgaat gttggtgtcc ctttggattt    1020
gaaggaaaga actgtgaatt agatgtaaca tgtaacatta agaatggcag atgcgagcag    1080
ttttgtaaaa atagtgctga taacaaggtg gtttgctcct gtactgaggg atatcgactt    1140
gcagaaaacc agaagtcctg tgaaccagca gtgccatttc catgtggaag agtttctgtt    1200
tcacaaactt ctaagctcac ccgtgctgag actgttttc ctgatgtgga ctatgtaaat     1260
tctactgaag ctgaaaccat tttggataac atcactcaaa gcacccaatc atttaatgac    1320
ttcactcggg ttgttggtgg agaagatgcc aaaccaggtc aattcccttg gcaggttgtt    1380
ttgaatggta agttgatgc attctgtgga ggctctatcg ttaatgaaaa atggattgta     1440
actgctgccc actgtgttga aactggtgtt aaaattacag ttgtcgcagg tgaacataat    1500
attgaggaga cagaacatac agagcaaaag cgaaatgtga ttcgaattat tcctcaccac    1560
aactacaatg cagctattaa taagtacaac catgacattg cccttctgga actggacgaa    1620
cccttagtgc taaacagcta cgttacacct atttgcattg ctgacaagga atacacgaac    1680
atcttcctca aatttggatc tggctatgta agtggctggg aagagtctt ccacaaaggg     1740 agatcagctt tagttcttca gtaccttaga gttccacttg ttgaccgagc cacatgtctt    1800
cgatctacaa agttcaccat ctataacaac atgttctgtg ctggcttcca tgaaggaggt    1860
agagattcat gtcaaggaga tagtggggga ccccatgtta ctgaagtgga agggaccagt    1920
ttcttaactg gaattattag ctggggtgaa gagtgtgcaa tgaaaggcaa atatggaata    1980
tataccaagg tatcccggta tgtcaactgg attaaggaaa aaacaaagct cacttaatga    2040
aagatggaga tctgcggcct cgactagagc tcgctgatca gcctcgactg tgccttctag    2100
ttgccagcca tctgttgttt gcccctcccc cgtgccttcc ttgaccctgg aaggtgccac    2160
tcccactgtc ctttcctaat aaaatgagga aattgcatcg cattgtctga gtaggtgtca    2220
ttctattctg gggggtgggg tggggcagga cagcaagggg gaggattggg aagacaatag    2280 caggaaccccc actccctctc tgcgcgctcg ctcgctcact gaggccgggc gaccaaaggt    2340
cgcccgacgc ccgggctttg cccgggcggc ctcagtgagc gagcgagcgc gcag          2394
```

<210> SEQ ID NO 35
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 35

```
tttagggtta gggttagggt tagggaaaaa tttagggtta gggttagggt tagggaaaaa     60
tttagggtta gggttagggt tagggaaaaa                                      90
```

<210> SEQ ID NO 36
<211> LENGTH: 3295
<212> TYPE: DNA
<213> ORGANISM: Artificial Sequence
<220> FEATURE:
<223> OTHER INFORMATION: Synthetic polynucleotide

<400> SEQUENCE: 36

```
tgcgcgctcg ctcgctcact gaggccgccc gggcaaagcc cgggcgtcgg gcgacctttg     60
gtcgcccggc ctcagtgagc gagcgagcgc gcagagaggg agtggccaac tccatcacta    120
ggggttcctt gtagttaatg attaacccgc catgctactt atctacgtag ccatgctcta    180
gcggcctcgg cctctgcata aataaaaaaa attagtcagc catgagcttg gcccattgca    240
```

```
tacgttgtat ccatatcata atatgtacat ttatattggc tcatgtccaa cattaccgcc      300
atgttgacat tgattattga ctagttatta atagtaatca attacggggt cattagttca      360
tagcccatat atggagttcc gcgttacata acttacggta aatggcccgc ctggctgacc      420
gcccaacgac ccccgcccat tgacgtcaat aatgacgtat gttcccatag taacgccaat      480
agggactttc cattgacgtc aatgggtgga gtatttacgg taaactgccc acttggcagt      540
acatcaagtg tatcatatgc caagtacgcc ccctattgac gtcaatgacg gtaaatggcc      600
cgcctggcat tatgcccagt acatgacctt atgggacttt cctacttggc agtacatcta      660
cgtattagtc atcgctatta ccatggtgat gcggttttgg cagtacatca atgggcgtgg      720
atagcggttt gactcacggg gatttccaag tctccacccc attgacgtca atgggagttt      780
gttttggcac caaaatcaac gggactttcc aaaatgtcgt aacaactccg ccccattgac      840
gcaaatgggc ggtaggcgtg tacggtggga ggtctatata agcagagctc gtttagtgaa      900
ccgtcagatc gcctggagac gccatccacg ctgttttgac ctccatagaa gacaccggga      960
ccgatccagc ctcccctcga agctgatcct gagaacttca gggtgagtct atgggaccct     1020
tgatgttttc tttccccttc ttttctatgg ttaagttcat gtcataggaa ggggagaagt     1080
aacagggtac acatattgac caaatcaggg taattttgca tttgtaattt taaaaaatgc     1140
tttcttcttt taatatactt ttttgtttat cttatttcta atactttccc taatctcttt     1200
ctttcagggc aataatgata caatgtatca tgcctctttg caccattcta agaataaca      1260 gtgataattt ctgggttaag gcaatagcaa tatttctgca tataaatatt tctgcatata     1320
aattgtaact gatgtaagag gtttcatatt gctaatagca gctacaatcc agctaccatt     1380
ctgcttttat tttatggttg ggataaggct ggattattct gagtccaagc taggcccttt     1440
tgctaatcat gttcatacct cttatcttcc tcccacagct cctgggcaac gtgctggtct     1500
gtgtgctggc ccatcacttt ggcaaagaat tccgcgggcc cgggatccac cggtcgccac     1560
catggtgagc aagggcgagg agctgttcac cggggtggtg cccatcctgg tcgagctgga     1620
cggcgacgta aacggccaca gtttcagcgt gtccggcgag ggcgagggcg atgccaccta     1680
cggcaagctg accctgaagt tcatctgcac caccggcaag ctgcccgtgc cctggcccac     1740
cctcgtgacc accctgacct acggcgtgca gtgcttcagc cgctaccccg accacatgaa     1800
gcagcacgac ttcttcaagt ccgccatgcc cgaaggctac gtccaggagc gcaccatctt     1860
cttcaaggac gacggcaact acaagacccg cgccgaggtg aagttcgagg gcgacaccct     1920
ggtgaaccgc atcgagctga agggcatcga cttcaaggag gacggcaaca tcctggggca     1980
caagctggag tacaactaca acagccacaa cgtctatatc atggccgaca agcagaagaa     2040
cggcatcaag gtgaacttca agatccgcca caacatcgag gacggcagcg tgcagctcgc     2100
cgaccactac cagcagaaca cccccatcgg cgacggcccc gtgctgctgc ccgacaacca     2160
ctacctgagc acccagtccg ccctgagcaa agaccccaac gagaagcgcg atcacatggt     2220
cctgctggag ttcgtgaccg ccgccgggat cactctcggc atggacgagc tgtacaagta     2280
aagcggccgc tctagaggat ccaagcttat cgataccgtc gacctcgagg gcccagatct     2340
aattcacccc accagtgcag gctgcctatc agaaagtggt ggctggtgtg gctaatgccc     2400
tggcccacaa gtatcactaa gctcgctttc ttgctgtcca atttctatta aaggttcctt     2460
tgttccctaa gtccaactac taaactgggg atattatga agggccttga gcatctggat     2520
tctgcctaat aaaaaacatt tattttcatt gcaatgatgt atttaaatta tttctgaata     2580
```

```
ttttactaaa aagggaatgt gggaggtcag tgcatttaaa acataaagaa atgaagagct    2640
agttcaaacc ttgggaaaat acactatatc ttaaactcca tgaaagaagg tgaggctgca    2700
aacagctaat gcacattggc aacagcccct gatgcctatg ccttattcat ccctcagaaa    2760
aggattcaag tagaggcttg atttggaggt taaagttttg ctatgctgta ttttacatta    2820
cttattgttt tagctgtcct catgaatgtc ttttcactac ccatttgctt atcctgcatc    2880
tctcagcctt gactccactc agttctcttg cttagagata ccacctttcc cctgaagtgt    2940
tccttccatg ttttacggcg agatggtttc tcctcgcctg gccactcagc cttagttgtc    3000
tctgttgtct tatagaggtc tacttgaaga aggaaaaaca gggggcatgg tttgactgtc    3060
ctgtgagccc ttcttccctg cctcccccac tcacagtgac ccggaatccc tcgacatcta    3120
gagcatggct acgtagataa gtagcatggc gggttaatca ttaactacaa ggaaccccta    3180
gtgatggagt tggccactcc ctctctgcgc gctcgctcgc tcactgaggc cgggcgacca    3240
aaggtcgccc gacgcccggg ctttgcccgg gcggcctcag tgagcgagcg agcgc    3295
```

<210> SEQ ID NO 37
<211> LENGTH: 3484
<212> TYPE: DNA
<213> ORGANISM: Artificial Sequence
<220> FEATURE:
<223> OTHER INFORMATION: Synthetic polynucleotide

<400> SEQUENCE: 37

```
tgcgcgctcg ctcgctcact gaggccgccc gggcaaagcc cgggcgtcgg gcgacctttg      60 gtcgccggc ctcagtgagc gagcgagcgc gcagagaggg agtggccaac tccatcacta     120
ggggttcctt gtagttaatg attaacccgc catgctactt atctacgtag ccatgctcta    180
gcggcctcgg cctctgcata aataaaaaaa attagtcagc catgagcttg gcccattgca    240
tacgttgtat ccatatcata atatgtacat ttatattggc tcatgtccaa cattaccgcc    300
atgttgacat tgattattga ctagttatta atagtaatca attacggggt cattagttca    360
tagcccatat atggagttcc gcgttacata acttacggta atggcccgc ctggctgacc    420 gcccaacgac ccccgcccat tgacgtcaat aatgacgtat gttcccatag taacgccaat    480
agggactttc cattgacgtc aatgggtgga gtatttacgg taaactgccc acttggcagt    540
acatcaagtg tatcatatgc caagtacgcc ccctattgac gtcaatgacg gtaaatggcc    600
cgcctggcat tatgcccagt acatgacctt atgggacttt cctacttggc agtacatcta    660
cgtattagtc atcgctatta ccatggtgat gcggttttgg cagtacatca atgggcgtgg    720
atagcggttt gactcacggg gatttccaag tctccacccc attgacgtca tgggagtttt    780
gttttggcac caaaatcaac gggactttcc aaaatgtcgt aacaactccg ccccattgac    840
gcaaatgggc ggtaggcgtg tacggtggga ggtctatata agcagagctc gtttagtgaa    900
ccgtcagatc gcctggagac gccatccacg ctgttttgac ctccatagaa gacaccggga    960
ccgatccagc ctcccctcga agctgatcct gagaacttca gggtgagtct atgggaccct   1020
tgatgttttc tttccccttc ttttctatgg ttaagttcat gtcataggaa ggggagaagt   1080
aacagggtac acatattgac caaatcaggg taattttgca tttgtaattt taaaaaatgc   1140
ttcttctttt aatatactt ttttgtttat cttatttcta atactttccc taatctcttt   1200
ctttcagggc aataatgata caatgtatca tgcctctttg caccattcta aagaataaca   1260
gtgataattt ctgggttaag gcaatagcaa tatttctgca tataaatatt tctgcatata   1320
aattgtaact gatgtaagag gtttcatatt gctaatagca gctacaatcc agctaccatt   1380
```

```
ctgcttttat tttatggttg ggataaggct ggattattct gagtccaagc taggcccttt    1440
tgctaatcat gttcatacct cttatcttcc tcccacagct cctgggcaac gtgctggtct    1500
gtgtgctggc ccatcacttt ggcaaagaat tccgcgggcc cgggatccac cggtcgccac    1560
catggtgagc aagggcgagg agctgttcac cggggtggtg cccatcctgg tcgagctgga    1620
cggcgacgta acggccaca agttcagcgt gtccggcgag ggcgagggcg atgccaccta    1680
cggcaagctg accctgaagt tcatctgcac caccggcaag ctgcccgtgc cctggcccac    1740
cctcgtgacc accctgacct acggcgtgca gtgcttcagc cgctaccccg accacatgaa    1800
gcagcacgac ttcttcaagt ccgccatgcc cgaaggctac gtccaggagc gcaccatctt    1860
cttcaaggac gacggcaact acaagacccg cgccgaggtg aagttcgagg gcgacaccct    1920
ggtgaaccgc atcgagctga agggcatcga cttcaaggag gacggcaaca tcctggggca    1980
caagctggag tacaactaca acagccacaa cgtctatatc atggccgaca agcagaagaa    2040
cggcatcaag gtgaacttca agatccgcca caacatcgag gacggcagcg tgcagctcgc    2100
cgaccactac cagcagaaca cccccatcgg cgacggcccc gtgctgctgc ccgacaacca    2160
ctacctgagc acccagtccg ccctgagcaa agaccccaac gagaagcgcg atcacatggt    2220
cctgctggag ttcgtgaccg ccgccgggat cactctcggc atggacgagc tgtacaagta    2280
aagcggccgc tctagaggat ccaagcttat cgataccgtc gacctcgagg gcccagatct    2340
aattcacccc accagtgcag gctgcctatc agaaagtggt ggctggtgtg gctaatgccc    2400
tggcccacaa gtatcactaa gctcgctttc ttgctgtcca atttctatta aaggttcctt    2460
tgttccctaa gtccaactac taaactgggg gatattatga agggccttga gcatctggat    2520
tctgcctaat aaaaaacatt tattttcatt gcaatgatgt atttaaatta tttctgaata    2580
ttttactaaa aagggaatgt gggaggtcag tgcatttaaa acataaagaa atgaagagct    2640
agttcaaacc ttgggaaaat acactatatc ttaaactcca tgaaagaagg tgaggctgca    2700
aacagctaat gcacattggc aacagcccct gatgcctatg ccttattcat ccctcagaaa    2760
aggattcaag tagaggcttg atttggaggt taaagttttg ctatgctgta ttttacatta    2820
cttattgttt tagctgtcct catgaatgtc ttttcactac ccatttgctt atcctgcatc    2880
tctcagcctt gactccactc agttctcttg cttagagata ccacctttcc cctgaagtgt    2940
tccttccatg ttttacggcg agatggtttc tcctcgcctg gccactcagc cttagttgtc    3000
tctgttgtct tatagaggtc tacttgaaga aggaaaaaca gggggcatgg tttgactgtc    3060
ctgtgagccc ttcttccctg cctcccccac tcacagtgac ccggaatccc tcgacaggta    3120
cctttagggt tagggttagg gttagggaaa aatttagggt tagggttagg gttagggaaa    3180
aatttagggt tagggttagg gttagggaaa aatgcagcgg taagttccca tccaggtttt    3240
ttgcagcggt aagttcccat ccaggttttt tgcagcggta agttcccatc caggttttg    3300 ctagctctag agcatggcta cgtagataag tagcatggcg ggttaatcat taactacaag    3360
gaacccctag tgatggagtt ggccactccc tctctgcgcg ctcgctcgct cactgaggcc    3420
gggcgaccaa aggtcgcccg acgcccgggc tttgcccggg cggcctcagt gagcgagcga    3480
gcgc                                                                  3484
```

<210> SEQ ID NO 38
<211> LENGTH: 3601
<212> TYPE: DNA
<213> ORGANISM: Artificial Sequence
<220> FEATURE:

<223> OTHER INFORMATION: Synthetic polynucleotide

<400> SEQUENCE: 38

```
tgcgcgctcg ctcgctcact gaggccgccc gggcaaagcc cgggcgtcgg gcgacctttg      60
gtcgccggc  ctcagtgagc gagcgagcgc gcagagaggg agtggccaac tccatcacta     120
ggggttcctt gtagttaatg attaacccgc catgctactt atctacgtag ccatgctcta     180
gcggcctcgg cctctgcata aataaaaaaa attagtcagc catgagcttg gcccattgca     240
tacgttgtat ccatatcata atatgtacat ttatattggc tcatgtccaa cattaccgcc     300
atgttgacat tgattattga ctagtcctgg atgggaaaaa aacctggatg ggaaaaaaac     360
ctggatggga aaaaaaactt ccccgccagg attttttactt ccccgccagg attttttactt     420
ccccgccagg attttttacta gttattaata gtaatcaatt acgggtcat tagttcatag     480
cccatatatg gagttccgcg ttacataact tacggtaaat ggcccgcctg gctgaccgcc     540
caacgacccc cgcccattga cgtcaataat gacgtatgtt cccatagtaa cgccaatagg     600
gactttccat tgacgtcaat gggtggagta tttacggtaa actgcccact tggcagtaca     660
tcaagtgtat catatgccaa gtacgccccc tattgacgtc aatgacggta aatggcccgc     720
ctggcattat gcccagtaca tgaccttatg gactttcct  acttggcagt acatctacgt     780
attagtcatc gctattacca tggtgatgcg gttttggcag tacatcaatg ggcgtggata     840
gcggtttgac tcacggggat ttccaagtct ccacccccatt gacgtcaatg ggagtttgtt     900
ttggcaccaa aatcaacggg actttccaaa atgtcgtaac aactccgccc cattgacgca     960
aatgggcggt aggcgtgtac ggtgggaggt ctatataagc agagctcgtt tagtgaaccg    1020
tcagatcgcc tggagacgcc atccacgctg ttttgacctc catagaagac accgggaccg    1080
atccagcctc ccctcgaagc tgatcctgag aacttcaggg tgagtctatg ggacccttga    1140
tgttttcttt ccccttcttt tctatggtta agttcatgtc ataggaaggg gagaagtaac    1200
agggtacaca tattgaccaa atcagggtaa ttttgcattt gtaattttaa aaaatgcttt    1260
cttcttttaa tatacttttt tgtttatctt atttctaata cttttccctaa tctctttctt    1320
tcagggcaat aatgatacaa tgtatcatgc ctctttgcac cattctaaag aataacagtg    1380
ataatttctg ggttaaggca atagcaatat ttctgcatat aaatatttct gcatataaat    1440
tgtaactgat gtaagaggtt tcatattgct aatagcagct acaatccagc taccattctg    1500
cttttatttt atggttggga taaggctgga ttattctgag tccaagctag gccccttttgc    1560
taatcatgtt catacctctt atcttcctcc cacagctcct gggcaacgtg ctggtctgtg    1620
tgctggccca tcactttggc aaagaattcc gcgggccggg gatccaccgg tcgccaccat    1680
ggtgagcaag ggcgaggagc tgttcaccgg ggtggtgccc atcctggtcg agctggacgg    1740
cgacgtaaac ggccacaagt tcagcgtgtc cggcgagggc gagggcgatg ccacctacgg    1800
caagctgacc ctgaagttca tctgcaccac cggcaagctg cccgtgccct ggcccaccct    1860
cgtgaccacc ctgacctacg gcgtgcagtg cttcagccgc taccccgacc acatgaagca    1920
gcacgacttc ttcaagtccg ccatgcccga aggctacgtc caggagcgca ccatcttctt    1980
caaggacgac ggcaactaca agacccgcgc cgaggtgaag ttcgagggcg acaccctggt    2040
gaaccgcatc gagctgaagg gcatcgactt caaggaggac ggcaacatcc tggggcacaa    2100
gctggagtac aactacaaca gccacaacgt ctatatcatg gccgacaagc agaagaacgg    2160
catcaaggtg aacttcaaga tccgccacaa catcgaggac ggcagcgtgc agctcgccga    2220
ccactaccag cagaacaccc ccatcggcga cggccccgtg ctgctgcccg acaaccacta    2280
```

```
cctgagcacc cagtccgccc tgagcaaaga ccccaacgag aagcgcgatc acatggtcct    2340
gctggagttc gtgaccgccg ccgggatcac tctcggcatg gacgagctgt acaagtaaag    2400
cggccgctct agaggatcca agcttatcga taccgtcgac ctcgagggcc cagatctaat    2460
tcaccccacc agtgcaggct gcctatcaga agtggtggc tggtgtggct aatgccctgg     2520
cccacaagta tcactaagct cgcttttctt ctgtccaatt tctattaaag gttccttttgt   2580 tccctaagtc caactactaa actgggggat attatgaagg gccttgagca tctggattct    2640
gcctaataaa aaacatttat tttcattgca atgatgtatt taaattattt ctgaatattt    2700
tactaaaaag ggaatgtggg aggtcagtgc atttaaaaca taaagaaatg aagagctagt    2760
tcaaaccttg ggaaaataca ctatatctta aactccatga aagaaggtga ggctgcaaac    2820
agctaatgca cattggcaac agcccctgat gcctatgcct tattcatccc tcagaaaagg    2880
attcaagtag aggcttgatt tggaggttaa agttttgcta tgctgtattt tacattactt    2940
attgttttag ctgtcctcat gaatgtcttt tcactaccca tttgcttatc ctgcatctct    3000
cagccttgac tccactcagt tctcttgctt agagatacca cctttcccct gaagtgttcc    3060 ttccatgtttt tacggcgaga tggtttctcc tcgcctggcc actcagcctt agttgtctct    3120
gttgtcttat agaggtctac ttgaagaagg aaaaacaggg ggcatggttt gactgtcctg    3180
tgagcccttc ttccctgcct cccccactca cagtgacccg gaatccctcg acaggtacct    3240
ttagggttag ggttagggtt agggaaaaat ttagggttag ggttagggtt agggaaaaat    3300
ttagggttag ggttagggtt agggaaaaat gcagcggtaa gttcccatcc aggttttttg    3360
cagcggtaag ttcccatcca ggttttttgc agcggtaagt tcccatccag gttttgcta    3420 gctctagagc atggctacgt agataagtag catggcgggt taatcattaa ctacaaggaa    3480
cccctagtga tggagttggc cactccctct ctgcgcgctc gctcgctcac tgaggccggg    3540
cgaccaaagg tcgcccgacg cccgggcttt gcccgggcgg cctcagtgag cgagcgagcg    3600
c                                                                     3601

<210> SEQ ID NO 39
<211> LENGTH: 177
<212> TYPE: DNA
<213> ORGANISM: Artificial Sequence
<220> FEATURE:
<223> OTHER INFORMATION: Synthetic polynucleotide

<400> SEQUENCE: 39
tttagggtta gggttagggt tagggaaaaa tttagggtta gggttagggt tagggaaaaa    60
tttagggtta gggttagggt tagggaaaaa tgcagcggta agttcccatc caggtttttt    120
gcagcggtaa gttcccatcc aggttttttg cagcggtaag ttcccatcca ggtttt        177

<210> SEQ ID NO 40
<211> LENGTH: 111
<212> TYPE: DNA
<213> ORGANISM: Artificial Sequence
<220> FEATURE:
<223> OTHER INFORMATION: Synthetic polynucleotide

<400> SEQUENCE: 40
cctggatggg aaaaaaacct ggatgggaaa aaaacctgga tgggaaaaaa aacttccccg    60
ccaggatttt tacttccccg ccaggatttt tacttccccg ccaggatttt t             111

<210> SEQ ID NO 41
```

<211> LENGTH: 2693
<212> TYPE: DNA
<213> ORGANISM: Artificial Sequence
<220> FEATURE:
<223> OTHER INFORMATION: Synthetic polynucleotide

<400> SEQUENCE: 41

| | | | | | |
|---|---|---|---|---|---:|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctacgta | gccatgctct | 180 |
| aggaagatcg | gaattcgccc | ttaagctagc | tagttattaa | tagtaatcaa | ttacggggtc | 240 |
| attagttcat | agcccatata | tggagttccg | cgttacataa | cttacggtaa | atggcccgcc | 300 |
| tggctgaccg | cccaacgacc | cccgcccatt | gacgtcaata | atgacgtatg | ttcccatagt | 360 |
| aacgccaata | gggactttcc | attgacgtca | atgggtggag | tatttacggt | aaactgccca | 420 |
| cttggcagta | catcaagtgt | atcatatgcc | aagtacgccc | cctattgacg | tcaatgacgg | 480 |
| taaatggccc | gcctggcatt | atgcccagta | catgacctta | tgggactttc | ctacttggca | 540 |
| gtacatctac | gtattagtca | tcgctattac | catggtgatg | cggttttggc | agtacatcaa | 600 |
| tgggcgtgga | tagcggtttg | actcacgggg | atttccaagt | ctccacccca | ttgacgtcaa | 660 |
| tgggagtttg | ttttggcacc | aaaatcaacg | ggactttcca | aaatgtcgta | acaactccgc | 720 |
| cccattgacg | caaatgggcg | gtaggcgtgt | acggtgggag | gtctatataa | gcagagctgg | 780 |
| tttagtgaac | cgtcagatcc | tgcagaagtt | ggtcgtgagg | cactgggcag | gtaagtatca | 840 |
| aggttacaag | acaggtttaa | ggagaccaat | agaaactggg | cttgtcgaga | cagagaagac | 900 |
| tcttgcgttt | ctgataggca | cctattggtc | ttactgacat | ccactttgcc | tttctctcca | 960 |
| caggtgtcca | gcggcgccgcc | atggtgagca | agggcgagga | gctgttcacc | ggggtggtgc | 1020 |
| ccatcctggt | cgagctggac | ggcgacgtaa | acggccacaa | gttcagcgtg | tccggcgagg | 1080 |
| gcgagggcga | tgccacctac | ggcaagctga | ccctgaagtt | catctgcacc | accggcaagc | 1140 |
| tgcccgtgcc | ctggcccacc | ctcgtgacca | ccctgaccta | cggcgtgcag | tgcttcagcc | 1200 |
| gctaccccga | ccacatgaag | cagcacgact | tcttcaagtc | cgccatgccc | gaaggctacg | 1260 |
| tccaggagcg | caccatcttc | ttcaaggacg | acggcaacta | caagacccgc | gccgaggtga | 1320 |
| agttcgaggg | cgacaccctg | gtgaaccgca | tcgagctgaa | gggcatcgac | ttcaaggagg | 1380 |
| acggcaacat | cctggggcac | aagctggagt | acaactacaa | cagccacaac | gtctatatca | 1440 |
| tggccgacaa | gcagaagaac | ggcatcaagg | tgaacttcaa | gatccgccac | aacatcgagg | 1500 |
| acggcagcgt | gcagctcgcc | gaccactacc | agcagaacac | cccatcggc | gacggccccg | 1560 |
| tgctgctgcc | cgacaaccac | tacctgagca | cccagtccgc | cctgagcaaa | gaccccaacg | 1620 |
| agaagcgcga | tcacatggtc | ctgctggagt | tcgtgaccgc | cgccgggatc | actctcggca | 1680 |
| tggacgagct | gtacaagtaa | taagcttgga | tccaatcaac | ctctggatta | caaaatttgt | 1740 |
| gaaagattga | ctggtattct | taactatgtt | gctccttta | cgctatgtgg | atacgctgct | 1800 |
| ttaatgcctt | tgtatcatgc | tattgcttcc | cgtatggctt | tcattttctc | ctccttgtat | 1860 |
| aaatcctggt | tgctgtctct | ttatgaggag | ttgtggcccg | ttgtcaggca | acgtggcgtg | 1920 |
| gtgtgcactg | tgtttgctga | cgcaacccccc | actggttggg | gcattgccac | cacctgtcag | 1980 |
| ctcctttccg | ggactttcgc | tttccccctc | cctattgcca | cggcggaact | catcgccgcc | 2040 |
| tgccttgccc | gctgctggac | aggggctcgg | ctgttgggca | ctgacaattc | cgtggtgttg | 2100 |
| tcggggaaat | catcgtcctt | tccttggctg | ctcgcctgtg | ttgccacctg | gattctgcgc | 2160 |

```
gggacgtcct tctgctacgt cccttcggcc ctcaatccag cggaccttcc ttcccgcggc   2220
ctgctgccgg ctctgcggcc tcttccgcgt cttcgagatc tgcctcgact gtgccttcta   2280
gttgccagcc atctgttgtt tgcccctccc ccgtgccttc cttgaccctg aaggtgcca    2340 ctcccactgt cctttcctaa taaaatgagg aaattgcatc gcattgtctg agtaggtgtc   2400
attctattct gggggggtggg gtggggcagg acagcaaggg ggaggattgg gaagacaata  2460
gcaggcatgc tggggactcg agttaagggc gaattcccga taaggatctt cctagagcat   2520
ggctacgtag ataagtagca tggcgggtta atcattaact acaaggaacc cctagtgatg   2580
gagttggcca ctccctctct gcgcgctcgc tcgctcactg aggccgggcg accaaaggtc   2640
gcccgacgcc cgggctttgc ccgggcggcc tcagtgagcg agcgagcgcg cag          2693
```

<210> SEQ ID NO 42
<211> LENGTH: 2876
<212> TYPE: DNA
<213> ORGANISM: Artificial Sequence
<220> FEATURE:
<223> OTHER INFORMATION: Synthetic polynucleotide

<400> SEQUENCE: 42

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatcg gaattcgccc ttaagctagc tagttattaa tagtaatcaa ttacggggtc   240
attagttcat agcccatata tggagttccg cgttacataa cttacggtaa atggcccgcc   300
tggctgaccg cccaacgacc cccgcccatt gacgtcaata atgacgtatg ttcccatagt   360
aacgccaata gggactttcc attgacgtca atgggtggag tatttacggt aaactgccca   420
cttggcagta catcaagtgt atcatatgcc aagtacgccc cctattgacg tcaatgacgg   480
taaatggccc gcctggcatt atgcccagta catgacctta tgggactttc ctacttggca   540
gtacatctac gtattagtca tcgctattac catggtgatg cggttttggc agtacatcaa   600
tgggcgtgga tagcggtttg actcacgggg atttccaagt ctccacccca ttgacgtcaa   660
tgggagtttg ttttggcacc aaaatcaacg ggactttcca aaatgtcgta caactccgc    720 cccattgacg caaatgggcg gtaggcgtgt acggtgggag gtctatataa gcagagctgg   780
tttagtgaac cgtcagatcc tgcagaagtt ggtcgtgagg cactgggcag gtaagtatca   840
aggttacaag acaggtttaa ggagaccaat agaaactggg cttgtcgaga cagagaagac   900
tcttgcgttt ctgataggca cctattggtc ttactgacat ccactttgcc tttctctcca   960
caggtgtcca gcggccgcc atggtgagca agggcgagga gctgttcacc ggggtggtgc   1020
ccatcctggt cgagctggac ggcgacgtaa acggccacaa gttcagcgtg tccggcgagg  1080
gcgagggcga tgccacctac ggcaagctga cctgaagtt catctgcacc accggcaagc   1140
tgcccgtgcc ctggcccacc ctcgtgacca ccctgaccta cggcgtgcag tgcttcagcc   1200
gctaccccga ccacatgaag cagcacgact tcttcaagtc cgccatgccc gaaggctacg   1260
tccaggagcg caccatcttc ttcaaggacg acggcaacta caagacccgc gccgaggtga   1320
agttcgaggg cgacaccctg gtgaaccgca tcgagctgaa gggcatcgac ttcaaggagg   1380
acggcaacat cctggggcac aagctggagt acaactacaa cagccacaac gtctatatca   1440
tggccgacaa gcagaagaac ggcatcaagg tgaacttcaa gatccgccac aacatcgagg   1500
```

```
acggcagcgt gcagctcgcc gaccactacc agcagaacac ccccatcggc gacggccccg      1560
tgctgctgcc cgacaaccac tacctgagca cccagtccgc cctgagcaaa gaccccaacg      1620
agaagcgcga tcacatggtc ctgctggagt tcgtgaccgc cgccgggatc actctcggca      1680
tggacgagct gtacaagtaa taagcttgga tccaatcaac ctctggatta caaaatttgt      1740
gaaagattga ctggtattct taactatgtt gctcctttta cgctatgtgg atacgctgct      1800
ttaatgcctt tgtatcatgc tattgcttcc cgtatggctt tcattttctc ctccttgtat      1860
aaatcctggt tgctgtctct ttatgaggag ttgtggcccg ttgtcaggca acgtggcgtg      1920
gtgtgcactg tgtttgctga cgcaaccccc actggttggg gcattgccac cacctgtcag      1980
ctcctttccg ggactttcgc tttccccctc cctattgcca cggcggaact catcgccgcc      2040
tgccttgccc gctgctggac aggggctcgg ctgttgggca ctgacaattc cgtggtgttg      2100
tcggggaaat catcgtcctt ccttggctgc tcgcctgtg ttgccacctg gattctgcgc      2160
gggacgtcct tctgctacgt cccttcggcc ctcaatccag cggaccttcc ttcccgcggc      2220
ctgctgccgg ctctgcggcc tcttccgcgt cttcgagatc tgcctcgact gtgccttcta      2280
gttgccagcc atctgttgtt tgcccctccc ccgtgccttc cttgaccctg gaaggtgcca      2340
ctcccactgt cctttcctaa taaaatgagg aaattgcatc gcattgtctg agtaggtgtc      2400
attctattct ggggggtggg gtggggcagg acagcaaggg ggaggattgg gaagacaata      2460
gcaggcatgc tggggaggta cctttagggt tagggttagg gttagggaaa aatttagggt      2520
tagggttagg gttagggaaa aatttagggt tagggttagg gttagggaaa aatgcagcgg      2580
taagttccca tccaggtttt ttgcagcggt aagttcccat ccaggttttt tgcagcggta      2640
agttcccatc caggtttttc tcgagttaag ggcgaattcc cgataaggat cttcctagag      2700
catggctacg tagataagta gcatggcggg ttaatcatta actacaagga accctagtg       2760 atggagttgg ccactccctc tctgcgcgct cgctcgctca ctgaggccgg gcgaccaaag      2820
gtcgcccgac gcccgggctt tgcccgggcg gcctcagtga gcgagcgagc gcgcag          2876
```

<210> SEQ ID NO 43
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 43
tcctgagctt gaagt                                                        15

<210> SEQ ID NO 44
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 44
ttattattat tattattatt atta                                              24

<210> SEQ ID NO 45
<211> LENGTH: 4369
<212> TYPE: DNA
<213> ORGANISM: Artificial Sequence
<220> FEATURE:
<223> OTHER INFORMATION: Synthetic polynucleotide

<400> SEQUENCE: 45

```
aaagcttccc ggggggatct gggccactcc ctctctgcgc gctcgctcgc tcactgaggc    60
cgggcgacca aaggtcgccc gacgcccggg ctttgcccgg gcggcctcag tgagcgagcg   120
agcgcgcaga gagggagtgg ccaactccat cactaggggt tcctggaggg gtggagtcgt   180
gacctaggca tatgccaagt acgcccccta ttgacgtcaa tgacggtaaa tggcccgcct   240
ggcattatgc ccagtacatg accttatggg actttcctac ttggcagtac atctacgtat   300
tagtcatcgc tattaccatg gtgatgcggt tttggcagta catcaatggg cgtggatagc   360
ggtttgactc acggggattt ccaagtctcc accccattga cgtcaatggg agtttgtttt   420
ggcaccaaaa tcaacgggac tttccaaaat gtcgtaacaa ctccgcccca ttgacgcaaa   480
tgggcggtag gcgtgtacgg tgggaggtct atataagcag agctcgttta gtgaaccgtc   540
agatcgcctg gagacgccat ccggactcta aggtaaatat aaaattttta agtgtataat   600
gtgttaaact actgattcta attgtttctc tcttttagat tccaacccttt ggaactgaat   660
tccgcgggcc cgggatccac cggtcgccac catggtgagc aagggcgagg agctgttcac   720
cggggtggtg cccatcctgg tcgagctgga cggcgacgta aacggccaca agttcagcgt   780
gtccggcgag ggcgagggcg atgccaccta cggcaagctg accctgaagt tcatctgcac   840
caccggcaag ctgcccgtgc cctggcccac cctcgtgacc accctgacct acggcgtgca   900
gtgcttcagc cgctaccccg accacatgaa gcagcacgac ttcttcaagt ccgccatgcc   960
cgaaggctac gtccaggagc gcaccatctt cttcaaggac gacggcaact acaagacccg  1020
cgccgaggtg aagttcgagg gcgacaccct ggtgaaccgc atcgagctga agggcatcga  1080
cttcaaggag gacggcaaca tcctggggca caagctggag tacaactaca acagccacaa  1140
cgtctatatc atggccgaca agcagaagaa cggcatcaag gtgaacttca agatccgcca  1200
caacatcgag gacggcagcg tgcagctcgc cgaccactac cagcagaaca cccccatcgg  1260
cgacggcccc gtgctgctgc ccgacaacca ctacctgagc acccagtccg ccctgagcaa  1320
agaccccaac gagaagcgcg atcacatggt cctgctggag ttcgtgaccg ccgccgggat  1380
cactctcggc atggacgagc tgtacaagta aagcggccgc taggcctcac ctgcgatctc  1440
gatgctttat ttgtgaaatt tgtgatgcta ttgctttatt tgtaaccatt ataagctgca  1500
ataaacaagt taacaacaac aattgcattc attttatgtt tcaggttcag ggggaggtgt  1560
gggaggtttt ttaaactagt ccactccctc tctgcgcgct cgtcgctca ctgaggccgg  1620
gcgaccaaag gtcgcccgac gcccgggctt tgcccgggcg gcctcagtga gcgagcgagc  1680
gcgcagagag ggacagatcc gggcccgcat gcgtcgacaa ttcactggcc gtcgttttac  1740
aacgtcgtga ctgggaaaac cctggcgtta cccaacttaa tcgccttgca gcacatcccc  1800
ctttcgccag ctggcgtaat agcgaagagg cccgcaccga tcgcccttcc caacagttgc  1860
gcagcctgaa tggcgaatgg cgcctgatgc ggtattttct ccttacgcat ctgtgcggta  1920
tttcacaccg catatggtgc actctcagta caatctgctc tgatgccgca tagttaagcc  1980
agccccgaca cccgccaaca cccgctgacg cgccctgacg gcttgtctg ctcccggcat   2040
ccgcttacag acaagctgtg accgtctccg ggagctgcat gtgtcagagg ttttcaccgt  2100
catcaccgaa acgcgcgaga cgaaagggcc tcgtgatacg cctatttta taggttaatg   2160
tcatgataat aatggtttct tagacgtcag gtggcacttt tcggggaaat gtgcgcggaa  2220
cccctatttg tttatttttc taaatacatt caaatatgta tccgctcatg agacaataac  2280
cctgataaat gcttcaataa tattgaaaaa ggaagagtat gagtattcaa catttccgtg  2340
```

```
tcgcccttat tccctttttt gcggcatttt gccttcctgt ttttgctcac ccagaaacgc      2400
tggtgaaagt aaaagatgct gaagatcagt tgggtgcacg agtgggttac atcgaactgg      2460
atctcaacag cggtaagatc cttgagagtt tcgccccga agaacgtttt ccaatgatga       2520
gcacttttaa agttctgcta tgtggcgcgg tattatcccg tattgacgcc gggcaagagc      2580
aactcggtcg ccgcatacac tattctcaga atgacttggt tgagtactca ccagtcacag      2640
aaaagcatct tacggatggc atgacagtaa gagaattatg cagtgctgcc ataaccatga      2700
gtgataacac tgcggccaac ttacttctga caacgatcgg aggaccgaag gagctaaccg      2760
cttttttgca caacatgggg gatcatgtaa ctcgccttga tcgttgggaa ccggagctga      2820
atgaagccat accaaacgac gagcgtgaca ccacgatgcc tgtagcaatg gcaacaacgt      2880
tgcgcaaact attaactggc gaactactta ctctagcttc ccggcaacaa ttaatagact      2940
ggatggaggc ggataaagtt gcaggaccac ttctgcgctc ggcccttccg gctggctggt      3000
ttattgctga taaatctgga gccggtgagc gtgggtctcg cggtatcatt gcagcactgg      3060
ggccagatgg taagccctcc cgtatcgtag ttatctacac gacggggagt caggcaacta      3120
tggatgaacg aaatagacag atcgctgaga taggtgcctc actgattaag cattggtaac      3180
tgtcagacca agtttactca tatatacttt agattgattt aaaacttcat ttttaattta      3240
aaaggatcta ggtgaagatc ctttttgata atctcatgac caaatccctt aacgtgagt       3300 tttcgttcca ctgagcgtca gaccccgtag aaaagatcaa aggatcttct tgagatcctt      3360 ttttctgcg cgtaatctgc tgcttgcaaa caaaaaaacc accgctacca gcggtggttt       3420
gtttgccgga tcaagagcta ccaactcttt ttccgaaggt aactggcttc agcagagcgc      3480
agataccaaa tactgttctt ctagtgtagc cgtagttagg ccaccacttc aagaactctg      3540
tagcaccgcc tacatacctc gctctgctaa tcctgttacc agtggctgct gccagtggcg      3600
ataagtcgtg tcttaccggg ttggactcaa gacgatagtt accggataag gcgcagcggt      3660
cgggctgaac ggggggttcg tgcacacagc ccagcttgga gcgaacgacc tacaccgaac      3720
tgagatacct acagcgtgag ctatgagaaa gcgccacgct tcccgaaggg agaaaggcgg      3780
acaggtatcc ggtaagcggc agggtcggaa caggagagcg cacgagggag cttccagggg      3840
gaaacgcctg gtatctttat agtcctgtcg ggtttcgcca cctctgactt gagcgtcgat      3900
ttttgtgatg ctcgtcaggg gggcggagcc tatggaaaaa cgccagcaac gcggcctttt      3960
tacggttcct ggccttttgc tggccttttg ctcacatgtt ctttcctgcg ttatcccctg      4020
attctgtgga taaccgtatt accgcctttg agtgagctga taccgctcgc cgcagccgaa      4080
cgaccgagcg cagcgagtca gtgagcgagg aagcggaaga gcgcccaata cgcaaaccgc      4140
ctctccccgc gcgttggccg attcattaat gcagctggca cgacaggttt cccgactgga      4200
aagcgggcag tgagcgcaac gcaattaatg tgagttagct cactcattag gcaccccagg      4260
ctttacactt tatgcttccg gctcgtatgt tgtgtggaat tgtgagcgga taacaatttc      4320
acacaggaaa cagctatgac catgattacg ccaagctctc gagatctag                  4369
```

<210> SEQ ID NO 46
<211> LENGTH: 4450
<212> TYPE: DNA
<213> ORGANISM: Artificial Sequence
<220> FEATURE:
<223> OTHER INFORMATION: Synthetic polynucleotide

<400> SEQUENCE: 46

```
aaagcttccc gggggggatct gggccactcc ctctctgcgc gctcgctcgc tcactgaggc        60
```

```
cgggcgacca aaggtcgccc gacgcccggg cttttgcccgg gcggcctcag tgagcgagcg    120
agcgcgcaga gagggagtgg ccaactccat cactaggggt tcctggaggg gtggagtcgt    180
gacctaggca tatgccaagt acgcccccta ttgacgtcaa tgacggtaaa tggcccgcct    240
ggcattatgc ccagtacatg acctttatggg actttcctac ttggcagtac atctacgtat    300
tagtcatcgc tattaccatg gtgatgcggt tttggcagta catcaatggg cgtggatagc    360
ggtttgactc acggggattt ccaagtctcc accccattga cgtcaatggg agtttgtttt    420
ggcaccaaaa tcaacgggac tttccaaaat gtcgtaacaa ctccgcccca ttgacgcaaa    480
tgggcggtag gcgtgtacgg tgggaggtct atataagcag agctcgttta gtgaaccgtc    540
agatcgcctg gagacgccat ccggactcta aggtaaatat aaaatttttta agtgtataat    600 gtgttaaact actgattcta attgtttctc tcttttagat tccaaccttt ggaactgaat    660
tccgcgggcc cgggatccac cggtcgccac catggtgagc aagggcgagg agctgttcac    720
cggggtggtg cccatcctgg tcgagctgga cggcgacgta aacggccaca agttcagcgt    780
gtccggcgag ggcgagggcg atgccaccta cggcaagctg accctgaagt tcatctgcac    840
caccggcaag ctgcccgtgc cctggcccac cctcgtgacc accctgacct acggcgtgca    900
gtgcttcagc cgctaccccg accacatgaa gcagcacgac ttcttcaagt ccgccatgcc    960
cgaaggctac gtccaggagc gcaccatctt cttcaaggac gacggcaact acaagacccg    1020
cgccgaggtg aagttcgagg gcgacaccct ggtgaaccgc atcgagctga agggcatcga    1080
cttcaaggag gacggcaaca tcctggggca caagctggag tacaactaca acagccacaa    1140
cgtctatatc atggccgaca agcagaagaa cggcatcaag gtgaacttca agatccgcca    1200
caacatcgag gacggcagcg tgcagctcgc cgaccactac cagcagaaca ccccccatcgg    1260 cgacggcccc gtgctgctgc ccgacaacca ctacctgagc acccagtccg ccctgagcaa    1320 agacccccaac gagaagcgcg atcacatggt cctgctggag ttcgtgaccg ccgccgggat    1380
cactctcggc atggacgagc tgtacaagta aagcggccgc taggcctcac ctgcgatctc    1440
gatgctttat ttgtgaaatt tgtgatgcta ttgctttatt tgtaaccatt ataagctgca    1500
ataaacaagt taacaacaac aattgcattc attttatgtt tcaggttcag ggggaggtgt    1560
gggaggtttt ttaaatcgat tggcgcgcac ccacggcctg aaaaatggcg cgcacccacg    1620
gcctgaaaaa tggcgcgcac ccacggcctg aaaaaactag tccactccct ctctgcgcgc    1680
tcgctcgctc actgaggccg ggcgaccaaa ggtcgcccga cgcccgggct ttgcccgggc    1740
ggcctcagtg agcgagcgag cgcgcagaga gggacagatc cgggcccgca tgcgtcgaca    1800
attcactggc cgtcgtttta caacgtcgtg actgggaaaa ccctggcgtt acccaactta    1860
atcgccttgc agcacatccc cctttcgcca gctggcgtaa tagcgaagag gcccgcaccg    1920
atcgcccttc ccaacagttg cgcagcctga atggcgaatg gcgcctgatg cggtattttc    1980
tccttacgca tctgtgcggt atttcacacc gcatatggtg cactctcagt acaatctgct    2040
ctgatgccgc atagttaagc cagccccgac acccgccaac acccgctgac gcgccctgac    2100
gggcttgtct gctcccggca tccgcttaca gacaagctgt gaccgtctcc gggagctgca    2160
tgtgtcagag gttttcaccg tcatcaccga acgcgcgag acgaaagggc ctcgtgatac    2220
gcctattttt ataggttaat gtcatgataa taatggtttc ttagacgtca ggtggcactt    2280
ttcggggaaa tgtgcgcgga accccctattt gtttattttt ctaaatacat tcaaatatgt    2340
atccgctcat gagacaataa ccctgataaa tgcttcaata atattgaaaa aggaagagta    2400
```

```
tgagtattca acatttccgt gtcgcccttta ttccctttt tgcggcattt tgccttcctg    2460
tttttgctca cccagaaacg ctggtgaaag taaaagatgc tgaagatcag ttgggtgcac    2520
gagtgggtta catcgaactg atctcaaca gcggtaagat ccttgagagt tttcgccccg    2580
aagaacgttt tccaatgatg agcactttta aagttctgct atgtggcgcg gtattatccc    2640
gtattgacgc cgggcaagag caactcggtc gccgcataca ctattctcag aatgacttgg    2700
ttgagtactc accagtcaca gaaaagcatc ttacggatgg catgacagta agagaattat    2760
gcagtgctgc cataaccatg agtgataaca ctgcggccaa cttacttctg acaacgatcg    2820
gaggaccgaa ggagctaacc gcttttttgc acaacatggg gatcatgta actcgccttg    2880 atcgttggga accggagctg aatgaagcca taccaaacga cgagcgtgac accacgatgc    2940
ctgtagcaat ggcaacaacg ttgcgcaaac tattaactgg cgaactactt actctagctt    3000
cccggcaaca attaatagac tggatggagg cggataaagt tgcaggacca cttctgcgct    3060
cggcccttcc ggctggctgg tttattgctg ataaatctgg agccggtgag cgtgggtctc    3120
gcggtatcat tgcagcactg gggccagatg gtaagccctc ccgtatcgta gttatctaca    3180
cgacggggag tcaggcaact atggatgaac gaaatagaca gatcgctgag ataggtgcct    3240
cactgattaa gcattggtaa ctgtcagacc aagtttactc atatatactt tagattgatt    3300
taaaacttca ttttaattt aaaaggatct aggtgaagat cctttttgat aatctcatga    3360
ccaaaatccc ttaacgtgag ttttcgttcc actgagcgtc agaccccgta gaaaagatca    3420
aaggatcttc ttgagatcct ttttttctgc gcgtaatctg ctgcttgcaa acaaaaaaac    3480
caccgctacc agcggtggtt tgtttgccgg atcaagagct accaactctt tttccgaagg    3540
taactggctt cagcagagcg cagataccaa atactgttct tctagtgtag ccgtagttag    3600
gccaccactt caagaactct gtagcaccgc ctacatacct cgctctgcta atcctgttac    3660
cagtggctgc tgccagtggc gataagtcgt gtcttaccgg gttggactca agacgatagt    3720
taccggataa ggcgcagcgg tcgggctgaa cggggggttc gtgcacacag cccagcttgg    3780
agcgaacgac ctacaccgaa ctgagatacc tacagcgtga gctatgagaa agcgccacgc    3840
ttcccgaagg gagaaaggcg gacaggtatc cggtaagcgg cagggtcgga acaggagagc    3900
gcacgaggga gcttccaggg ggaaacgcct ggtatcttta tagtcctgtc gggtttcgcc    3960
acctctgact tgagcgtcga ttttttgtgat gctcgtcagg ggggcggagc ctatggaaaa    4020
acgccagcaa cgcggccttt ttacggttcc tggccttttg ctggccttt gctcacatgt    4080 tctttcctgc gttatcccct gattctgtgg ataaccgtat taccgccttt gagtgagctg    4140
ataccgctcg ccgcagccga acgaccgagc gcagcgagtc agtgagcgag gaagcggaag    4200
agcgcccaat acgcaaaccg cctctccccg cgcgttggcc gattcattaa tgcagctggc    4260
acgacaggtt tcccgactgg aaagcgggca gtgagcgcaa cgcaattaat gtgagttagc    4320
tcactcatta ggcaccccag gctttacact ttatgcttcc ggctcgtatg ttgtgtggaa    4380
ttgtgagcgg ataacaattt cacacaggaa acagctatga ccatgattac gccaagctct    4440
cgagatctag                                                             4450
```

<210> SEQ ID NO 47
<211> LENGTH: 4465
<212> TYPE: DNA
<213> ORGANISM: Artificial Sequence
<220> FEATURE:
<223> OTHER INFORMATION: Synthetic polynucleotide

<400> SEQUENCE: 47

```
aaagcttccc ggggggatct gggccactcc ctctctgcgc gctcgctcgc tcactgaggc    60
cgggcgacca aaggtcgccc gacgcccggg ctttgcccgg gcggcctcag tgagcgagcg   120
agcgcgcaga gagggagtgg ccaactccat cactaggggt tcctggaggg gtggagtcgt   180
gacctaggca tatgccaagt acgcccccta ttgacgtcaa tgacggtaaa tggcccgcct   240
ggcattatgc ccagtacatg accttatggg actttcctac ttggcagtac atctacgtat   300
tagtcatcgc tattaccatg gtgatgcggt tttggcagta catcaatggg cgtggatagc   360
ggtttgactc acggggattt ccaagtctcc accccattga cgtcaatggg agtttgtttt   420
ggcaccaaaa tcaacgggac tttccaaaat gtcgtaacaa ctccgcccca ttgacgcaaa   480
tgggcggtag gcgtgtacgg tgggaggtct atataagcag agctcgttta gtgaaccgtc   540
agatcgcctg gagacgccat ccggactcta aggtaaatat aaaattttta agtgtataat   600
gtgttaaact actgattcta attgtttctc tcttttagat tccaaccttt ggaactgaat   660
tccgcgggcc cggatccac cggtcgccac catggtgagc aagggcgagg agctgttcac   720
cggggtggtg cccatcctgg tcgagctgga cggcgacgta aacggccaca gttcagcgt   780
gtccggcgag ggcgagggcg atgccaccta cggcaagctg accctgaagt tcatctgcac   840
caccggcaag ctgcccgtgc cctggcccac cctcgtgacc accctgacct acggcgtgca   900
gtgcttcagc cgctaccccg accacatgaa gcagcacgac ttcttcaagt ccgccatgcc   960
cgaaggctac gtccaggagc gcaccatctt cttcaaggac gacggcaact acaagacccg  1020
cgccgaggtg aagttcgagg gcgacaccct ggtgaaccgc atcgagctga agggcatcga  1080
cttcaaggag gacggcaaca tcctggggca caagctggag tacaactaca acagccacaa  1140
cgtctatatc atggccgaca gcagaagaa cggcatcaag gtgaacttca gatccgcca  1200
caacatcgag gacggcagcg tgcagctcgc cgaccactac cagcagaaca cccccatcgg  1260
cgacggcccc gtgctgctgc ccgacaacca ctacctgagc acccagtccg ccctgagcaa  1320
agacccccaac gagaagcgcg atcacatggt cctgctggag ttcgtgaccg ccgccgggat  1380
cactctcggc atgacgagc tgtacaagta aagcggccgc taggcctcac ctgcgatctc  1440
gatgctttat ttgtgaaatt tgtgatgcta ttgctttatt tgtaaccatt ataagctgca  1500
ataaacaagt taacaacaac aattgcattc attttatgtt tcaggttcag ggggaggtgt  1560
gggaggtttt ttaaatcgat tttagggtta gggttagggt tagggaaaaa tttagggtta  1620
gggttagggt tagggaaaaa tttagggtta gggttagggt tagggaaaaa actagtccac  1680
tccctctctg cgcgctcgct cgctcactga ggccgggcga ccaaaggtcg cccgacgccc  1740
gggctttgcc cggcggcct cagtgagcga gcgagcgcgc agagagggac agatccgggc  1800
ccgcatgcgt cgacaattca ctggccgtcg ttttacaacg tcgtgactgg gaaaaccctg  1860
gcgttaccca acttaatcgc cttgcagcac atccccttt cgccagctgg cgtaatagcg  1920
aagaggcccg caccgatcgc ccttcccaac agttgcgcag cctgaatggc gaatggcgcc  1980
tgatgcggta ttttctcctt acgcatctgt gcggtatttc acaccgcata tggtgcactc  2040
tcagtacaat ctgctctgat gccgcatagt taagccagcc ccgacacccg ccaacacccg  2100
ctgacgcgcc ctgacgggct tgtctgctcc cggcatccgc ttacagacaa gctgtgaccg  2160
tctccgggag ctgcatgtgt cagaggtttt caccgtcatc accgaaacgc gcgagacgaa  2220
agggcctcgt gatacgccta tttttatagg ttaatgtcat gataataatg gtttcttaga  2280
cgtcaggtgg cacttttcgg ggaaatgtgc gcggaacccc tatttgttta ttttctaaa   2340
```

```
tacattcaaa tatgtatccg ctcatgagac aataaccctg ataaatgctt caataatatt    2400
gaaaaaggaa gagtatgagt attcaacatt tccgtgtcgc ccttattccc ttttttgcgg    2460
cattttgcct tcctgttttt gctcacccag aaacgctggt gaaagtaaaa gatgctgaag    2520
atcagttggg tgcacgagtg ggttacatcg aactggatct caacagcggt aagatccttg    2580
agagttttcg ccccgaagaa cgttttccaa tgatgagcac ttttaaagtt ctgctatgtg    2640
gcgcggtatt atcccgtatt gacgccgggc aagagcaact cggtcgccgc atacactatt    2700
ctcagaatga cttggttgag tactcaccag tcacagaaaa gcatcttacg gatggcatga    2760
cagtaagaga attatgcagt gctgccataa ccatgagtga taacactgcg gccaacttac    2820
ttctgacaac gatcggagga ccgaaggagc taaccgcttt tttgcacaac atggggatc    2880 atgtaactcg ccttgatcgt tgggaaccgg agctgaatga agccatacca aacgacgagc    2940
gtgacaccac gatgcctgta gcaatggcaa caacgttgcg caaactatta actggcgaac    3000
tacttactct agcttcccgg caacaattaa tagactggat ggaggcggat aaagttgcag    3060
gaccacttct gcgctcggcc cttccggctg gctggtttat tgctgataaa tctggagccg    3120
gtgagcgtgg gtctcgcggt atcattgcag cactggggcc agatggtaag ccctcccgta    3180
tcgtagttat ctacacgacg gggagtcagg caactatgga tgaacgaaat agacagatcg    3240
ctgagatagg tgcctcactg attaagcatt ggtaactgtc agaccaagtt tactcatata    3300
tactttagat tgatttaaaa cttcattttt aatttaaaag gatctaggtg aagatccttt    3360
ttgataatct catgaccaaa atcccttaac gtgagttttc gttccactga gcgtcagacc    3420
ccgtagaaaa gatcaaagga tcttcttgag atcctttttt tctgcgcgta atctgctgct    3480
tgcaaacaaa aaaaccaccg ctaccagcgg tggtttgttt gccggatcaa gagctaccaa    3540 ctcttttttcc gaaggtaact ggcttcagca gagcgcagat accaaatact gttcttctag    3600
tgtagccgta gttaggccac cacttcaaga actctgtagc accgcctaca tacctcgctc    3660
tgctaatcct gttaccagtg gctgctgcca gtggcgataa gtcgtgtctt accgggttgg    3720
actcaagacg atagttaccg gataaggcgc agcggtcggg ctgaacgggg ggttcgtgca    3780
cacagcccag cttggagcga acgacctaca ccgaactgag atacctacag cgtgagctat    3840
gagaaagcgc cacgcttccc gaagggagaa aggcggacag gtatccggta agcggcaggg    3900
tcggaacagg agagcgcacg agggagcttc caggggggaaa cgcctggtat ctttatagtc    3960
ctgtcgggtt tcgccacctc tgacttgagc gtcgattttt gtgatgctcg tcagggggc    4020 ggagcctatg gaaaaacgcc agcaacgcgg cctttttacg gttcctggcc ttttgctggc    4080
cttttgctca catgttcttt cctgcgttat ccctgattc tgtggataac cgtattaccg    4140
cctttgagtg agctgatacc gctcgccgca gccgaacgac cgagcgcagc gagtcagtga    4200
gcgaggaagc ggaagagcgc ccaatacgca aaccgcctct ccccgcgcgt tggccgattc    4260
attaatgcag ctggcacgac aggtttcccg actggaaagc gggcagtgag cgcaacgcaa    4320
ttaatgtgag ttagctcact cattaggcac cccaggcttt acactttatg cttccggctc    4380
gtatgttgtg tggaattgtg agcggataac aatttcacac aggaaacagc tatgaccatg    4440
attacgccaa gctctcgaga tctag                                         4465
```

<210> SEQ ID NO 48
<211> LENGTH: 4465
<212> TYPE: DNA
<213> ORGANISM: Artificial Sequence
<220> FEATURE:
<223> OTHER INFORMATION: Synthetic polynucleotide

<400> SEQUENCE: 48

```
aaagcttccc gggggatct gggccactcc ctctctgcgc gctcgctcgc tcactgaggc    60
cgggcgacca aaggtcgccc gacgcccggg ctttgcccgg gcggcctcag tgagcgagcg   120
agcgcgcaga gagggagtgg ccaactccat cactaggggt tcctggaggg gtggagtcgt   180
gacctaggtt tagggttagg gttagggtta gggaaaaatt tagggttagg gttagggtta   240
gggaaaaatt tagggttagg gttagggtta gggaaaaacc taggcatatg ccaagtacgc   300
cccctattga cgtcaatgac ggtaaatggc ccgcctggca ttatgcccag tacatgacct   360
tatgggactt tcctacttgg cagtacatct acgtattagt catcgctatt accatggtga   420
tgcggttttg gcagtacatc aatgggcgtg gatagcggtt tgactcacgg ggatttccaa   480
gtctccaccc cattgacgtc aatgggagtt tgttttggca ccaaaatcaa cgggactttc   540
caaaatgtcg taacaactcc gccccattga cgcaaatggg cggtaggcgt gtacggtggg   600
aggtctatat aagcagagct cgtttagtga accgtcagat cgcctggaga cgccatccgg   660
actctaaggt aaatataaaa ttttttaagtg tataatgtgt taaactactg attctaattg   720
tttctctctt ttagattcca acctttggaa ctgaattccg cgggcccggg atccaccggt   780
cgccaccatg gtgagcaagg gcgaggagct gttcaccggg gtggtgccca tcctggtcga   840
gctggacggc gacgtaaacg gccacaagtt cagcgtgtcc ggcgagggcg agggcgatgc   900
cacctacggc aagctgaccc tgaagttcat ctgcaccacc ggcaagctgc ccgtgccctg   960
gcccaccctc gtgaccaccc tgacctacgg cgtgcagtgc ttcagccgct accccgacca  1020
catgaagcag cacgacttct tcaagtccgc catgcccgaa ggctacgtcc aggagcgcac  1080
catcttcttc aaggacgacg gcaactacaa gacccgcgcc gaggtgaagt tcgagggcga  1140
caccctggtg aaccgcatcg agctgaaggg catcgacttc aaggaggacg gcaacatcct  1200
ggggcacaag ctggagtaca actacaacag ccacaacgtc tatatcatgg ccgacaagca  1260
gaagaacggc atcaaggtga acttcaagat ccgccacaac atcgaggacg gcagcgtgca  1320
gctcgccgac cactaccagc agaacacccc catcggcgac ggccccgtgc tgctgcccga  1380
caaccactac ctgagcaccc agtccgccct gagcaaagac cccaacgaga gcgcgatca  1440
catggtcctg ctggagttcg tgaccgccgc cgggatcact ctcggcatgg acgagctgta  1500
caagtaaagc ggccgctagg cctcacctgc gatctcgatg ctttatttgt gaaatttgtg  1560
atgctattgc tttatttgta accattataa gctgcaataa acaagttaac aacaacaatt  1620
gcattcattt tatgtttcag gttcagggggg aggtgtggga ggttttttaa actagtccac  1680
tccctctctg cgcgctcgct cgctcactga ggccgggcga ccaaaggtcg cccgacgccc  1740
gggctttgcc cgggcggcct cagtgagcga gcgagcgcgc agagagggac agatccgggc  1800
ccgcatgcgt cgacaattca ctggccgtcg ttttacaacg tcgtgactgg gaaaaccctg  1860
gcgttaccca acttaatcgc cttgcagcac atccccctttt cgccagctgg cgtaatagcg  1920
aagaggcccg caccgatcgc ccttcccaac agttgcgcag cctgaatggc gaatggcgcc  1980
tgatgcggta ttttctcctt acgcatctgt gcggtatttc acaccgcata tggtgcactc  2040
tcagtacaat ctgctctgat gccgcatagt taagccagcc ccgacacccg ccaacacccg  2100
ctgacgcgcc ctgacgggct tgtctgctcc cggcatccgc ttacagacaa gctgtgaccg  2160
tctccgggag ctgcatgtgt cagaggtttt caccgtcatc accgaaacgc gcgagacgaa  2220
agggcctcgt gatacgccta tttttatagg ttaatgtcat gataataatg gtttcttaga  2280
```

```
cgtcaggtgg cactttcgg ggaaatgtgc gcggaacccc tatttgttta tttttctaaa    2340
tacattcaaa tatgtatccg ctcatgagac aataaccctg ataaatgctt caataatatt    2400
gaaaaaggaa gagtatgagt attcaacatt tccgtgtcgc ccttattccc ttttttgcgg    2460
cattttgcct tcctgttttt gctcacccag aaacgctggt gaaagtaaaa gatgctgaag    2520
atcagttggg tgcacgagtg ggttacatcg aactggatct caacagcggt aagatccttg    2580
agagttttcg ccccgaagaa cgttttccaa tgatgagcac ttttaaagtt ctgctatgtg    2640
gcgcggtatt atcccgtatt gacgccgggc aagagcaact cggtcgccgc atacactatt    2700
ctcagaatga cttggttgag tactcaccag tcacagaaaa gcatcttacg gatggcatga    2760
cagtaagaga attatgcagt gctgccataa ccatgagtga taacactgcg gccaacttac    2820
ttctgacaac gatcggagga ccgaaggagc taaccgcttt tttgcacaac atggggatc     2880
atgtaactcg ccttgatcgt tgggaaccgg agctgaatga agccatacca aacgacgagc    2940
gtgacaccac gatgcctgta gcaatggcaa caacgttgcg caaactatta actggcgaac    3000
tacttactct agcttcccgg caacaattaa tagactggat ggaggcggat aaagttgcag    3060
gaccacttct gcgctcggcc cttccggctg gctggtttat tgctgataaa tctggagccg    3120
gtgagcgtgg gtctcgcggt atcattgcag cactggggcc agatggtaag ccctcccgta    3180
tcgtagttat ctacacgacg gggagtcagg caactatgga tgaacgaaat agacagatcg    3240
ctgagatagg tgcctcactg attaagcatt ggtaactgtc agaccaagtt tactcatata    3300
tactttagat tgatttaaaa cttcattttt aatttaaaag gatctaggtg aagatccttt    3360
ttgataatct catgaccaaa atcccttaac gtgagttttc gttccactga gcgtcagacc    3420
ccgtagaaaa gatcaaagga tcttcttgag atcctttttt tctgcgcgta atctgctgct    3480
tgcaaacaaa aaaaccaccg ctaccagcgg tggtttgttt gccggatcaa gagctaccaa    3540
ctctttttcc gaaggtaact ggcttcagca gagcgcagat accaaatact gttcttctag    3600
tgtagccgta gttaggccac cacttcaaga actctgtagc accgcctaca tacctcgctc    3660
tgctaatcct gttaccagtg gctgctgcca gtggcgataa gtcgtgtctt accgggttgg    3720
actcaagacg atagttaccg gataaggcgc agcggtcggg ctgaacgggg gttcgtgca    3780
cacagcccag cttggagcga acgacctaca ccgaactgag atacctacag cgtgagctat    3840
gagaaagcgc cacgcttccc gaagggagaa aggcggacag gtatccggta agcggcaggg    3900
tcggaacagg agagcgcacg agggagcttc caggggggaaa cgcctggtat ctttatagtc    3960
ctgtcgggtt tcgccacctc tgacttgagc gtcgatttt gtgatgctcg tcaggggggc    4020
ggagcctatg gaaaaacgcc agcaacgcgg cctttttacg gttcctggcc ttttgctggc    4080
cttttgctca catgttcttt cctgcgttat cccctgattc tgtggataac cgtattaccg    4140
cctttgagtg agctgatacc gctcgccgca gccgaacgac cgagcgcagc gagtcagtga    4200
gcgaggaagc ggaagagcgc ccaatacgca aaccgcctct ccccgcgcgt tggccgattc    4260
attaatgcag ctggcacgac aggtttcccg actggaaagc gggcagtgag cgcaacgcaa    4320
ttaatgtgag ttagctcact cattaggcac cccaggcttt acactttatg cttccggctc    4380
gtatgttgtg tggaattgtg agcggataac aatttcacac aggaaacagc tatgaccatg    4440
attacgccaa gctctcgaga tctag                                          4465
```

<210> SEQ ID NO 49
<211> LENGTH: 6940
<212> TYPE: DNA
<213> ORGANISM: Artificial Sequence
<220> FEATURE:
<223> OTHER INFORMATION: Synthetic polynucleotide

<400> SEQUENCE: 49

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagcg gcctcggcct ctgcataaat aaaaaaaatt agtcagccat gagcttggcc     240
cattgcatac gttgtatcca tatcataata tgtacattta tattggctca tgtccaacat     300
taccgccatg ttgacattga ttattgacta gttattaata gtaatcaatt acggggtcat     360
tagttcatag cccatatatg gagttccgcg ttacataact tacggtaaat ggcccgcctg     420
gctgaccgcc caacgacccc cgcccattga cgtcaataat gacgtatgtt cccatagtaa     480
cgccaatagg gactttccat tgacgtcaat gggtggagta tttacggtaa actgcccact     540
tggcagtaca tcaagtgtat catatgccaa gtacgccccc tattgacgtc aatgacggta     600
aatgcccgc ctggcattat gcccagtaca tgaccttatg gactttcct acttggcagt      660
acatctacgt attagtcatc gctattacca tggtgatgcg gttttggcag tacatcaatg     720
ggcgtggata gcggtttgac tcacggggat ttccaagtct ccaccccatt gacgtcaatg     780
ggagtttgtt ttggcaccaa atcaacggg actttccaaa atgtcgtaac aactccgccc      840
cattgacgca aatgggcggt aggcgtgtac ggtgggaggt ctatataagc agagctcgtt     900
tagtgaaccg tcagatcgcc tggagacgcc atccacgctg ttttgacctc catagaagac     960
accgggaccg atccagcctc ccctcgaagc tgatcctgag aacttcaggg tgagtctatg    1020
ggacccttga tgttttcttt cccttcttt tctatggtta agttcatgtc ataggaaggg     1080
gagaagtaac agggtacaca tattgaccaa atcagggtaa ttttgcattt gtaattttaa    1140
aaaatgcttt cttcttttaa tatactttt tgtttatctt atttctaata ctttccctaa     1200
tctctttctt tcagggcaat aatgatacaa tgtatcatgc ctctttgcac cattctaaag    1260
aataacagtg ataatttctg ggttaaggca atagcaatat ttctgcatat aaatatttct    1320
gcatataaat tgtaactgat gtaagaggtt tcatattgct aatagcagct acaatccagc    1380
taccattctg cttttatttt atggttggga taaggctgga ttattctgag tccaagctag    1440
gccctttgc taatcatgtt catacctctt atcttcctcc cacagctcct gggcaacgtg     1500
ctggtctgtg tgctggccca tcactttggc aaagaattcc gcgggccgg gatccaccgg     1560
tcgccaccat ggtgagcaag ggcgaggagc tgttcaccgg ggtggtgccc atcctggtcg    1620
agctggacgg cgacgtaaac ggccacaagt tcagcgtgtc cggcgagggc gagggcgatg    1680
ccacctacgg caagctgacc ctgaagttca tctgcaccac cggcaagctg cccgtgccct    1740
ggcccaccct cgtgaccacc ctgacctacg gcgtgcagtg cttcagccgc taccccgacc    1800
acatgaagca gcacgacttc ttcaagtccg ccatgcccga aggctacgtc caggagcgca    1860
ccatcttctt caaggacgac ggcaactaca agacccgcgc cgaggtgaag ttcgagggcg    1920
acaccctggt gaaccgcatc gagctgaagg gcatcgactt caaggaggac ggcaacatcc    1980
tggggcacaa gctggagtac aactacaaca gccacaacgt ctatatcatg gccgacaagc    2040
agaagaacgg catcaaggtg aacttcaaga tccgccacaa catcgaggac ggcagcgtgc    2100
agctcgccga ccactaccag cagaacaccc ccatcggcga cggccccgtg ctgctgcccg    2160
acaaccacta cctgagcacc cagtccgccc tgagcaaaga ccccaacgag aagcgcgatc    2220
```

-continued

| | |
|---|---|
| acatggtcct gctggagttc gtgaccgccg ccgggatcac tctcggcatg gacgagctgt | 2280 |
| acaagtaaag cggccgctct agaggatcca agcttatcga taccgtcgac ctcgagggcc | 2340 |
| cagatctaat tcaccccacc agtgcaggct gcctatcaga aagtggtggc tggtgtggct | 2400 |
| aatgccctgg cccacaagta tcactaagct cgctttcttg ctgtccaatt tctattaaag | 2460 |
| gttcctttgt tccctaagtc caactactaa actgggggat attatgaagg gccttgagca | 2520 |
| tctggattct gcctaataaa aaacatttat tttcattgca atgatgtatt taaattattt | 2580 |
| ctgaatattt tactaaaaag ggaatgtggg aggtcagtgc atttaaaaca taagaaatg | 2640 |
| aagagctagt tcaaaccttg ggaaaataca ctatatctta aactccatga agaaggtga | 2700 |
| ggctgcaaac agctaatgca cattggcaac agcccctgat gcctatgcct tattcatccc | 2760 |
| tcagaaaagg attcaagtag aggcttgatt tggaggttaa agttttgcta tgctgtattt | 2820 |
| tacattactt attgttttag ctgtcctcat gaatgtcttt tcactaccca tttgcttatc | 2880 |
| ctgcatctct cagccttgac tccactcagt tctcttgctt agagatacca cctttcccct | 2940 |
| gaagtgttcc ttccatgttt tacggcgaga tggtttctcc tcgcctggcc actcagcctt | 3000 |
| agttgtctct gttgtcttat agaggtctac ttgaagaagg aaaaacaggg ggcatggttt | 3060 |
| gactgtcctg tgagcccttc ttccctgcct ccccactca cagtgacccg gaatccctcg | 3120 |
| acatctagag catggctacg tagataagta gcatggcggg ttaatcatta actacaagga | 3180 |
| accccctagt atggagttgg ccactccctc tctgcgcgct cgctcgctca ctgaggccgg | 3240 |
| gcgaccaaag gtcgcccgac gcccgggctt tgcccgggcg gcctcagtga gcgagcgagc | 3300 |
| gcgccagctg gcgtaatagc gaagaggccc gcaccgatcg cccttcccaa cagttgcgca | 3360 |
| gcctgaatgg cgaatggaat tccagacgat tgagcgtcaa aatgtaggta tttccatgag | 3420 |
| cgttttccct gttgcaatgg ctggcggtaa tattgttctg gatattacca gcaaggccga | 3480 |
| tagtttgagt tcttctactc aggcaagtga tgttattact aatcaaagaa gtattgcgac | 3540 |
| aacggttaat ttgcgtgatg gacagactct tttactcggt ggcctcactg attataaaaa | 3600 |
| cacttctcag gattctggcg taccgttcct gtctaaaatc cctttaatcg gcctcctgtt | 3660 |
| tagctcccgc tctgattcta acgaggaaag cacgttatac gtgctcgtca aagcaaccat | 3720 |
| agtacgcgcc ctgtagcggc gcattaagcg cggcgggtgt ggtggttacg cgcagcgtga | 3780 |
| ccgctacact tgccagcgcc ctagcgcccg ctcctttcgc tttcttccct tcctttctcg | 3840 |
| ccacgttcgc cggctttccc cgtcaagctc taaatcgggg gctccctta gggttccgat | 3900 |
| ttagtgcttt acggcacctc gaccccaaaa aacttgatta gggtgatggt tcacgtagtg | 3960 |
| ggccatcgcc ctgatagacg gttttcgcc ctttgacgtt ggagtccacg ttctttaata | 4020 |
| gtggactctt gttccaaact ggaacaacac tcaaccctat ctcggtctat tcttttgatt | 4080 |
| tataagggat tttgccgatt tcggcctatt ggttaaaaaa tgagctgatt taacaaaaat | 4140 |
| ttaacgcgaa ttttaacaaa atattaacgt ttacaattta aatatttgct tatacaatct | 4200 |
| tcctgttttt ggggcttttc tgattatcaa ccggggtaca tatgattgac atgctagttt | 4260 |
| tacgattacc gttcatcgat tctcttgttt gctccagact ctcaggcaat gacctgatag | 4320 |
| cctttgtaga gacctctcaa aaatagctac cctctccggc atgaatttat cagctagaac | 4380 |
| ggttgaatat catattgatg gtgatttgac tgtctccggc ctttctcacc cgtttgaatc | 4440 |
| tttacctaca cattactcag gcattgcatt taaaatatat gagggttcta aaaattttta | 4500 |
| tccttgcgtt gaaataaagg cttctcccgc aaaagtatta cagggtcata atgttttgg | 4560 |
| tacaaccgat ttagctttat gctctgaggc tttattgctt aattttgcta attctttgcc | 4620 |

```
ttgcctgtat gatttattgg atgttggaat tcctgatgcg gtattttctc cttacgcatc    4680
tgtgcggtat ttcacaccgc atatggtgca ctctcagtac aatctgctct gatgccgcat    4740
agttaagcca gccccgacac ccgccaacac ccgctgacgc gccctgacgg gcttgtctgc    4800
tcccggcatc cgcttacaga caagctgtga ccgtctccgg gagctgcatg tgtcagaggt    4860
tttcaccgtc atcaccgaaa cgcgcgagac gaaagggcct cgtgatacgc ctatttttat    4920
aggttaatgt catgataata atggtttctt agacgtcagg tggcactttt cggggaaatg    4980
tgcgcggaac ccctatttgt ttatttttct aaatacattc aaatatgtat ccgctcatga    5040
gacaataacc ctgataaatg cttcaataat attgaaaaag gaagagtatg agtattcaac    5100
atttccgtgt cgcccttatt cccttttttg cggcattttg ccttcctgtt tttgctcacc    5160
cagaaacgct ggtgaaagta aaagatgctg aagatcagtt gggtgcacga gtgggttaca    5220
tcgaactgga tctcaacagc ggtaagatcc ttgagagttt tcgccccgaa gaacgttttc    5280
caatgatgag cacttttaaa gttctgctat gtggcgcggt attatcccgt attgacgccg    5340
ggcaagagca actcggtcgc cgcatacact attctcagaa tgacttggtt gagtactcac    5400
cagtcacaga aaagcatctt acggatggca tgacagtaag agaattatgc agtgctgcca    5460
taaccatgag tgataacact gcggccaact tacttctgac aacgatcgga ggaccgaagg    5520
agctaaccgc ttttttgcac aacatggggg atcatgtaac tcgccttgat cgttgggaac    5580
cggagctgaa tgaagccata ccaaacgacg agcgtgacac cacgatgcct gtagcaatgg    5640
caacaacgtt gcgcaaacta ttaactggcg aactacttac tctagcttcc cggcaacaat    5700
taatagactg gatggaggcg gataaagttg caggaccact tctgcgctcg gcccttccgg    5760
ctggctggtt tattgctgat aaatctggag ccggtgagcg tgggtctcgc ggtatcattg    5820
cagcactggg gccagatggt aagccctccc gtatcgtagt tatctacacg acggggagtc    5880
aggcaactat ggatgaacga atagacaga tcgctgagat aggtgcctca ctgattaagc    5940
attggtaact gtcagaccaa gtttactcat atatacttta gattgattta aaacttcatt    6000
tttaatttaa aaggatctag gtgaagatcc ttttttgataa tctcatgacc aaaatccctt    6060
aacgtgagtt ttcgttccac tgagcgtcag accccgtaga aaagatcaaa ggatcttctt    6120
gagatccttt ttttctgcgc gtaatctgct gcttgcaaac aaaaaaacca ccgctaccag    6180
cggtggtttg tttgccggat caagagctac caactctttt tccgaaggta actggcttca    6240
gcagagcgca gataccaaat actgtccttc tagtgtagcc gtagttaggc caccacttca    6300
agaactctgt agcaccgcct acatacctcg ctctgctaat cctgttacca gtggctgctg    6360
ccagtggcga taagtcgtgt cttaccgggt tggactcaag acgatagtta ccggataagg    6420
cgcagcggtc gggctgaacg gggggttcgt gcacacagcc cagcttggag cgaacgacct    6480
acaccgaact gagatacctac agcgtgagc tatgagaaag cgccacgctt cccgaaggga    6540
gaaaggcgga caggtatccg gtaagcggca gggtcggaac aggagagcgc acgagggagc    6600
ttccagggggg aaacgcctgg tatctttata gtcctgtcgg gtttcgccac ctctgacttg    6660
agcgtcgatt tttgtgatgc tcgtcagggg ggcggagcct atggaaaaac gccagcaacg    6720
cggccttttt acgttcctg gccttttgct ggccttttgc tcacatgttc tttcctgcgt    6780
tatcccctga ttctgtggat aaccgtatta ccgcctttga gtgagctgat accgctcgcc    6840
gcagccgaac gaccgagcgc agcgagtcag tgagcgagga agcggaagag cgcccaatac    6900
gcaaaccgcc tctccccgcg cgttggccga ttcattaatg                          6940
```

<210> SEQ ID NO 50
<211> LENGTH: 7257
<212> TYPE: DNA
<213> ORGANISM: Artificial Sequence
<220> FEATURE:
<223> OTHER INFORMATION: Synthetic polynucleotide

<400> SEQUENCE: 50

| | | | | | |
|---|---|---|---|---|---|
| cagcagctgc | gcgctcgctc | gctcactgag | gccgcccggg | caaagcccgg | gcgtcgggcg | 60 |
| acctttggtc | gcccggcctc | agtgagcgag | cgagcgcgca | gagagggagt | ggccaactcc | 120 |
| atcactaggg | gttccttgta | gttaatgatt | aacccgccat | gctacttatc | tacgtagcca | 180 |
| tgctctagcg | gcctcggcct | ctgcataaat | aaaaaaaatt | agtcagccat | gagcttggcc | 240 |
| cattgcatac | gttgtatcca | tatcataata | tgtacattta | tattggctca | tgtccaacat | 300 |
| taccgccatg | ttgacattga | ttattgacta | gttattaata | gtaatcaatt | acgggtcat | 360 |
| tagttcatag | cccatatatg | gagttccgcg | ttacataact | tacggtaaat | ggcccgcctg | 420 |
| gctgaccgcc | caacgacccc | cgcccattga | cgtcaataat | gacgtatgtt | cccatagtaa | 480 |
| cgccaatagg | gactttccat | tgacgtcaat | gggtggagta | tttacggtaa | actgcccact | 540 |
| tggcagtaca | tcaagtgtat | catatgccaa | gtacgccccc | tattgacgtc | aatgacggta | 600 |
| aatggcccgc | ctggcattat | gcccagtaca | tgaccttatg | ggactttcct | acttggcagt | 660 |
| acatctacgt | attagtcatc | gctattacca | tggtgatgcg | gttttggcag | tacatcaatg | 720 |
| ggcgtggata | gcggtttgac | tcacggggat | ttccaagtct | ccaccccatt | gacgtcaatg | 780 |
| ggagtttgtt | ttggcaccaa | aatcaacggg | actttccaaa | atgtcgtaac | aactccgccc | 840 |
| cattgacgca | aatgggcggt | aggcgtgtac | ggtgggaggt | ctatataagc | agagctcgtt | 900 |
| tagtgaaccg | tcagatcgcc | tggagacgcc | atccacgctg | ttttgacctc | catagaagac | 960 |
| accgggaccg | atccagcctc | ccctcgaagc | tgatcctgag | aacttcaggg | tgagtctatg | 1020 |
| ggacccttga | tgttttcttt | ccccttcttt | tctatggtta | agttcatgtc | ataggaaggg | 1080 |
| gagaagtaac | agggtacaca | tattgaccaa | atcagggtaa | ttttgcattt | gtaattttaa | 1140 |
| aaaatgcttt | cttcttttaa | tatacttttt | tgtttatctt | atttctaata | ctttccctaa | 1200 |
| tctctttctt | tcagggcaat | aatgatacaa | tgtatcatgc | ctctttgcac | cattctaaag | 1260 |
| aataacagtg | ataatttctg | ggttaaggca | atagcaatat | ttctgcatat | aaatatttct | 1320 |
| gcatataaat | tgtaactgat | gtaagaggtt | tcatattgct | aatagcagct | acaatccagc | 1380 |
| taccattctg | cttttatttt | atggttggga | taaggctgga | ttattctgag | tccaagctag | 1440 |
| gcccttttgc | taatcatgtt | catacctctt | atcttcctcc | cacagctcct | gggcaacgtg | 1500 |
| ctggtctgtg | tgctggccca | tcactttggc | aaagaattcc | gcgggccgg | gatccaccgg | 1560 |
| tcgccaccat | ggtgagcaag | ggcgaggagc | tgttcaccgg | ggtggtgccc | atcctggtcg | 1620 |
| agctggacgg | cgacgtaaac | ggccacaagt | tcagcgtgtc | cggcgagggc | gagggcgatg | 1680 |
| ccacctacgg | caagctgacc | ctgaagttca | tctgcaccac | cggcaagctg | cccgtgccct | 1740 |
| ggcccaccct | cgtgaccacc | ctgacctacg | gcgtgcagtg | cttcagccgc | taccccgacc | 1800 |
| acatgaagca | gcacgacttc | ttcaagtccg | ccatgcccga | aggctacgtc | caggagcgca | 1860 |
| ccatcttctt | caaggacgac | ggcaactaca | agacccgcgc | cgaggtgaag | ttcgagggcg | 1920 |
| acaccctggt | gaaccgcatc | gagctgaagg | gcatcgactt | caaggaggac | ggcaacatcc | 1980 |
| tggggcacaa | gctggagtac | aactacaaca | gccacaacgt | ctatatcatg | gccgacaagc | 2040 |
| agaagaacgg | catcaaggtg | aacttcaaga | tccgccacaa | catcgaggac | ggcagcgtgc | 2100 |

```
agctcgccga ccactaccag cagaacaccc ccatcggcga cggccccgtg ctgctgcccg    2160
acaaccacta cctgagcacc cagtccgccc tgagcaaaga ccccaacgag aagcgcgatc    2220
acatggtcct gctggagttc gtgaccgccg ccgggatcac tctcggcatg gacgagctgt    2280
acaagtaaag cggccgctct agaggatcca agcttatcga taccgtcgac ctcgagggcc    2340
cagatctaat tcaccccacc agtgcaggct gcctatcaga aagtggtggc tggtgtggct    2400
aatgccctgg cccacaagta tcactaagct cgctttcttg ctgtccaatt tctattaaag    2460
gttcctttgt tccctaagtc caactactaa actgggggat attatgaagg ccttgagca    2520 tctggattct gcctaataaa aaacatttat tttcattgca atgatgtatt taaattattt    2580
ctgaatattt tactaaaaag ggaatgtggg aggtcagtgc atttaaaaca taaagaaatg    2640
aagagctagt tcaaaccttg ggaaaataca ctatatctta aactccatga agaaggtga    2700 ggctgcaaac agctaatgca cattggcaac agcccctgat gcctatgcct tattcatccc    2760
tcagaaaagg attcaagtag aggcttgatt tggaggttaa agttttgcta tgctgtattt    2820
tacattactt attgttttag ctgtcctcat gaatgtcttt tcactaccca tttgcttatc    2880
ctgcatctct cagccttgac tccactcagt tctcttgctt agagatacca cctttcccct    2940
gaagtgttcc ttccatgttt tacggcgaga tggtttctcc tcgcctggcc actcagcctt    3000
agttgtctct gttgtcttat agaggtctac ttgaagaagg aaaaacaggg ggcatggttt    3060
gactgtcctg tgagcccttc ttccctgcct cccccactca cagtgacccg gaatccctcg    3120
acaggtacct ttagggttag ggttagggtt agggaaaaat ttagggttag ggttagggtt    3180
agggaaaaat ttagggttag ggttagggtt agggaaaaat ttagggttag ggttagggtt    3240
agggaaaaat ttagggttag ggttagggtt agggaaaaac cctaacccta accctaaccc    3300 taaattttt ccctaaccct aaccctaacc ctaaattttt tccctaaccc taaccctaac    3360
cctaaatttt ttccctaacc ctaaccctaa ccctaaattt tttccctaac cctaacccta    3420
accctaaatt ttttgctagc tctagagcat ggctacgtag ataagtagca tggcgggtta    3480
atcattaact acaaggaacc cctagtgatg gagttggcca ctccctctct gcgcgctcgc    3540
tcgctcactg aggccgggcg accaaaggtc gcccgacgcc cgggctttgc ccgggcggcc    3600
tcagtgagcg agcgagcgcg ccagctggcg taatagcgaa gaggcccgca ccgatcgccc    3660
ttcccaacag ttgcgcagcc tgaatggcga atggaattcc agacgattga gcgtcaaaat    3720
gtaggtattt ccatgagcgt ttttcctgtt gcaatggctg gcggtaatat tgttctggat    3780
attaccagca aggccgatag tttgagttct tctactcagg caagtgatgt tattactaat    3840
caaagaagta ttgcgacaac ggttaatttg cgtgatggac agactctttt actcggtggc    3900
ctcactgatt ataaaaacac ttctcaggat tctggcgtac cgttcctgtc taaaatccct    3960
ttaatcggcc tcctgtttag ctcccgctct gattctaacg aggaaagcac gttatacgtg    4020
ctcgtcaaag caaccatagt acgcgccctg tagcggcgca ttaagcgcgg cgggtgtggt    4080
ggttacgcgc agcgtgaccg ctacacttgc cagcgcccta gcgcccgctc ctttcgcttt    4140
cttcccttcc tttctcgcca cgttcgccgg ctttccccgt caagctctaa atcgggggct    4200
ccctttaggg ttccgattta gtgctttacg gcacctcgac cccaaaaaac ttgattaggg    4260
tgatggttca cgtagtgggc catcgccctg atagacggtt tttcgccctt gacgttgga    4320 gtccacgttc tttaatagtg gactcttgtt ccaaactgga acaacactca acctatctc    4380 ggtctattct tttgatttat aagggatttt gccgatttcg gcctattggt taaaaatga    4440
```

| | | | | | |
|---|---|---|---|---|---|
| gctgatttaa | caaaaattta | acgcgaattt | taacaaaata | ttaacgttta | caatttaaat | 4500 |
| atttgcttat | acaatcttcc | tgttttgg | gcttttctga | ttatcaaccg | gggtacatat | 4560 |
| gattgacatg | ctagttttac | gattaccgtt | catcgattct | cttgtttgct | ccagactctc | 4620 |
| aggcaatgac | ctgatagcct | ttgtagagac | ctctcaaaaa | tagctaccct | ctccggcatg | 4680 |
| aatttatcag | ctagaacggt | tgaatatcat | attgatggtg | atttgactgt | ctccggcctt | 4740 |
| tctcacccgt | ttgaatcttt | acctacacat | tactcaggca | ttgcatttaa | aatatatgag | 4800 |
| ggttctaaaa | attttatcc | ttgcgttgaa | ataaaggctt | ctcccgcaaa | agtattacag | 4860 |
| ggtcataatg | ttttggtac | aaccgattta | gctttatgct | ctgaggcttt | attgcttaat | 4920 |
| tttgctaatt | ctttgccttg | cctgtatgat | ttattggatg | ttggaattcc | tgatgcggta | 4980 |
| tttctcctt | acgcatctgt | gcggtatttc | acaccgcata | tggtgcactc | tcagtacaat | 5040 |
| ctgctctgat | gccgcatagt | taagccagcc | ccgacacccg | ccaacacccg | ctgacgcgcc | 5100 |
| ctgacgggct | tgtctgctcc | cggcatccgc | ttacagacaa | gctgtgaccg | tctccgggag | 5160 |
| ctgcatgtgt | cagaggtttt | caccgtcatc | accgaaacgc | gcgagacgaa | agggcctcgt | 5220 |
| gatacgccta | tttttatagg | ttaatgtcat | gataataatg | gtttcttaga | cgtcaggtgg | 5280 |
| cacttttcgg | ggaaatgtgc | gcggaacccc | tatttgttta | tttttctaaa | tacattcaaa | 5340 |
| tatgtatccg | ctcatgagac | aataaccctg | ataaatgctt | caataatatt | gaaaaggaa | 5400 |
| gagtatgagt | attcaacatt | tccgtgtcgc | ccttattccc | ttttttgcgg | cattttgcct | 5460 |
| tcctgttttt | gctcacccag | aaacgctggt | gaaagtaaaa | gatgctgaag | atcagttggg | 5520 |
| tgcacgagtg | ggttacatcg | aactggatct | caacagcggt | aagatccttg | agagttttcg | 5580 |
| ccccgaagaa | cgttttccaa | tgatgagcac | ttttaaagtt | ctgctatgtg | gcgcggtatt | 5640 |
| atcccgtatt | gacgccgggc | aagagcaact | cggtcgccgc | atacactatt | ctcagaatga | 5700 |
| cttggttgag | tactcaccag | tcacagaaaa | gcatcttacg | gatggcatga | cagtaagaga | 5760 |
| attatgcagt | gctgccataa | ccatgagtga | taacactgcg | gccaacttac | ttctgacaac | 5820 |
| gatcggagga | ccgaaggagc | taaccgcttt | tttgcacaac | atgggggatc | atgtaactcg | 5880 |
| ccttgatcgt | tgggaaccgg | agctgaatga | agccatacca | aacgacgagc | gtgacaccac | 5940 |
| gatgcctgta | gcaatggcaa | caacgttgcg | caaactatta | actggcgaac | tacttactct | 6000 |
| agcttcccgg | caacaattaa | tagactggat | ggaggcggat | aaagttgcag | gaccacttct | 6060 |
| gcgctcggcc | cttccggctg | gctggtttat | tgctgataaa | tctggagccg | gtgagcgtgg | 6120 |
| gtctcgcggt | atcattgcag | cactggggcc | agatggtaag | ccctcccgta | tcgtagttat | 6180 |
| ctacacgacg | gggagtcagg | caactatgga | tgaacgaaat | agacagatcg | ctgagatagg | 6240 |
| tgcctcactg | attaagcatt | ggtaactgtc | agaccaagtt | tactcatata | tactttagat | 6300 |
| tgatttaaaa | cttcatttt | aatttaaaag | gatctaggtg | aagatccttt | ttgataatct | 6360 |
| catgaccaaa | atcccttaac | gtgagttttc | gttccactga | gcgtcagacc | ccgtagaaaa | 6420 |
| gatcaaagga | tcttcttgag | atcctttttt | tctgcgcgta | atctgctgct | tgcaaacaaa | 6480 |
| aaaaccaccg | ctaccagcgg | tggtttgttt | gccggatcaa | gagctaccaa | ctcttttcc | 6540 |
| gaaggtaact | ggcttcagca | gagcgcagat | accaaatact | gtccttctag | tgtagccgta | 6600 |
| gttaggccac | cacttcaaga | actctgtagc | accgcctaca | tacctcgctc | tgctaatcct | 6660 |
| gttaccagtg | gctgctgcca | gtggcgataa | gtcgtgtctt | accgggttgg | actcaagacg | 6720 |
| atagttaccg | gataaggcgc | agcggtcggg | ctgaacgggg | ggttcgtgca | cacagcccag | 6780 |
| cttggagcga | acgacctaca | ccgaactgag | atacctacag | cgtgagctat | gagaaagcgc | 6840 |

| | |
|---|---|
| cacgcttccc gaagggagaa aggcggacag gtatccggta agcggcaggg tcggaacagg | 6900 |
| agagcgcacg agggagcttc caggggggaaa cgcctggtat ctttatagtc ctgtcgggtt | 6960 |
| tcgccacctc tgacttgagc gtcgattttt gtgatgctcg tcaggggggc ggagcctatg | 7020 |
| gaaaaacgcc agcaacgcgg ccttttttacg gttcctggcc ttttgctggc cttttgctca | 7080 |
| catgttcttt cctgcgttat cccctgattc tgtggataac cgtattaccg cctttgagtg | 7140 |
| agctgatacc gctcgccgca gccgaacgac cgagcgcagc gagtcagtga gcgaggaagc | 7200 |
| ggaagagcgc ccaatacgca aaccgcctct ccccgcgcgt tggccgattc attaatg | 7257 |

<210> SEQ ID NO 51
<211> LENGTH: 4369
<212> TYPE: DNA
<213> ORGANISM: Artificial Sequence
<220> FEATURE:
<223> OTHER INFORMATION: Synthetic polynucleotide

<400> SEQUENCE: 51

| | |
|---|---|
| aaagcttccc gggggggatct gggccactcc ctctctgcgc gctcgctcgc tcactgaggc | 60 |
| cgggcgacca aggtcgccc gacgcccggg ctttgcccgg cggcctcag tgagcgagcg | 120 |
| agcgcgcaga gagggagtgg ccaactccat cactaggggt tcctggaggg gtggagtcgt | 180 |
| gacctaggca tatgccaagt acgccccta ttgacgtcaa tgacggtaaa tggcccgcct | 240 |
| ggcattatgc ccagtacatg accttatggg actttcctac ttggcagtac atctacgtat | 300 |
| tagtcatcgc tattaccatg gtgatgcggt tttggcagta catcaatggg cgtggatagc | 360 |
| ggtttgactc acggggattt ccaagtctcc accccattga cgtcaatggg agtttgtttt | 420 |
| ggcaccaaaa tcaacgggac tttccaaaat gtcgtaacaa ctccgcccca ttgacgcaaa | 480 |
| tgggcggtag gcgtgtacgg tgggaggtct atataagcag agctcgttta gtgaaccgtc | 540 |
| agatcgcctg gagacgccat ccggactcta aggtaaatat aaaattttta agtgtataat | 600 |
| gtgttaaact actgattcta attgtttctc tcttttagat tccaaccttt ggaactgaat | 660 |
| tccgcgggcc cgggatccac cggtcgccac catggtgagc aagggcgagg agctgttcac | 720 |
| cggggtggtg cccatcctgg tcgagctgga cggcgacgta aacggccaca agttcagcgt | 780 |
| gtccggcgag ggcgagggcg atgccaccta cggcaagctg accctgaagt tcatctgcac | 840 |
| caccggcaag ctgcccgtgc cctggcccac cctcgtgacc accctgacct acggcgtgca | 900 |
| gtgcttcagc cgctaccccg accacatgaa gcagcacgac ttcttcaagt ccgccatgcc | 960 |
| cgaaggctac gtccaggagc gcaccatctt cttcaaggac gacggcaact acaagacccg | 1020 |
| cgccgaggtg aagttcgagg gcgacaccct ggtgaaccgc atcgagctga agggcatcga | 1080 |
| cttcaaggag gacggcaaca tcctggggca caagctggag tacaactaca acagccacaa | 1140 |
| cgtctatatc atggccgaca agcagaagaa cggcatcaag gtgaacttca agatccgcca | 1200 |
| caacatcgag gacggcagcg tgcagctcgc cgaccactac cagcagaaca cccccatcgg | 1260 |
| cgacggcccc gtgctgctgc cgacaaccca ctacctgagc acccagtccg ccctgagcaa | 1320 |
| agaccccaac gagaagcgcg atcacatggt cctgctggag ttcgtgaccg ccgccgggat | 1380 |
| cactctcggc atggacgagc tgtacaagta aagcggccgc taggcctcac ctgcgatctc | 1440 |
| gatgctttat ttgtgaaatt tgtgatgcta ttgctttatt tgtaaccatt ataagctgca | 1500 |
| ataaacaagt taacaacaac aattgcattc attttatgtt tcaggttcag ggggaggtgt | 1560 |
| gggaggtttt ttaaactagt ccactccctc tctgcgcgct cgctcgctca ctgaggccgg | 1620 |

```
gcgaccaaag gtcgcccgac gcccgggctt tgcccgggcg gcctcagtga gcgagcgagc   1680
gcgcagagag ggacagatcc gggcccgcat gcgtcgacaa ttcactggcc gtcgttttac   1740
aacgtcgtga ctgggaaaac cctggcgtta cccaacttaa tcgccttgca gcacatcccc   1800
ctttcgccag ctggcgtaat agcgaagagg cccgcaccga tcgcccttcc caacagttgc   1860
gcagcctgaa tggcgaatgg cgcctgatgc ggtattttct ccttacgcat ctgtgcggta   1920
tttcacaccg catatggtgc actctcagta caatctgctc tgatgccgca tagttaagcc   1980
agccccgaca cccgccaaca cccgctgacg cgccctgacg gcttgtctg ctcccggcat    2040 ccgcttacag acaagctgtg accgtctccg ggagctgcat gtgtcagagg ttttcaccgt   2100
catcaccgaa acgcgcgaga cgaaagggcc tcgtgatacg cctatttta taggttaatg    2160 tcatgataat aatggtttct tagacgtcag gtggcacttt tcggggaaat gtgcgcggaa   2220
cccctatttg tttatttttc taaatacatt caaatatgta tccgctcatg agacaataac   2280
cctgataaat gcttcaataa tattgaaaaa ggaagagtat gagtattcaa catttccgtg   2340
tcgcccttat tcccttttt gcggcatttt gccttcctgt ttttgctcac ccagaaacgc    2400
tggtgaaagt aaaagatgct gaagatcagt tgggtgcacg agtgggttac atcgaactgg   2460
atctcaacag cggtaagatc cttgagagtt tcgccccga agaacgtttt ccaatgatga    2520
gcacttttaa agttctgcta tgtggcgcgg tattatcccg tattgacgcc gggcaagagc   2580
aactcggtcg ccgcatacac tattctcaga atgacttggt tgagtactca ccagtcacag   2640
aaaagcatct tacggatggc atgacagtaa gagaattatg cagtgctgcc ataaccatga   2700
gtgataacac tgcggccaac ttacttctga caacgatcgg aggaccgaag gagctaaccg   2760
cttttttgca caacatgggg gatcatgtaa ctcgccttga tcgttgggaa ccggagctga   2820
atgaagccat accaaacgac gagcgtgaca ccacgatgcc tgtagcaatg gcaacaacgt   2880
tgcgcaaact attaactggc gaactactta ctctagcttc ccggcaacaa ttaatagact   2940
ggatggaggc ggataaagtt gcaggaccac ttctgcgctc ggcccttccg gctggctggt   3000
ttattgctga taaatctgga gccggtgagc gtgggtctcg cggtatcatt gcagcactgg   3060
ggccagatgg taagccctcc cgtatcgtag ttatctacac gacggggagt caggcaacta   3120
tggatgaacg aaatagacag atcgctgaga taggtgcctc actgattaag cattggtaac   3180
tgtcagacca agtttactca tatatacttt agattgattt aaaacttcat ttttaattta   3240
aaaggatcta ggtgaagatc ctttttgata atctcatgac caaaatccct aacgtgagt    3300 tttcgttcca ctgagcgtca gaccccgtag aaaagatcaa aggatcttct tgagatcctt   3360 ttttttctgcg cgtaatctgc tgcttgcaaa caaaaaaacc accgctacca gcggtggttt   3420
gtttgccgga tcaagagcta ccaactcttt ttccgaaggt aactggcttc agcagagcgc   3480
agataccaaa tactgttctt ctagtgtagc cgtagttagg ccaccacttc aagaactctg   3540
tagcaccgcc tacataccctc gctctgctaa tcctgttacc agtggctgct gccagtggcg   3600
ataagtcgtg tcttaccggg ttggactcaa gacgatagtt accggataag gcgcagcggt   3660
cgggctgaac ggggggttcg tgcacacagc ccagcttgga gcgaacgacc tacaccgaac   3720
tgagatacct acagcgtgag ctatgagaaa gcgccacgct tcccgaaggg agaaaggcgg   3780
acaggtatcc ggtaagcggc agggtcggaa caggagagcg cacgagggag cttccagggg   3840
gaaacgcctg gtatctttat agtcctgtcg ggtttcgcca cctctgactt gagcgtcgat   3900
ttttgtgatg ctcgtcaggg gggcggagcc tatggaaaaa cgccagcaac gcggcctttt   3960
tacggttcct ggccttttgc tggccttttg ctcacatgtt ctttcctgcg ttatcccctg   4020
```

-continued

```
attctgtgga taaccgtatt accgcctttg agtgagctga taccgctcgc cgcagccgaa      4080
cgaccgagcg cagcgagtca gtgagcgagg aagcggaaga gcgcccaata cgcaaaccgc      4140
ctctccccgc gcgttggccg attcattaat gcagctggca cgacaggttt cccgactgga      4200
aagcgggcag tgagcgcaac gcaattaatg tgagttagct cactcattag gcaccccagg      4260
ctttacactt tatgcttccg gctcgtatgt tgtgtggaat tgtgagcgga taacaatttc      4320
acacaggaaa cagctatgac catgattacg ccaagctctc gagatctag                 4369

<210> SEQ ID NO 52
<211> LENGTH: 4450
<212> TYPE: DNA
<213> ORGANISM: Artificial Sequence
<220> FEATURE:
<223> OTHER INFORMATION: Synthetic polynucleotide

<400> SEQUENCE: 52
aaagcttccc gggggatct gggccactcc ctctctgcgc gctcgctcgc tcactgaggc        60
cgggcgacca aggtcgccc gacgcccggg ctttgcccgg gcggcctcag tgagcgagcg       120
agcgcgcaga gagggagtgg ccaactccat cactaggggt tcctggaggg gtggagtcgt      180
gacctaggca tatgccaagt acgcccccta ttgacgtcaa tgacggtaaa tggcccgcct      240
ggcattatgc ccagtacatg acctatggg actttcctac ttggcagtac atctacgtat      300
tagtcatcgc tattaccatg gtgatgcggt tttggcagta catcaatggg cgtggatagc      360
ggtttgactc acggggattt ccaagtctcc accccattga cgtcaatggg agtttgtttt      420
ggcaccaaaa tcaacgggac tttccaaaat gtcgtaacaa ctccgcccca ttgacgcaaa      480
tgggcggtag gcgtgtacgg tgggaggtct atataagcag agctcgttta gtgaaccgtc      540
agatcgcctg gagacgccat ccggactcta aggtaaatat aaaattttta agtgtataat      600
gtgttaaact actgattcta attgtttctc tcttttagat tccaaccttt ggaactgaat      660
tccgcgggcc cgggatccac cggtcgccac catggtgagc aagggcgagg agctgttcac      720
cggggtggtg cccatcctgg tcgagctgga cggcgacgta acggccaca agttcagcgt      780 gtccggcgag ggcgagggcg atgccaccta cggcaagctg accctgaagt tcatctgcac      840
caccggcaag ctgcccgtgc cctggcccac cctcgtgacc accctgacct acggcgtgca      900
gtgcttcagc cgctacccg accacatgaa gcagcacgac ttcttcaagt ccgccatgcc      960
cgaaggctac gtccaggagc gcaccatctt cttcaaggac gacggcaact acaagacccg     1020
cgccgaggtg aagttcgagg gcgacaccct ggtgaaccgc atcgagctga agggcatcga     1080
cttcaaggag gacggcaaca tcctggggca agctggag tacaactaca cagccacaa      1140 cgtctatatc atggccgaca gcagaagaa cggcatcaag gtgaacttca agatccgcca     1200
caacatcgag gacggcagcg tgcagctcgc cgaccactac cagcagaaca ccccatcgg     1260 cgacggcccc gtgctgctgc ccgacaacca ctacctgagc acccagtccg ccctgagcaa     1320
agaccccaac gagaagcgcg atcacatggt cctgctggag ttcgtgaccg ccgccgggat     1380
cactctcggc atggacgagc tgtacaagta aagcggccgc taggcctcac ctgcgatctc     1440
gatgctttat ttgtgaaatt tgtgatgcta ttgctttatt tgtaaccatt ataagctgca     1500
ataaacaagt taacaacaac aattgcattc attttatgtt tcaggttcag ggggaggtgt     1560
gggaggtttt ttaaatcgat tggcgcgcac ccacggcctg aaaaatgcgc gcacccacg     1620 gcctgaaaaa tggcgcgcac ccacggcctg aaaaaactag tccactccct ctctgcgcgc     1680
```

```
tcgctcgctc actgaggccg ggcgaccaaa ggtcgcccga cgcccgggct tgcccgggc      1740
ggcctcagtg agcgagcgag cgcgcagaga gggacagatc cgggcccgca tgcgtcgaca     1800
attcactggc cgtcgtttta caacgtcgtg actgggaaaa ccctggcgtt acccaactta     1860
atcgccttgc agcacatccc cctttcgcca gctggcgtaa tagcgaagag gcccgcaccg     1920
atcgccttc ccaacagttg cgcagcctga atggcgaatg gcgcctgatg cggtattttc      1980
tccttacgca tctgtgcggt atttcacacc gcatatggtg cactctcagt acaatctgct     2040
ctgatgccgc atagttaagc cagccccgac acccgccaac acccgctgac gcgccctgac     2100
gggcttgtct gctcccggca tccgcttaca gacaagctgt gaccgtctcc gggagctgca     2160
tgtgtcagag gttttcaccg tcatcaccga aacgcgcgag acgaaagggc ctcgtgatac     2220
gcctattttt ataggttaat gtcatgataa taatggtttc ttagacgtca ggtggcactt     2280
ttcggggaaa tgtgcgcgga accctatt tgttatttttt ctaaatacat tcaaatatgt     2340
atccgctcat gagacaataa ccctgataaa tgcttcaata atattgaaaa aggaagagta     2400
tgagtattca acatttccgt gtcgccctta ttccctttttt tgcggcatttt tgccttcctg    2460
ttttttgctca cccagaaacg ctggtgaaag taaaagatgc tgaagatcag ttgggtgcac    2520
gagtgggtta catcgaactg gatctcaaca gcggtaagat ccttgagagt tttcgccccg     2580
aagaacgttt tccaatgatg agcactttta aagttctgct atgtggcgcg gtattatccc     2640
gtattgacgc cgggcaagag caactcggtc gccgcataca ctattctcag aatgacttgg     2700
ttgagtactc accagtcaca gaaaagcatc ttacggatgg catgacagta agagaattat     2760
gcagtgctgc cataaccatg agtgataaca ctgcggccaa cttacttctg acaacgatcg     2820
gaggaccgaa ggagctaacc gcttttttgc acaacatggg ggatcatgta actcgccttg     2880
atcgttggga accggagctg aatgaagcca taccaaacga cgagcgtgac accacgatgc     2940
ctgtagcaat ggcaacaacg ttgcgcaaac tattaactgg cgaactactt actctagctt     3000
cccggcaaca attaatagac tggatggagg cggataaagt tgcaggacca cttctgcgct     3060
cggcccttcc ggctggctgg tttattgctg ataaatctgg agccggtgag cgtgggtctc    3120
gcggtatcat tgcagcactg gggccagatg gtaagccctc ccgtatcgta gttatctaca     3180
cgacggggag tcaggcaact atggatgaac gaaatagaca gatcgctgag ataggtgcct     3240
cactgattaa gcattggtaa ctgtcagacc aagtttactc atatatactt tagattgatt     3300
taaaacttca ttttttaatttt aaaaggatct aggtgaagat cctttttgat aatctcatga    3360
ccaaaatccc ttaacgtgag ttttcgttcc actgagcgtc agaccccgta gaaaagatca     3420
aaggatcttc ttgagatcct ttttttctgc gcgtaatctg ctgcttgcaa acaaaaaaac     3480
caccgctacc agcggtggtt tgtttgccgg atcaagagct accaactctt tttccgaagg     3540
taactggctt cagcagagcg cagataccaa atactgttct tctagtgtag ccgtagttag     3600
gccaccactt caagaactct gtagcaccgc ctacatacct cgctctgcta atcctgttac     3660
cagtggctgc tgccagtggc gataagtcgt gtcttaccgg gttggactca agacgatagt     3720
taccggataa ggcgcagcgg tcgggctgaa cggggggttc gtgcacacag cccagcttgg     3780
agcgaacgac ctacaccgaa ctgagatacc tacagcgtga gctatgagaa agcgccacgc     3840
ttcccgaagg gagaaaggcg gacaggtatc cggtaagcgg cagggtcgga acaggagagc     3900
gcacgaggga gcttccaggg ggaaacgcct ggtatcttta tagtcctgtc gggtttcgcc     3960
acctctgact tgagcgtcga ttttgtgat gctcgtcagg ggggcggagc ctatggaaaa    4020
acgccagcaa cgcggccttt ttacggttcc tggccttttg ctggccttttt gctcacatgt    4080
```

-continued

| tctttcctgc gttatccct gattctgtgg ataaccgtat taccgccttt gagtgagctg | 4140 |
| atccgctcg ccgcagccga acgaccgagc gcagcgagtc agtgagcgag gaagcggaag | 4200 |
| agcgcccaat acgcaaaccg cctctccccg cgcgttggcc gattcattaa tgcagctggc | 4260 |
| acgacaggtt tcccgactgg aaagcgggca gtgagcgcaa cgcaattaat gtgagttagc | 4320 |
| tcactcatta ggcaccccag gctttacact ttatgcttcc ggctcgtatg ttgtgtggaa | 4380 |
| ttgtgagcgg ataacaattt cacacaggaa acagctatga ccatgattac gccaagctct | 4440 |
| cgagatctag | 4450 |

<210> SEQ ID NO 53
<211> LENGTH: 4425
<212> TYPE: DNA
<213> ORGANISM: Artificial Sequence
<220> FEATURE:
<223> OTHER INFORMATION: Synthetic polynucleotide

<400> SEQUENCE: 53

| aaagcttccc gggggatct gggccactcc ctctctgcgc gctcgctcgc tcactgaggc | 60 |
| cgggcgacca aggtcgccc gacgcccggg ctttgcccgg gcggcctcag tgagcgagcg | 120 |
| agcgcgcaga gagggagtgg ccaactccat cactagggt tcctggaggg gtggagtcgt | 180 |
| gacctaggca tatgccaagt acgccccta ttgacgtcaa tgacggtaaa tggcccgcct | 240 |
| ggcattatgc ccagtacatg accttatggg actttcctac ttggcagtac atctacgtat | 300 |
| tagtcatcgc tattaccatg gtgatgcggt tttggcagta catcaatggg cgtggatagc | 360 |
| ggtttgactc acggggattt ccaagtctcc accccattga cgtcaatggg agtttgtttt | 420 |
| ggcaccaaaa tcaacgggac tttccaaaat gtcgtaacaa ctccgcccca ttgacgcaaa | 480 |
| tgggcggtag gcgtgtacgg tgggaggtct atataagcag agctcgttta gtgaaccgtc | 540 |
| agatcgcctg gagacgccat ccggactcta aggtaaatat aaaattttta agtgtataat | 600 |
| gtgttaaact actgattcta attgtttctc tcttttagat tccaaccttt ggaactgaat | 660 |
| tccgcgggcc cgggatccac cggtcgccac catggtgagc aagggcgagg agctgttcac | 720 |
| cggggtggtg cccatcctgg tcgagctgga cggcgacgta aacggccaca agttcagcgt | 780 |
| gtccggcgag ggcgagggcg atgccaccta cggcaagctg accctgaagt tcatctgcac | 840 |
| caccggcaag ctgcccgtgc cctggcccac cctcgtgacc accctgacct acggcgtgca | 900 |
| gtgcttcagc cgctacccg accacatgaa gcagcacgac ttcttcaagt ccgccatgcc | 960 |
| cgaaggctac gtccaggagc gcaccatctt cttcaaggac gacggcaact acaagacccg | 1020 |
| cgccgaggtg aagttcgagg gcgacaccct ggtgaaccgc atcgagctga agggcatcga | 1080 |
| cttcaaggag gacggcaaca tcctggggca caagctggag tacaactaca acagccacaa | 1140 |
| cgtctatatc atggccgaca agcagaagaa cggcatcaag gtgaacttca agatccgcca | 1200 |
| caacatcgag gacggcagcg tgcagctcgc cgaccactac cagcagaaca cccccatcgg | 1260 |
| cgacggcccc gtgctgctgc ccgacaacca ctacctgagc acccagtccg ccctgagcaa | 1320 |
| agacccccaac gagaagcgcg atcacatggt cctgctggag ttcgtgaccg ccgccgggat | 1380 |
| cactctcggc atggacgagc tgtacaagta aagcggccgc taggcctcac ctgcgatctc | 1440 |
| gatgctttat ttgtgaaatt tgtgatgcta ttgctttatt tgtaaccatt ataagctgca | 1500 |
| ataaacaagt taacaacaac aattgcattc attttatgtt tcaggttcag ggggaggtgt | 1560 |
| gggaggtttt ttaaatcgat tggcgcgcac ccacggcctg aaaaatggcg cgcacccacg | 1620 |

```
gcctgaaaaa actagtccac tccctctctg cgcgctcgct cgctcactga ggccgggcga    1680
ccaaaggtcg cccgacgccc gggctttgcc cgggcggcct cagtgagcga gcgagcgcgc    1740
agagagggac agatccgggc ccgcatgcgt cgacaattca ctggccgtcg ttttacaacg    1800
tcgtgactgg gaaaaccctg gcgttaccca acttaatcgc cttgcagcac atcccccttt    1860
cgccagctgg cgtaatagcg aagaggcccg caccgatcgc ccttcccaac agttgcgcag    1920
cctgaatggc gaatggcgcc tgatgcggta ttttctcctt acgcatctgt gcggtatttc    1980
acaccgcata tggtgcactc tcagtacaat ctgctctgat gccgcatagt taagccagcc    2040
ccgacacccg ccaacacccg ctgacgcgcc ctgacgggct tgtctgctcc cggcatccgc    2100
ttacagacaa gctgtgaccg tctccgggag ctgcatgtgt cagaggtttt caccgtcatc    2160
accgaaacgc gcgagacgaa agggcctcgt gatacgccta ttttataggt taatgtcat    2220
gataataatg gtttcttaga cgtcaggtgg cacttttcgg ggaaatgtgc gcggaacccc    2280
tatttgttta ttttctaaa tacattcaaa tatgtatccg ctcatgagac aataaccctg    2340
ataaatgctt caataatatt gaaaaaggaa gagtatgagt attcaacatt tccgtgtcgc    2400
ccttattccc ttttttgcgg cattttgcct tcctgttttt gctcacccag aaacgctggt    2460
gaaagtaaaa gatgctgaag atcagttggg tgcacgagtg ggttacatcg aactggatct    2520
caacagcggt aagatccttg agagttttcg ccccgaagaa cgttttccaa tgatgagcac    2580
ttttaaagtt ctgctatgtg gcgcggtatt atcccgtatt gacgccgggc aagagcaact    2640
cggtcgccgc atacactatt ctcagaatga cttggttgag tactcaccag tcacagaaaa    2700
gcatcttacg gatggcatga cagtaagaga attatgcagt gctgccataa ccatgagtga    2760
taacactgcg gccaacttac ttctgacaac gatcggagga ccgaaggagc taaccgcttt    2820
tttgcacaac atgggggatc atgtaactcg ccttgatcgt tgggaaccgg agctgaatga    2880
agccatacca aacgacgagc gtgacaccac gatgcctgta gcaatggcaa caacgttgcg    2940
caaactatta actggcgaac tacttactct agcttcccgg caacaattaa tagactggat    3000
ggaggcggat aaagttgcag gaccacttct gcgctcggcc cttccggctg gctggtttat    3060
tgctgataaa tctggagccg gtgagcgtgg gtctcgcggt atcattgcag cactggggcc    3120
agatggtaag ccctcccgta tcgtagttat ctacacgacg gggagtcagg caactatgga    3180
tgaacgaaat agacagatcg ctgagatagg tgcctcactg attaagcatt ggtaactgtc    3240
agaccaagtt tactcatata ctttagat tgatttaaaa cttcattttt aatttaaaag    3300
gatctaggtg aagatccttt ttgataatct catgaccaaa atcccttaac gtgagttttc    3360
gttccactga gcgtcagacc ccgtagaaaa gatcaaagga tcttcttgag atcctttttt    3420
tctgcgcgta atctgctgct tgcaaacaaa aaaaccaccg ctaccagcgg tggtttgttt    3480
gccggatcaa gagctaccaa ctcttttttcc gaaggtaact ggcttcagca gagcgcagat    3540
accaaatact gttcttctag tgtagccgta gttaggccac cacttcaaga actctgtagc    3600
accgcctaca tacctcgctc tgctaatcct gttaccagtg gctgctgcca gtggcgataa    3660
gtcgtgtctt accgggttgg actcaagacg atagttaccg gataaggcgc agcggtcggg    3720
ctgaacgggg ggttcgtgca cacagcccag cttggagcga acgacctaca ccgaactgag    3780
atacctacag cgtgagctat gagaaagcgc cacgcttccc gaagggagaa aggcggacag    3840
gtatccggta agcggcaggg tcggaacagg agagcgcacg agggagcttc caggggggaaa   3900
cgcctggtat ctttatagtc ctgtcgggtt tcgccacctc tgacttgagc gtcgattttt    3960
gtgatgctcg tcaggggggc ggagcctatg gaaaaacgcc agcaacgcgg cctttttacg    4020
```

```
gttcctggcc ttttgctggc cttttgctca catgttcttt cctgcgttat ccctgattc       4080 tgtggataac cgtattaccg cctttgagtg agctgatacc gctcgccgca gccgaacgac       4140
cgagcgcagc gagtcagtga gcgaggaagc ggaagagcgc ccaatacgca aaccgcctct       4200
ccccgcgcgt tggccgattc attaatgcag ctggcacgac aggtttcccg actggaaagc       4260
gggcagtgag cgcaacgcaa ttaatgtgag ttagctcact cattaggcac cccaggcttt       4320
acactttatg cttccggctc gtatgttgtg tggaattgtg agcggataac aatttcacac       4380
aggaaacagc tatgaccatg attacgccaa gctctcgaga tctag                      4425
```

<210> SEQ ID NO 54
<211> LENGTH: 4465
<212> TYPE: DNA
<213> ORGANISM: Artificial Sequence
<220> FEATURE:
<223> OTHER INFORMATION: Synthetic polynucleotide

<400> SEQUENCE: 54

```
aaagcttccc gggggatct gggccactcc ctctctgcgc gctcgctcgc tcactgaggc         60
cgggcgacca aggtcgccc gacgcccggg ctttgcccgg gcggcctcag tgagcgagcg        120
agcgcgcaga gaggagtgg ccaactccat cactaggggt tcctggaggg gtggagtcgt        180
gacctaggca tatgccaagt acgccccta ttgacgtcaa tgacggtaaa tggcccgcct        240
ggcattatgc ccagtacatg accttatggg actttcctac ttggcagtac atctacgtat       300
tagtcatcgc tattaccatg gtgatgcggt tttggcagta catcaatggg cgtggatagc       360
ggtttgactc acggggattt ccaagtctcc accccattga cgtcaatggg agtttgtttt       420
ggcaccaaaa tcaacgggac tttccaaaat gtcgtaacaa ctccgcccca ttgacgcaaa       480
tgggcggtag gcgtgtacgg tgggaggtct atataagcag agctcgttta gtgaaccgtc       540
agatcgcctg gagacgccat ccggactcta aggtaaatat aaaatttta agtgtataat       600 gtgttaaact actgattcta attgtttctc tcttttagat tccaacctt ggaactgaat        660 tccgcgggcc cgggatccac cggtcgccac catggtgagc aagggcgagg agctgttcac       720
cggggtggtg cccatcctgg tcgagctgga cggcgacgta aacggccaca gttcagcgt        780 gtccggcgag ggcgagggcg atgccaccta cggcaagctg accctgaagt tcatctgcac       840
caccggcaag ctgcccgtgc cctggcccac cctcgtgacc accctgacct acggcgtgca       900
gtgcttcagc cgctacccg accacatgaa gcagcacgac ttcttcaagt ccgccatgcc       960
cgaaggctac gtccaggagc gcaccatctt cttcaaggac gacggcaact acaagacccg      1020
cgccgaggtg aagttcgagg gcgacaccct ggtgaaccgc atcgagctga agggcatcga      1080
cttcaaggag gacggcaaca tcctggggca caagctggag tacaactaca acagccacaa      1140
cgtctatatc atggccgaca agcagaagaa cggcatcaag gtgaacttca agatccgcca      1200
caacatcgag gacggcagcg tgcagctcgc cgaccactac cagcagaaca ccccccatcgg     1260 cgacggcccc gtgctgctgc ccgacaacca ctacctgagc acccagtccg ccctgagcaa      1320 agacccaac gagaagcgcg atcacatggt cctgctggag ttcgtgaccg ccgccgggat       1380
cactctcggc atggacgagc tgtacaagta aagcggccgc taggcctcac ctgcgatctc      1440
gatgctttat ttgtgaaatt tgtgatgcta ttgctttatt tgtaaccatt ataagctgca      1500
ataaacaagt taacaacaac aattgcattc attttatgtt tcaggttcag ggggaggtgt     1560
gggaggtttt ttaaatcgat tttagggtta gggttaggggt tagggaaaaa tttagggtta     1620
```

```
gggttagggt tagggaaaaa tttagggtta gggttagggt tagggaaaaa actagtccac   1680
tccctctctg cgcgctcgct cgctcactga ggccgggcga ccaaaggtcg cccgacgccc   1740
gggctttgcc cgggcggcct cagtgagcga gcgagcgcgc agagagggac agatccgggc   1800
ccgcatgcgt cgacaattca ctggccgtcg ttttacaacg tcgtgactgg gaaaaccctg   1860
gcgttaccca acttaatcgc cttgcagcac atcccccttt cgccagctgg cgtaatagcg   1920
aagaggcccg caccgatcgc ccttcccaac agttgcgcag cctgaatggc gaatggcgcc   1980
tgatgcggta ttttctcctt acgcatctgt gcggtatttc acaccgcata tggtgcactc   2040
tcagtacaat ctgctctgat gccgcatagt taagccagcc ccgacacccg ccaacacccg   2100
ctgacgcgcc ctgacgggct tgtctgctcc cggcatccgc ttacagacaa gctgtgaccg   2160
tctccgggag ctgcatgtgt cagaggtttt caccgtcatc accgaaacgc gcgagacgaa   2220
agggcctcgt gatacgccta ttttttatagg ttaatgtcat gataataatg gtttcttaga   2280
cgtcaggtgg cacttttcgg ggaaatgtgc gcggaacccc tatttgttta ttttttctaaa   2340
tacattcaaa tatgtatccg ctcatgagac aataaccctg ataaatgctt caataatatt   2400
gaaaaaggaa gagtatgagt attcaacatt tccgtgtcgc ccttattccc ttttttgcgg   2460
cattttgcct tcctgttttt gctcacccag aaacgctggt gaaagtaaaa gatgctgaag   2520
atcagttggg tgcacgagtg ggttacatcg aactggatct caacagcggt aagatccttg   2580
agagttttcg ccccgaagaa cgttttccaa tgatgagcac ttttaaagtt ctgctatgtg   2640
gcgcggtatt atcccgtatt gacgccgggc aagagcaact cggtcgccgc atacactatt   2700
ctcagaatga cttggttgag tactcaccag tcacagaaaa gcatcttacg gatggcatga   2760
cagtaagaga attatgcagt gctgccataa ccatgagtga taacactgcg gccaacttac   2820
ttctgacaac gatcggagga ccgaaggagc taaccgcttt tttgcacaac atgggggatc   2880
atgtaactcg ccttgatcgt tgggaaccgg agctgaatga agccatacca aacgacgagc   2940
gtgacaccac gatgcctgta gcaatggcaa caacgttgcg caaactatta actggcgaac   3000
tacttactct agcttcccgg caacaattaa tagactggat ggaggcggat aaagttgcag   3060
gaccacttct gcgctcggcc cttccggctg gctggtttat tgctgataaa tctggagccg   3120
gtgagcgtgg gtctcgcggt atcattgcag cactggggcc agatggtaag ccctcccgta   3180
tcgtagttat ctacacgacg gggagtcagg caactatgga tgaacgaaat agacagatcg   3240
ctgagatagg tgcctcactg attaagcatt ggtaactgtc agaccaagtt tactcatata   3300
tactttagat tgatttaaaa cttcattttt aatttaaaag gatctaggtg aagatccttt   3360
ttgataatct catgaccaaa atcccttaac gtgagttttc gttccactga gcgtcagacc   3420
ccgtagaaaa gatcaaagga tcttcttgag atcctttttt tctgcgcgta atctgctgct   3480
tgcaaacaaa aaaaccaccg ctaccagcgg tggtttgttt gccggatcaa gagctaccaa   3540
ctctttttcc gaaggtaact ggcttcagca gagcgcagat accaaatact gttcttctag   3600
tgtagccgta gttaggccac cacttcaaga actctgtagc accgcctaca tacctcgctc   3660
tgctaatcct gttaccagtg gctgctgcca gtggcgataa gtcgtgtctt accgggttgg   3720
actcaagacg atagttaccg gataaggcgc agcggtcggg ctgaacgggg gttcgtgca   3780
cacagcccag cttggagcga acgacctaca ccgaactgag atacctacag cgtgagctat   3840
gagaaagcgc cacgcttccc gaagggagaa aggcggacag gtatccggta agcggcaggg   3900
tcggaacagg agagcgcacg agggagcttc caggggaaa cgcctggtat ctttatagtc   3960
ctgtcgggtt tcgccacctc tgacttgagc gtcgattttt gtgatgctcg tcaggggggc   4020
```

```
ggagcctatg gaaaaacgcc agcaacgcgg ccttttacg gttcctggcc ttttgctggc    4080
cttttgctca catgttcttt cctgcgttat cccctgattc tgtggataac cgtattaccg    4140
cctttgagtg agctgatacc gctcgccgca gccgaacgac cgagcgcagc gagtcagtga    4200
gcgaggaagc ggaagagcgc ccaatacgca aaccgcctct ccccgcgcgt tggccgattc    4260
attaatgcag ctggcacgac aggtttcccg actggaaagc gggcagtgag cgcaacgcaa    4320
ttaatgtgag ttagctcact cattaggcac cccaggcttt acactttatg cttccggctc    4380
gtatgttgtg tggaattgtg agcggataac aatttcacac aggaaacagc tatgaccatg    4440
attacgccaa gctctcgaga tctag                                          4465
```

<210> SEQ ID NO 55
<211> LENGTH: 4405
<212> TYPE: DNA
<213> ORGANISM: Artificial Sequence
<220> FEATURE:
<223> OTHER INFORMATION: Synthetic polynucleotide

<400> SEQUENCE: 55

```
aaagcttccc gggggatct gggccactcc ctctctgcgc gctcgctcgc tcactgaggc     60
cgggcgacca aggtcgccc gacgcccggg ctttgcccgg gcggcctcag tgagcgagcg    120
agcgcgcaga gagggagtgg ccaactccat cactaggggt tcctggaggg gtggagtcgt    180
gacctaggca tatgccaagt acgcccccta ttgacgtcaa tgacggtaaa tggcccgcct    240
ggcattatgc ccagtacatg acctatggg actttcctac ttggcagtac atctacgtat    300
tagtcatcgc tattaccatg gtgatgcggt tttggcagta catcaatggg cgtggatagc    360
ggtttgactc acggggattt ccaagtctcc accccattga cgtcaatggg agtttgtttt    420
ggcaccaaaa tcaacgggac tttccaaaat gtcgtaacaa ctccgcccca ttgacgcaaa    480
tgggcggtag gcgtgtacgg tgggaggtct atataagcag agctcgttta gtgaaccgtc    540
agatcgcctg gagacgccat ccggactcta aggtaaatat aaaatttta agtgtataat    600 gtgttaaact actgattcta attgtttctc tcttttagat tccaacctt ggaactgaat    660 tccgcgggcc cgggatccac cggtcgccac catggtgagc aagggcgagg agctgttcac    720
cggggtggtg cccatcctgg tcgagctgga cggcgacgta aacggccaca agttcagcgt    780
gtccggcgag ggcgagggcg atgccaccta cggcaagctg accctgaagt tcatctgcac    840
caccggcaag ctgcccgtgc cctggcccac cctcgtgacc accctgacct acggcgtgca    900
gtgcttcagc cgctaccccg accacatgaa gcagcacgac ttcttcaagt ccgccatgcc    960
cgaaggctac gtccaggagc gcaccatctt cttcaaggac gacggcaact acaagacccg   1020
cgccgaggtg aagttcgagg gcgacaccct ggtgaaccgc atcgagctga agggcatcga   1080
cttcaaggag gacggcaaca tcctggggca caagctggag tacaactaca acagccacaa   1140
cgtctatatc atggccgaca agcagaagaa cggcatcaag gtgaacttca gatccgcca   1200 caacatcgag gacggcagcg tgcagctcgc cgaccactac cagcagaaca ccccatcgg   1260 cgacggcccc gtgctgctgc ccgacaacca ctacctgagc acccagtccg ccctgagcaa   1320
agaccccaac gagaagcgcg atcacatggt cctgctggag ttcgtgaccg ccgccgggat   1380
cactctcggc atggacgagc tgtacaagta aagcggccgc taggcctcac ctgcgatctc   1440
gatgctttat ttgtgaaatt tgtgatgcta ttgctttatt tgtaaccatt ataagctgca   1500
ataaacaagt taacaacaac aattgcattc attttatgtt tcaggttcag ggggaggtgt   1560
```

-continued

```
gggaggttttt ttaaatcgat tttagggtta gggttagggt tagggaaaaa actagtccac    1620
tccctctctg cgcgctcgct cgctcactga ggccgggcga ccaaaggtcg cccgacgccc    1680
gggctttgcc cgggcggcct cagtgagcga gcgagcgcgc agagagggac agatccgggc    1740
ccgcatgcgt cgacaattca ctggccgtcg ttttacaacg tcgtgactgg gaaaaccctg    1800
gcgttaccca acttaatcgc cttgcagcac atcccccttt cgccagctgg cgtaatagcg    1860
aagaggcccg caccgatcgc ccttcccaac agttgcgcag cctgaatggc gaatggcgcc    1920
tgatgcggta ttttctcctt acgcatctgt gcggtatttc acaccgcata tggtgcactc    1980
tcagtacaat ctgctctgat gccgcatagt taagccagcc ccgacacccg ccaacacccg    2040
ctgacgcgcc ctgacgggct tgtctgctcc cggcatccgc ttacagacaa gctgtgaccg    2100
tctccgggag ctgcatgtgt cagaggtttt caccgtcatc accgaaacgc gcgagacgaa    2160
agggcctcgt gatacgccta tttttatagg ttaatgtcat gataataatg gtttcttaga    2220
cgtcaggtgg cacttttcgg ggaaatgtgc gcggaacccc tatttgttta ttttctaaa    2280
tacattcaaa tatgtatccg ctcatgagac aataaccctg ataaatgctt caataatatt    2340
gaaaaaggaa gagtatgagt attcaacatt tccgtgtcgc ccttattccc ttttttgcgg    2400
cattttgcct tcctgttttt gctcacccag aaacgctggt gaaagtaaaa gatgctgaag    2460
atcagttggg tgcacgagtg ggttacatcg aactggatct caacagcggt aagatccttg    2520
agagttttcg ccccgaagaa cgttttccaa tgatgagcac ttttaaagtt ctgctatgtg    2580
gcgcggtatt atcccgtatt gacgccgggc aagagcaact cggtcgccgc atacactatt    2640
ctcagaatga cttggttgag tactcaccag tcacagaaaa gcatcttacg gatggcatga    2700
cagtaagaga attatgcagt gctgccataa ccatgagtga taacactgcg gccaacttac    2760
ttctgacaac gatcggagga ccgaaggagc taaccgcttt tttgcacaac atggggatc    2820
atgtaactcg ccttgatcgt tgggaaccgg agctgaatga agccatacca aacgacgagc    2880
gtgacaccac gatgcctgta gcaatggcaa caacgttgcg caaactatta actggcgaac    2940
tacttactct agcttcccgg caacaattaa tagactggat ggaggcggat aaagttgcag    3000
gaccacttct gcgctcggcc cttccggctg gctggtttat tgctgataaa tctggagccg    3060
gtgagcgtgg gtctcgcggt atcattgcag cactggggcc agatggtaag ccctcccgta    3120
tcgtagttat ctacacgacg gggagtcagg caactatgga tgaacgaaat agacagatcg    3180
ctgagatagg tgcctcactg attaagcatt ggtaactgtc agaccaagtt tactcatata    3240
tactttagat tgatttaaaa cttcattttt aatttaaaag gatctaggtg aagatccttt    3300
ttgataatct catgaccaaa atcccttaac gtgagttttc gttccactga gcgtcagacc    3360
ccgtagaaaa gatcaaagga tcttcttgag atccttttt tctgcgcgta atctgctgct    3420
tgcaaacaaa aaaaccaccg ctaccagcgg tggtttgttt gccggatcaa gagctaccaa    3480
ctcttttttcc gaaggtaact ggcttcagca gagcgcagat accaaatact gttcttctag    3540
tgtagccgta gttaggccac cacttcaaga actctgtagc accgcctaca tacctcgctc    3600
tgctaatcct gttaccagtg gctgctgcca gtggcgataa gtcgtgtctt accgggttgg    3660
actcaagacg atagttaccg gataaggcgc agcggtcggg ctgaacgggg gttcgtgca    3720
cacagcccag cttggagcga acgacctaca ccgaactgag atacctacag cgtgagctat    3780
gagaaagcgc cacgcttccc gaagggagaa aggcggacag gtatccggta agcggcaggg    3840
tcggaacagg agagcgcacg agggagcttc caggggggaaa cgcctggtat ctttatagtc    3900
ctgtcgggtt tcgccacctc tgacttgagc gtcgattttt gtgatgctcg tcagggggc    3960
```

```
ggagcctatg gaaaaacgcc agcaacgcgg cctttttacg gttcctggcc ttttgctggc    4020
cttttgctca catgttcttt cctgcgttat ccctgattc tgtggataac cgtattaccg     4080
cctttgagtg agctgatacc gctcgccgca gccgaacgac cgagcgcagc gagtcagtga    4140
gcgaggaagc ggaagagcgc ccaatacgca aaccgcctct ccccgcgcgt tggccgattc    4200
attaatgcag ctggcacgac aggtttcccg actggaaagc gggcagtgag cgcaacgcaa    4260
ttaatgtgag ttagctcact cattaggcac cccaggcttt acactttatg cttccggctc    4320
gtatgttgtg tggaattgtg agcggataac aatttcacac aggaaacagc tatgaccatg    4380
attacgccaa gctctcgaga tctag                                          4405
```

<210> SEQ ID NO 56
<211> LENGTH: 4465
<212> TYPE: DNA
<213> ORGANISM: Artificial Sequence
<220> FEATURE:
<223> OTHER INFORMATION: Synthetic polynucleotide

<400> SEQUENCE: 56

```
aaagcttccc gggggatct gggccactcc ctctctgcgc gctcgctcgc tcactgaggc       60
cgggcgacca aggtcgccc gacgcccggg ctttgcccgg gcggcctcag tgagcgagcg      120
agcgcgcaga gagggagtgg ccaactccat cactaggggt tcctggaggg gtggagtcgt    180
gacctaggtt tagggttagg gttagggtta gggaaaaatt tagggttagg gttagggtta    240
gggaaaaatt tagggttagg gttagggtta gggaaaaacc taggcatatg ccaagtacgc    300
cccctattga cgtcaatgac ggtaaatggc ccgcctggca ttatgcccag tacatgacct    360
tatgggactt tcctacttgg cagtacatct acgtattagt catcgctatt accatggtga    420
tgcggttttg gcagtacatc aatgggcgtg gatagcggtt tgactcacgg ggatttccaa    480
gtctccaccc cattgacgtc aatgggagtt tgttttggca ccaaaatcaa cgggactttc    540
caaaatgtcg taacaactcc gccccattga cgcaaatggg cggtaggcgt gtacggtggg    600
aggtctatat aagcagagct cgtttagtga accgtcagat cgcctggaga cgccatccgg    660
actctaaggt aaatataaaa ttttttaagtg tataatgtgt taaactactg attctaattg    720
tttctctctt ttagattcca accttttggaa ctgaattccg cgggcccggg atccaccggt    780
cgccaccatg gtgagcaagg gcgaggagct gttcaccggg gtggtgccca tcctggtcga    840
gctggacggc gacgtaaacg gccacaagtt cagcgtgtcc ggcgagggcg agggcgatgc    900
cacctacggc aagctgaccc tgaagttcat ctgcaccacc ggcaagctgc ccgtgccctg    960
gcccaccctc gtgaccaccc tgacctacgg cgtgcagtgc ttcagccgct accccgacca   1020
catgaagcag cacgacttct tcaagtccgc catgcccgaa ggctacgtcc aggagcgcac   1080
catcttcttc aaggacgacg gcaactacaa gacccgcgcc gaggtgaagt tcgagggcga   1140
caccctggtg aaccgcatcg agctgaaggg catcgacttc aaggaggacg gcaacatcct   1200
ggggcacaag ctggagtaca actacaacag ccacaacgtc tatatcatgg ccgacaagca   1260
gaagaacggc atcaaggtga acttcaagat ccgccacaac atcgaggacg gcagcgtgca   1320
gctcgccgac cactaccagc agaacacccc catcggcgac ggccccgtgc tgctgcccga   1380
caaccactac ctgagcaccc agtccgccct gagcaaagac cccaacgaga gcgcgatca    1440 catggtcctg ctggagttcg tgaccgccgc cgggatcact ctcggcatgg acgagctgta   1500
caagtaaagc ggccgctagg cctcacctgc gatctcgatg ctttatttgt gaaatttgtg   1560
```

-continued

```
atgctattgc tttatttgta accattataa gctgcaataa acaagttaac aacaacaatt    1620
gcattcattt tatgtttcag gttcaggggg aggtgtggga ggttttttaa actagtccac    1680
tccctctctg cgcgctcgct cgctcactga ggccgggcga ccaaaggtcg cccgacgccc    1740
gggcttttgcc cgggcggcct cagtgagcga gcgagcgcgc agagagggac agatccgggc    1800
ccgcatgcgt cgacaattca ctggccgtcg ttttacaacg tcgtgactgg gaaaaccctg    1860
gcgttaccca acttaatcgc cttgcagcac atccccttt cgccagctgg cgtaatagcg    1920
aagaggcccg caccgatcgc ccttcccaac agttgcgcag cctgaatggc gaatggcgcc    1980
tgatgcggta ttttctcctt acgcatctgt gcggtatttc acaccgcata tggtgcactc    2040
tcagtacaat ctgctctgat gccgcatagt taagccagcc ccgacacccg ccaacacccg    2100
ctgacgcgcc ctgacgggct tgtctgctcc cggcatccgc ttacagacaa gctgtgaccg    2160
tctccgggag ctgcatgtgt cagaggtttt caccgtcatc accgaaacgc gcgagacgaa    2220
agggcctcgt gatacgccta ttttatagg ttaatgtcat gataataatg gtttcttaga    2280
cgtcaggtgg cacttttcgg ggaaatgtgc gcggaacccc tatttgttta ttttctaaa    2340
tacattcaaa tatgtatccg ctcatgagac aataaccctg ataaatgctt caataatatt    2400
gaaaaaggaa gagtatgagt attcaacatt tccgtgtcgc ccttattccc ttttttgcgg    2460
cattttgcct tcctgttttt gctcacccag aaacgctggt gaaagtaaaa gatgctgaag    2520
atcagttggg tgcacgagtg ggttacatcg aactggatct caacagcggt aagatccttg    2580
agagttttcg ccccgaagaa cgttttccaa tgatgagcac ttttaaagtt ctgctatgtg    2640
gcgcggtatt atcccgtatt gacgccgggc aagagcaact cggtcgccgc atacactatt    2700
ctcagaatga cttggttgag tactcaccag tcacagaaaa gcatcttacg gatggcatga    2760
cagtaagaga attatgcagt gctgccataa ccatgagtga taacactgcg gccaacttac    2820
ttctgacaac gatcggagga ccgaaggagc taaccgcttt tttgcacaac atggggatc    2880
atgtaactcg ccttgatcgt tgggaaccgg agctgaatga agccatacca aacgacgagc    2940
gtgacaccac gatgcctgta gcaatggcaa caacgttgcg caaactatta actggcgaac    3000
tacttactct agcttcccgg caacaattaa tagactggat ggaggcggat aaagttgcag    3060
gaccacttct gcgctcggcc cttccggctg gctggtttat tgctgataaa tctggagccg    3120
gtgagcgtgg gtctcgcggt atcattgcag cactggggcc agatggtaag ccctcccgta    3180
tcgtagttat ctacacgacg gggagtcagg caactatgga tgaacgaaat agacagatcg    3240
ctgagatagg tgcctcactg attaagcatt ggtaactgtc agaccaagtt tactcatata    3300
tactttagat tgatttaaaa cttcattttt aatttaaaag gatctaggtg aagatccttt    3360
ttgataatct catgaccaaa atcccttaac gtgagttttc gttccactga gcgtcagacc    3420
ccgtagaaaa gatcaaagga tcttcttgag atcctttttt tctgcgcgta atctgctgct    3480
tgcaaacaaa aaaaccaccg ctaccagcgg tggtttgttt gccggatcaa gagctaccaa    3540
ctcttttttcc gaaggtaact ggcttcagca gagcgcagat accaaatact gttcttctag    3600
tgtagccgta gttaggccac cacttcaaga actctgtagc accgcctaca tacctcgctc    3660
tgctaatcct gttaccagtg gctgctgcca gtggcgataa gtcgtgtctt accgggttgg    3720
actcaagacg atagttaccg gataaggcgc agcggtcggg ctgaacgggg ggttcgtgca    3780
cacagcccag cttggagcga acgacctaca ccgaactgag atacctacag cgtgagctat    3840
gagaaagcgc cacgcttccc gaagggagaa aggcggacag gtatccggta agcggcaggg    3900
tcggaacagg agagcgcacg agggagcttc caggggggaaa cgcctggtat ctttatagtc    3960
```

```
ctgtcgggtt tcgccacctc tgacttgagc gtcgatttttt gtgatgctcg tcagggggc     4020 ggagcctatg gaaaaacgcc agcaacgcgg ccttttttacg gttcctggcc ttttgctggc    4080
cttttgctca catgttcttt cctgcgttat ccctgattc tgtggataac cgtattaccg      4140
cctttgagtg agctgatacc gctcgccgca gccgaacgac cgagcgcagc gagtcagtga    4200
gcgaggaagc ggaagagcgc ccaatacgca aaccgcctct ccccgcgcgt tggccgattc    4260
attaatgcag ctggcacgac aggtttcccg actggaaagc gggcagtgag cgcaacgcaa    4320
ttaatgtgag ttagctcact cattaggcac cccaggcttt acactttatg cttccggctc    4380
gtatgttgtg tggaattgtg agcggataac aatttcacac aggaaacagc tatgaccatg    4440
attacgccaa gctctcgaga tctag                                           4465

<210> SEQ ID NO 57
<211> LENGTH: 4435
<212> TYPE: DNA
<213> ORGANISM: Artificial Sequence
<220> FEATURE:
<223> OTHER INFORMATION: Synthetic polynucleotide

<400> SEQUENCE: 57
aaagcttccc gggggggatct gggccactcc ctctctgcgc gctcgctcgc tcactgaggc     60
cgggcgacca aaggtcgccc gacgcccggg cttttgcccgg gcggcctcag tgagcgagcg    120
agcgcgcaga gagggagtgg ccaactccat cactagggtt tcctggaggg gtggagtcgt    180
gacctaggca tatgccaagt acgccccta ttgacgtcaa tgacggtaaa tggcccgcct     240
ggcattatgc ccagtacatg accttatggg actttcctac ttggcagtac atctacgtat     300
tagtcatcgc tattaccatg gtgatgcggt tttggcagta catcaatggg cgtggatagc     360
ggtttgactc acggggattt ccaagtctcc accccattga cgtcaatggg agtttgtttt     420
ggcaccaaaa tcaacgggac tttccaaaat gtcgtaacaa ctccgcccca ttgacgcaaa     480
tgggcggtag gcgtgtacgg tgggaggtct atataagcag agctcgttta gtgaaccgtc     540
agatcgcctg gagacgccat ccggactcta aggtaaatat aaaatttttta agtgtataat     600 gtgttaaact actgattcta attgtttctc tcttttagat tccaaccttt ggaactgaat      660
tccgcgggcc cggatccac cggtcgccac catggtgagc aagggcgagg agctgttcac       720
cggggtggtg cccatcctgg tcgagctgga cggcgacgta aacggccaca agttcagcgt      780
gtccggcgag ggcgagggcg atgccaccta cggcaagctg accctgaagt tcatctgcac      840
caccggcaag ctgcccgtgc cctggcccac cctcgtgacc accctgacct acggcgtgca      900
gtgcttcagc cgctaccccg accacatgaa gcagcacgac ttcttcaagt ccgccatgcc      960
cgaaggctac gtccaggagc gcaccatctt cttcaaggac gacggcaact acaagacccg     1020
cgccgaggtg aagttcgagg gcgacaccct ggtgaaccgc atcgagctga agggcatcga     1080
cttcaaggag gacggcaaca tcctggggca caagctggag tacaactaca acagccacaa     1140
cgtctatatc atggccgaca agcagaagaa cggcatcaag gtgaacttca gatccgcca      1200 caacatcgag gacggcagcg tgcagctcgc cgaccactac cagcagaaca cccccatcgg     1260
cgacggcccc gtgctgctgc ccgacaacca ctacctgagc acccagtccg ccctgagcaa     1320
agacccaaac gagaagcgcg atcacatggt cctgctggag ttcgtgaccg ccgccgggat     1380
cactctcggc atggacgagc tgtacaagta aagcggccgc taggcctcac ctgcgatctc     1440
gatgctttat ttgtgaaatt tgtgatgcta ttgctttatt tgtaaccatt ataagctgca     1500
```

```
ataaacaagt taacaacaac aattgcattc attttatgtt tcaggttcag ggggaggtgt    1560
gggaggtttt ttaaatcgat gctagatgtt agcgtaaaaa gctagatgtt agcgtaaaaa    1620
gctagatgtt agcgtaaaaa actagtccac tccctctctg cgcgctcgct cgctcactga    1680
ggccgggcga ccaaaggtcg cccgacgccc gggctttgcc cgggcggcct cagtgagcga    1740
gcgagcgcgc agagagggac agatccgggc ccgcatgcgt cgacaattca ctggccgtcg    1800
ttttacaacg tcgtgactgg gaaaaccctg gcgttaccca acttaatcgc cttgcagcac    1860 atccccettt cgccagctgg cgtaatagcg aagaggcccg caccgatcgc ccttcccaac    1920
agttgcgcag cctgaatggc gaatggcgcc tgatgcggta ttttctcctt acgcatctgt    1980
gcggtatttc acaccgcata tggtgcactc tcagtacaat ctgctctgat gccgcatagt    2040
taagccagcc ccgacacccg ccaacacccg ctgacgcgcc ctgacgggct tgtctgctcc    2100
cggcatccgc ttacagacaa gctgtgaccg tctccgggag ctgcatgtgt cagaggtttt    2160
caccgtcatc accgaaacgc gcgagacgaa agggcctcgt gatacgccta tttttatagg    2220
ttaatgtcat gataataatg gtttcttaga cgtcaggtgg cacttttcgg ggaaatgtgc    2280 gcggaaccec tatttgttta ttttttctaaa tacattcaaa tatgtatccg ctcatgagac    2340
aataaccctg ataaatgctt caataatatt gaaaaaggaa gagtatgagt attcaacatt    2400
tccgtgtcgc ccttattccc ttttttgcgg cattttgcct tcctgttttt gctcacccag    2460
aaacgctggt gaaagtaaaa gatgctgaag atcagttggg tgcacgagtg ggttacatcg    2520
aactggatct caacagcggt aagatccttg agagttttcg ccccgaagaa cgttttccaa    2580
tgatgagcac ttttaaagtt ctgctatgtg gcgcggtatt atcccgtatt gacgccgggc    2640
aagagcaact cggtcgccgc atacactatt ctcagaatga cttggttgag tactcaccag    2700
tcacagaaaa gcatcttacg gatggcatga cagtaagaga attatgcagt gctgccataa    2760
ccatgagtga taacactgcg gccaacttac ttctgacaac gatcggagga ccgaaggagc    2820
taaccgcttt tttgcacaac atgggggatc atgtaactcg ccttgatcgt tgggaaccgg    2880
agctgaatga agccatacca aacgacgagc gtgacaccac gatgcctgta gcaatggcaa    2940
caacgttgcg caaactatta actggcgaac tacttactct agcttcccgg caacaattaa    3000
tagactggat ggaggcggat aaagttgcag gaccacttct gcgctcggcc cttccggctg    3060
gctggtttat tgctgataaa tctggagccg gtgagcgtgg gtctcgcggt atcattgcag    3120
cactggggcc agatggtaag ccctcccgta tcgtagttat ctacacgacg gggagtcagg    3180
caactatgga tgaacgaaat agacagatcg ctgagatagg tgcctcactg attaagcatt    3240
ggtaactgtc agaccaagtt tactcatata cttagat tgatttaaaa cttcattttt    3300
aatttaaaag gatctaggtg aagatccttt ttgataatct catgaccaaa atcccttaac    3360
gtgagttttc gttccactga gcgtcagacc ccgtagaaaa gatcaaagga tcttcttgag    3420
atcctttttt tctgcgcgta atctgctgct tgcaaacaaa aaaaccaccg ctaccagcgg    3480
tggtttgttt gccggatcaa gagctaccaa ctctttttcc gaaggtaact ggcttcagca    3540
gagcgcagat accaaatact gttcttctag tgtagccgta gttaggccac cacttcaaga    3600
actctgtagc accgcctaca tacctcgctc tgctaatcct gttaccagtg gctgctgcca    3660
gtggcgataa gtcgtgtctt accgggttgg actcaagacg atagttaccg gataaggcgc    3720
agcggtcggg ctgaacgggg gttcgtgcac acagcccag cttggagcga acgacctaca    3780
ccgaactgag atacctacag cgtgagctat gagaaagcgc cacgcttccc gaagggagaa    3840
aggcggacag gtatccggta agcggcaggg tcggaacagg agagcgcacg agggagcttc    3900
```

```
cagggggaaa cgcctggtat ctttatagtc ctgtcgggtt tcgccacctc tgacttgagc    3960
gtcgattttt gtgatgctcg tcagggggc ggagcctatg gaaaaacgcc agcaacgcgg    4020 ccttttacg gttcctggcc ttttgctggc cttttgctca catgttcttt cctgcgttat    4080
cccctgattc tgtggataac cgtattaccg cctttgagtg agctgatacc gctcgccgca    4140
gccgaacgac cgagcgcagc gagtcagtga gcgaggaagc ggaagagcgc ccaatacgca    4200
aaccgcctct ccccgcgcgt tggccgattc attaatgcag ctggcacgac aggtttcccg    4260
actggaaagc gggcagtgag cgcaacgcaa ttaatgtgag ttagctcact cattaggcac    4320
cccaggcttt acactttatg cttccggctc gtatgttgtg tggaattgtg agcggataac    4380
aatttcacac aggaaacagc tatgaccatg attacgccaa gctctcgaga tctag        4435

<210> SEQ ID NO 58
<211> LENGTH: 6940
<212> TYPE: DNA
<213> ORGANISM: Artificial Sequence
<220> FEATURE:
<223> OTHER INFORMATION: Synthetic polynucleotide

<400> SEQUENCE: 58
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagcg gcctcggcct ctgcataaat aaaaaaaatt agtcagccat gagcttggcc     240
cattgcatac gttgtatcca tatcataata tgtacattta tattggctca tgtccaacat     300
taccgccatg ttgacattga ttattgacta gttattaata gtaatcaatt acggggtcat     360
tagttcatag cccatatatg gagttccgcg ttacataact tacggtaaat ggcccgcctg     420
gctgaccgcc caacgacccc cgcccattga cgtcaataat gacgtatgtt cccatagtaa     480
cgccaatagg gactttccat tgacgtcaat gggtggagta tttacggtaa actgcccact     540
tggcagtaca tcaagtgtat catatgccaa gtacgccccc tattgacgtc aatgacggta     600
aatggcccgc ctggcattat gcccagtaca tgaccttatg gactttcct acttggcagt     660 acatctacgt attagtcatc gctattacca tggtgatgcg gttttggcag tacatcaatg     720
ggcgtggata gcggtttgac tcacggggat ttccaagtct ccaccccatt gacgtcaatg     780
ggagtttgtt ttggcaccaa aatcaacggg actttccaaa atgtcgtaac aactccgccc     840
cattgacgca aatgggcggt aggcgtgtac ggtgggaggt ctatataagc agagctcgtt     900
tagtgaaccg tcagatcgcc tggagacgcc atccacgctg ttttgacctc catagaagac     960
accgggaccg atccagcctc ccctcgaagc tgatcctgag aacttcaggg tgagtctatg    1020
ggacccttga tgttttcttt ccccttcttt tctatggtta agttcatgtc ataggaaggg    1080
gagaagtaac agggtacaca tattgaccaa atcaggtaa ttttgcattt gtaattttaa    1140
aaaatgcttt cttcttttaa tatactttttt tgtttatctt atttctaata ctttccctaa    1200
tctctttctt tcagggcaat aatgatacaa tgtatcatgc ctctttgcac cattctaaag    1260
aataacagtg ataatttctg ggttaaggca atagcaatat ttctgcatat aaatatttct    1320
gcatataaat tgtaactgat gtaagaggtt tcatattgct aatagcagct acaatccagc    1380
taccattctg ctttatttt atggttggga taaggctgga ttattctgag tccaagctag    1440
gcccttttgc taatcatgtt catacctctt atcttcctcc cacagctcct gggcaacgtg    1500
```

```
ctggtctgtg tgctggccca tcactttggc aaagaattcc gcgggcccgg gatccaccgg    1560
tcgccaccat ggtgagcaag ggcgaggagc tgttcaccgg ggtggtgccc atcctggtcg    1620
agctggacgg cgacgtaaac ggccacaagt tcagcgtgtc cggcgagggc gagggcgatg    1680
ccacctacgg caagctgacc ctgaagttca tctgcaccac cggcaagctg cccgtgccct    1740
ggcccaccct cgtgaccacc ctgacctacg gcgtgcagtg cttcagccgc taccccgacc    1800
acatgaagca gcacgacttc ttcaagtccg ccatgcccga aggctacgtc caggagcgca    1860
ccatcttctt caaggacgac ggcaactaca agacccgcgc cgaggtgaag ttcgagggcg    1920
acaccctggt gaaccgcatc gagctgaagg gcatcgactt caaggaggac ggcaacatcc    1980
tggggcacaa gctggagtac aactacaaca gccacaacgt ctatatcatg gccgacaagc    2040
agaagaacgg catcaaggtg aacttcaaga tccgccacaa catcgaggac ggcagcgtgc    2100
agctcgccga ccactaccag cagaacaccc ccatcggcga cggccccgtg ctgctgcccg    2160
acaaccacta cctgagcacc cagtccgccc tgagcaaaga ccccaacgag aagcgcgatc    2220
acatggtcct gctggagttc gtgaccgccg ccgggatcac tctcggcatg gacgagctgt    2280
acaagtaaag cggccgctct agaggatcca agcttatcga taccgtcgac ctcgagggcc    2340
cagatctaat tcaccccacc agtgcaggct gcctatcaga aagtggtggc tggtgtggct    2400
aatgccctgg cccacaagta tcactaagct cgctttcttg ctgtccaatt tctattaaag    2460
gttcctttgt tccctaagtc aactactaa actgggggat attatgaagg ccttgagca    2520 tctggattct gcctaataaa aaacatttat tttcattgca atgatgtatt taaattattt    2580
ctgaatattt tactaaaaag ggaatgtggg aggtcagtgc atttaaaaca taagaaatg    2640 aagagctagt tcaaaccttg ggaaaataca ctatatctta aactccatga agaaggtga    2700 ggctgcaaac agctaatgca cattggcaac agccccgat gcctatgcct tattcatccc    2760
tcagaaaagg attcaagtag aggcttgatt tggaggttaa agttttgcta tgctgtattt    2820
tacattactt attgttttag ctgtcctcat gaatgtcttt tcactaccca tttgcttatc    2880
ctgcatctct cagccttgac tccactcagt tctcttgctt agagatacca cctttcccct    2940
gaagtgttcc ttccatgttt tacggcgaga tggtttctcc tcgcctggcc actcagcctt    3000
agttgtctct gttgtcttat agaggtctac ttgaagaagg aaaaacaggg ggcatggttt    3060
gactgtcctg tgagcccttc ttccctgcct cccccactca cagtgacccg gaatccctcg    3120
acatctagag catggctacg tagataagta gcatggcggg ttaatcatta actacaagga    3180 accccctagtg atggagttgg ccactccctc tctgcgcgct cgctcgctca ctgaggccgg    3240
gcgaccaaag gtcgcccgac gcccgggctt tgcccgggcg gcctcagtga gcgagcgagc    3300 gcgcagctg gcgtaatagc gaagaggccc gcaccgatcg cccttcccaa cagttgcgca    3360
gcctgaatgg cgaatggaat tccagacgat tgagcgtcaa aatgtaggta tttccatgag    3420
cgttttccct gttgcaatgg ctggcggtaa tattgttctg gatattacca gcaaggccga    3480
tagtttgagt tcttctactc aggcaagtga tgttattact aatcaaagaa gtattgcgac    3540
aacggttaat ttgcgtgatg gacagactct tttactcggt ggcctcactg attataaaaa    3600
cacttctcag gattctggcg taccgttcct gtctaaaatc cctttaatcg gcctcctgtt    3660
tagctcccgc tctgattcta acgaggaaag cacgttatac gtgctcgtca aagcaaccat    3720
agtacgcgcc ctgtagcggc gcattaagcg cggcgggtgt ggtggttacg cgcagcgtga    3780
ccgctacact tgccagcgcc ctagcgcccg ctcctttcgc tttcttccct tcctttctcg    3840
ccacgttcgc cggctttccc cgtcaagctc taaatcgggg gctcccttta gggttccgat    3900
```

```
ttagtgcttt acggcacctc gacccccaaaa aacttgatta gggtgatggt tcacgtagtg    3960
ggccatcgcc ctgatagacg gttttttcgcc ctttgacgtt ggagtccacg ttctttaata    4020
gtggactctt gttccaaact ggaacaaacac tcaaccctat ctcggtctat tctttgatt    4080
tataagggat tttgccgatt tcggcctatt ggttaaaaaa tgagctgatt taacaaaaat    4140
ttaacgcgaa ttttaacaaa atattaacgt ttacaattta aatatttgct tatacaatct    4200
tcctgttttt ggggcttttc tgattatcaa ccggggtaca tatgattgac atgctagttt    4260
tacgattacc gttcatcgat tctcttgttt gctccagact ctcaggcaat gacctgatag    4320
cctttgtaga gacctctcaa aaatagctac cctctccggc atgaatttat cagctagaac    4380
ggttgaatat catattgatg gtgatttgac tgtctccggc ctttctcacc cgtttgaatc    4440
tttacctaca cattactcag gcattgcatt taaaatatat gagggttcta aaaattttta    4500
tccttgcgtt gaaataaagg cttctcccgc aaaagtatta cagggtcata atgttttggg    4560
tacaaccgat ttagctttat gctctgaggc tttattgctt aattttgcta attctttgcc    4620
ttgcctgtat gatttattgg atgttggaat tcctgatgcg gtattttctc cttacgcatc    4680
tgtgcggtat ttcacaccgc atatggtgca ctctcagtac aatctgctct gatgccgcat    4740
agttaagcca gccccgacac ccgccaacac ccgctgacgc gccctgacgg gcttgtctgc    4800
tcccggcatc cgcttacaga caagctgtga ccgtctccgg gagctgcatg tgtcagaggt    4860
tttcaccgtc atcaccgaaa cgcgcgagac gaaagggcct cgtgatacgc ctattttat    4920
aggttaatgt catgataata atggtttctt agacgtcagg tggcactttt cggggaaatg    4980
tgcgcggaac ccctatttgt ttatttttct aaatacattc aaatatgtat ccgctcatga    5040
gacaataacc ctgataaatg cttcaataat attgaaaaag gaagagtatg agtattcaac    5100
atttccgtgt cgcccttatt cccttttttg cggcattttg ccttcctgtt tttgctcacc    5160
cagaaacgct ggtgaaagta aaagatgctg aagatcagtt gggtgcacga gtgggttaca    5220
tcgaactgga tctcaacagc ggtaagatcc ttgagagttt cgccccgaa gaacgttttc    5280
caatgatgag cacttttaaa gttctgctat gtggcgcggt attatcccgt attgacgccg    5340
ggcaagagca actcggtcgc cgcatacact attctcagaa tgacttggtt gagtactcac    5400
cagtcacaga aaagcatctt acggatggca tgacagtaag agaattatgc agtgctgcca    5460
taaccatgag tgataacact gcggccaact tacttctgac aacgatcgga ggaccgaagg    5520
agctaaccgc ttttttgcac aacatggggg atcatgtaac tcgccttgat cgttgggaac    5580
cggagctgaa tgaagccata ccaaacgacg agcgtgacac cacgatgcct gtagcaatgg    5640
caacaacgtt gcgcaaacta ttaactggcg aactacttac tctagcttcc cggcaacaat    5700
taatagactg gatggaggcg gataaagttg caggaccact tctgcgctcg gcccttccgg    5760
ctggctggtt tattgctgat aaatctggag ccggtgagcg tgggtctcgc ggtatcattg    5820
cagcactggg gccagatggt aagccctccc gtatcgtagt tatctacacg acggggagtc    5880
aggcaactat ggatgaacga aatagacaga tcgctgagat aggtgcctca ctgattaagc    5940
attggtaact gtcagaccaa gtttactcat atatacttta gattgattta aaacttcatt    6000
tttaatttaa aaggatctag gtgaagatcc ttttgataa tctcatgacc aaaatccctt    6060
aacgtgagtt ttcgttccac tgagcgtcag accccgtaga aaagatcaaa ggatcttctt    6120
gagatccttt ttttctgcgc gtaatctgct gcttgcaaac aaaaaaacca ccgctaccag    6180
cggtggtttg tttgccggat caagagctac caactctttt tccgaaggta actggcttca    6240
```

| | | | | |
|---|---|---|---|---|
| gcagagcgca | gataccaaat | actgtccttc | tagtgtagcc | gtagttaggc caccacttca | 6300 |
| agaactctgt | agcaccgcct | acatacctcg | ctctgctaat | cctgttacca gtggctgctg | 6360 |
| ccagtggcga | taagtcgtgt | cttaccgggt | tggactcaag | acgatagtta ccggataagg | 6420 |
| cgcagcggtc | gggctgaacg | gggggttcgt | gcacacagcc | cagcttggag cgaacgacct | 6480 |
| acaccgaact | gagataccta | cagcgtgagc | tatgagaaag | cgccacgctt cccgaaggga | 6540 |
| gaaaggcgga | caggtatccg | gtaagcggca | gggtcggaac | aggagagcgc acagggagc | 6600 |
| ttccagggg | aaacgcctgg | tatctttata | gtcctgtcgg | gtttcgccac ctctgacttg | 6660 |
| agcgtcgatt | tttgtgatgc | tcgtcagggg | ggcggagcct | atggaaaaac gccagcaacg | 6720 |
| cggccttttt | acggttcctg | gccttttgct | ggccttttgc | tcacatgttc tttcctgcgt | 6780 |
| tatccctga | ttctgtggat | aaccgtatta | ccgcctttga | gtgagctgat accgctcgcc | 6840 |
| gcagccgaac | gaccgagcgc | agcgagtcag | tgagcgagga | agcggaagag cgcccaatac | 6900 |
| gcaaaccgcc | tctccccgcg | cgttggccga | ttcattaatg | | 6940 |

<210> SEQ ID NO 59
<211> LENGTH: 7257
<212> TYPE: DNA
<213> ORGANISM: Artificial Sequence
<220> FEATURE:
<223> OTHER INFORMATION: Synthetic polynucleotide

<400> SEQUENCE: 59

| | | | | |
|---|---|---|---|---|
| cagcagctgc | gcgctcgctc | gctcactgag | gccgcccggg | caaagcccgg gcgtcgggcg | 60 |
| acctttggtc | gcccggcctc | agtgagcgag | cgagcgcgca | gagagggagt ggccaactcc | 120 |
| atcactaggg | gttccttgta | gttaatgatt | aacccgccat | gctacttatc tacgtagcca | 180 |
| tgctctagcg | gcctcggcct | ctgcataaat | aaaaaaaatt | agtcagccat gagcttggcc | 240 |
| cattgcatac | gttgtatcca | tatcataata | tgtacattta | tattggctca tgtccaacat | 300 |
| taccgccatg | ttgacattga | ttattgacta | gttattaata | gtaatcaatt acggggtcat | 360 |
| tagttcatag | cccatatatg | gagttccgcg | ttacataact | tacggtaaat ggcccgcctg | 420 |
| gctgaccgcc | caacgacccc | cgcccattga | cgtcaataat | gacgtatgtt cccatagtaa | 480 |
| cgccaatagg | gactttccat | tgacgtcaat | gggtggagta | tttacggtaa actgcccact | 540 |
| tggcagtaca | tcaagtgtat | catatgccaa | gtacgccccc | tattgacgtc aatgacggta | 600 |
| aatggcccgc | ctggcattat | gcccagtaca | tgaccttatg | ggactttcct acttggcagt | 660 |
| acatctacgt | attagtcatc | gctattacca | tggtgatgcg | gttttggcag tacatcaatg | 720 |
| ggcgtggata | gcggtttgac | tcacggggat | ttccaagtct | ccaccccatt gacgtcaatg | 780 |
| ggagtttgtt | ttggcaccaa | aatcaacggg | actttccaaa | atgtcgtaac aactccgccc | 840 |
| cattgacgca | aatgggcggt | aggcgtgtac | ggtgggaggt | ctatataagc agagctcgtt | 900 |
| tagtgaaccg | tcagatcgcc | tggagacgcc | atccacgctg | ttttgacctc catagaagac | 960 |
| accgggaccg | atccagcctc | ccctcgaagc | tgatcctgag | aacttcaggg tgagtctatg | 1020 |
| ggacccttga | tgttttcttt | cccttcttt | tctatggtta | agttcatgtc ataggaaggg | 1080 |
| gagaagtaac | agggtacaca | tattgaccaa | atcagggtaa | ttttgcattt gtaattttaa | 1140 |
| aaaatgcttt | cttcttttaa | tatactttt | tgtttatctt | atttctaata ctttccctaa | 1200 |
| tctctttctt | tcagggcaat | aatgatacaa | tgtatcatgc | ctctttgcac cattctaaag | 1260 |
| aataacagtg | ataatttctg | ggttaaggca | atagcaatat | ttctgcatat aaatatttct | 1320 |
| gcatataaat | tgtaactgat | gtaagaggtt | tcatattgct | aatagcagct acaatccagc | 1380 |

```
taccattctg cttttatttt atggttggga taaggctgga ttattctgag tccaagctag    1440 gccctttttgc taatcatgtt catacctctt atcttcctcc cacagctcct gggcaacgtg   1500
ctggtctgtg tgctggccca tcactttggc aaagaattcc gcgggcccgg gatccaccgg    1560
tcgccaccat ggtgagcaag ggcgaggagc tgttcaccgg ggtggtgccc atcctggtcg    1620
agctggacgg cgacgtaaac ggccacaagt tcagcgtgtc cggcgagggc gagggcgatg    1680
ccacctacgg caagctgacc ctgaagttca tctgcaccac cggcaagctg cccgtgccct    1740
ggcccaccct cgtgaccacc ctgacctacg gcgtgcagtg cttcagccgc taccccgacc    1800
acatgaagca gcacgacttc ttcaagtccg ccatgcccga aggctacgtc caggagcgca    1860
ccatcttctt caaggacgac ggcaactaca agacccgcgc cgaggtgaag ttcgagggcg    1920
acaccctggt gaaccgcatc gagctgaagg gcatcgactt caaggaggac ggcaacatcc    1980
tggggcacaa gctggagtac aactacaaca gccacaacgt ctatatcatg gccgacaagc    2040
agaagaacgg catcaaggtg aacttcaaga tccgccacaa catcgaggac ggcagcgtgc    2100
agctcgccga ccactaccag cagaacaccc ccatcggcga cggccccgtg ctgctgcccg    2160
acaaccacta cctgagcacc cagtccgccc tgagcaaaga ccccaacgag aagcgcgatc    2220
acatggtcct gctggagttc gtgaccgccg ccgggatcac tctcggcatg gacgagctgt    2280
acaagtaaag cggccgctct agaggatcca agcttatcga taccgtcgac ctcgagggcc    2340
cagatctaat tcaccccacc agtgcaggct gcctatcaga aagtggtggc tggtgtggct    2400
aatgccctgg cccacaagta tcactaagct cgctttcttg ctgtccaatt tctattaaag    2460
gttcctttgt tccctaagtc caactactaa actgggggat attatgaagg gccttgagca    2520
tctggattct gcctaataaa aaacatttat tttcattgca atgatgtatt taaattattt    2580
ctgaatattt tactaaaaag ggaatgtggg aggtcagtgc atttaaaaca taagaaatg    2640 aagagctagt tcaaaccttg ggaaaataca ctatatctta aactccatga agaaggtga    2700 ggctgcaaac agctaatgca cattggcaac agcccctgat gcctatgcct tattcatccc    2760
tcagaaaagg attcaagtag aggcttgatt tggaggttaa agttttgcta tgctgtattt    2820
tacattactt attgttttag ctgtcctcat gaatgtcttt tcactaccca tttgcttatc    2880
ctgcatctct cagccttgac tccactcagt tctcttgctt agagatacca cctttcccct    2940
gaagtgttcc ttccatgttt tacgcgaga tggtttctcc tcgcctggcc actcagcctt    3000
agttgtctct gttgtcttat agaggtctac ttgaagaagg aaaaacaggg ggcatggttt    3060
gactgtcctg tgagcccttc ttccctgcct cccccactca cagtgacccg gaatccctcg    3120
acaggtacct ttagggttag ggttagggtt agggaaaaat ttagggttag ggttagggtt    3180
agggaaaaat ttagggttag ggttagggtt agggaaaaat ttagggttag ggttagggtt    3240
agggaaaaat ttagggttag ggttagggtt agggaaaaac cctaaccta accctaaccc    3300 taaattttt ccctaacccct aaccctaacc ctaaatttt tccctaaccc taaccctaac    3360
cctaaatttt ttccctaacc ctaaccctaa ccctaaattt tttccctaac cctaaccta    3420 accctaaatt ttttgctagc tctagagcat ggctacgtag ataagtagca tggcgggtta    3480
atcattaact acaaggaacc cctagtgatg gagttggcca ctccctctct gcgcgctcgc    3540
tcgctcactg aggccgggcg accaaaggtc gcccgacgcc cgggctttgc ccgggcggcc    3600
tcagtgagcg agcgagcgcg ccagctggcg taatagcgaa gaggcccgca ccgatcgccc    3660
ttcccaacag ttgcgcagcc tgaatggcga atggaattcc agacgattga gcgtcaaaat    3720
```

```
gtaggtattt ccatgagcgt ttttcctgtt gcaatggctg gcggtaatat tgttctggat    3780
attaccagca aggccgatag tttgagttct tctactcagg caagtgatgt tattactaat    3840
caaagaagta ttgcgacaac ggttaatttg cgtgatggac agactctttt actcggtggc    3900
ctcactgatt ataaaaacac ttctcaggat tctggcgtac cgttcctgtc taaaatccct    3960
ttaatcggcc tcctgtttag ctcccgctct gattctaacg aggaaagcac gttatacgtg    4020
ctcgtcaaag caaccatagt acgcgccctg tagcggcgca ttaagcgcgg cgggtgtggt    4080
ggttacgcgc agcgtgaccg ctacacttgc cagcgcccta gcgcccgctc ctttcgcttt    4140
cttcccttcc tttctcgcca cgttcgccgg ctttccccgt caagctctaa atcgggggct    4200
ccctttaggg ttccgattta gtgctttacg gcacctcgac cccaaaaaac ttgattaggg    4260
tgatggttca cgtagtgggc catcgccctg atagacggtt tttcgccctt gacgttgga    4320 gtccacgttc tttaatagtg gactcttgtt ccaaactgga caacactca accctatctc    4380 ggtctattct tttgatttat aagggatttt gccgatttcg gcctattggt taaaaaatga    4440
gctgatttaa caaaaattta acgcgaattt taacaaaata ttaacgttta caatttaaat    4500
atttgcttat acaatcttcc tgttttgggg cttttctga ttatcaaccg gggtacatat    4560
gattgacatg ctagttttac gattaccgtt catcgattct cttgtttgct ccagactctc    4620
aggcaatgac ctgatagcct ttgtagagac ctctcaaaaa tagctaccct ctccggcatg    4680
aatttatcag ctagaacggt tgaatatcat attgatggtg atttgactgt ctccggcctt    4740
tctcacccgt ttgaatcttt acctacacat tactcaggca ttgcatttaa aatatatgag    4800
ggttctaaaa attttatcc ttgcgttgaa ataaaggctt ctcccgcaaa agtattacag    4860
ggtcataatg tttttggtac aaccgattta gctttatgct ctgaggcttt attgcttaat    4920
tttgctaatt ctttgccttg cctgtatgat ttattggatg ttggaattcc tgatgcggta    4980
ttttctcctt acgcatctgt gcggtatttc acaccgcata tggtgcactc tcagtacaat    5040
ctgctctgat gccgcatagt taagccagcc ccgacacccg ccaacacccg ctgacgcgcc    5100
ctgacgggct tgtctgctcc cggcatccgc ttacagacaa gctgtgaccg tctccgggag    5160
ctgcatgtgt cagaggtttt caccgtcatc accgaaacgc gcgagacgaa agggcctcgt    5220
gatacgccta ttttatatgg ttaatgtcat gataataatg gtttcttaga cgtcaggtgg    5280
cacttttcgg ggaaatgtgc gcggaacccc tatttgttta ttttctaaa tacattcaaa    5340 tatgtatccg ctcatgagac aataaccctg ataaatgctt caataatatt gaaaaaggaa    5400
gagtatgagt attcaacatt tccgtgtcgc ccttattccc ttttttgcgg cattttgcct    5460
tcctgttttt gctcacccag aaacgctggt gaaagtaaaa gatgctgaag atcagttggg    5520
tgcacgagtg ggttacatcg aactggatct caacagcggt aagatccttg agagttttcg    5580
ccccgaagaa cgttttccaa tgatgagcac ttttaaagtt ctgctatgtg gcgcggtatt    5640
atcccgtatt gacgccgggc aagagcaact cggtcgccgc atacactatt ctcagaatga    5700
cttggttgag tactcaccag tcacagaaaa gcatcttacg gatggcatga cagtaagaga    5760
attatgcagt gctgccataa ccatgagtga taacactgcg gccaacttac ttctgacaac    5820
gatcggagga ccgaaggagc taaccgcttt tttgcacaac atgggggatc atgtaactcg    5880
ccttgatcgt tgggaaccgg agctgaatga agccatacca aacgacgagc gtgacaccac    5940
gatgcctgta gcaatggcaa caacgttgcg caaactatta actggcgaac tacttactct    6000
agcttcccgg caacaattaa tagactggat ggaggcggat aaagttgcag gaccacttct    6060
gcgctcggcc cttccggctg gctggtttat tgctgataaa tctggagccg gtgagcgtgg    6120
```

```
gtctcgcggt atcattgcag cactggggcc agatggtaag ccctcccgta tcgtagttat   6180
ctacacgacg gggagtcagg caactatgga tgaacgaaat agacagatcg ctgagatagg   6240
tgcctcactg attaagcatt ggtaactgtc agaccaagtt tactcatata tactttagat   6300
tgatttaaaa cttcattttt aatttaaaag gatctaggtg aagatccttt ttgataatct   6360
catgaccaaa atcccttaac gtgagttttc gttccactga gcgtcagacc ccgtagaaaa   6420
gatcaaagga tcttcttgag atccttttttt tctgcgcgta atctgctgct tgcaaacaaa   6480
aaaaccaccg ctaccagcgg tggtttgttt gccggatcaa gagctaccaa ctctttttcc   6540
gaaggtaact ggcttcagca gagcgcagat accaaatact gtccttctag tgtagccgta   6600
gttaggccac cacttcaaga actctgtagc accgcctaca tacctcgctc tgctaatcct   6660
gttaccagtg gctgctgcca gtggcgataa gtcgtgtctt accgggttgg actcaagacg   6720
atagttaccg gataaggcgc agcggtcggg ctgaacgggg ggttcgtgca cacagcccag   6780
cttggagcga acgacctaca ccgaactgag atacctacag cgtgagctat gagaaagcgc   6840
cacgcttccc gaagggagaa aggcggacag gtatccggta agcggcaggg tcggaacagg   6900
agagcgcacg agggagcttc caggggggaaa cgcctggtat ctttatagtc ctgtcgggtt   6960
tcgccacctc tgacttgagc gtcgattttt gtgatgctcg tcaggggggc ggagcctatg   7020
gaaaaacgcc agcaacgcgg cctttttacg gttcctggcc ttttgctggc cttttgctca   7080
catgttcttt cctgcgttat cccctgattc tgtggataac cgtattaccg cctttgagtg   7140
agctgatacc gctcgccgca gccgaacgac cgagcgcagc gagtcagtga gcgaggaagc   7200
ggaagagcgc ccaatacgca aaccgcctct ccccgcgcgt tggccgattc attaatg      7257
```

<210> SEQ ID NO 60
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 60

```
gctagatgtt agcgt                                                      15
```

<210> SEQ ID NO 61
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 61

```
ttaggg                                                                 6
```

<210> SEQ ID NO 62
<211> LENGTH: 18
<212> TYPE: DNA
<213> ORGANISM: Artificial Sequence
<220> FEATURE:
<223> OTHER INFORMATION: Synthetic

<400> SEQUENCE: 62

```
ttagggttag ggttaggg                                                   18
```

<210> SEQ ID NO 63
<211> LENGTH: 10
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(5)
<223> OTHER INFORMATION: d is a or g or t; not c
<220> FEATURE:
<221> NAME/KEY: misc_feature
<222> LOCATION: (6)..(7)
<223> OTHER INFORMATION: n is a, c, g, or t

<400> SEQUENCE: 63 ccnddnnggg                                                              10
```